US012780813B2

(12) United States Patent
Adams et al.

(10) Patent No.: US 12,780,813 B2
(45) Date of Patent: Nov. 3, 2026

(54) HSD17B13 INHIBITORS AND/OR DEGRADERS

(71) Applicant: Pfizer Inc., New York, NY (US)

(72) Inventors: Jan Antoinette Cusi Romero Adams, Arlington, MA (US); Bruce Michael Bechle, Oakdale, CT (US); Jason Kenneth Dutra, Gales Ferry, CT (US); Michelle Renee Garnsey, Medford, MA (US); Xinjun Hou, Winchester, MA (US); Jisun Lee, Mystic, CT (US); Deane Milford Nason, II, Norwich, CT (US); Steven Victor O'Neil, East Lyme, CT (US); Danica Antonia Rankic, East Lyme, CT (US); Yang Wang, Newton, MA (US); Ann Sorrentino Wright, Old Lyme, CT (US); Lei Zhang, Auburndale, MA (US); Liying Zhang, Lexington, MA (US); David James Edmonds, Riehen (CH)

(73) Assignee: Pfizer, Inc., New York, NY (US)

( * ) Notice: Subject to any disclaimer, the term of this patent is extended or adjusted under 35 U.S.C. 154(b) by 454 days.

(21) Appl. No.: 18/482,129

(22) Filed: Oct. 6, 2023

(65) Prior Publication Data

US 2024/0150334 A1 May 9, 2024

Related U.S. Application Data

(60) Provisional application No. 63/378,807, filed on Oct. 7, 2022.

(51) Int. Cl.

| | |
|---|---|
| ***C07D 413/04*** | (2006.01) |
| ***C07D 231/56*** | (2006.01) |
| ***C07D 263/56*** | (2006.01) |
| ***C07D 401/04*** | (2006.01) |
| ***C07D 403/04*** | (2006.01) |
| ***C07D 405/14*** | (2006.01) |
| ***C07D 413/14*** | (2006.01) |
| ***C07D 417/04*** | (2006.01) |
| ***C07D 471/04*** | (2006.01) |
| ***C07D 487/04*** | (2006.01) |
| ***C07D 491/048*** | (2006.01) |
| ***C07D 498/04*** | (2006.01) |
| ***C07D 513/04*** | (2006.01) |

(52) U.S. Cl.

CPC ......... *C07D 413/04* (2013.01); *C07D 231/56* (2013.01); *C07D 263/56* (2013.01); *C07D 401/04* (2013.01); *C07D 403/04* (2013.01); *C07D 405/14* (2013.01); *C07D 413/14* (2013.01); *C07D 417/04* (2013.01); *C07D 471/04* (2013.01); *C07D 487/04* (2013.01); *C07D 491/048* (2013.01); *C07D 498/04* (2013.01); *C07D 513/04* (2013.01)

(58) Field of Classification Search

CPC ................ C07D 413/04; C07D 231/56; C07D 263/56; C07D 401/04; C07D 403/04; C07D 405/14

USPC ...................................................... 514/234.5

See application file for complete search history.

(56) References Cited

U.S. PATENT DOCUMENTS

2023/0248851 A1 8/2023 Alonso Silva et al.

FOREIGN PATENT DOCUMENTS

| | | | | |
|---|---|---|---|---|
| CN | 115916761 A | | 4/2023 | |
| EP | 3695012 A1 | | 8/2020 | |
| WO | WO-2010011917 A1 | * | 1/2010 | ............. A61K 31/41 |
| WO | WO-2024075051 A1 | * | 4/2024 | ......... C07D 491/048 |

OTHER PUBLICATIONS

Abul-Husn N., et al., "A Protein-Truncating HSD17B13 Variant and Protection from Chronic Liver Disease," The New England Journal of Medicine, 2018, 378(12), 1096-1106.

International Search Report, Mailed on Jan. 19, 2024 for WO Application No. PCT/IB2023/059988, 4 pages.

Marchais-Oberwinkler, S., et al., "17ß-Hydroxysteroid dehydrogenases (17ß-HSDs) as therapeutic targets: protein structures, functions, and recent progress in inhibitor development," Journal of Steroid Biochemistry and Molecular Biology, 2010, 125(1-2), 66-82.

Written Opinion, Mailed on Jan. 19, 2024 for WO Application No. PCT/IB2023/059988, 5 pages.

* cited by examiner

*Primary Examiner* — James H Alstrum-Acevedo
*Assistant Examiner* — Sahar Inam
(74) *Attorney, Agent, or Firm* — Hamilton, Brook, Smith & Reynolds, P.C.

(57) ABSTRACT

Described herein are compounds of Formula I,

I

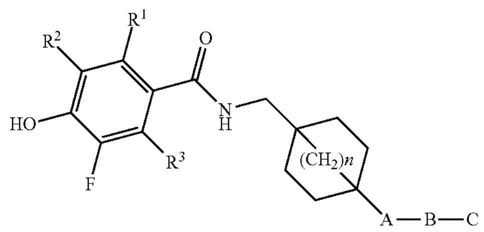

wherein the variables are defined herein, their use as HSD17B13 inhibitors and/or degraders, pharmaceutical compositions containing such compounds and their use to treat, for example, NAFLD and NASH.

16 Claims, No Drawings

HSD17B13 INHIBITORS AND/OR DEGRADERS

FIELD

This application provides compounds that are hydroxysteroid 17β-dehydrogenase13 (HSD17B13) inhibitors and/or degraders, pharmaceutical compositions containing such compounds and their use to treat conditions, diseases or disorders associated with HSD17B13 activity.

BACKGROUND OF THE INVENTION

Hydroxysteroid 17β-dehydrogenase13 (HSD17B13) is a hepatic lipid droplet associated steroid dehydrogenase family enzyme. From 2018 to present, multiple human genetic variants of HSD17B13 have been identified as protective against NASH progression, where these human variants result in reduced hepatic inflammation, ballooning and fibrosis. Abul-Husn et al., 2018 reported a truncation variant was over enriched in individuals with simple steatosis and under enriched in NASH and NASH+fibrosis individuals, implying its protection against disease progression. Abul-Husn, et al., "Protein-Truncating HSD17B13 Variant and Protection from Chronic Liver Disease", N Engl J Med 2018; 378:1096-1106. Later that year a second truncation variant was reported by Kozlitina et al. with reduced allele frequency in blacks and Hispanics with chronic liver disease. Kozlitina, et al., "HSD17B13 and Chronic Liver Disease in Blacks and Hispanics", N Engl J Med 2018; 379:1876-1877. In 2019 a coding variant, P260S, was found by Ma et al. to be associated with reduced inflammation and ballooning. It has been shown that HSD17B13 expression is significantly upregulated in humans with non-alcoholic fatty liver disease (NAFLD). Ma, et al., "17-Beta Hydroxysteroid Dehydrogenase 13 Is a Hepatic Retinol Dehydrogenase Associated With Histological Features of Nonalcoholic Fatty Liver Disease", Hepatology 2019; 69(4):1504-1519. Murine models placed on pro-NASH diets also demonstrate upregulation of the protein. As such, inhibition or degradation of HSD17B13 enzymatic activity is hypothesized to slow or prevent the progression of liver diseases such as nonalcoholic fatty liver diseases (NAFLDs) including NASH (nonalcoholic steatohepatitis), hepatic inflammation, fibrosis, cirrhosis, and development of hepatocellular carcinoma.

Although there has been some early research related to HSD17B13 there remains a need for pharmaceutical agents that have HSD17B13 inhibiting/degrading activity and are useful in the treatment, prevention or diminution of the manifestations of the maladies described herein.

SUMMARY OF THE INVENTION

This application is directed to compounds of the Formula I

Formula I

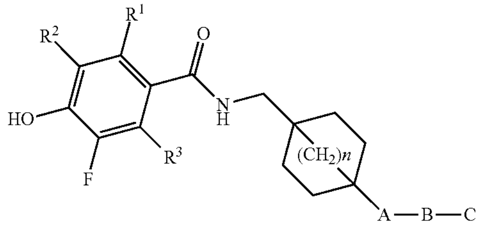

wherein

A is —NH—C(O)— or a heteroaryl having 1, 2, 3, or 4 heteroatoms selected from O, N, and S and wherein A is optionally substituted with one or two $R^4$;

B is absent or is H, aryl, heteroaryl, heterocyclyl, fluoro, chloro, bromo, oxo, cyano, hydroxyl, $(C_1\text{-}C_6)$alkyl, $(C_3\text{-}C_6)$cycloalkyl, $(C_1\text{-}C_6)$fluoroalkyl, $(C_1\text{-}C_6)$alkoxy, or $(C_1\text{-}C_6)$fluoroalkoxy, wherein the heteroaryl or heterocyclyl has 1, 2, or 3 heteroatoms selected from O, N, and S and wherein B is optionally substituted with one or two $R^5$;

C is absent or is H, —NH—C(O)—$R^7$, —$S(O)_2$—$R^7$, —O—$S(O)_2$—$R^7$, fluoro, chloro, bromo, oxo, cyano, hydroxyl, $(C_1\text{-}C_6)$alkyl, $(C_3\text{-}C_6)$cycloalkyl, $(C_1\text{-}C_6)$alkoxy, $(C_3\text{-}C_6)$cycloether, $(C_1\text{-}C_6)$fluoroalkyl, $(C_1\text{-}C_6)$fluoroalkoxy, aryl, heteroaryl or heterocyclyl, wherein the heteroaryl or heterocyclyl has 1, 2, or 3 heteroatoms selected from ON, and S, and wherein C is optionally substituted with one, two or three $R^6$;

$R^1$, $R^2$, and $R^3$ are each independently selected from H and fluoro;

each $R^4$, $R^5$ and $R^6$ are independently selected from oxo, hydroxyl, chloro, fluoro, $(C_1\text{-}C_6)$alkyl, $(C_1\text{-}C_6)$alkoxy, $(C_1\text{-}C_6)$fluoroalkyl, $(C_3\text{-}C_6)$cycloalkyl, and heterocyclyl having 1, 2, or 3 heteroatoms selected from O and N;

$R^7$ is hydroxyl, chloro, fluoro, $(C_1\text{-}C_6)$alkyl, $(C_1\text{-}C_6)$alkoxy, $(C_1\text{-}C_6)$fluoroalkyl, or $(C_3\text{-}C_6)$cycloalkyl; and n is 0, 1 or 2;

or a pharmaceutically acceptable salt of said compound.

This application is also directed at methods of treating fatty liver, nonalcoholic fatty liver disease, nonalcoholic steatohepatitis, nonalcoholic steatohepatitis with liver fibrosis, nonalcoholic steatohepatitis with cirrhosis, nonalcoholic steatohepatitis with cirrhosis, hepatocellular carcinoma, alcoholic fatty liver disease, alcoholic steatohepatitis, hepatitis B, hepatitis C, biliary cirrhosis, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma, Type I diabetes, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, restenosis after angioplasty, peripheral vascular disease, intermittent claudication, postprandial lipemia, metabolic acidosis, ketosis, arthritis, diabetic retinopathy, macular degeneration, cataract, diabetic nephropathy, glomerulosclerosis, chronic renal failure, diabetic neuropathy, skin and connective tissue disorders, foot ulcerations and ulcerative colitis, endothelial dysfunction and impaired vascular compliance, kidney disease, end-stage kidney disease, chronic kidney disease at risk of progression, and maple syrup urine disease by administering to a human in need of such treatment a therapeutically effective amount of a compound of Formula I or a pharmaceutically acceptable salt of said compound.

This application is also directed at methods of reducing the development of liver cirrhosis, cirrhotic decompensation, progression to model of end-stage liver disease (MELD) score >=15, liver transplant, death (liver-related), hepatocellular carcinoma by administering to a human in need of such treatment a therapeutically effective amount of a compound of Formula I or a pharmaceutically acceptable salt of said compound.

This application is also directed at pharmaceutical compositions having a therapeutically effective amount of a compound of Formula I or a pharmaceutically acceptable salt of said compound and a pharmaceutically acceptable carrier, vehicle or diluent.

This application is also directed at pharmaceutical combination compositions that include: a therapeutically effective amount of a composition having:

a first compound, said first compound being a compound of Formula I or a pharmaceutically acceptable salt of said compound;

a second compound, said second compound being an anti-diabetic agent; a non-alcoholic steatohepatitis treatment agent, a non-alcoholic fatty liver disease treatment agent or an anti-heart failure treatment agent and a pharmaceutical carrier, vehicle or diluent.

It is to be understood that both the foregoing general description and the following detailed description are exemplary and explanatory only and are not restrictive of the invention, as claimed.

DETAILED DESCRIPTION OF THE INVENTION

This application may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

The term "and/or" means one or more. For example, "X and/or Y" shall be understood to mean either "X and Y" or "X or Y" and shall be taken to provide explicit support for both meanings or for either meaning. Similarly, when more than 2 expressions are listed, such as in "X, Y and/or Z", it shall be understood to mean either i) "X and Y", "X, Y and Z", "X and Z", or "Y and Z", or ii) "X or Y or Z" and shall be taken to provide explicit support for all meanings.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, butyl, sec-butyl, isobutyl and t-butyl. The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_3$ alkyl refers to alkyl of one to three carbon atoms, inclusive.

"Fluoroalkyl" means an alkyl as defined herein substituted with one, two or three fluoro atoms. Exemplary $(C_1)$fluoroalkyl compounds include fluoromethyl, difluoromethyl and trifluoromethyl; exemplary $(C_2)$fluoroalkyl compounds include 1-fluoroethyl, 2-fluoroethyl, 1,1-difluoroethyl, 1,2-difluoroethyl, 1,1,1-trifluoroethyl, 1,1,2-trifluoroethyl, and the like.

"Cycloalkyl" refers to a nonaromatic ring that is fully hydrogenated group of the formula $C_nH_{2n-1}$. Examples of such carbocyclic rings include cyclopropyl and cyclobutyl.

"Fluorocycloalkyl" means a nonaromatic cycloalkyl ring as defined herein substituted with one, two or three fluoro atoms. Exemplary $(C_3)$fluorocycloalkyl compounds include fluorocyclopropyl, difluorocyclopropyl and trifluorocyclopropyl; exemplary (C4)fluorocycloalkyl compounds include 1-fluorocyclobutyl, 2-fluorocyclobutyl, 1,1-difluorocyclobutyl, 1,2-difluorocyclobutyl, 1,1,1-trifluorocyclobutyl, 1,1,2-trifluorocyclobutyl, and the like.

By "alkoxy" is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

"Fluoroalkoxy" means an alkoxy as defined herein substituted with one, two or three fluoro atoms. Exemplary $(C_1)$fluoroalkoxy compounds include fluoromethoxy, difluoromethoxy and trifluoromethoxy; exemplary $(C_2)$fluoroalkyl compounds include 1-fluoroethoxy, 2-fluoroethoxy, 1,1-difluoroethoxy, 1,2-difluoroethoxy, 1,1,1-trifluoroethoxy, 1,1,2-trifluoroethoxy, and the like.

"Halo" refers to bromo, chloro, fluoro or iodo.

The term "heteroaryl" refers to a monovalent or bivalent group containing at least one aromatic ring and at least one ring member that is a heteroatom (e.g., 1 to 5 heteroatoms, each independently N, O, or S). The total number of ring members may be indicated (e.g., a 5- to 10-membered heteroaryl). The heteroaryl group can include two fused rings, where at least one of the rings is aromatic and the other is aromatic, saturated, or partially unsaturated and at least one of the fused rings contains the heteroatom.

When "ene" is added after "yl" at the end a term to form a new term, the new term refers to a diradical formed by removing one hydrogen atom from the original term of which the new term derived. For example, an alkylene refers to a diradical group formed by removing one hydrogen atom from an alkyl group and that a "methylene" refers to a divalent radical $—CH_2$-derived from removing one hydrogen atom from methyl. More examples of such diradicals include, but are not limited to: alkenylene, alkynylene, cycloalkylene, phenylene, heterocyclylene, and heteroarylene which are derived from alkenyl, alkynyl, cycloalkyl, phenyl, heterocyclyl, and heteroarylene Non-limiting examples of "$C_{13}$ alkylene" include: $—CH_2—$, $—CH(CH_3)—$, $—CH_2—CH_2—$, $—CH_2—CH_2—CH_2—$, $—CH(CH_3)—CH_2—$, and $—CH(CH_2CH_3)—$. For a cyclic moiety, the removal of the hydrogen can occur on any atom of sufficient valency.

"Compounds" when used herein includes any pharmaceutically acceptable derivative or variation, including conformational isomers (e.g., cis and trans isomers), atropisomers (i.e., stereoisomers from hindered rotation), and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of Formula I include but are not limited to those having a carboxyl moiety wherein the free hydrogen is replaced by ($C_1$-$C_4$)alkyl, ($C_2$-$C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

As used herein, an arrowhead, "" or wavy line, "" denotes a point of attachment of a substituent to another group.

"Deuterium enrichment factor" as used herein means the ratio between the deuterium abundance and the natural abundance of deuterium, each relative to hydrogen abundance. An atomic position designated as having deuterium typically has a deuterium enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "mammal" refers to human, livestock or companion animals.

The term "companion animal" or "companion animals" refers to animals kept as pets or household animals. Examples of companion animals include dogs, cats, and rodents including hamsters, guinea pigs, gerbils and the like, rabbits, ferrets.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits.

"Patient" refers to warm blooded animals such as, for example, guinea pigs, mini pigs, mice, rats, gerbils, cats, rabbits, dogs, cattle, goats, sheep, horses, monkeys, chimpanzees, and humans.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation in combination with other therapies.

"Therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "pharmaceutically acceptable" means the substance (e.g., the compounds of the invention) and any salt thereof, or composition containing the substance or salt of the invention that is suitable for administration to a patient. When referring to a compound of Formula I, unless otherwise stated, it is understood that a pharmaceutically acceptable salt of said compound is also considered.

In an embodiment of the compound, the compound has the Formula IA

Formula IA

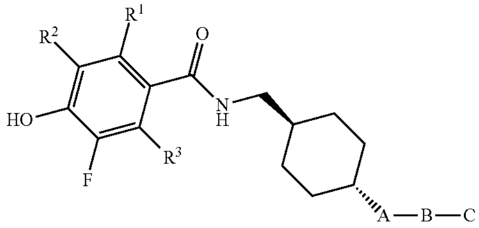

or a pharmaceutically acceptable salt of said compound.

In an embodiment of the compound, the compound has the Formula IB

Formula IB

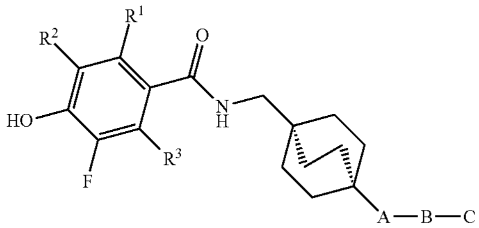

or a pharmaceutically acceptable salt of said compound.

In an embodiment of the compound, $R^2$ is F, or a pharmaceutically acceptable salt of said compound.

In an embodiment of the compound, A is thiazolyl, pyrazolyl, oxazolyl, imidazolyl, isoxazolyl, isothiazolyl, imidazotriazinyl, imidazopyridazinyl, imidazopyridinyl, benzoimidazolyl, benzothiazolyl, purinyl, pyridopyridazinyl, quinazolinyl, indazolyl, imidazopyridinyl, benzooxazolyl, pyrazolopyridinyl, isoindolinonyl, triazolyl, or oxadiazolyl, or a pharmaceutically acceptable salt of said compound.

In another embodiment of the compound, A is

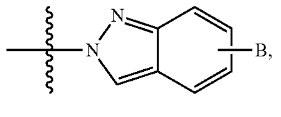

-continued

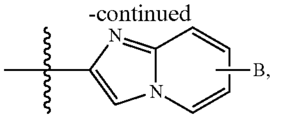

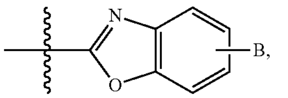

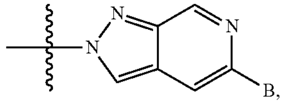

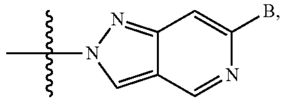

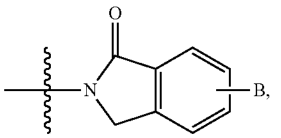

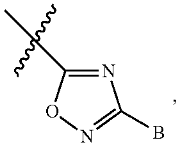,

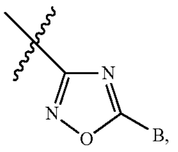

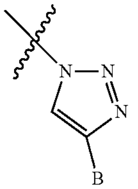, or

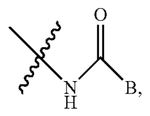

In another embodiment of the compound, B is absent or is H, pyridinyl, pyrimidinyl, pyridazinyl, pyrazinyl, pyrazolyl, piperazinyl, quinoxalinyl, phenyl, triazolyl, thiazolyl, thiadiazolyl, oxazolyl, imidazolyl, indazolyl, ($C_1$-$C_6$)alkyl, ($C_1$-$C_6$)fluoroalkyl, ($C_1$-$C_6$)alkoxy, bromo, chloro, fluoro, or oxo, and wherein B is optionally substituted with one or two fluoro, oxo, hydroxyl, ($C_1$-$C_6$)alkyl, ($C_3$-$C_6$)cycloalkyl, ($C_1$-$C_6$)fluoroalkyl, ($C_1$-$C_6$)alkoxy, or ($C_3$-$C_6$)cycloether;

or a pharmaceutically acceptable salt of said compound.

In another embodiment of the compound, B is pyrimidinyl, ($C_1$-$C_3$)fluoroalkyl substituted pyrimidinyl, ($C_1$-$C_3$)alkyl substituted pyrazolyl, methoxy substituted pyridazinyl, difluoromethyl substituted pyrazinyl, trifluoromethyl substituted pyrimidinyl, or methoxy substituted pyrimidinyl;

or a pharmaceutically acceptable salt of said compound.

In another embodiment of the compound, C is absent or is H, pyridinyl, piperazinyl, oxolanyl, ($C_3$-$C_6$)cycloalkyl, ($C_1$-$C_6$)alkyl, ($C_1$-$C_6$)fluoroalkyl, ($C_1$-$C_6$)alkoxy, cyano, bromo, chloro, fluoro, or oxo, and wherein C is optionally substituted with one, two or three fluoro, oxo, hydroxyl, ($C_1$-$C_6$)alkyl, ($C_3$-$C_6$)cycloalkyl, ($C_1$-$C_6$)fluoroalkyl, or ($C_1$-$C_6$)alkoxy;

or a pharmaceutically acceptable salt of said compound.

In another embodiment of the compound, C is absent or is pyridinyl, piperazinyl, ($C_3$-$C_6$)cycloalkyl, ($C_1$-$C_6$)alkyl, ($C_1$-$C_6$)fluoroalkyl; and wherein C is optionally substituted with one, two or three fluoro, oxo, hydroxyl, or ($C_1$-$C_6$) alkyl;

or a pharmaceutically acceptable salt of said compound.

In an embodiment of the compound, the compound is 2,3,5-Trifluoro-4-hydroxy-N-[(4-{3-[5-(trifluoromethyl)pyrimidin-2-yl]-1,2,4-oxadiazol-5-yl}bicyclo[2.2.2]octan-1-yl)methyl]benzamide; 2,3,5-Trifluoro-4-hydroxy-N-({(1r,4r)-4-[6-(1-methyl-1H-pyrazol-4-yl)-2H-indazol-2-yl]cyclohexyl}methyl)benzamide; 2,3,5-Trifluoro-4-hydroxy-N-({4-[6-(pyrimidin-2-yl)-2H-indazol-2-yl]bicyclo[2.2.2]octan-1-yl}methyl)benzamide; 2,3,5-Trifluoro-4-hydroxy-N-({(1r,4r)-4-[6-(pyrimidin-5-yl)-2H-indazol-2-yl]cyclohexyl}methyl)benzamide; 2,3,5-Trifluoro-4-hydroxy-N-({4-[3-(6-methoxypyridazin-3-yl)-1,2,4-oxadiazol-5-yl]bicyclo[2.2.2]octan-1-yl}methyl)benzamide; N-[(4-{5-[5-(Difluoromethyl)pyrazin-2-yl]-1,2,4-oxadiazol-3-yl}bicyclo[2.2.2]octan-1-yl)methyl]-3,5-difluoro-4-hydroxybenzamide; 3,5-Difluoro-4-hydroxy-N-{[(1r,4r)-4-{3-[5-(trifluoromethyl)pyrimidin-2-yl]-1,2,4-oxadiazol-5-yl}cyclohexyl]methyl}benzamide; 3,5-Difluoro-4-hydroxy-N-({(1r,4r)-4-[6-(2-methoxypyrimidin-5-yl)-2H-pyrazolo[4,3-c]pyridin-2-yl]cyclohexyl}methyl)benzamide; 2,3,5-Trifluoro-4-hydroxy-N-[(4-{5-[2-(piperazin-1-yl)pyrimidin-4-yl]-1,2,4-oxadiazol-3-yl}bicyclo[2.2.2]octan-1-yl)methyl]benzamide or 2,3,5-Trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide, or a pharmaceutically acceptable salt of said compound.

In an embodiment of the compound, the compound is 2,3,5-trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide or a pharmaceutically acceptable salt of said compound.

In an embodiment of the invention, a method of treating fatty liver, nonalcoholic fatty liver disease, nonalcoholic steatohepatitis, nonalcoholic steatohepatitis with liver fibrosis, nonalcoholic steatohepatitis with cirrhosis or nonalcoholic steatohepatitis with cirrhosis and hepatocellular carcinoma comprising administering to a human in need of such treatment a therapeutically effective amount of the compound of Formula I or a pharmaceutically acceptable salt of said compound.

In an embodiment of the invention, the method includes treating nonalcoholic steatohepatitis.

In an embodiment of the invention, a pharmaceutical composition comprises a therapeutically effective amount of the compound of Formula I or a pharmaceutically acceptable salt of said compound and a pharmaceutically acceptable carrier, vehicle or diluent.

In an embodiment of the invention, a pharmaceutical combination composition comprises a therapeutically effective amount of a composition comprising: a first compound, said first compound being a compound of Formula I or a pharmaceutically acceptable salt of said compound; a second compound, said second compound being an anti-diabetic agent; a non-alcoholic steatohepatitis treatment agent, a non-alcoholic fatty liver disease treatment agent or an anti-heart failure treatment agent; and a pharmaceutical carrier, vehicle or diluents.

In an embodiment of the invention, the non-alcoholic steatohepatitis treatment agent or non-alcoholic fatty liver disease treatment agent in the pharmaceutical combination composition is an ACC inhibitor, a KHK inhibitor, a DGAT-2 inhibitor, an FXR agonist, metformin, incretin analogs, or an incretin receptor modulator.

In an embodiment of the disclosure, the anti-diabetic agent is an SGLT-2 inhibitor, metformin, incretin analogs, an incretin receptor modulator, a DPP-4 inhibitor, or a PPAR agonist.

The invention includes compounds of the present invention that are targeted protein ligands covalently linked to E3 ligase ligands or ligands known to interact with the ubiquitin proteasome system (Degrons) through a Linker of varying length and functionality. The compounds of the present invention, when so linked to Degrons are referred to herein as bifunctional compounds of the present invention. The compounds of the present invention are generally referred to as a Targeting Ligand within these bifunctional compounds of the present invention. These bifunctional compounds of the present invention can be used as therapeutics for treating various diseases including various liver diseases.

The bifunctional compounds of the present invention have the general structure: Degron-Linker-Targeting Ligand, wherein the Linker is covalently bound to at least one Degron and at least one Targeting Ligand, wherein the Degron is a compound capable of binding to a ubiquitin ligase such as an E3 Ubiquitin Ligase (e.g., cereblon (CRBN), von Hippel-Lindau (VHL), and the like), and the Targeting Ligand is capable of binding to the targeted protein(s) HSD17B13, and is a compound of the present invention as presented in any embodiment described herein. Such bifunctional compounds of the present invention are generally presented as compounds of Formula II, where L is the Linker and D is the Degron:

(II)

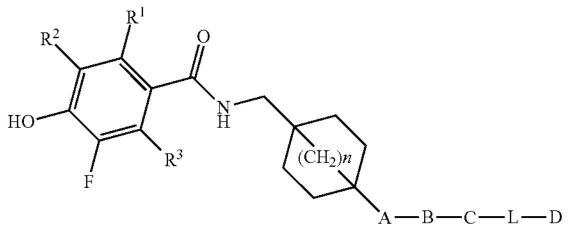

The Degron is small in size and highly effective in recruiting targeted proteins for degradation. The Degron is a compound that serves to link a targeted protein, through the Linker and Targeting Ligand, to a ubiquitin ligase for proteasomal degradation. In certain embodiments, the Degron is a compound that is capable of binding to or binds to a ubiquitin ligase. In further embodiments, the Degron is a compound that is capable of binding to or binds to a E3 Ubiquitin Ligase, including cereblon, wherein the Degron is a thalidomide, lenalidomide, pomalidomide, or iberdomide, or newer IMiDs CRBN ligands disclosed in WO2019/060693, WO2019/140387, WO2019/236483 or analogs thereof. In further embodiments, the Degron is a compound that is capable of binding to or binds to a E3 Ubiquitin Ligase, including von Hippel-Lindau ligand. See, e.g., WO2020/092907; WO2013106643; Buckley et al. *J. Am. Chem. Soc.* 2012, 134, 4465-4468, "Targeting the Von Hippel-Lindau E3 Ubiquitin Ligase Using Small Molecules to Disrupt the VHL/Hif-1alpha Interaction", Soares et al. *J. Med. Chem.* 2019, 61, 599-618, "Group-Based Optimization of Potent and Cell-Active Inhibitors of the von Hippel-Lindau (VHL) E3 Ubiquitin Ligase: Structure-Activity Relationships Leading to the Chemical Probe (2S,4R)-1-((S)-2-(1-Cyanocyclopropanecarboxamido)-3,3-dimethylbutanoyl)-4-hydroxy-N-(4-(4-methylthiazol-5-yl)benzyl)pyrrolidine-2-carboxamide (VH298)". In further embodiments, the Degron is a compound that is capable of binding to or binds to a E3 Ubiquitin Ligase, including inhibitors of apoptosis protein ligases (IAP1, IAP2, XIAP). See, e.g. Itoh et al, *J. Am. Chem. Soc.* 2010, 132, 5820-5826 "Protein Knockdown Using Methyl Bestatin-Ligand Hybrid Molecules: Design and Synthesis of Inducers of Ubiquitination-Mediated Degradation of Cellular Retinoic Acid-Binding Proteins', Mares et al. Commun. Biol. 2020, 3, 140, "Extended pharmacodynamic responses observed upon PROTAC-mediated degradation of RIPK2', and Tinworth et al. ACS Chem. Biol. 2019, 14, 342-347, "PROTAC-Mediated Degradation of Bruton's Tyrosine Kinase Is Inhibited by Covalent Binding.' In further embodiments, the Degron is a compound that is capable of binding to or binds other ubiquitin proteasome proteins that can induce degradation including, but not limited to, the Hsp70/90 chaperone complex (WO2020/207395), Usp14 (WO2019/238886), UchL5 (WO2019238816), BILO (WO201719705), and Rpn11 (WO2019/238817).

In certain embodiments, the Linker is designed and optimized based on SAR (structure-activity relationship) and X-ray crystallography of the Targeting Ligand with regard to the location of attachment for the Linker.

In certain embodiments, the optimal Linker length and composition vary by target and can be estimated based upon X-ray structures of the original Targeting Ligand bound to its target. Linker length and composition can be also modified to modulate metabolic stability and pharmacokinetic (PK) and pharmacodynamics (PD) parameters.

In certain embodiments, where the Target Ligand binds multiple targets, selectivity may be achieved by varying Linker length where the ligand binds some of its targets in different binding pockets, e.g., deeper or shallower binding pockets than others.

The Linker ("L") provides a covalent attachment between the Targeting Ligand and the Degron. The Linker has two terminating groups, wherein one terminating group attaches to the Degron and the other terminating group attaches to the Targeting Ligand. The structure of the Linker may not be critical, provided it does not substantially interfere with the activity of the Targeting Ligand or the Degron. In some embodiments, the Linker is an alkyl chain (e.g., having 2-20 alkyl units), or a polyethylene glycol (PEG) chain ($CH_2CH_2$—O or (O—$CH_2CH_2$)). In other embodiments, the Linker may be an alkylene chain, a PEG chain, or a bivalent alkylene chain, any of which may be interrupted by, and/or terminate (at either or both termini) by at least one of the following: —O—, —S—, —N($R^L$)—, —C≡C—, —C(O)—, —C(O)O—, —OC(O)—, —OC(O)O—, —C(NOR$^L$)—, —C(O)N($R^L$)—, —C(O)N($R^L$)C(O)—, —C(O)N($R^L$)C(O)N($R^L$)—, —N($R^L$)C(O)—, —N($R^L$)C(O)N($R^L$)—, —N($R^L$)C(O)O—, —OC(O)N($R^L$)—, —C(NR$^L$)—, —N($R^L$)C(NR$^L$)—, —C(NR$^L$)N($R^L$)—, —N($R^L$)C(NR$^L$)N($R^L$)—, —OB($CH_3$)O—, —S$(O)_2$—, —OS(O)—, —S(O)O—, —S(O)—, —OS$(O)_2$—, —S$(O)_2$O—, —N($R^L$)S$(O)_2$—, —S$(O)_2$N($R^L$)—, —N($R^L$)S(O)—, —S(O)N($R^L$)—, —N($R^L$)S$(O)_2$N($R^L$)—, —N(R')S(O)N(R')—, $C_{3-12}$ carbocyclene, 3- to 12-membered heterocyclene, 5- to 12-membered heteroarylene, or arylene, or any combination thereof, wherein $R^L$ is H or $C_{1-6}$ alkyl, wherein the interrupting and the one or both terminating groups may be the same or different.

In some embodiments, the Linker may be $C_{1-10}$ alkylene chain terminating in NH-group wherein the nitrogen is also bound to the Degron, or the Linker may be a $C_{1-10}$ alkylene chain or a PEG chain having 1-8 PEG units and interrupted by or terminating in —$(CH_2)_{n'}$, —C(O)—NH—, where n' is 0 to about 5. For the Linker, "Carbocyclene" refers to a bivalent carbocycle radical, which is optionally substituted. "Heterocyclylene" refers to a bivalent heterocyclyl radical which may be optionally substituted. "Heteroarylene" refers to a bivalent heteroaryl radical which may be optionally substituted.

Nonlimiting examples of a Linker include —$(CH_2)_{n'}$—, —$(CH_2CH_2$—$O)_{n''}$—$(CH_2)_{n'}$, —C(O)—, $(CH_2)_{n'}$—C(O)—

$N(R^L)—(CH_2CH_2—O)_{n''}—(CH_2)_{n'}—C(O)—$, $—(CH_2CH_2—O)_{n''}—(CH_2)_{n'}—N(R^L)—C(O)—$, $—(CH_2CH_2—O)_{n''}—(CH_2)_{n'}—C(O)—N(R^L)—$, $—(CH_2)_{n'}$-phenylene-$N(R^L)—C(O)—(CH_2)_{n'}—$, $—N(R^L)—(CH_2)_{n'}—$O-phenylene-$(CH_2)_{n''}—N(R^L)—(CH_2)_{n'}—$, $—(CH_2)_{n'}—C(O)—N(R^L)$-phenylene-$C(O)—$, $—N(R^L)—(CH_2)_{n'}$-phenylene-$(CH_2)_{n''}$-heterocyclylene-, $—(CH_2)_{n'}$-phenylene-$N(R^L)—C(O)—(CH_2CH_2—O)_{n''}—(CH_2)_{n'}—$, $—(CH_2)_{n'}$-phenylene-$(CH_2)_{n''}$-heterocyclylene-$(CH_2)_{n''}—C(O)—N(R^L)—(CH_2)_{n'}—$, $—(CH_2)_{n'}$-phenylene-O—$(CH_2)_{n'}$-heterocyclylene-$(CH_2)_{n'}—$, $—(CH_2)_{n'}$-phenylene-$(CH_2)_{n'}$-heterocyclylene-$(CH_2)_{n'}—O—$, $—(CH_2)_{n'}$-heterocyclylene-$(CH_2)_{n'}$, wherein $R^L$ is H or $C_{1-6}$ alkyl; n' is 0 to about 10; and n" is 1 to about 10.

Another embodiment includes a compound selected from any of the Examples described herein, or a pharmaceutically acceptable salt thereof.

Another embodiment includes a prodrug of any of the Examples described herein, or a pharmaceutically acceptable salt thereof.

Another embodiment includes a phosphate ester prodrug of any of the Examples described herein, or a pharmaceutically acceptable salt thereof.

Another embodiment includes any novel genus of intermediates described in the General Schemes or Examples.

Another embodiment includes any novel specific intermediate described in the Preparations and Examples described herein.

Another embodiment includes any novel process described herein.

All pharmaceutically acceptable isotopically-labelled compounds of Formula I are within scope of this application wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$, and $^{14}C$, chlorine, such as $^{36}Cl$, fluorine, such as $^{18}F$, nitrogen, such as $^{13}N$ and $^{15}N$, oxygen, such as $^{15}O$, $^{17}O$ and $^{18}O$, and sulphur, such as $^{35}S$.

Certain isotopically-labelled compounds of Formula I for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labelled compounds of Formula I can generally be prepared by conventional techniques known to those skilled in the art or by processes analogous to those described in the accompanying Examples and Preparations using an appropriate isotopically-labelled reagent in place of the non-labelled reagent previously employed.

Certain compounds of Formula I and intermediates described herein may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

Salts encompassed within the term "pharmaceutically acceptable salts" refer to the compounds of this invention which are generally prepared by reacting the free base or free acid with a suitable organic or inorganic acid, or a suitable organic or inorganic base, respectively, to provide a salt of the compound of the invention that is suitable for administration to a patient. Base salts are preferred, however, some compounds may also form acid salts. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, calcium, choline, diethylamine, glycine, lysine, magnesium, meglumine, olamine, potassium, sodium, trimethamine and zinc salts. Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Hemisalts of acids and bases may also be formed, for example, hemisulfate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of Formula I, and pharmaceutically acceptable salts thereof, may exist in unsolvated and solvated forms. The term 'solvate' is used herein to describe a molecular complex comprising the compound of Formula I, or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

Also included within the scope of the invention are active metabolites of compounds of Formula I (including prodrugs), that is, compounds formed in vivo upon administration of the drug, often by oxidation or dealkylation. Some examples of metabolites in accordance with the invention include:

(i) where the compound of Formula I contains a methyl group, a hydroxymethyl derivative thereof ($—CH_3 \rightarrow —CH_2OH$) and (ii) where the compound of Formula I contains an alkoxy group, a hydroxy derivative thereof (—OR→—OH).

The compounds of the invention may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of Formula I may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^-Na^+$, $—COO^-K^+$, or $—SO_3^-Na^+$) or non-ionic (such as $—N^-N^+(CH_3)_3$) polar head group. For more information, see Crystals and the Polarizing Microscope by N. H. Hartshorne and A. Stuart, $4^{th}$ Edition (Edward Arnold, 1970).

The compounds of Formula I may exhibit polymorphism and/or one or more kinds of isomerism (e.g., optical, geometric or tautomeric isomerism). The compounds of Formula I may also be isotopically labelled. Such variation is implicit to the compounds of Formula I defined as they are by reference to their structural features and therefore within the scope of the invention.

The terms "concentrated," "evaporated," and "concentrated in vacuo" refer to the removal of solvent at reduced pressure on a rotary evaporator with a bath temperature less than 60° C. The abbreviation "min" and "h" stand for "minutes" and "hours" respectively. The term "room temperature or ambient temperature" means a temperature between 18 to 25° C., "GCMS" refers to gas chromatography-mass spectrometry, "LCMS" refers to liquid chromatography-mass spectrometry, "UPLC" refers to ultra-performance liquid chromatography, "SFC" refers to supercritical fluid chromatography, "HPLC" refers to high-pressure liquid chromatography, "MPLC" refers to medium-pressure liquid chromatography, "TLC" refers to thin-layer chromatography, "MS" refers to mass spectrum or mass spectroscopy or mass spectrometry, "NMR" refers to nuclear magnetic resonance spectroscopy, "DCM" refers to dichloromethane, "DMSO" refers to dimethyl sulfoxide, "DME" refers to 1,2-dimethoxyethane, "EtOAc" refers to ethyl acetate, "MeOH" refers to methanol, "Ph" refers to the phenyl group, "Pr" refers to propyl, "trityl" refers to the triphenylmethyl group, "ACN" refers to acetonitrile, "DEAD" refers to diethyl azodicarboxylate, and "DIAD" refers to diisopropyl azodicarboxylate.

In general, the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section. Specific synthetic schemes for preparation of the compounds of Formula I are outlined below.

As used herein, the expressions "reaction-inert solvent" and "inert solvent" refer to a solvent or a mixture thereof which does not interact with starting materials, reagents, intermediates or products in a manner which adversely affects the yield of the desired product.

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-tert-butoxycarbonyl, benzyloxycarbonyl, and 9-fluorenylmethylenoxycarbonyl for amines and lower alkyl or benzyl esters for carboxylic acids), which are generally not chemically reactive under the reaction conditions described and can typically be removed without chemically altering other functionality in the Formula I compound.

The compounds of Formula I and intermediates may contain asymmetric or chiral centers, and, therefore, exist in different stereoisomeric forms. Unless specified otherwise, it is intended that all stereoisomeric forms of the compounds as well as mixtures thereof, including racemic mixtures are included herein. In addition, all geometric and positional isomers are included within the scope of the compounds. For example, if a compound incorporates a double bond or a fused ring, both the cis- and trans-forms, as well as mixtures, are embraced within the scope of the invention.

In addition, the compounds of Formula I and intermediates embrace all atropisomers and stereoisomeric mixtures thereof, including racemic mixtures. Atropisomers include those that can be isolated as separate stereoisomers and retain their stereoisomeric purity for various lengths of time including moderate and long times. Atropisomers also include those isomers that cannot be readily separated as separate stereoisomers due to interconversion over some time period including short to moderate times.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds possess one or more stereogenic centers and no stereochemistry is given in the name or structure, it is understood that the name or structure is intended to encompass all forms of the compound, including the racemic form.

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

It is also possible that the intermediates and compounds of Formula I may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the tetrazole moiety where the proton may migrate between the four ring nitrogen as follows.

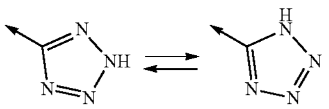

Valence tautomers include interconversions by reorganization of some of the bonding electrons.

Included within the scope of the claimed compounds present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Compounds of Formula I may be prepared according to the General Schemes and Examples provided herein.

General Schemes

In general, the compounds of this invention may be made by processes described herein and by analogous processes known to those skilled in the art. Certain processes for the manufacture of the compounds of this invention are described in the following reaction schemes. Other processes are described in the experimental section. The schemes and examples provided herein (including the corresponding description) are for illustration only. The substituent groups labelled in Schemes 1-7 are as described in this application, wherein PMB is p-methocybenzyl ether and Boc is tert-butyloxycarbonyl.

Scheme 1 refers to the preparation of compounds of Formula IA. Compounds of Formula IA can be readily prepared from intermediates IV, VI, and VIII. Intermediate IV can be prepared from an amide bond forming reaction between carboxylic acid intermediate II and amine intermediate III. Similarly, intermediates VI and VIII can be prepared from an amide bond forming reaction between intermediate II and intermediates V and VII, respectively. Amide bond forming reactions of this type can be achieved by combining a carboxylic acid (such as II) with an amine (such as III, V or VII) in the presence of an activating reagent (such as O-(7-azabenzotriazol-1-yl)-N,N,N',N'-tetramethyluronium hexafluorophosphate; HATU) and a base (such as N,N-diisopropylethylamine) in a suitable solvent (such as dichloromethane).

Scheme 1
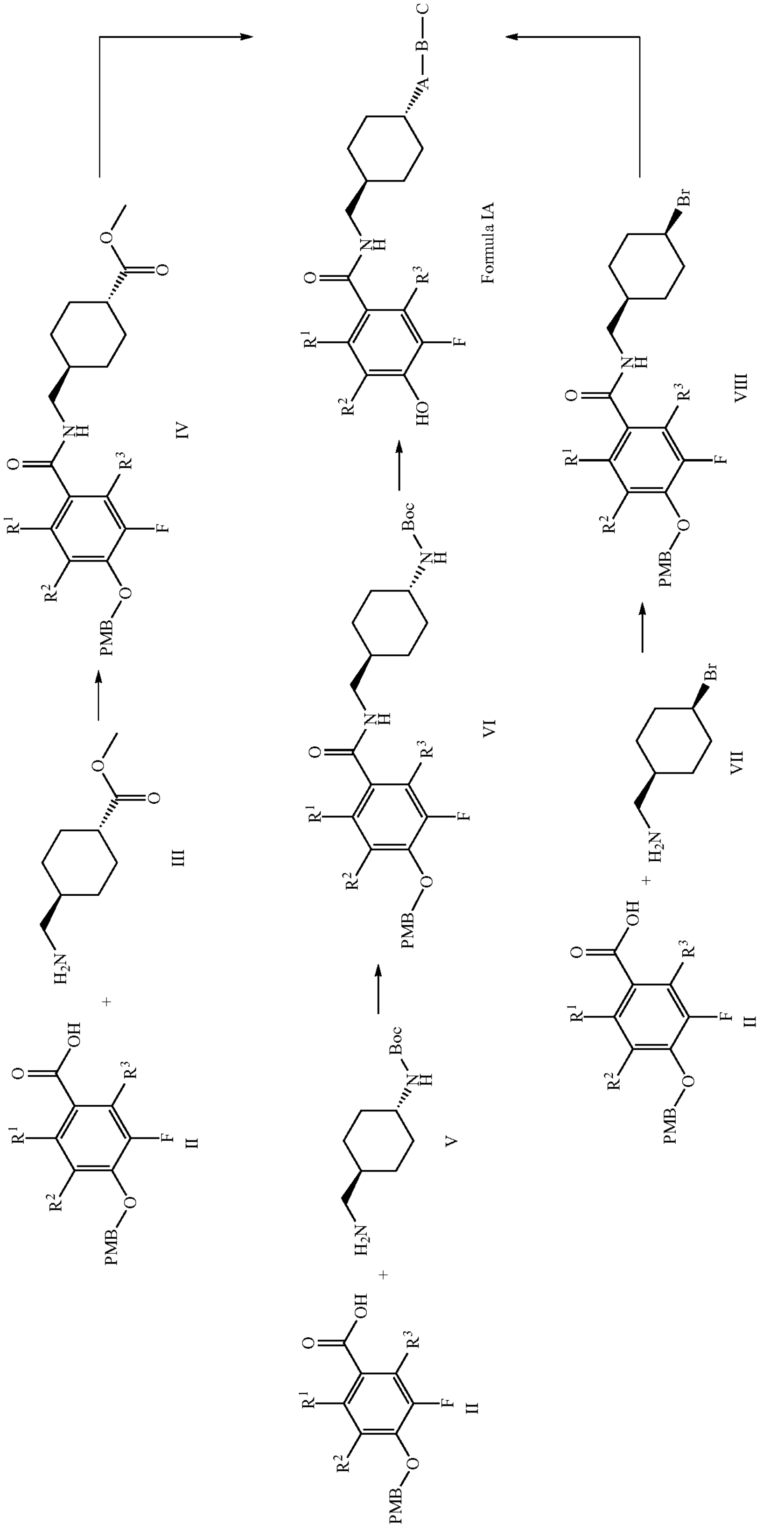

Scheme 2 refers to the preparation of compounds of Formulas IA-1, IA-2, IA-3 and IA-4 from intermediate IV. The ester in intermediate IV may be hydrolyzed to afford intermediate IX. The carboxylic acid functional group in intermediate IX can be converted to various heteroaryl rings systems by methods known to those skilled in the art. For example, intermediate IX can be reacted with aminophenols such as X under suitable conditions to afford compounds of Formula IA-1 after removal of the PMB protecting group. Alternatively, intermediate IX can be coupled with intermediates of the structure XI, and the resulting compound can be further dehydrated and deprotected to afford compounds of Formula IA-2. One skilled in the art may also recognize that the carboxylic acid in intermediate IX can be converted to an alternate functional group that may have further functionality for the construction of other heteroaryl ring systems. For example, the carboxylic acid in compound IX can be converted to a bromoketone by methods known in the art to afford intermediate XII. Intermediate XII can be reacted with aminopyridines (XIII) and subsequently deprotected to prepare compounds of Formula IA-3. Alternatively, the carboxylic acid in IX can be converted to a primary amide and subsequently dehydrated to afford a nitrile-containing intermediate of structure XIV. Intermediate XIV can be reacted with hydroxylamine to afford compound XV. Compounds of structure XV can be reacted with carboxylic acids of structure XVI. The resulting compounds can be dehydrated and deprotected to form oxadiazole-containing compounds of Formula IA-4.

Scheme 2
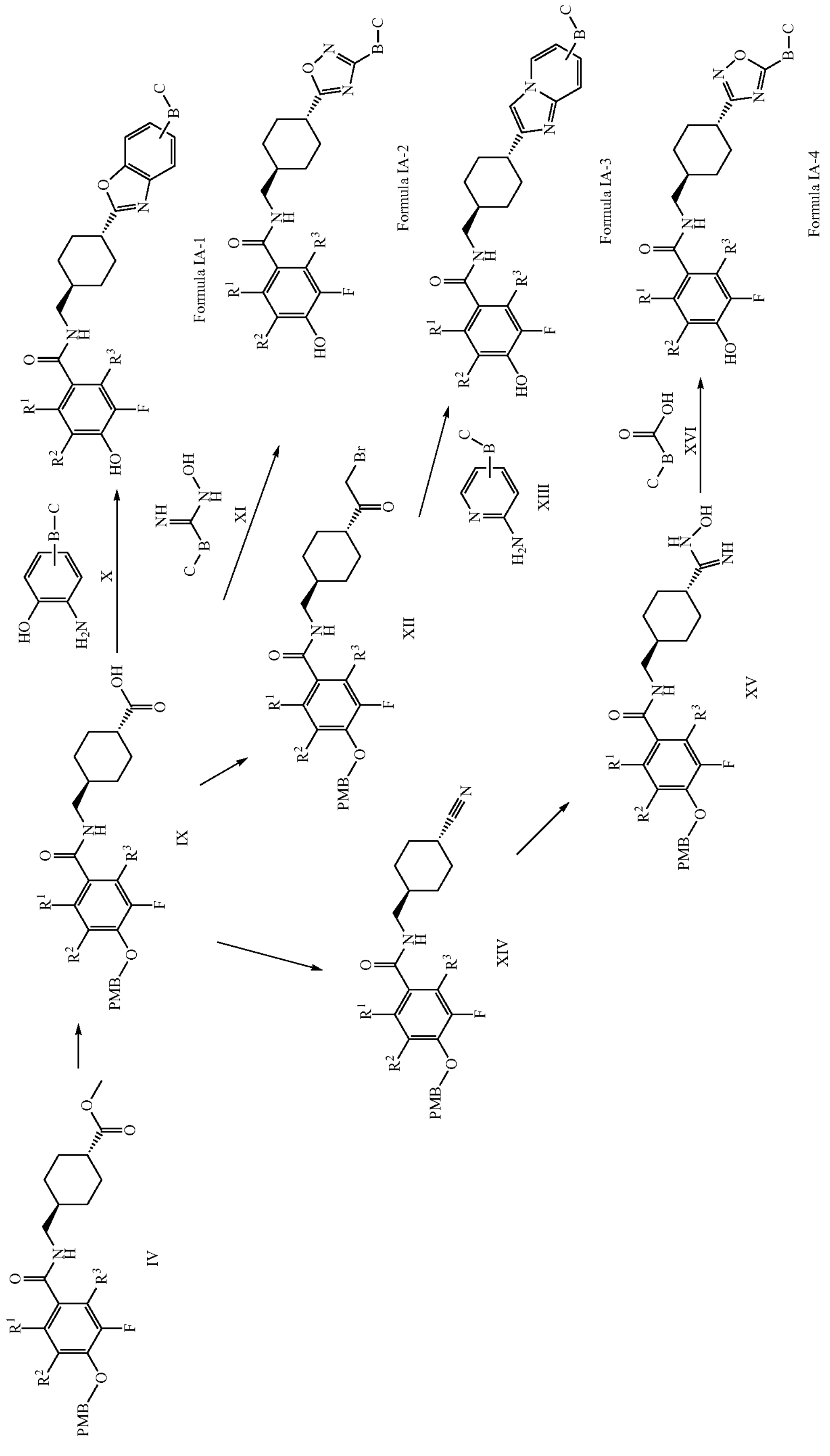
IV
IX
X
XI
XII
XIII
XIV
XV
XVI
Formula IA-1
Formula IA-2
Formula IA-3
Formula IA-4

Scheme 3 refers to the preparation of compounds of Formulas IA-5 and IA-6 from intermediate VI. The Boc protecting group in intermediate VI can be selectively removed to afford intermediate XVII. Intermediate XVII can be reacted with a nitroaldehyde-containing compound (XVIII) in the presence of a trialkylphosphine to afford a compound of Formula IA-5 after removal of the PMB protecting group. Alternatively, compound XVII can be reacted with bromoester-containing compound (XIX) and subsequently deprotected to afford a compound of Formula IA-6.

Scheme 3

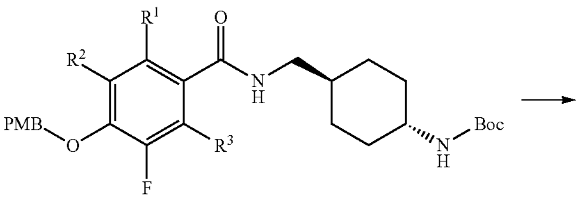

VI

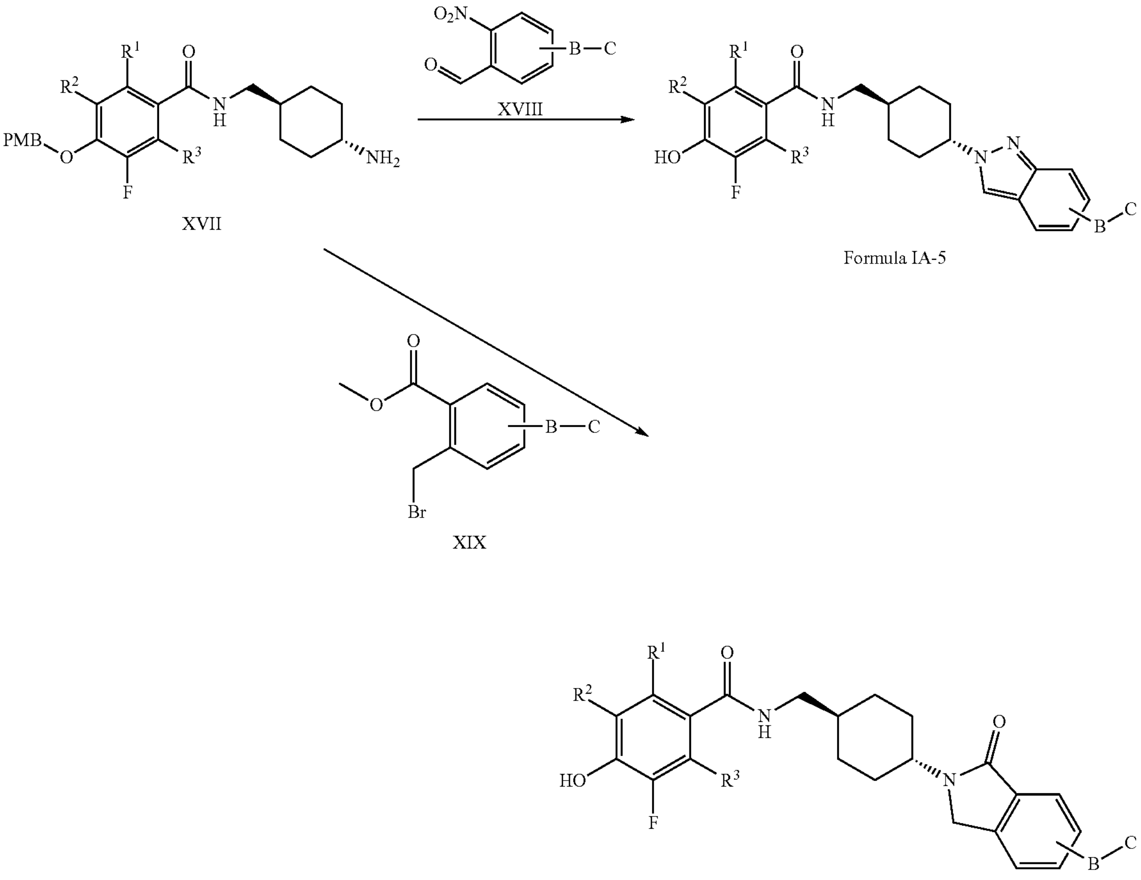

XVII

XVIII

Formula IA-5

XIX

Formula IA-6

Scheme 4 refers to the preparation of compounds of Formulas IA and IA-7 from intermediate VIII. Intermediates of the structure VIII can be reacted with aryl and heteroaryl halides ~(XX) in the presence of suitable metal-containing catalysts and ligands to afford compounds of Formula IA after removal of the PMB protecting group. Alternatively, bromide can be displaced from intermediate VIII with sodium azide. The resulting intermediate can be reacted with an alkyne-containing compound (XXI) in the presence of a copper catalyst to afford a compound of Formula IA-7.

Scheme 4

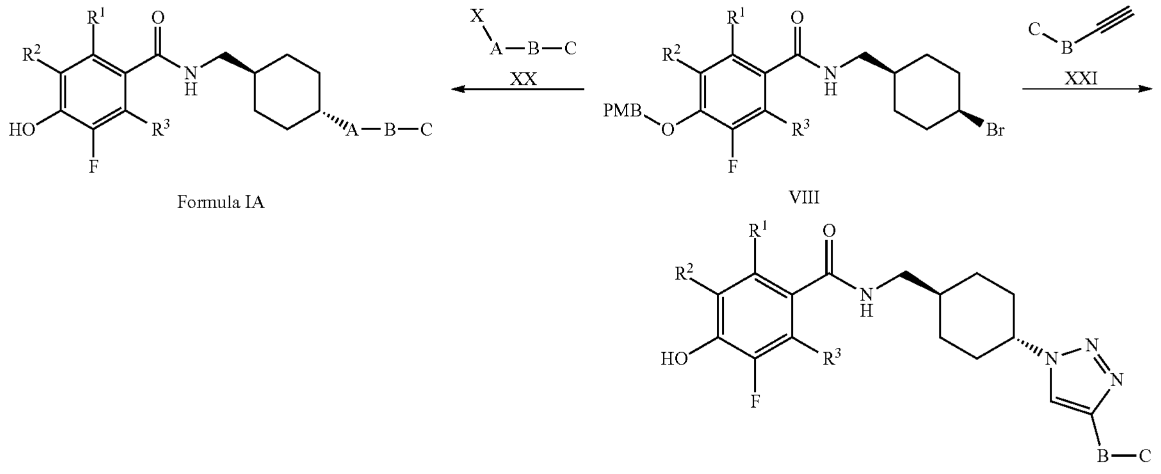

Formula IA

VIII

Formula IA-7

Scheme 5 refers to an alternate preparation of compounds of Formula IA-5. In some instances, compounds may be prepared by the methods described herein that contain substituents that can be utilized synthetically to prepare alternate compounds of Formula IA. For example, an intermediate of the structure XXII may be prepared by the method described for the preparation of compounds of Formula IA-5. The bromine substituent in intermediate XXII can be reacted with boronic acids (XXIII) or boronate esters (XXIII) by a Suzuki reaction to afford a compound of Formula IA-5. Additionally, compounds of structure XXII can be reacted with intermediates of structure XXIV, where B—H represents a primary or secondary amine. In this instance, XXII and XXIV can react with one another under Buchwald reaction conditions to afford another variation on compounds or Formula IA-5. Alternatively, the bromine substituent in XXII can be converted to a boronic acid (XXV; R=H) or boronate ester (XXV; R=alkyl). Compounds of the structure XXV can be reacted with aryl and heteroaryl halides of the structure XXVI to afford compounds of Formula IA-5. Additionally, compounds of structure XXV can be reacted with aromatic heterocycles bearing an N—H (XXIV') under Cham-Lam coupling conditions to afford compounds of Formula IA-5. The example transformations provided in Scheme 5 are not intended to be comprehensive. The examples provided are just isolated examples of synthetic sequences that can be used to make modifications to the B-substituents and the C-substituents of Compounds of Formula IA. One skilled in the art will also recognize that similar transformations can be achieved with compounds containing alternate A-substituents from that depicted in Scheme 5.

Scheme 5
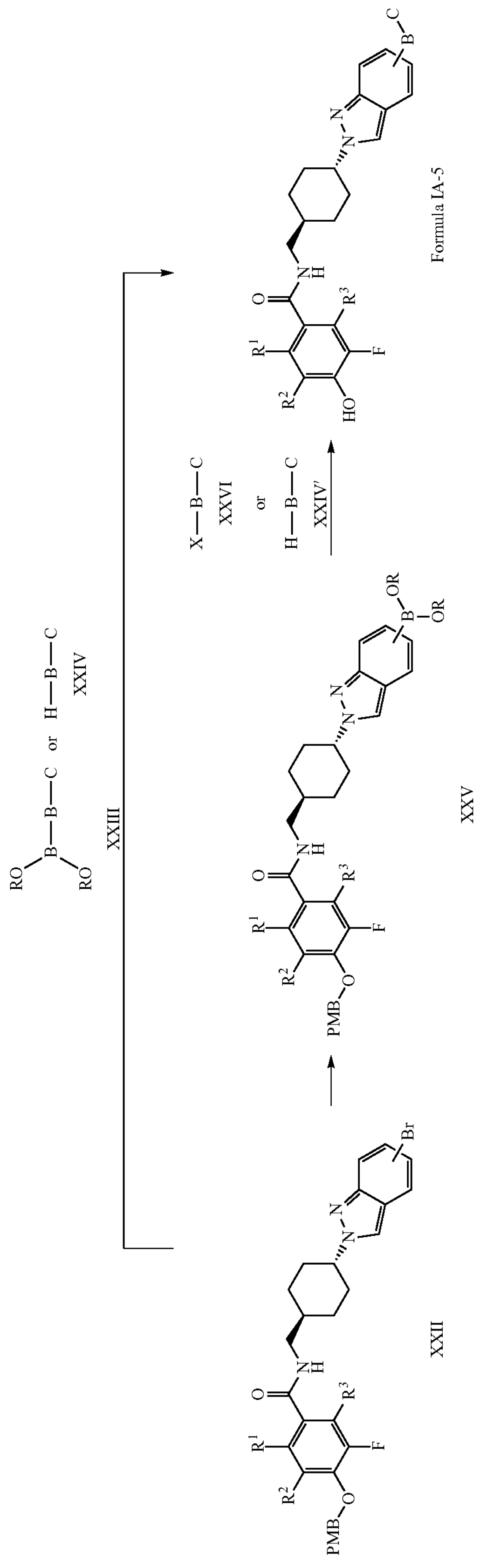

Scheme 6 refers to the preparation of compounds of Formula IB. Compounds of Formula IB can be readily prepared from intermediates XXIX and XXX. Intermediate XXIX can be prepared from an amide bond forming reaction between carboxylic acid intermediate II and amine intermediate XXVII. Similarly, intermediate XXX can be prepared from an amide bond forming reaction between intermediate II and intermediates XXVIII. Amide bond forming reactions of this type can be achieved by combining a carboxylic acid (such as II) with an amine (such as XXVII or XXVIII) in the presence of an activating reagent (such as O-(7-azabenzotriazol-1-yl)-N,N,N',N'-tetramethyluronium hexafluorophosphate; HATU) and a base (such as N,N-diisopropylethylamine) in a suitable solvent (such as dichloromethane). The preparation of compounds of Formula IB can be achieved from intermediate XXIX by methods analogous to those described for the preparation of compounds of Formula IA from intermediate IV in Scheme 2 and Scheme 5. Likewise, the preparation of compounds of Formula IB can be achieved from intermediate XXX by methods analogous to those described for the preparation of compounds of Formula IA from intermediate VI in Scheme 3 and Scheme 5.

Scheme 7

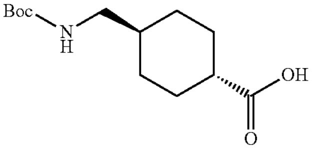
or

XXXI

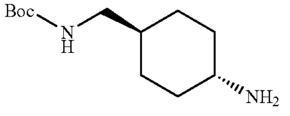
or

XXXII

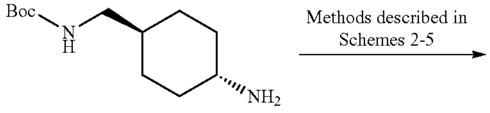

XXXIII

Scheme 6

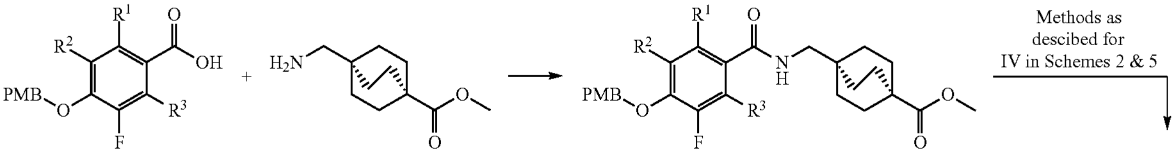

II XXVII XXIX

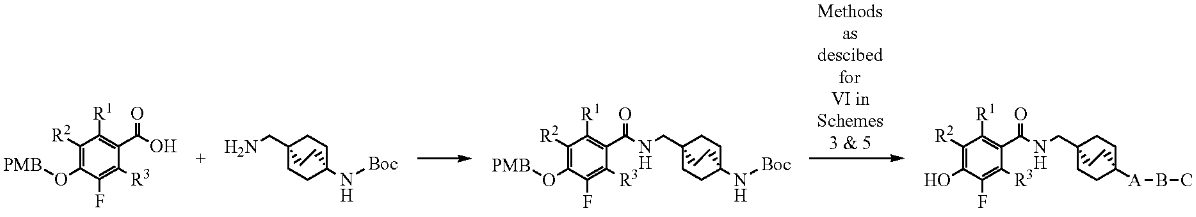

II XXVIII XXX Formula IB

Scheme 7 refers to an alternate ordering of synthetic steps that can be utilized to prepare compounds of Formula IA or compounds of Formula IB. For example, intermediates such as XXXI, XXXII, or XXXIII can be converted to intermediates of the structure XXXIV via methods described herein. Amine intermediates of the structure XXXIV can be reacted with a carboxylic acid of the structure II in an amide bond forming reaction. The resulting product can be deprotected to afford compounds of Formula IA. Likewise, intermediates such as XXXV and XXXVI can be converted to intermediates of the structure XXXVII. Amine intermediates of the structure XXXVII can be reacted with a carboxylic acid of the structure II and subsequently deprotected to afford compounds of Formula IB.

-continued

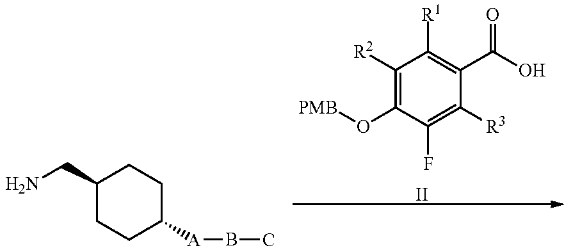

II

XXXIV

-continued

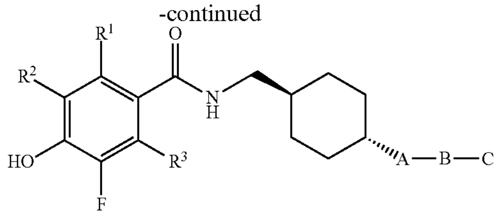

Formula IA

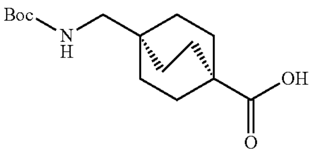

or

XXXV

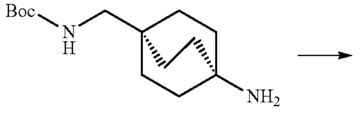

XXXVI

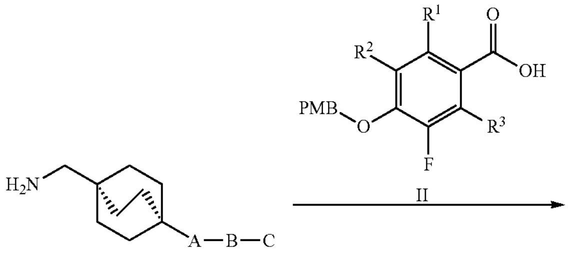

II

XXXVII

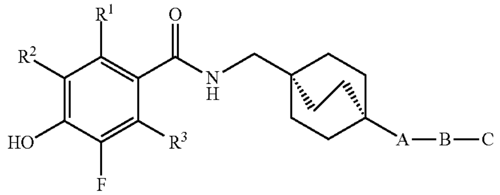

Formula IB

The starting materials and reagents for the above-described Formula I compounds are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

This application is also directed at pharmaceutical compositions having a therapeutically effective amount of a compound of Formula I or a pharmaceutically acceptable salt of said compound and a pharmaceutically acceptable carrier, vehicle or diluent.

The compounds of this invention may also be used in conjunction with other pharmaceutical agents (e.g., antiatherosclerotic and antithrombotic agents) for the treatment of the disease/conditions described herein. This application is also directed at pharmaceutical combination compositions that include: a therapeutically effective amount of a composition having:

a first compound, said first compound being a compound of any of Formula I or a pharmaceutically acceptable salt of said compound;

a second compound, said second compound being a treatment agent for kidney disease, an anti-diabetic agent; a non-alcoholic steatohepatitis treatment agent, a non-alcoholic fatty liver disease treatment agent or an anti-heart failure treatment agent and a pharmaceutical carrier, vehicle or diluents.

In one embodiment, said treatment agent for kidney disease is useful for treating acute and/or chronic kidney disease.

In one embodiment, said non-alcoholic steatohepatitis treatment agent or non-alcoholic fatty liver disease treatment agent is an ACC inhibitor, a KHK inhibitor, a DGAT-2 inhibitor, an FXR agonist, a GLP-1R agonist, metformin, incretin analogs, or an incretin receptor modulator.

In another embodiment, said anti-diabetic agent is an SGLT-2 inhibitor, metformin, incretin analogs, an incretin receptor modulator, a DPP-4 inhibitor, or a PPAR agonist. In another embodiment, said anti-diabetic agent is metfomin, sitagliptin or ertuglifozin.

In another embodiment, said anti-heart failure agent is an ACE inhibitor, an angiotensin receptor blocker, an angiotensin-receptor neprilysin inhibitor, a beta adrenergic receptor blocker, a calcium channel blocker, or a vasodilator.

Combination Agents

The compounds can be administered alone or in combination with one or more additional therapeutic agents. By "administered in combination" or "combination therapy" it is meant that a compound and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect. The phrases "concurrent administration," "co-administration," "simultaneous administration," and "administered simultaneously" mean that the compounds are administered in combination. Thus, the methods of prevention and treatment described herein include use of combination agents.

The combination agents are administered to a mammal in a therapeutically effective amount. By "therapeutically effective amount" it is meant an amount of a compound of Formula I that, when administered alone or in combination with an additional therapeutic agent to a mammal, is effective to treat the desired disease/condition (e.g., NASH, heart failure, kidney disease or diabetes).

Given the NASH/NAFLD activity of the compounds of this invention, they may be co-administered with other agents for the treatment of non-alcoholic steatohepatitis (NASH) and/or non-alcoholic fatty liver disease (NAFLD) and associated disease/conditions, such as Orlistat, TZDs and other insulin-sensitizing agents, FGF21 analogs, Metformin, Omega-3-acid ethyl esters (e.g., Lovaza), Fibrates, HMG-CoA reductase inhibitors (e.g., pravastatin, lovastatin, atorvastatin, simvastatin, fluvastatin, NK-104 (a.k.a. itavastatin or nisvastatin or nisbastatin) and ZD-4522 (a.k.a. rosuvastatin or atavastatin or visastatin)), Ezetimibe, proprotein convertase subtilisin kexin type-9 (PCSK9) inhibitors (e.g., evolocumab, alirocumab), Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 inhibitors (including dapagliflozin, canagliflozin, empagliflozin, tofogliflozin, ertugliflozin, ASP-1941, THR1474, TS-071, ISIS388626 and LX4211 as well as those in WO2010023594), Phentermine, Topiramate, GLP-1 receptor agonists, GIP receptor agonists, dual GLP-1 receptor/glucagon receptor agonists (i.e., OPK88003, MED10382, JNJ-64565111, NN9277, BI 456906), dual GLP-1 receptor/GIP receptor agonists (i.e., Tirzepatide (LY3298176), NN9423), Angiotensin-receptor blockers an acetyl-CoA carboxylase (ACC) inhibitor, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a PNPLA3 inhibitor, an FGF21 analog, an FGF19 analog, a PPAR agonist, an FXR agonist, an AMPK activator, an SCD1 inhibitor or an MPO inhibitor.

Exemplary GLP-1 receptor agonists include liraglutide, albiglutide, exenatide, albiglutide, lixisenatide, dulaglutide, semaglutide, HM15211, LY3298176, Medi-0382, NN-9924, TTP-054, TTP-273, efpeglenatide, those described in WO2018109607, and those described in PCT/IB2019/054867 filed Jun. 11, 2019 including the following:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2; and 2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid, or pharmaceutically acceptable salts thereof.

Exemplary ACC inhibitors include 4-(4-[(1-isopropyl-7-oxo-1,4,6,7-tetrahydro-1'H-spiro[indazole-5,4'-piperidin]-1'-yl)carbonyl]-6-methoxypyridin-2-yl)benzoic acid; and firsocostat (GS-0976) and pharmaceutically acceptable salts thereof.

Exemplary FXR Agonists include tropifexor (2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid); cilofexor (GS-9674); obeticholic acid; LY2562175; Met409; TERN-101; and EDP-305 and pharmaceutically acceptable salts thereof.

Exemplary DGAT2 inhibitors include (S)-2-(5-((3-ethoxypyridin-2-yl)oxy)pyridin-3-yl)-N-(tetrahydrofuran-3-yl)pyrimidine-5-carboxamide;

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide, or a pharmaceutically acceptable salt thereof.

Exemplary KHK inhibitors include [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid and pharmaceutically acceptable salts thereof.

Given the anti-diabetic activity of the compounds of this invention they may be co-administered with other anti-diabetic agents. Suitable anti-diabetic agents include insulin, metformin, GLP-1 receptor agonists (described herein above), an acetyl-CoA carboxylase (ACC) inhibitor (described herein above), SGLT2 inhibitors (described herein above), monoacylglycerol O-acyltransferase inhibitors, phosphodiesterase (PDE)-10 inhibitors, AMPK activators, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, α-amylase inhibitors (e.g., tendamistat, trestatin and AL-3688), an α-glucoside hydrolase inhibitor (e.g., acarbose), α-glucosidase inhibitors (e.g., adiposine, camiglibose, emiglitate, miglitol, voglibose, pradimicin-Q, and salbostatin), PPARγ agonists (e.g., balaglitazone, ciglitazone, darglitazone, englitazone, isaglitazone, pioglitazone and rosiglitazone), PPAR α/γ agonists (e.g., CLX-0940, GW-1536, GW-1929, GW-2433, KRP-297, L-796449, LR-90, MK-0767 and SB-219994), protein tyrosine phosphatase-1B (PTP-1B) inhibitors (e.g., trodusquemine, hyrtiosal extract, and compounds disclosed by Zhang, S., et al., Drug Discovery Today, 12(9/10), 373-381 (2007)), SIRT-1 activators (e.g., resveratrol, GSK2245840 or GSK184072), dipeptidyl peptidease IV (DPP-IV) inhibitors (e.g., those in WO2005116014, sitagliptin, vildagliptin, alogliptin, dutogliptin, linagliptin and saxagliptin), insulin secreatagogues, fatty acid oxidation inhibitors, A2 antagonists, c-jun amino-terminal kinase (JNK) inhibitors, glucokinase activators (GKa) such as those described in WO2010103437, WO201010343f8, WO2010013161, WO2007122482, TTP-399, TTP-355, TTP-547, AZD1656, ARRY403, MK-0599, TAK-329, AZD5658 or GKM-001, insulin, insulin mimetics, glycogen phosphorylase inhibitors (e.g., GSK1362885), VPAC2 receptor agonists, glucagon receptor modulators such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g., MBX-2982, GSK1292263, APD597 and PSN821), FGF21 derivatives or analogs such as those described in Kharitonenkov, A. et al. et al., Current Opinion in Investigational Drugs 2009, 10(4) 359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of this application can be found, for example, at page 28, line 35 through page 30, line 19 of WO2011005611.

Other anti-diabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKC□, PKC□, PKC□), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors (e.g., SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Given the anti-heart failure activity of the compounds of this application, they may be co-administered with other anti-heart failure agents such as ACE inhibitors (e.g., captopril, enalapril, fosinopril, Lisinopril, perindopril, quinapril, Ramipril, trandolapril), Angiotensin II receptor blockers (e.g., Candesartan, Losartan, Valsartan), Angiotensin-receptor neprilysin inhibitors (sacubitril/valsartan), $I_f$ channel blocker Ivabradine, Beta-Adrenergic blocking agents (e.g., bisoprolol, metoprolol succinate, carvedilol), SGLT2 inhibitors, Aldosterone antagonists (e.g., spironolactone, eplerenone), cardiac myosin activator (e.g., omecamtiv mecarbil), guanylate cyclase stimulator (e.g., vericiguat), cardiac myosin inhibitor (e.g., mavacamten), SERCA2a activator (e.g., istaroxime), hydralazine and isosorbide dinitrate, diuretics (e.g., furosemide, bumetanide, torsemide, chlorothiazide, amiloride, hydrochlorothiazide, Indapamide, Metolazone, Triamterene), or digoxin.

The compounds of Formula I may also be used in combination with antihypertensive agents and such antihypertensive activity is readily determined by those skilled in the art according to standard assays (e.g., blood pressure measurements). Examples of suitable antihypertensive agents include: alpha adrenergic blockers; beta adrenergic blockers; calcium channel blockers (e.g., diltiazem, verapamil, nifedipine and amlodipine); vasodilators (e.g., hydralazine), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I may be co-administered with furosemide. In still another embodiment, one or more compounds of Formula I may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I may be co-administered with chlorothiazide. In still another embodiment, one or more compounds of Formula I may be co-administered with hydrochlorothiazide. In another embodiment, one or more compounds of Formula I may be co-administered with a phthalimidine-type diuretic. In still another embodiment, the phthalimidine-type diuretic is chlorthalidone.

Examples of suitable mineralocorticoid receptor antagonists include spironolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug-eluting stents, stem cell therapy and medical devices such as implanted pacemakers, defibrillators, or cardiac resynchronization therapy.

The compounds of Formula I may also be used in combination with drugs used in the management of chronic kidney disease including phosphate binders (e.g., sucroferric oxyhydroxide, sevelamer, calcium acetate), sodium bicarbonate, erythropoietin-stimulating agents, oral or intravenous iron agents (e.g., iron sucrose, ferric carboxymaltose, ferumoxytol), potassium binders, calcitriol, or SGLT2 inhibitors (e.g., dapagliflozin, empagliflozin, or other SGLT2 inhibitors recited herein).

Particularly when provided as a single dosage unit, the potential exists for a chemical interaction between the combined active ingredients. For this reason, when a Formula I compound and a second therapeutic agent are combined in a single dosage unit they may be formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Sustained-release preparations may be used. Suitable examples of sustained-release preparations include semipermeable matrices of solid hydrophobic polymers containing the compound of the invention, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

These as well as other ways of minimizing contact between the components of combination products, whether administered in a single dosage form or administered in separate forms but at the same time by the same manner, will be readily apparent to those skilled in the art, once armed with the present disclosure.

In combination therapy treatment, both the compounds of this invention and the other drug therapies are administered to mammals (e.g., humans, male or female) by conventional methods.

The Formula I compound of this invention, their prodrugs and the salts of such compounds and prodrugs are all adapted to therapeutic use as agents that inhibit and/or degrade HSD17B13 in mammals, particularly humans and thus are useful for the treatment of the various conditions (e.g., those described herein) in which such action is implicated.

The disease/conditions that can be treated with compounds of Formula I, include, but are not limited to NASH/NAFLD, diabetes, kidney disease, and heart failure and associated disease/conditions.

Accordingly, given the positive correlation between activation of HSD17B13 with the development of NASH/NAFLD and associated disease/conditions, Formula I compounds of this invention, their prodrugs and the salts of such compounds and prodrugs, by virtue of their pharmacologic action, are useful for the prevention, arrestment and/or regression of fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma.

Administration of the compounds of this invention can be via any method that delivers a compound of this invention systemically and/or locally. These methods include oral routes, parenteral, intraduodenal routes, buccal, intranasal etc. Generally, the compounds of this invention are administered orally, but parenteral administration (e.g., intravenous, intramuscular, subcutaneous or intramedullary) may be utilized, for example, where oral administration is inappropriate for the target or where the patient is unable to ingest the drug.

For administration to human patients, an oral daily dose of the compounds herein may be in the range 1 mg to 5000 mg depending, of course, on the mode of and frequency of administration, the disease state, and the age and condition of the patient, etc. An oral daily dose is in the range of 3 mg to 3000 mg may be used. A further oral daily dose is in the range of 5 mg to 1000 mg. For convenience, the compounds of Formula I can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 500, or 1000 mg of the compound. The total daily dose may be administered in single or divided doses and may, at the physician's discretion, fall outside of the typical ranges given herein.

For administration to human patients, an infusion daily dose of the compounds herein may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

These compounds may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjunction with the Formula I compound is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention is dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient.

It is to be noted that dosage values may vary with the type and severity of the condition to be alleviated, and may include single or multiple doses. It is to be further understood that for any particular subject, specific dosage regimens should be adjusted overtime according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, intra-patient dose-escalation may be used as determined by the skilled artisan. Determining appropriate dosages and regiments for administration of the chemotherapeutic agent are well-known in the relevant art and would be understood to be encompassed by the skilled artisan once provided the teachings disclosed herein.

This application further comprises use of a compound of Formula I for use as a medicament (such as a unit dosage tablet or unit dosage capsule). In another embodiment, this application comprises the use of a compound of Formula I for the manufacture of a medicament (such as a unit dosage tablet or unit dosage capsule) to treat one or more of the conditions previously identified in the above sections discussing methods of treatment.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerin or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of Formula I or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel® from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab® from Edward Mendell Co.), cross-linked polyvinyl pyrrolidone, croscarmellose sodium A-type (available as Ac-di-sol®), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated castor oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of Formula I and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol®, Explotab®, starch and sodium lauryl sulphate. When present, a disintegrant will usually comprise less than 10% by weight of the formulation or less than 5%, for example about 3%. A preferred lubricant is magnesium stearate. When present a lubricant will usually comprise less than 5% by weight of the formulation or less than 3%, for example about 1%.

Tablets may be manufactured by standard tableting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of Formula I or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyol® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex® 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglycerides, from Gattefosse), Captex® 500P (glyceryl triacetate i.e., triacetin, from Abitec), Capmul® MCM (medium chain mono- and diglycerides, from Abitec), Miglyol® 812 (caprylic/capric triglyceride, from Condea, Cranford N.J.), Migyol®829 (caprylic/capric/succinic triglyceride, from Condea), Migyol® 840 (propylene glycol dicaprylate/dicaprate, from Condea), Labrafil® M1944CS (oleoyl macrogol-6 glycerides, from Gattefosse), Peceol™ (glyceryl monooleate, from Gattefosse) and Maisine® 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50% by weight, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of Formula I or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of Formula I or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of Formula I or combinations include ointments, creams, lotions, powders and sprays. The drugs are admixed with a pharmaceutically acceptable excipient, diluent or carrier, and any preservatives, buffers, or propellants that may be required.

Many of the present compounds are poorly soluble in water, e.g., less than about 1 μg/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g., 1-8). The polymer can be neutral or ionizable, and should have an aqueous-solubility of at least 0.1 mg/mL over at least a portion of the pH range of 1-8.

Water-soluble polymers suitable for use with the compounds of Formula I may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60% by weight) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoat.sup.(R)-LF, Aqoat.sup.(R)-MF and Aqoat.sup.(R)—HF respectively from Shin-Etsu Chemical Co., LTD, Tokyo, Japan. The higher MF and HF grades are generally preferred.

The compound of Formula I or a pharmaceutically acceptable salt of said compound can be used for treating non-human animals. The administration of the compounds of Formula I and combinations with another effective agent used to treat the relevant condition can be effected orally or non-orally.

An amount of a compound of Formula I or combination of a compound of Formula I with another effective agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of Formula I (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of Formula I (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of Formula I with a sufficient amount of animal feed to provide from about 0.001 to about 500 ppm of the compound in the feed or water.

The preferred medicated swine, cattle, sheep and goat feed generally contain from about 1 to about 400 grams of a compound of Formula I (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound (or combination) per ton of feed.

For parenteral administration in animals, the compounds of Formula I (or combination) may be prepared in the form of a paste or a pellet and administered as an implant, usually under the skin of the head or ear of the animal in which increase in lean meat deposition and improvement in lean meat to fat ratio is sought.

Paste formulations may be prepared by dispersing the drug in a pharmaceutically acceptable oil such as peanut oil, sesame oil, corn oil or the like.

Pellets containing an effective amount of a compound of Formula I, pharmaceutical composition, or combination may be prepared by admixing a compound of Formula I or combination with a diluent such as carbowax, carnauba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and polymethylmethacrylate microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid®, Liposyn®, Infonutrol™, Lipofundin® and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device, or the nebulizing device may be attached to a face mask, tent or intermittent positive pressure breathing machine. Solution, suspension or powder compositions may be administered, preferably orally or nasally, from devices which deliver the formulation in an appropriate manner.

The compounds herein may be formulated for oral, buccal, intranasal, parenteral (e.g., intravenous, intramuscular or subcutaneous) or rectal administration or in a form suitable for administration by inhalation. The compounds of the invention may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see Remington's Pharmaceutical Sciences, 20th Edition (Lippincott Williams & Wilkins, 2000).

Pharmaceutical compositions according to the invention may contain 0.1%-95% by weight of the compound(s) of this invention, preferably 1%-70%. In any event, the composition to be administered will contain a quantity of a compound(s) according to the invention in an amount effective to treat the disease/condition of the subject being treated.

Since this application has an aspect that relates to the treatment of the disease/conditions described herein with a combination of active ingredients which may be administered separately, the invention also relates to combining separate pharmaceutical compositions in kit form. The kit can comprise a composition that includes a compound of the Formula I or it can contain at least two separate pharmaceutical compositions: a compound of Formula I, a prodrug thereof, or a salt of such compound or prodrug and a second compound as described above. The kit comprises a means for containing the separate compositions such as a container, a divided bottle or a divided foil packet. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of an optional second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Also, as this application has an aspect that relates to the treatment of the disease/conditions described herein with a combination of active ingredients which may be administered jointly, the invention also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

The active ingredient may be formulated as a solid dispersion or as a self-emulsified drug delivery system (SEDDS) with pharmaceutically acceptable excipients.

The active ingredient may be formulated as an immediate release or modified release tablet or capsule. Alternatively, the active ingredient may be delivered as the active ingredient alone within a capsule shell, without additional excipients.

Experimental Procedures

The following illustrate the synthesis of various compounds of the present invention. Additional compounds within the scope of this invention may be prepared using the methods illustrated in these Examples, either alone or in combination with techniques generally known in the art. All starting materials in these Preparations and Examples are either commercially available or can be prepared by methods known in the art or as described herein.

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wisconsin or DriSolv™ products from EMD Chemicals, Gibbstown, NJ) were employed. In some cases, commercial solvents were passed through columns packed with 4 Å molecular sieves, until the following QC standards for water were attained: a) <100 ppm by weight for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Other commercial solvents and reagents were used without further purification. For syntheses referencing procedures in other Examples or Methods, reaction conditions (reaction time and temperature) may vary. Products were generally dried under vacuum before being carried on to further reactions or submitted for biological testing.

When indicated, reactions were heated by microwave irradiation using Biotage Initiator or Personal Chemistry Emrys Optimizer microwave instruments. Reaction progress was monitored using thin-layer chromatography (TLC), liquid chromatography-mass spectrometry (LCMS), high-performance liquid chromatography (HPLC), and/or gas chromatography-mass spectrometry (GCMS) analyses. TLC was performed on pre-coated silica gel plates with a fluorescence indicator (254 nm excitation wavelength) and visualized under UV light and/or with $I_2$, $KMnO_4$, $CoCl_2$, phosphomolybdic acid, or ceric ammonium molybdate stains. LCMS data were acquired on an Agilent 1100 Series instrument with a Leap Technologies autosampler, Gemini C18 columns, acetonitrile/water gradients, and either trifluoroacetic acid, formic acid, or ammonium hydroxide modifiers. The column eluent was analyzed using a Waters ZQ mass spectrometer scanning in both positive and negative ion modes from 100 to 1200 Da. Other similar instruments were also used. HPLC data were generally acquired on an Agilent 1100 Series instrument using Gemini or XBridge C18 columns, acetonitrile/water gradients, and either trifluoroacetic acid or ammonium hydroxide modifiers. GCMS data were acquired using a Hewlett Packard 6890 oven with an HP 6890 injector, HP-1 column (12 m×0.2 mm×0.33 μm), and helium carrier gas. Samples were analyzed on an HP 5973 mass selective detector, scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were generally performed by chiral supercritical fluid chromatography (SFC) using Berger or Thar instruments; ChiralPAK-AD, -AS, -IC, Chiralcel-OD, or -OJ columns; and $CO_2$ mixtures with methanol, ethanol, propan-2-ol, or acetonitrile, alone or modified using trifluoroacetic acid or propan-2-amine. UV detection was used to trigger fraction collection. For syntheses referencing procedures in other Examples or Methods, purifications may vary: in general, solvents and the solvent ratios used for eluents/gradients were chosen to provide appropriate $R_f$s or retention times.

Mass spectrometry data are reported from LCMS analyses. Mass spectrometry (MS) was performed via atmospheric pressure chemical ionization (APCI), electrospray ionization (ESI), electron impact ionization (EI) or electron scatter (ES) ionization sources. Proton nuclear magnetic spectroscopy ($^1H$ NMR) chemical shifts are given in parts per million downfield from tetramethylsilane and were recorded on 300, 400, 500, or 600 MHz Varian, Bruker, or Jeol spectrometers. Chemical shifts are expressed in parts per million (ppm, d) referenced to the deuterated solvent residual peaks (chloroform, 7.26 ppm; $CD_2HOD$, 3.31 ppm; acetonitrile-$d_2$, 1.94 ppm; dimethyl sulfoxide-$d_5$, 2.50 ppm; DHO, 4.79 ppm). The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using medium-pressure Biotage or ISCO systems using columns pre-packaged by various commercial vendors including Biotage and ISCO. Microanalyses were performed by Quantitative Technologies Inc. and were within 0.4% of the calculated values.

Unless otherwise noted, chemical reactions were performed at room temperature (about 23 degrees Celsius).

Unless noted otherwise, all reactants were obtained commercially without further purifications or were prepared using methods known in the literature.

Hydrogenation may be performed in a Parr Shaker under pressurized hydrogen gas, or in a Thales-nano H-Cube flow hydrogenation apparatus at full hydrogen and a flow rate between 1 and 2 mL/minute at the specified temperature.

HPLC, UPLC, LCMS, GCMS, and SFC retention times were measured using the methods noted in the procedures.

In some examples, chiral separations were carried out to separate enantiomers or diastereomers of certain compounds of the invention (in some examples, the separated enantiomers are designated as ENANT-1 and ENANT-2, according to their order of elution; similarly, separated diastereomers are designated as DIAST-1 and DIAST-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, the indicated stereochemistry represents just one of the two enantiomers that make up the racemic mixture.

The compounds and intermediates described below were named using the naming convention provided with ACD/ChemSketch 2017.2.1, File Version C40H41, Build 99535 (Advanced Chemistry Development, Inc., Toronto, Ontario, Canada). The naming convention provided with ACD/ChemSketch 2017.2.1 is well known by those skilled in the art and it is believed that the naming convention provided with ACD/ChemSketch 2017.2.1 generally comports with the IUPAC (International Union for Pure and Applied Chemistry) recommendations on Nomenclature of Organic Chemistry and the CAS Index rules.

EXAMPLES

Preparation P1: 3,5-Difluoro-4-[(4-methoxyphenyl)methoxy]benzoic acid (P1)

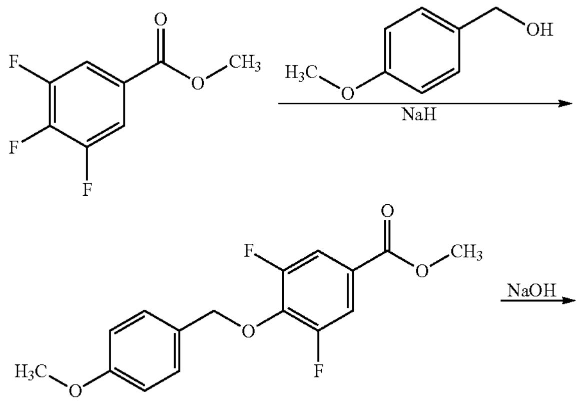

C1

-continued

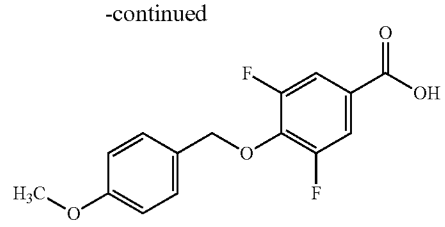

P1

Step 1. Synthesis of methyl 3,5-difluoro-4-[(4-methoxyphenyl)methoxy]benzoate (C1)

To a 0° C. solution of sodium hydride (60% dispersion in mineral oil; 1.60 g, 40.0 mmol) in tetrahydrofuran (200 mL) was added (4-methoxyphenyl)methanol (5.25 g, 38.0 mmol). After the reaction mixture had been stirred at 0° C. for 30 minutes, a solution of methyl 3,4,5-trifluorobenzoate (7.00 g, 36.8 mmol) in tetrahydrofuran (50 mL) was added, whereupon the reaction mixture was allowed to warm to 25° C. and stir for 1 hour. It was then quenched by addition of saturated aqueous ammonium chloride solution, and the aqueous layer was extracted with ethyl acetate; the combined organic layers were dried over sodium sulfate, filtered, and concentrated in vacuo to provide C1 as a solid (11.2 g). This material was progressed directly to the following step.

Step 2. Synthesis of 3,5-difluoro-4-[(4-methoxyphenyl)methoxy]benzoic acid (P1)

To a solution of C1 (from the previous step; 11.2 g, 536.3 mmol) in methanol (200 mL) was added a solution of sodium hydroxide (4.36 g, 109 mmol) in water (20 mL), whereupon the reaction mixture was stirred at 26° C. for 4 hours. It was then concentrated in vacuo, and the aqueous residue was washed with dichloromethane (2×150 mL). After the aqueous layer had been acidified to pH 5, it was extracted with dichloromethane (3×300 mL), and these three dichloromethane layers were combined and washed with saturated aqueous sodium chloride solution, dried over sodium sulfate, filtered, and concentrated under reduced pressure to afford P1 as a white solid. Yield: 10 g, 34 mmol, 92% over 2 steps. $^1H$ NMR (400 MHz, DMSO-$d_6$) δ 7.61-7.53 (m, 2H), 7.34 (d, J=8.6 Hz, 2H), 6.92 (d, J=8.7 Hz, 2H), 5.20 (s, 2H), 3.74 (s, 3H).

Preparation P2: 2,3,5-Trifluoro-4-[(4-methoxyphenyl)methoxy]benzoic acid (P2)

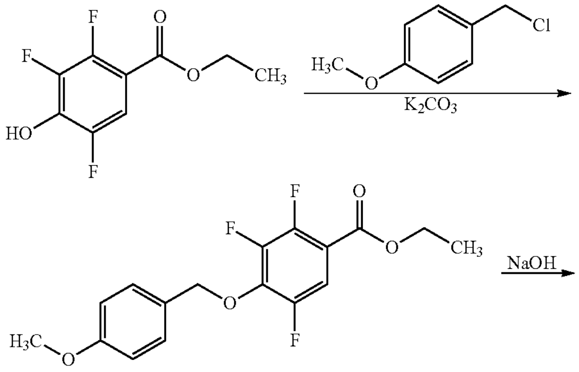

C2

-continued

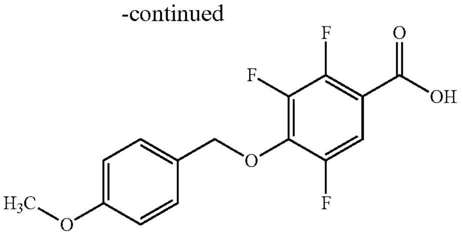

P2

Step 1. Synthesis of ethyl 2,3,5-trifluoro-4-[(4-methoxyphenyl)methoxy]benzoate (C2)

1-(Chloromethyl)-4-methoxybenzene (40.1 g, 256 mmol) was added to a mixture of ethyl 2,3,5-trifluoro-4-hydroxybenzoate (51.3 g, 233 mmol) and potassium carbonate (64.3 g, 465 mmol) in acetonitrile (100 mL). After the reaction mixture had been stirred at 80° C. for 16 hours, LCMS analysis indicated conversion to C2: LCMS m/z 363.1 $[M+Na^+]$. Solids were removed via filtration, and the filtrate was concentrated in vacuo to provide C2 as a yellow oil. Yield: 71.0 g, 209 mmol, 90%.

Step 2. Synthesis of 2,3,5-trifluoro-4-[(4-methoxyphenyl)methoxy]benzoic acid (P2)

To a solution of C2 (71.0 g, 209 mmol) in methanol (500 mL) was added an aqueous solution of sodium hydroxide (3 M; 300 mL). After the reaction mixture had been stirred at 50° C. for 4 hours, it was concentrated in vacuo. The aqueous residue was acidified by addition of 1 M hydrochloric acid, and the resulting solid was collected via filtration to afford P2 as a white solid. Yield: 51.7 g, 166 mmol, 79%. LCMS m/z 335.1 $[M+Na^+]$. $^1H$ NMR (400 MHz, DMSO-$d_6$) δ 7.38-7.29 (m, 1H), 7.34 (d, J=8.6 Hz, 2H), 6.93 (d, J=8.7 Hz, 2H), 5.18 (s, 2H), 3.75 (s, 3H).

Preparation P3: N-{[(1r,4r)-4-Aminocyclohexyl]methyl}-3,5-difluoro-4-[(4-methoxyphenyl)methoxy]benzamide (P3)

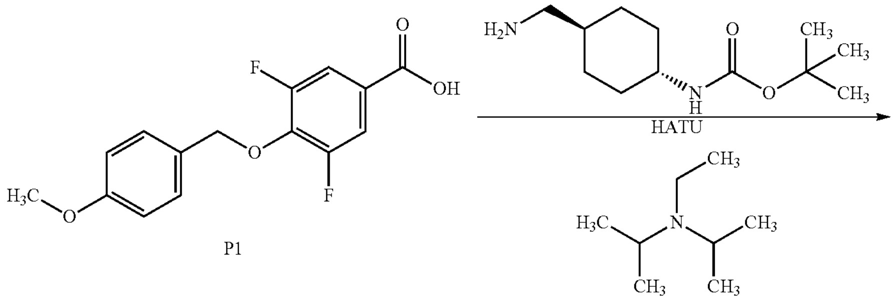

P1

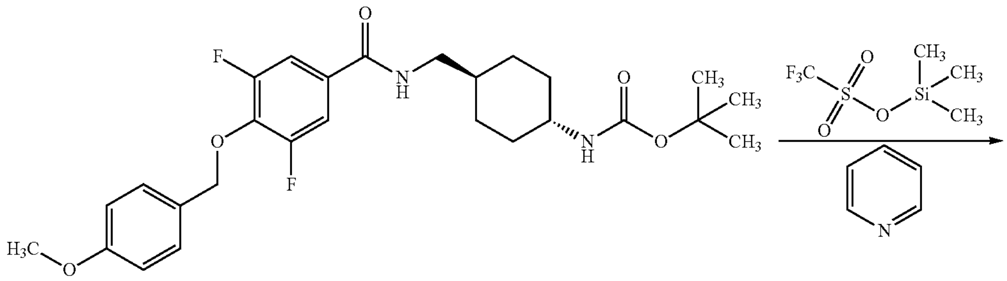

C3

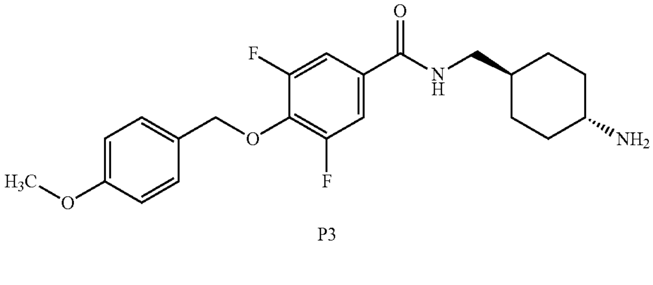

P3

Step 1. Synthesis of tert-butyl [(1r,4r)-4-({3,5-difluoro-4-[(4-methoxyphenyl)methoxy]benzamido}methyl)cyclohexyl]carbamate (C3)

To a solution of P1 (19.3 g, 65.6 mmol), N,N-diisopropylethylamine (25.4 g, 197 mmol), and O-(7-azabenzotriazol-1-yl)-N,N,N',N'-tetramethyluronium hexafluorophosphate (HATU; 27.5 g, 72.3 mmol) in dichloromethane (700 mL) was added tert-butyl [(1r,4r)-4-(aminomethyl)cyclohexyl]carbamate (15.0 g, 65.7 mmol). After the reaction mixture had been stirred at 25° C. for 16 hours, LCMS analysis indicated the presence of C3: LCMS m/z 527.3 $[M+Na^+]$. Filtration was followed by washing of the filter cake with water and with a mixture of dichloromethane and ethyl acetate, affording C3 as a white solid. Yield: 26.5 g, 52.5 mmol, 80%. $^1H$ NMR (400 MHz, DMSO-$d_6$) δ 8.48 (br t, J=6 Hz, 1H), 7.63-7.53 (m, 2H), 7.33 (d, J=8.6 Hz, 2H), 6.92 (d, J=8.7 Hz, 2H), 6.67 (br d, J=8.0 Hz, 1H), 5.16 (s, 2H), 3.74 (s, 3H), 3.22-3.10 (m, 1H), 3.06 (dd, J=6.1, 6.1 Hz, 2H), 1.83-1.65 (m, 4H), 1.48-1.36 (m, 1H), 1.36 (s, 9H), 1.16-1.02 (m, 2H), 1.00-0.85 (m, 2H).

Step 2. Synthesis of N-{[(1r,4r)-4-aminocyclohexyl]methyl}-3,5-difluoro-4-[(4-methoxyphenyl)methoxy]benzamide (P3)

To a 0° C. solution of C3 (21.5 g, 42.6 mmol) and pyridine (27.0 g, 341 mmol) in dichloromethane (500 mL) was added trimethylsilyl trifluoromethanesulfonate (37.9 g, 170 mmol) in a drop-wise manner. After the reaction mixture had been stirred at 25° C. for 16 hours, aqueous sodium bicarbonate solution (100 mL) was added, and the mixture was filtered. The filter cake was washed with water and with a mixture of dichloromethane and ethyl acetate, providing P3 as a white solid. Yield: 10.0 g, 24.7 mmol, 58%. LCMS m/z 405.3 $[M+H]^+$. $^1H$ NMR (400 MHz, DMSO-$d_6$) δ 8.50 (br t, J=6 Hz, 1H), 7.71-7.41 (m, 4H), 7.33 (d, J=8.2 Hz, 2H), 6.92 (d, J=8.2 Hz, 2H), 5.17 (s, 2H), 3.74 (s, 3H), 3.09 (dd, J=6 Hz, 2H), 3.00-2.86 (m, 1H), 1.96-1.85 (m, 2H), 1.82-1.70 (m, 2H), 1.54-1.38 (m, 1H), 1.31-1.15 (m, 2H), 1.07-0.92 (m, 2H).

Preparation P4: (1r,4r)-4-({3,5-Difluoro-4-[(4-methoxyphenyl)methoxy]benzamido}methyl)cyclohexane-1-carboxylic acid (P4)

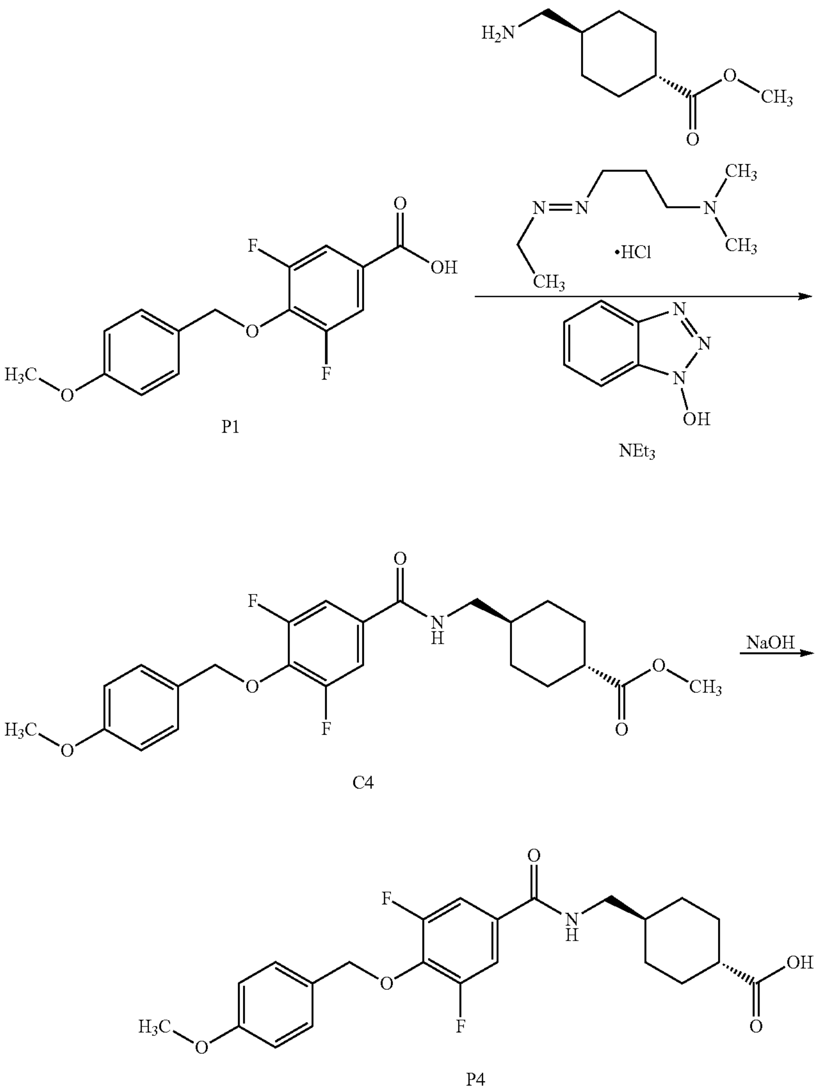

P1

C4

P4

Step 1. Synthesis of methyl (1r,4r)-4-({3,5-difluoro-4-[(4-methoxyphenyl)methoxy]benzamido}methyl) cyclohexane-1-carboxylate (C4)

To a solution of P1 (18.0 g, 61.2 mmol), 1-[3-(dimethylamino)propyl]-3-ethylcarbodiimide hydrochloride (14.1 g, 73.5 mmol), and 1H-benzotriazol-1-ol (9.92 g, 73.4 mmol) in dichloromethane (500 mL) were added triethylamine (7.41 g, 73.2 mmol) and methyl (1r,4r)-4-(aminomethyl) cyclohexane-1-carboxylate (10.5 g, 61.3 mmol). After the reaction mixture had been stirred at 28° C. for 4 hours, it was extracted with dichloromethane. The combined organic layers were washed with saturated aqueous sodium chloride solution, dried over sodium sulfate, filtered, concentrated in vacuo, and purified via silica gel chromatography (Eluent: 6% methanol in dichloromethane), providing C4 as a white solid. Yield: 22.0 g, 49.2 mmol, 80%. LCMS m/z 448.2 $[M+H]^+$.

Step 2. Synthesis of (1r,4r)-4-({3,5-difluoro-4-[(4-methoxyphenyl)methoxy]benzamido}methyl)cyclohexane-1-carboxylic acid (P4)

A solution of sodium hydroxide (8.05 g, 201 mmol) in water (20 mL) was added to a solution of $C_4$ (18.0 g, 40.2 mmol) in methanol (200 mL). The reaction mixture was stirred at 26° C. for 6 hours, whereupon methanol was removed under reduced pressure and the aqueous residue was washed with dichloromethane (2×20 mL). The aqueous layer was then adjusted to pH 5 and extracted with dichloromethane (3×50 mL); these three extracts were combined, washed with saturated aqueous sodium chloride solution, dried over sodium sulfate, filtered, and concentrated in vacuo to afford P4 as a white solid. Yield: 14.0 g, 32.3 mmol, 80%. LCMS m/z 434.2 $[M+H]^+$. $^1H$ NMR (400 MHz, DMSO-$d_6$) δ 8.50 (br t, J=5.7 Hz, 1H), 7.64-7.54 (m, 2H), 7.33 (d, J=8.5 Hz, 2H), 6.92 (d, J=8.4 Hz, 2H), 5.16 (s, 2H), 3.74 (s, 3H), 3.08 (dd, J=6, 6 Hz, 2H), 2.18-2.05 (m, 1H), 1.95-1.82 (m, 2H), 1.80-1.68 (m, 2H), 1.54-1.39 (m, 1H), 1.33-1.16 (m, 2H), 1.02-0.85 (m, 2H).

Preparation P5: 3,5-Difluoro-N-{[(1r,4r)-4-(N-hydroxycarbamimidoyl)cyclohexyl]methyl}-4-[(4-methoxyphenyl)methoxy]benzamide (P5)

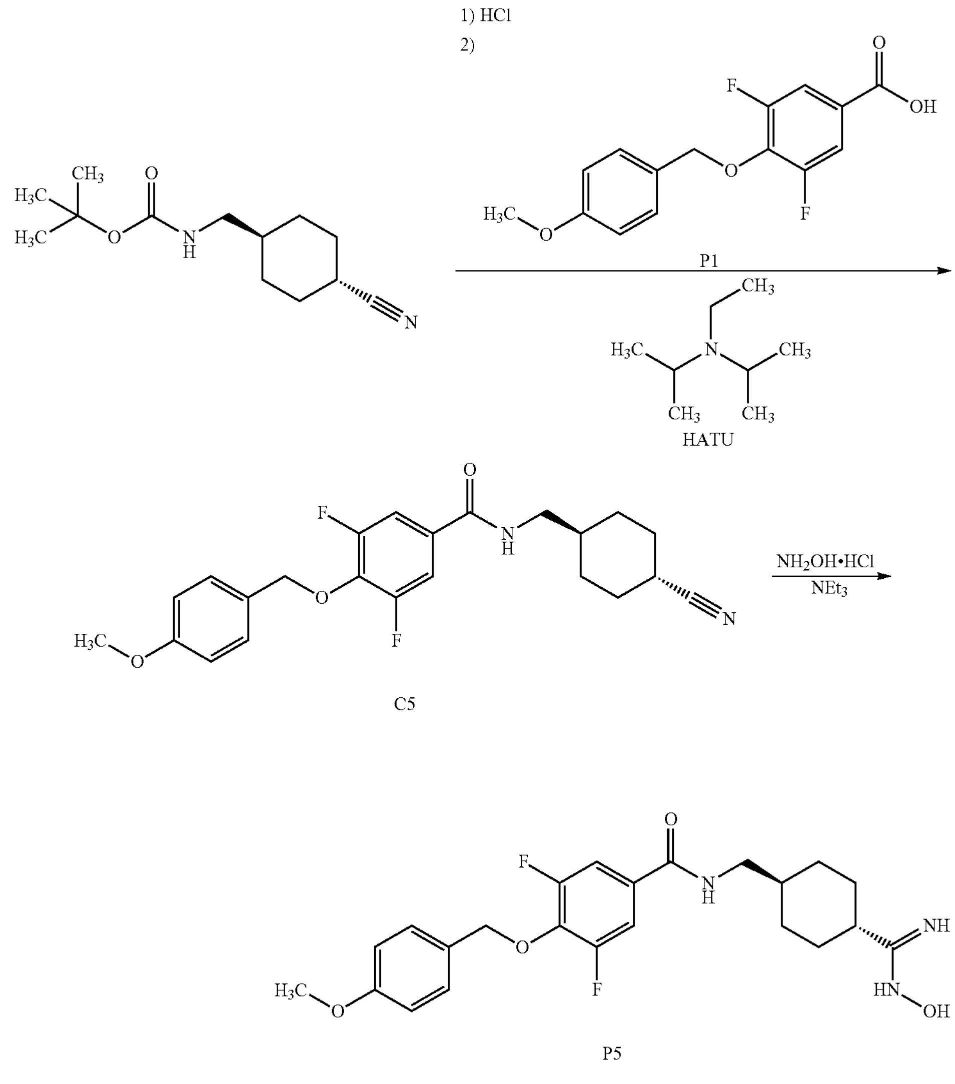

Step 1. Synthesis of N-{[(1r,4r)-4-cyanocyclohexyl]methyl}-3,5-difluoro-4-[(4-methoxyphenyl)methoxy]benzamide (C5)

A solution of hydrogen chloride in 1,4-dioxane (4 M; 50 mL, 200 mmol) was added to a solution of tert-butyl {[(1r,4r)-4-cyanocyclohexyl]methyl}carbamate (4.86 g, 20.4 mmol) in tetrahydrofuran (50 mL), and the mixture was stirred at room temperature overnight. After removal of solvents via concentration under reduced pressure, the residue was triturated with diethyl ether to provide (1r,4r)-4-(aminomethyl)cyclohexane-1-carbonitrile, hydrochloride salt.

O-(7-Azabenzotriazol-1-yl)-N,N,N',N'-tetramethyluronium hexafluorophosphate (HATU; 95%, 8.16 g, 20.4 mmol) was added to a solution of P1 (5.0 g, 17 mmol) in dichloromethane (113 mL). After this mixture had been stirred for 1 hour, it was treated with N,N-diisopropylethylamine (8.88 mL, 51.0 mmol) and the (1r,4r)-4-(aminomethyl)cyclohexane-1-carbonitrile, hydrochloride salt from above. The reaction mixture was stirred at room temperature for 3 days, whereupon it was washed sequentially with water, 1 M hydrochloric acid, water, saturated aqueous sodium bicarbonate solution, and saturated aqueous sodium chloride solution, dried over sodium sulfate, filtered, and concentrated in vacuo. The residue was dissolved in a minimal quantity of a hot 10:1 mixture of ethyl acetate and heptane; after cooling to room temperature, this was filtered, and the filtrate was concentrated under reduced pressure. Silica gel chromatography provided C5 as a white solid. Yield: 5.80 g, 14.0 mmol, 82%. LCMS m/z 415.3 $[M+H]^+$. $^1H$ NMR (400 MHz, DMSO-$d_6$) δ 8.50 (br t, J=5.8 Hz, 1H), 7.62-7.53 (m, 2H), 7.33 (d, J=8.6 Hz, 2H), 6.92 (d, J=8.6 Hz, 2H), 5.16 (s, 2H), 3.74 (s, 3H), 3.08 (dd, J=6, 6 Hz, 2H), 2.62 (tt, J=11.9, 3.6 Hz, 1H), 2.04-1.95 (m, 2H), 1.77-1.67 (m, 2H), 1.60-1.37 (m, 3H), 1.04-0.89 (m, 2H).

Step 2. Synthesis of 3,5-difluoro-N-{[(1r,4r)-4-(N-hydroxycarbamimidoyl)cyclohexyl]methyl}-4-[(4-methoxyphenyl)methoxy]benzamide (P5)

Hydroxylamine hydrochloride (8.38 g, 121 mmol) and triethylamine (16.8 mL, 121 mmol) were added to a solution of C5 (5.00 g, 12.1 mmol) in methanol (50 mL). The reaction mixture was heated at 50° C. for 24 hours, whereupon it was cooled to room temperature and concentrated in vacuo. The residue was partitioned between water (100 mL) and ethyl acetate (100 mL) and the mixture was vigorously stirred for 15 minutes. Filtration, followed by rinsing of the collected solids with water (50 mL) and with ethyl acetate (50 mL) provided P5 as a white solid. Yield: 4.50 g, 10.1 mmol, 83%. LCMS m/z 448.4 [M+H]*. $^1H$ NMR (400 MHz, DMSO-$d_6$), characteristic peaks: d 9.42 (s, 1H), 8.47 (br t, J=5.8 Hz, 1H), 8.19 (br s, 1H), 7.81 (br s, 1H), 7.63-7.54 (m, 2H), 7.33 (d, J=8.6 Hz, 2H), 6.92 (d, J=8.7 Hz, 2H), 5.16 (s, 2H), 3.74 (s, 3H), 3.09 (dd, J=6, 6 Hz, 2H), 2.5-2.40 (m, 1H, assumed; partially obscured by solvent peak), 1.96-1.84 (m, 2H), 1.56-1.41 (m, 1H), 1.02-0.87 (m, 2H).

Preparation P6: N-{[(1s,4s)-4-Bromocyclohexyl]methyl}-3,5-difluoro-4-[(4-methoxyphenyl)methoxy]benzamide (P6)

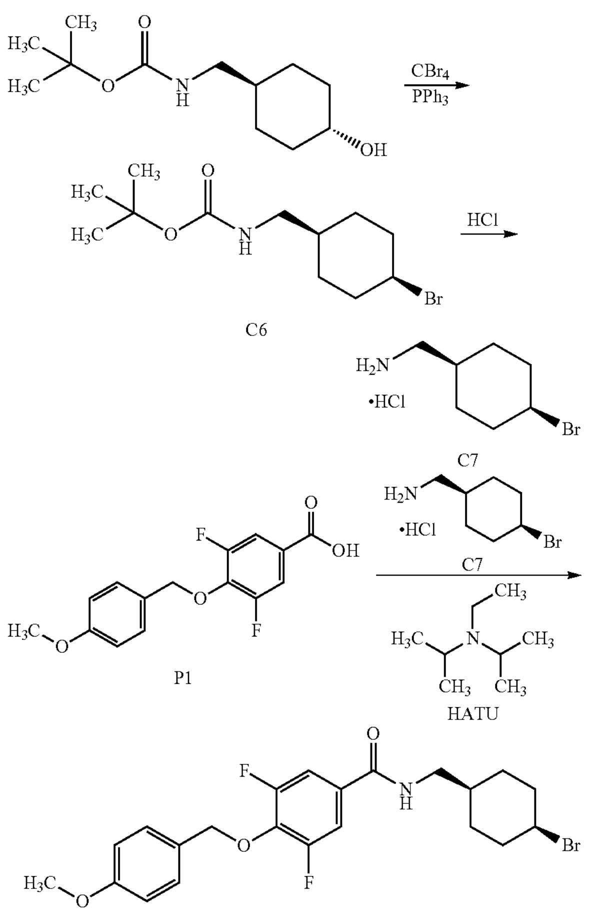

P6

Step 1. Synthesis of tert-butyl {[(1s,4s)-4-bromocyclohexyl]methyl}carbamate (C6)

To a 0° C. solution of tert-butyl {[(1r,4r)-4-hydroxycyclohexyl]methyl}carbamate (5.00 g, 21.8 mmol) in dichloromethane (150 mL) was added carbon tetrabromide (10.8 g, 32.6 mmol). Triphenylphosphine (8.58 g, 32.7 mmol) was added portion-wise, and the reaction mixture was stirred at 25° C. for 48 hours. After removal of solvent in vacuo, purification via silica gel chromatography (Gradient: 0% to 20% ethyl acetate in petroleum ether) afforded C6. Yield: 1.30 g, 4.45 mmol, 20%. LCMS m/z 314.1 (bromine isotope pattern observed) $[M+Na^+]$. $^1H$ NMR (400 MHz, DMSO-$d_6$) δ 6.86 (br t, J=6.0 Hz, 1H), 4.78-4.71 (m, 1H), 2.82 (dd, J=6, 6 Hz, 2H), 1.99-1.89 (m, 2H), 1.87-1.75 (m, 2H), 1.57-1.26 (m, 5H), 1.37 (s, 9H).

Step 2. Synthesis of 1-[(1s,4s)-4-bromocyclohexyl]methanamine, hydrochloride salt (C7)

To a solution of C6 (1.30 g, 4.45 mmol) in dichloromethane (20 mL) was added a solution of hydrogen chloride in 1,4-dioxane (4 M; 15 mL). After the reaction mixture had been stirred at 25° C. for 2.5 hours, LCMS analysis indicated conversion to C7: LCMS m/z 192.1 (bromine isotope pattern observed) $[M+H]^+$. Removal of solvents in vacuo afforded C7 (900 mg), which was used directly in the following step.

Step 3. Synthesis of N-{[(1s,4s)-4-bromocyclohexyl]methyl}-3,5-difluoro-4-[(4-methoxyphenyl)methoxy]benzamide (P6)

To a solution of P1 (1.65 g, 5.61 mmol), 0-(7-azabenzotriazol-1-yl)-N,N,N',N' tetramethyluronium hexafluorophosphate (HATU; 2.67 g, 7.02 mmol), and N,N-diisopropylethylamine (1.82 g, 14.1 mmol) in dichloromethane (80 mL) was added C7 (from the previous step; 900 mg, 54.45 mmol), whereupon the reaction mixture was stirred at room temperature for 3 hours. After the reaction mixture had been concentrated in vacuo, chromatography on silica gel (Gradient: 0% to 30% ethyl acetate in petroleum ether) provided P6. Yield: 1.40 g, 2.99 mmol, 67% over 2 steps. LCMS m/z 490.0 (bromine isotope pattern observed $[M+Na^+]$. $^1H$ NMR (400 MHz, DMSO-$d_6$) δ 8.55 (br t, J=5.8 Hz, 1H), 7.63-7.54 (m, 2H), 7.33 (d, J=8.7 Hz, 2H), 6.92 (d, J=8.6 Hz, 2H), 5.17 (s, 2H), 4.80-4.72 (m, 1H), 3.74 (s, 3H), 3.15 (dd, J=6, 6 Hz, 2H), 2.02-1.91 (m, 2H), 1.89-1.77 (m, 2H), 1.70-1.53 (m, 3H), 1.47-1.33 (m, 2H).

Preparation P7: 3,5-Difluoro-N-{[4-(N-hydroxycarbamimidoyl)bicyclo[2.2.2]octan-1-yl]methyl}-4-[(4-methoxyphenyl)methoxy]benzamide (P7)

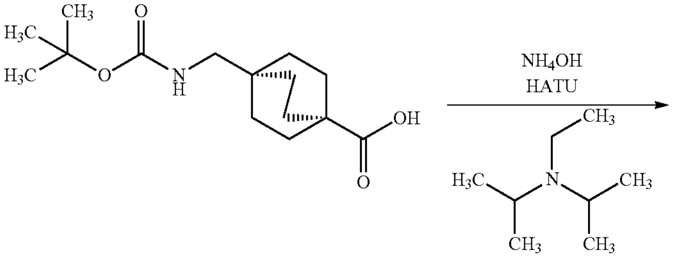

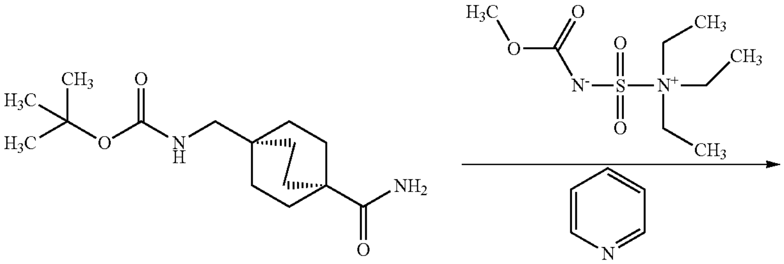

C8

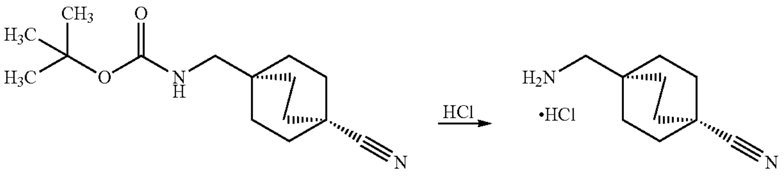

C9

C10

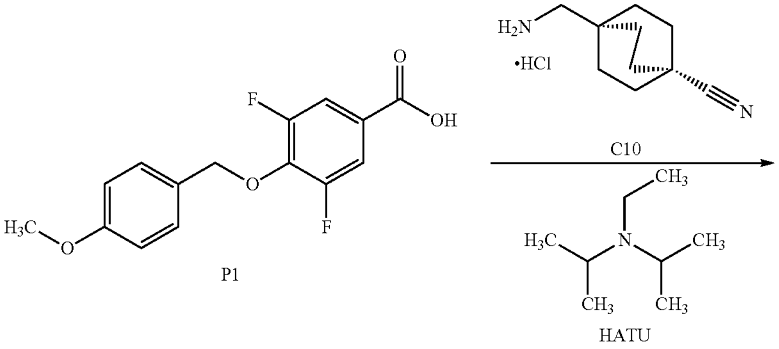

P1

-continued

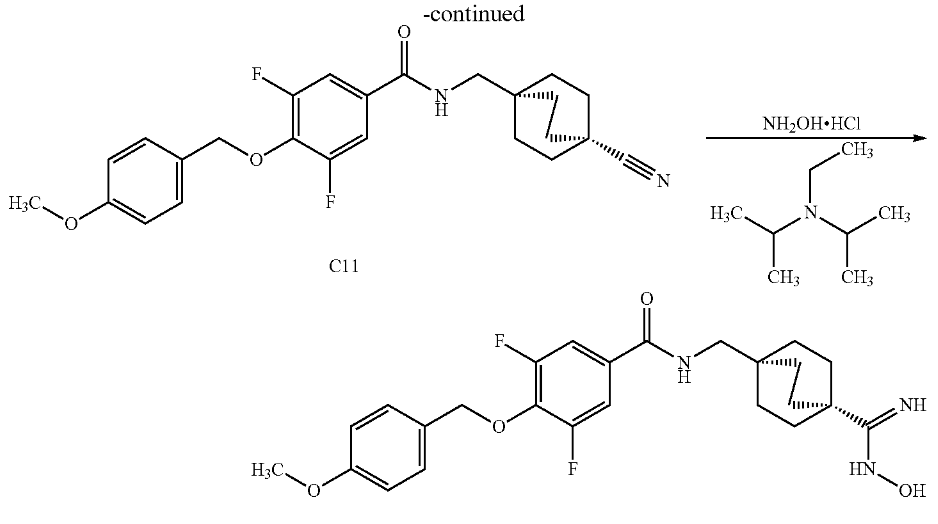

C11

P7

Step 1. Synthesis of tert-butyl [(4-carbamoylbicyclo [2.2.2]octan-1-yl)methyl]carbamate (C8)

To a solution of 4-{[(tert-butoxycarbonyl)amino] methyl}bicyclo[2.2.2]octane-1-carboxylic acid (1.50 g, 5.29 mmol) in dichloromethane (20 mL) were added O-(7-azabenzotriazol-1-yl)-N,N,N',N'-tetramethyluronium hexafluorophosphate (HATU; 3.02 g, 7.94 mmol), N,N-diisopropylethylamine (2.05 g, 15.9 mmol), and aqueous ammonium hydroxide solution (0.3 M; 22.9 mL, 6.87 mmol). After the reaction mixture had been stirred at 25° C. for 2 hours, it was diluted with dichloromethane (25 mL), washed sequentially with water (2×20 mL) and saturated aqueous sodium chloride solution (20 mL), dried over sodium sulfate, filtered, and concentrated in vacuo. Trituration with water (20 mL) afforded C8 as a white solid. Yield: 1.20 g, 4.25 mmol, 80%. LCMS m/z 283.2 $[M+H]^+$.

Step 2. Synthesis of tert-butyl [(4-cyanobicyclo [2.2.2]octan-1-yl)methyl]carbamate ($C_9$)

(Methoxycarbonylsulfamoyl)triethylammonium hydroxide, inner salt (Burgess reagent; 1.86 g, 7.81 mmol) was added to a solution of C8 (1.10 g, 3.90 mmol) in a mixture of pyridine (15 mL) and dichloromethane (10 mL). After the reaction mixture had been stirred at 25° C. for 2 hours, it was concentrated in vacuo; the residue was diluted with water (30 mL) and extracted with dichloromethane (2×20 mL). The combined organic layers were washed with saturated aqueous sodium chloride solution (2×20 mL), dried over sodium sulfate, filtered, and concentrated under reduced pressure, providing C9 as a white solid. Yield: 1.00 g, 3.78 mmol, 97%. LCMS m/z 209.2 $[(M\text{-}2\text{-methylprop-1-ene})+H]^+$. $^1H$ NMR (400 MHz, DMSO-$d_6$) δ 6.80 (br t, J=6.4 Hz, 1H), 2.66 (d, J=6.4 Hz, 2H), 1.86-1.76 (m, 6H), 1.36 (s, 9H), 1.36-1.27 (m, 6H).

Step 3. Synthesis of 4-(aminomethyl)bicyclo[2.2.2] octane-1-carbonitrile, hydrochloride salt (C10)

To a 0° C. solution of C9 (1.00 g, 3.78 mmol) in dichloromethane (15 mL) was added a solution of hydrogen chloride in 1,4-dioxane (4 M; 3.8 mL, 15 mmol), whereupon the reaction mixture was stirred at 25° C. for 16 hours. Removal of solvents in vacuo afforded C10 as a white solid. Yield: 750 mg, 3.74 mmol, 99%. LCMS m/z 165.2 $[M+H]^+$.

Step 4. Synthesis of N-[(4-cyanobicyclo[2.2.2]octan-1-yl)methyl]-3,5-difluoro-4-[(4-methoxyphenyl) methoxy]benzamide (C11)

O-(7-Azabenzotriazol-1-yl)-N,N,N',N'-tetramethyluronium hexafluorophosphate (HATU; 1.60 g, 4.21 mmol) and N,N-diisopropylethylamine (1.81 g, 14.0 mmol) were added to a solution of P1 (1.13 g, 3.84 mmol) in N,N-dimethylformamide (10 mL). After the reaction mixture had been stirred at 25° C. for 10 minutes, C10 (700 mg, 3.49 mmol) was added and stirring was continued at 25° C. for 4 hours. Water (25 mL) was then added, and the resulting mixture was extracted with ethyl acetate (2×25 mL); the combined organic layers were washed sequentially with water (2×10 mL) and saturated aqueous sodium chloride solution (2×10 mL), dried over sodium sulfate, filtered, and concentrated in vacuo. Silica gel chromatography (Gradient: 0% to 50% ethyl acetate in petroleum ether) provided C11 as a light-yellow solid. Yield: 1.29 g, 2.93 mmol, 84%. LCMS m/z 441.2 $[M+H]^+$. $^1H$ NMR (400 MHz, DMSO-$d_6$) δ 8.36 (br t, J=6.3 Hz, 1H), 7.64-7.54 (m, 2H), 7.34 (d, J=8.7 Hz, 2H), 6.92 (d, J=8.6 Hz, 2H), 5.17 (s, 2H), 3.75 (s, 3H), 3.01 (d, J=6.2 Hz, 2H), 1.87-1.78 (m, 6H), 1.46-1.36 (m, 6H).

Step 5. Synthesis of 3,5-difluoro-N-{[4-(N-hydroxycarbamimidoyl)bicyclo[2.2.2]octan-1-yl] methyl}-4-[(4-methoxyphenyl)methoxy]benzamide (P7)

To a solution of C11 (1.20 g, 2.72 mmol) in methanol (25 mL) were added hydroxylamine hydrochloride (1.14 g, 16.4 mmol) and N,N-diisopropylethylamine (2.82 g, 21.8 mmol), whereupon the reaction mixture was stirred at 70° C. for 16 hours. Removal of solvent in vacuo provided a residue, which was purified via silica gel chromatography (Gradient: 0% to 5% methanol in dichloromethane) to afford P7 as a white solid. Yield: 748 mg, 1.58 mmol, 58%. LCMS m/z 474.2 $[M+H]^+$. $^1H$ NMR (400 MHz, DMSO-$d_6$) δ 8.85 (s, 1H), 8.30 (br t, J=6.2 Hz, 1H), 7.64-7.55 (m, 2H), 7.34 (d, J=8.7 Hz, 2H), 6.92 (d, J=8.7 Hz, 2H), 5.16 (s, 2H), 5.11 (br s, 2H), 3.74 (s, 3H), 3.01 (d, J=6.2 Hz, 2H), 1.66-1.56 (m, 6H), 1.41-1.31 (m, 6H).

Preparation P8: N-[(4-Aminobicyclo[2.2.2]octan-1-yl)methyl]-2,3,5-trifluoro-4-[(4-methoxyphenyl)methoxy]benzamide (P8)

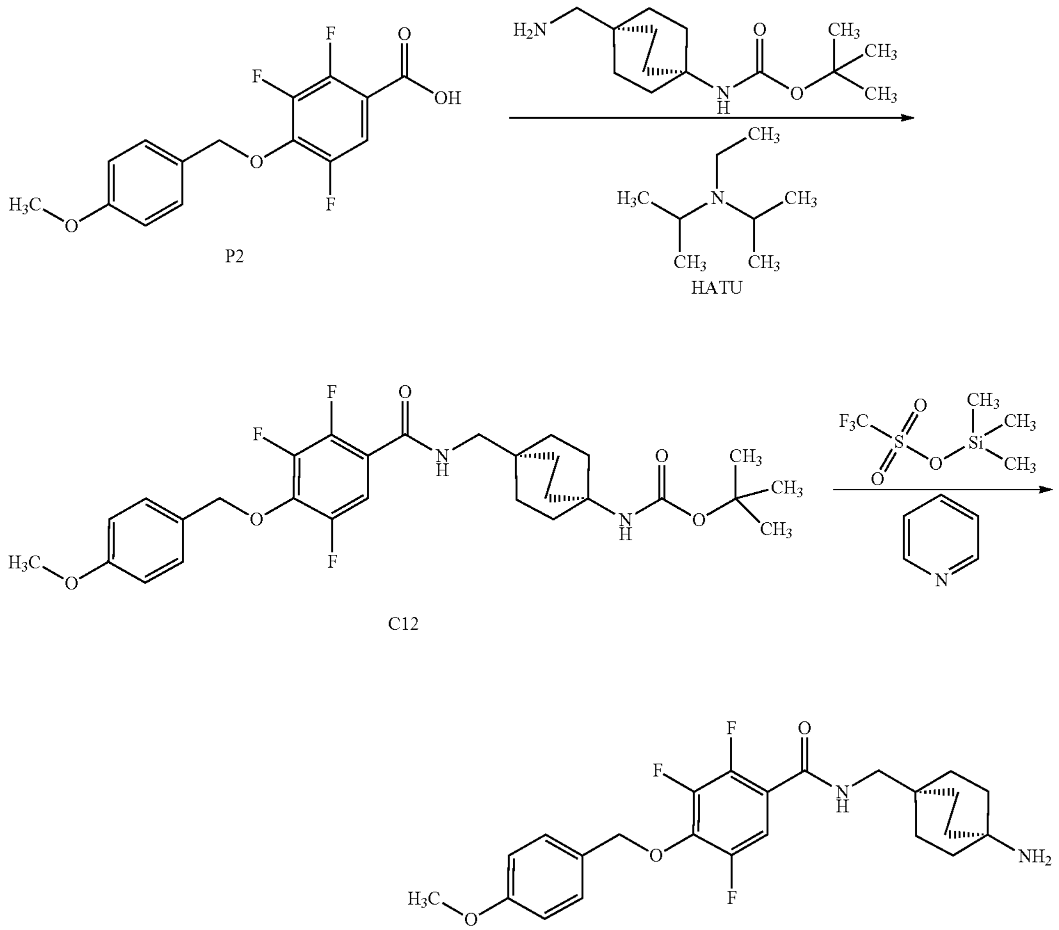

P2

C12

P8

Step 1. Synthesis of tert-butyl [4-({2,3,5-trifluoro-4-[(4-methoxyphenyl)methoxy]benzamido}methyl)bicyclo[2.2.2]octan-1-yl]carbamate (C12)

N,N-Diisopropylethylamine (826 mg, 6.39 mmol) was added to a solution of P2 (1.00 g, 3.20 mmol) and O-(7-azabenzotriazol-1-yl)-N,N,N',N'-tetramethyluronium hexafluorophosphate (HATU; 1.46 g, 3.84 mmol) in N,N-dimethylformamide (20 mL). After the mixture had been stirred at 25° C. for 2 minutes, tert-butyl [4-(aminomethyl)bicyclo[2.2.2]octan-1-yl]carbamate (855 mg, 3.36 mmol) was added, and stirring was continued at 20° C. for 1 hour. The reaction mixture was then extracted with ethyl acetate (2×50 mL), and the combined organic layers were dried over sodium sulfate, filtered, and concentrated in vacuo. Chromatography on silica gel (Eluent: 1:1 petroleum ether/ethyl acetate) provided C12 as a white solid. Yield: 1.35 g, 2.46 mmol, 77%. LCMS m/z 549.3 $[M+H]^+$. $^1H$ NMR (400 MHz, DMSO-$d_6$) δ 8.25 (t, J=6.3 Hz, 1H), 7.35 (d, J=8.6 Hz, 2H), 7.30 (ddd, J=10.9, 6.0, 2.3 Hz, 1H), 6.94 (d, J=8.7 Hz, 2H), 6.32 (br s, 1H), 5.21 (s, 2H), 3.75 (s, 3H), 2.96 (d, J=6.2 Hz, 2H), 1.76-1.64 (m, 6H), 1.46-1.37 (m, 6H), 1.35 (s, 9H).

Step 2. Synthesis of N-[(4-aminobicyclo[2.2.2]octan-1-yl)methyl]-2,3,5-trifluoro-4-[(4-methoxyphenyl)methoxy]benzamide (P8)

To a solution of C12 (1.30 g, 2.37 mmol) and pyridine (1.50 g, 19.0 mmol) in dichloromethane (20 mL) was added trimethylsilyl trifluoromethanesulfonate (3.69 g, 16.6 mmol), whereupon the reaction mixture was stirred at 20° C. for 30 minutes. Aqueous sodium bicarbonate solution (2 M; 50 mL) was then added, and the resulting mixture was extracted with dichloromethane (2×50 mL). The combined organic layers were washed with saturated aqueous sodium chloride solution (30 mL), dried over sodium sulfate, filtered, and concentrated in vacuo; purification using silica gel chromatography (Gradient: 13% to 17% methanol in dichloromethane) provided P8 as a white solid. Yield: 765 mg, 1.71 mmol, 72%. LCMS m/z 449.2 $[M+H]^+$. $^1H$ NMR (400 MHz, chloroform-d) δ 7.57 (ddd, J=11.8, 6.8, 2.3 Hz, 1H), 7.33 (d, J=8.6 Hz, 2H), 6.87 (d, J=8.5 Hz, 2H), 6.55-6.44 (m, 1H), 5.24 (s, 2H), 3.80 (s, 3H), 3.23 (d, J=6.1 Hz, 2H), 1.71-1.60 (m, 6H), 1.59-1.49 (m, 6H).

Preparation P9: 4-({2,3,5-Trifluoro-4-[(4-methoxyphenyl)methoxy]benzamido}methyl)bicyclo[2.2.2]octane-1-carboxylic acid (P9)

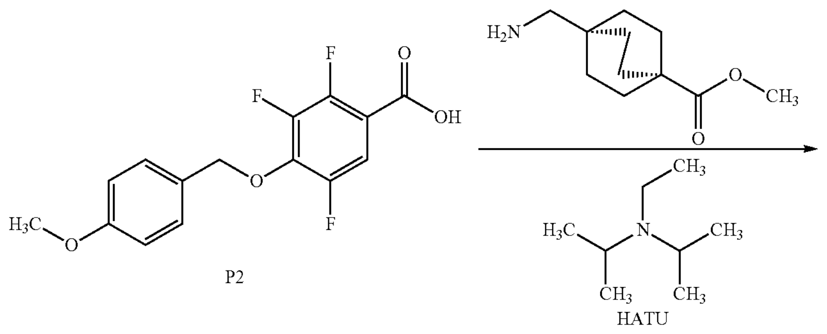

P2

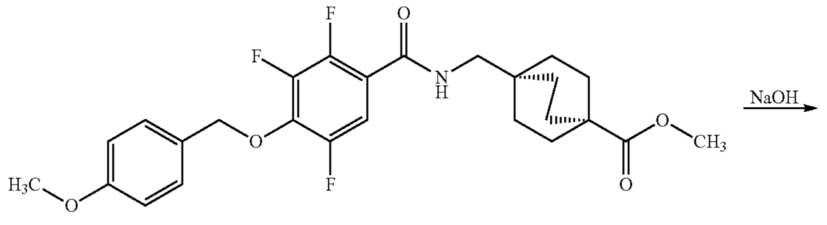

C13

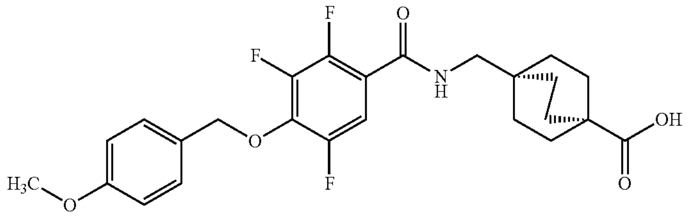

P9

Step 1. Synthesis of methyl 4-({2,3,5-trifluoro-4-[(4-methoxyphenyl)methoxy]benzamido}methyl)bicyclo[2.2.2]octane-1-carboxylate (C13)

To a solution of P2 (8.00 g, 25.6 mmol) and methyl 4-(aminomethyl)bicyclo[2.2.2]octane-1-carboxylate (5.05 g, 25.6 mmol) in N,N-dimethylformamide (60 mL) were added N,N-diisopropylethylamine (4.97 g, 38.4 mmol) and O-(7-azabenzotriazol-1-yl)-N,N,N',N'-tetramethyluronium hexafluorophosphate (HATU; 11.7 g, 30.8 mmol). After the reaction mixture had been stirred at room temperature for 4 hours, LCMS analysis indicated conversion to C13: LCMS m/z 492.2 $[M+H]^+$. The reaction mixture was poured into ice water, and the solid was collected via filtration and washed with water, providing C13 as a gray solid. Yield: 11.6 g, 23.6 mmol, 92%.

Step 2. Synthesis of 4-({2,3,5-trifluoro-4-[(4-methoxyphenyl)methoxy]benzamido}methyl)bicyclo[2.2.2]octane-1-carboxylic acid (P9)

A solution of C13 (11.6 g, 23.6 mmol) in methanol (120 mL) was treated with aqueous sodium hydroxide solution (3 M; 120 mL). The reaction mixture was stirred at 50° C. for 6 hours, then acidified by addition of hydrochloric acid. The resulting solid was collected via filtration and washed with water, then suspended in a mixture of ethyl acetate and methanol (10:1 ratio, 80 mL). This was stirred at 80° C., and treated slowly with methanol until a solution was obtained, whereupon it was cooled to room temperature. The resulting precipitate was collected via filtration and washed with ethyl acetate to afford P9 as a white solid. Yield: 9.0 g, 18.8 mmol, 80%. LCMS m/z 478.1 $[M+H]^+$. $^1H$ NMR (400 MHz, DMSO-$d_6$) δ 8.26 (br t, J=6.2 Hz, 1H), 7.42-7.23 (m, 3H), 6.94 (d, J=8.3 Hz, 2H), 5.21 (s, 2H), 3.75 (s, 3H), 2.98 (d, J=6.2 Hz, 2H), 1.71-1.55 (m, 6H), 1.44-1.29 (m, 6H).

Preparation P10: 2,3,5-Trifluoro-N-{[4-(N-hydroxy-carbamimidoyl)bicyclo[2.2.2]octan-1-yl]methyl}-4-[(4-methoxyphenyl)methoxy]benzamide (P10)

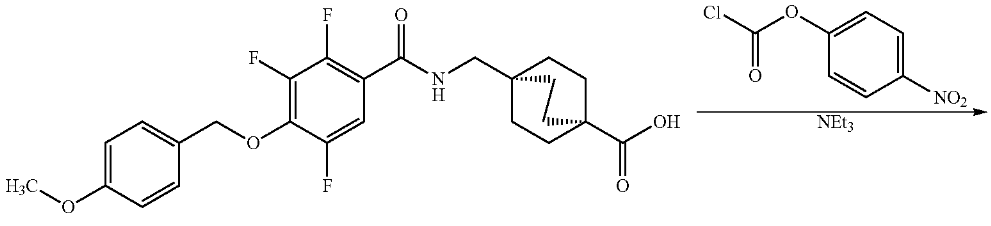

P9

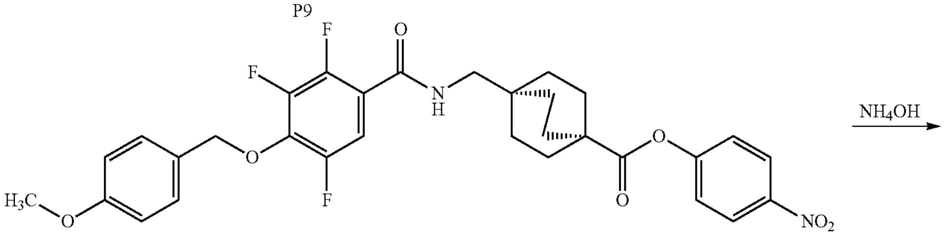

C14

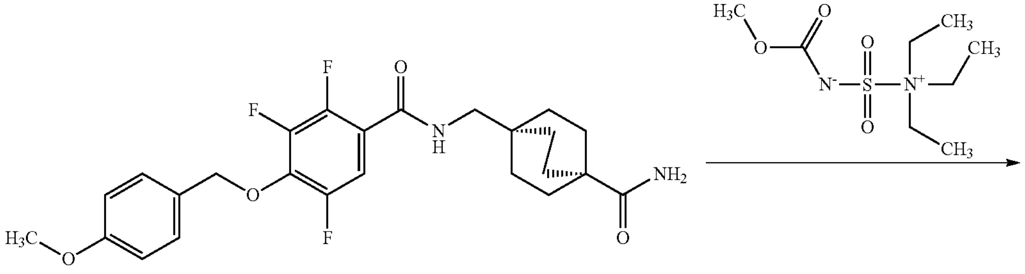

C15

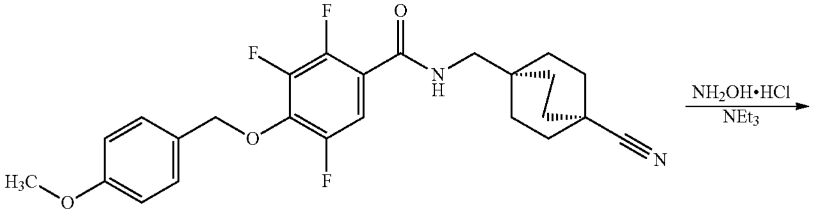

C16

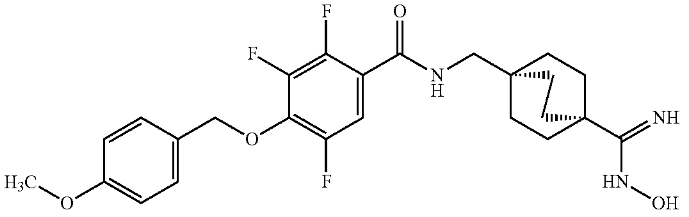

P10

Step 1. Synthesis of 4-nitrophenyl 4-({2,3,5-trifluoro-4-[(4-methoxyphenyl)methoxy]benzamido}methyl)bicyclo[2.2.2]octane-1-carboxylate (C14)

To a 0° C. suspension of P9 (962 mg, 2.01 mmol) in dichloromethane (8 mL) was added 4-nitrophenyl chloroformate (425 mg, 2.11 mmol), followed by triethylamine (0.842 mL, 6.04 mmol). The reaction mixture was allowed to warm to room temperature, then stir overnight at room temperature, whereupon it was concentrated in vacuo, providing C14 as a solid (1.20 g). This material was taken directly to the following step. LCMS m/z 599.4 $[M+H]^+$. $^1H$ NMR (400 MHz, DMSO-$d_6$), characteristic peaks: d 5.21 (s, 2H), 3.75 (s, 3H), 3.05 (d, J=6.3 Hz, 2H), 1.93-1.83 (m, 6H), 1.53-1.43 (m, 6H).

Step 2. Synthesis of 4-({2,3,5-trifluoro-4-[(4-methoxyphenyl)methoxy]benzamido}methyl)bicyclo[2.2.2]octane-1-carboxamide (C15)

A solution of C14 (from the previous step; 1.20 g, 52.01 mmol) in N,N-dimethylformamide (10 mL) was treated with concentrated ammonium hydroxide (14.5 M; 0.415 mL, 6.02 mmol), and the reaction mixture was stirred at room temperature for 5 hours. It was then added to water (100 mL) and the resulting mixture was extracted with ethyl acetate (3×80 mL); the combined organic layers were washed with saturated aqueous sodium chloride solution, dried over sodium sulfate, filtered, and concentrated in vacuo to provide C15 as an off-white solid. Yield: 919 mg, 1.93 mmol, 96% over 2 steps. LCMS m/z 477.3 [M+H]$^+$. $^1$H NMR (400 MHz, DMSO-$d_6$) δ 8.27 (br t, J=6 Hz, 1H), 7.35 (d, J=8.6 Hz, 2H), 7.30 (ddd, J=11.0, 6.1, 2.4 Hz, 1H), 6.94 (d, J=8.6 Hz, 2H), 6.88 (br s, 1H), 6.66 (br s, 1H), 5.21 (s, 2H), 3.75 (s, 3H), 2.99 (d, J=6.2 Hz, 2H), 1.66-1.57 (m, 6H), 1.41-1.33 (m, 6H).

Step 3. Synthesis of N-[(4-cyanobicyclo[2.2.2]octan-1-yl)methyl]-2,3,5-trifluoro-4-[(4-methoxyphenyl)methoxy]benzamide (C16)

To a solution of C15 (797 mg, 1.67 mmol) in ethyl acetate (10 mL) was added (methoxycarbonylsulfamoyl)triethylammonium hydroxide, inner salt (Burgess reagent; 997 mg, 4.18 mmol). The reaction mixture was stirred at room temperature overnight, whereupon it was diluted with ethyl acetate (40 mL) and washed sequentially with water (2×30 mL) and saturated aqueous sodium chloride solution (30 mL). The organic layer was then dried over sodium sulfate, filtered, and concentrated in vacuo, affording C16 as a solid. Yield: 658 mg, 1.44 mmol, 86%. LCMS m/z 459.3 [M+H]$^+$. $^1$H NMR (400 MHz, DMSO-$d_6$) δ 8.32 (br t, J=6.3 Hz, 1H), 7.35 (d, J=8.7 Hz, 2H), 7.34-7.28 (m, 1H), 6.94 (d, J=8.6 Hz, 2H), 5.21 (s, 2H), 3.75 (s, 3H), 2.99 (d, J=6.3 Hz, 2H), 1.88-1.79 (m, 6H), 1.46-1.37 (m, 6H).

Step 4. Synthesis of 2,3,5-trifluoro-N-{[4-(N-hydroxycarbamimidoyl)bicyclo[2.2.2]octan-1-yl]methyl}-4-[(4-methoxyphenyl)methoxy]benzamide (P10)

To a suspension of C16 (658 mg, 1.44 mmol) in methanol (8.0 mL) was added triethylamine (0.440 mL, 3.16 mmol), followed by hydroxylamine hydrochloride (219 mg, 3.15 mmol). No reaction was observed over several hours at room temperature. Hydroxylamine hydrochloride (219 mg, 3.15 mmol) was again added and the reaction mixture was heated at 50° C. for 24 hours. After cooling, it was diluted with ethyl acetate (30 mL) and washed sequentially with water (2×40 mL) and saturated aqueous sodium chloride solution (30 mL). The organic layer was then dried over sodium sulfate, filtered, and concentrated in vacuo, providing P10 as a solid. Yield: 330 mg, 0.671 mmol, 47%. LCMS m/z 492.4 [M+H]$^+$. $^1$H NMR (400 MHz, DMSO-$d_6$) d 11.82 (br s, 1H), 10.64 (br s, 1H), 8.59 (v br s, 1H), 8.33 (br t, J=6.3 Hz, 1H), 7.35 (d, J=8.6 Hz, 2H), 7.34-7.28 (m, 1H), 6.94 (d, J=8.6 Hz, 2H), 5.21 (s, 2H), 3.75 (s, 3H), 3.03 (d, J=6.3 Hz, 2H), 1.78-1.67 (m, 6H), 1.49-1.38 (m, 6H).

Preparation P11: tert-Butyl {[(1r,4r)-4-(7-bromoimidazo[1,2-a]pyridin-2-yl)cyclohexyl]methyl}carbamate (P11)

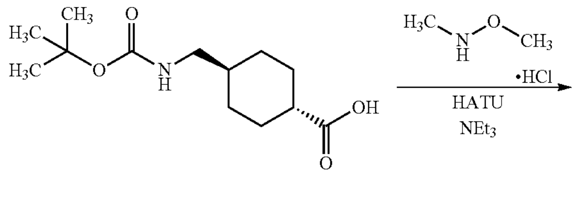

-continued

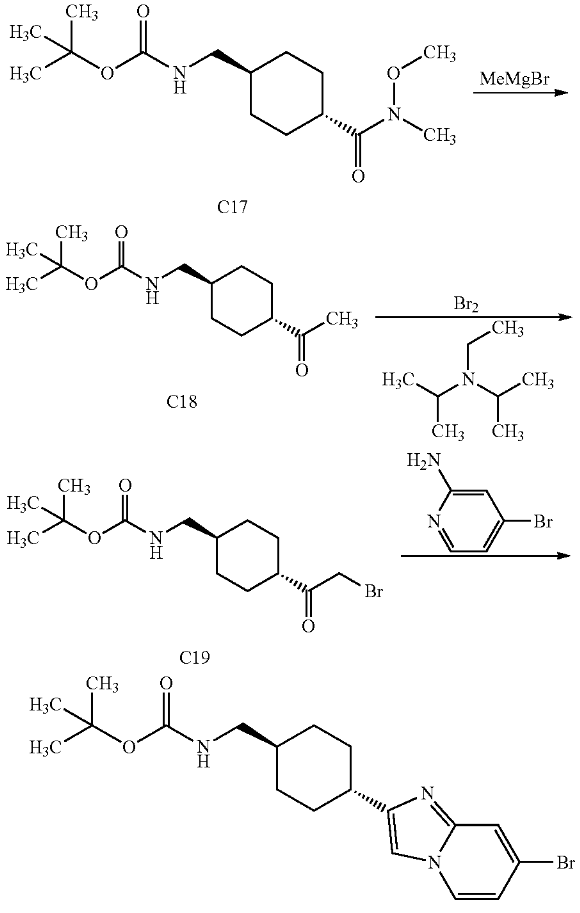

C17
C18
C19
P11

Step 1. Synthesis of tert-butyl ({(1r,4r)-4-[methoxy(methyl)carbamoyl]cyclohexyl}methyl)carbamate (C17)

To a solution of (1r,4r)-4-{[(tert-butoxycarbonyl)amino]methyl}cyclohexane-1-carboxylic acid (10.2 g, 39.6 mmol) in N,N-dimethylformamide (100 mL) were added N,O-dimethylhydroxylamine hydrochloride (4.66 g, 47.8 mmol), 0-(7-azabenzotriazol-1-yl)-N,N,N',N'-tetramethyluronium hexafluorophosphate (HATU; 19.7 g, 51.8 mmol), and triethylamine (16.7 mL, 120 mmol). After the reaction mixture had been stirred overnight at room temperature, LCMS analysis indicated formation of C17: LCMS m/z 301.5 [M+H]$^+$. In pilot reactions run on smaller scale, the reaction mixture was then concentrated under reduced pressure, diluted with a 1:1 mixture of ethyl acetate and dichloromethane, and filtered; concentration of the filtrate in vacuo provided C17. The product from this 39.6 mmol-scale reaction was combined with that from a similar reaction carried out using (1r,4r)-4-{[(tert-butoxycarbonyl)amino]methyl}cyclohexane-1-carboxylic acid (9.50 g, 36.9 mmol) to provide C17 as an oil. Combined yield: 22.8 g, 75.9 mmol, 99%. $^1$H NMR (500 MHz, chloroform-d) δ 4.56 (br s, 1H), 3.68 (s, 3H), 3.16 (s, 3H), 2.98 (br d, J=6.4 Hz, 2H), 2.69-2.57 (m, 1H), 1.87-1.77 (m, 4H), 1.57-1.38 (m, 3H), 1.44 (s, 9H), 1.05-0.94 (m, 2H).

Step 2. Synthesis of tert-butyl {[(1r,4r)-4-acetylcyclohexyl]methyl}carbamate (C18)

Methylmagnesium bromide (3.0 M; 81.7 mL, 245 mmol) was added drop-wise to a 0° C. solution of C17 (23.0 g, 76.6 mmol) in tetrahydrofuran (219 mL), whereupon the reaction mixture was allowed to warm to room temperature. After 2 hours, it was cooled to 0° C., treated with water (50 mL), and then diluted with ethyl acetate. The aqueous layer was extracted twice with ethyl acetate, and the combined organic layers were washed with saturated aqueous sodium chloride solution, dried over sodium sulfate, filtered, and concentrated in vacuo. Silica gel chromatography (Eluents: 0%, then 10%, then 25%, then 50% ethyl acetate in heptane) afforded C18 as a solid. Yield: 13.3 g, 52.1 mmol, 68%. $^{1}$H NMR (500 MHz, chloroform-d) δ 4.56 (br s, 1H), 2.98 (br dd, J=6, 6 Hz, 2H), 2.28 (tt, J=12.2, 3.5 Hz, 1H), 2.13 (s, 3H), 1.98-1.91 (m, 2H), 1.88-1.81 (m, 2H), 1.44 (s, 9H), 1.44-1.37 (m, 1H), 1.37-1.26 (m, 2H), 1.02-0.92 (m, 2H).

Step 3. Synthesis of tert-butyl {[(1r,4r)-4-(bromoacetyl)cyclohexyl]methyl}carbamate (C19)

Bromine (2.57 mL, 50.2 mmol) was added portion-wise to a 0° C. solution of C18 (12.1 g, 47.4 mmol) in methanol (158 mL). After the mixture had been stirred at 0° C. for 1 hour, and at room temperature for 1 hour, N,N-diisopropylethylamine (29.6 mL, 170 mmol) was added in a portion-wise manner. Stirring was continued at room temperature for 20 minutes, whereupon the mixture was concentrated in vacuo and combined with the product of a similar reaction carried out using C18 (1.03 g, 4.03 mmol). Silica gel chromatography (Eluents: 0%, then 10%, then 25% ethyl acetate in heptane) provided C19 as a solid. Combined yield: 9.07 g, 27.1 mmol, 53%. $^{1}$H NMR (500 MHz, chloroform-d) δ 4.56 (br s, 1H), 3.95 (s, 2H), 2.99 (dd, J=6, 6 Hz, 2H), 2.68 (tt, J=12.1, 3.4 Hz, 1H), 2.00-1.92 (m, 2H), 1.90-1.82 (m, 2H), 1.48-1.34 (m, 3H), 1.44 (s, 9H), 1.06-0.95 (m, 2H).

Step 4. Synthesis of tert-butyl {[(1r,4r)-4-(7-bromoimidazo[1,2-a]pyridin-2-yl)cyclohexyl]methyl}carbamate (P11)

A suspension of C19 (1.00 g, 2.99 mmol) and 4-bromopyridin-2-amine (1.04 g, 6.01 mmol) in ethanol (20 mL) was heated at 70° C. overnight. After the reaction mixture had cooled to room temperature, it was poured into water (150 mL) with stirring, and stirred for 20 minutes. Solids were collected via filtration and washed with water to afford P11 as a white solid. Yield: 976 mg, 2.39 mmol, 80%. LCMS m/z 408.2 (bromine isotope pattern observed) [M+H]$^{+}$. $^{1}$H NMR (400 MHz, DMSO-$d_6$) δ 8.41 (br d, J=7.1 Hz, 1H), 7.75 (br d, J=2.0 Hz, 1H), 7.69 (s, 1H), 6.97 (dd, J=7.2, 2.0 Hz, 1H), 6.83 (br t, J=5.9 Hz, 1H), 2.81 (dd, J=6, 6 Hz, 2H), 2.64-2.53 (m, 1H), 2.09-1.99 (m, 2H), 1.82-1.73 (m, 2H), 1.45-1.29 (m, 3H), 1.38 (s, 9H), 1.08-0.94 (m, 2H).

Preparation P12: tert-Butyl ({(1r,4r)-4-[6-(4,4,5,5-tetramethyl-1,3,2-dioxaborolan-2-yl)-2H-indazol-2-yl]cyclohexyl}methyl)carbamate (P12)

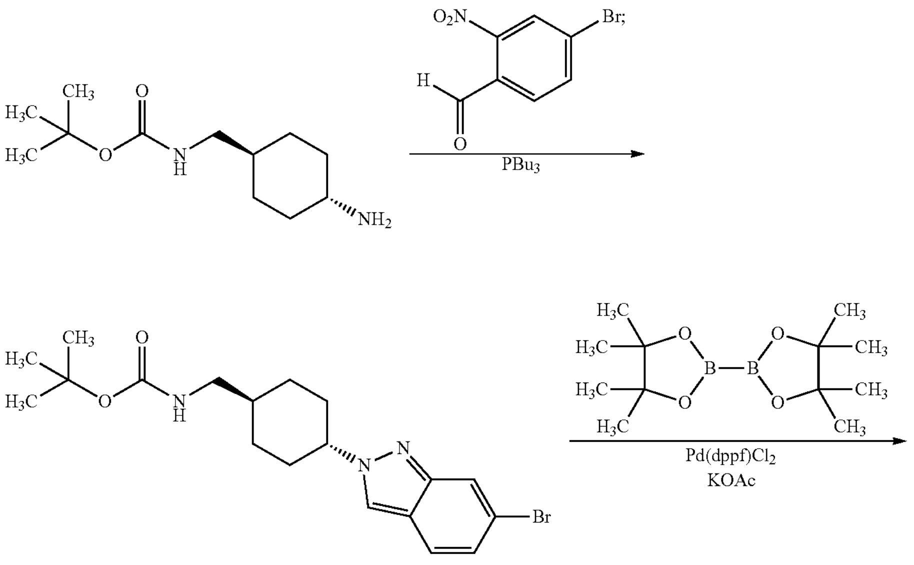

C20

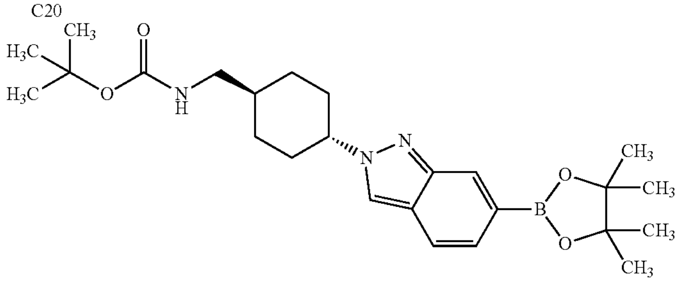

P12

Step 1. Synthesis of tert-butyl {[(1r,4r)-4-(6-bromo-2H-indazol-2-yl)cyclohexyl]methyl}carbamate (C20)

A suspension of tert-butyl {[(1r,4r)-4-aminocyclohexyl] methyl}carbamate (5.00 g, 21.9 mmol) and 4-bromo-2-nitrobenzaldehyde (5.04 g, 21.9 mmol) in propan-2-ol (70 mL) was heated at 80° C. for 4 hours. After the reaction mixture had cooled to room temperature, tributylphosphine (94%, 12 mL, 45 mmol) was added via syringe over 5 minutes; the reaction mixture was then heated at 80° C. overnight. Upon cooling to room temperature, the reaction mixture was filtered, and the filter cake was washed with heptane to afford C20 as a tan solid. Yield: 6.52 g, 16.0 mmol, 73%. LCMS m/z 408.1 (bromine isotope pattern observed) $[M+H]^+$. $^1H$ NMR (400 MHz, DMSO-$d_6$) 8.45 (s, 1H), 7.86-7.82 (m, 1H), 7.67 (d, J=8.8 Hz, 1H), 7.12 (dd, J=8.8, 1.7 Hz, 1H), 6.89 (br t, J=6.0 Hz, 1H), 4.50-4.38 (m, 1H), 2.85 (dd, J=6.3, 6.3 Hz, 2H), 2.17-2.07 (m, 2H), 1.93-1.78 (m, 4H), 1.54-1.41 (m, 1H), 1.39 (s, 9H), 1.20-1.04 (m, 2H).

Step 2. Synthesis of tert-butyl ({(1r,4r)-4-[6-(4,4,5,5-tetramethyl-1,3,2-dioxaborolan-2-yl)-2H-indazol-2-yl]cyclohexyl}methyl)carbamate (P12)

A mixture of C20 (6.52 g, 16.0 mmol), 4,4,4',4',5,5,5',5'-octamethyl-2,2'-bi-1,3,2-dioxaborolane (6.08 g, 23.9 mmol), and potassium acetate (95%, 4.95 g, 47.9 mmol) in 1,4-dioxane (200 mL) was degassed with nitrogen for 10 minutes, whereupon [1,1'-bis(diphenylphosphino)ferrocene]dichloropalladium(II), dichloromethane complex (Pd(dppf) $Cl_2$; 652 mg, 0.798 mmol) was added. After the reaction mixture had been heated at 100° C. for 1 hour, it was allowed to cool and filtered through a pad of diatomaceous earth. The filter cake was rinsed with ethyl acetate, and the combined filtrates were concentrated in vacuo; silica gel chromatography (Gradient: 30% to 70% ethyl acetate in heptane; loaded as a solution in dichloromethane) provided P12 as a colorless foam. Yield: 7.20 g, 15.8 mmol, 99%. LCMS m/z 456.4 $[M+H]^+$. $^1H$ NMR (400 MHz, DMSO-$d_6$), characteristic peaks: d 8.40 (s, 1H), 7.96-7.93 (m, 1H), 7.65 (br d, J=8.4 Hz, 1H), 7.25 (br d, J=8.4 Hz, 1H), 6.89 (br t, J=6.0 Hz, 1H), 4.53-4.39 (m, 1H), 2.85 (dd, J=6, 6 Hz, 2H), 2.19-2.08 (m, 2H), 1.93-1.78 (m, 4H), 1.56-1.43 (m, 1H), 1.39 (s, 9H), 1.31 (s, 12H).

Preparation P13: 1-{(1r,4r)-4-[6-(1-Methyl-1H-pyrazol-4-yl)-2H-indazol-2-yl]cyclohexyl}methanamine, hydrochloride salt (P13)

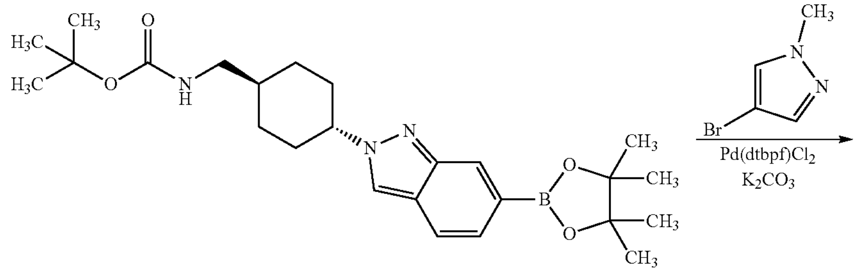

P12

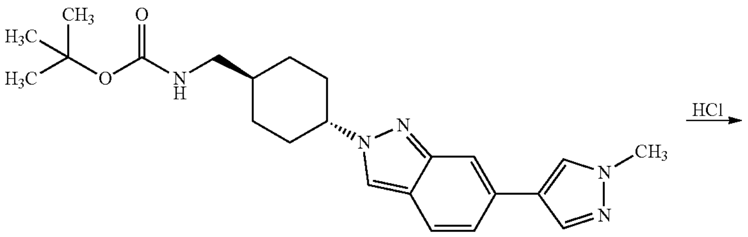

C21

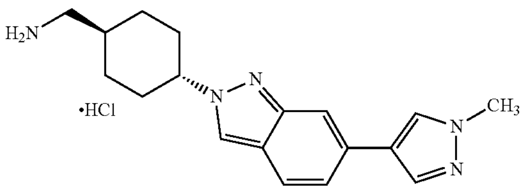

P13

Step 1. Synthesis of tert-butyl ({(1r,4r)-4-[6-(1-methyl-1H-pyrazol-4-yl)-2H-indazol-2-yl]cyclohexyl}methyl)carbamate (C21)

4-Bromo-1-methyl-1H-pyrazole (233 mg, 1.45 mmol), P12 (600 mg, 1.32 mmol), aqueous potassium carbonate solution (2 M; 1.98 mL, 3.96 mmol), [1,1'-bis(di-tert-butylphosphino)ferrocene]dichloropalladium(II) [Pd(dtbpf)$Cl_2$; 85.9 mg, 0.132 mmol], ethanol (5 mL), and water (1 mL) were combined in a pressure-relief vial, and the reaction mixture was heated at 85° C. for 1 hour. After the reaction mixture had cooled, concentration in vacuo was used to remove ethanol, and the resulting mixture was partitioned between ethyl acetate and water. The organic layer was washed with saturated aqueous sodium chloride solution, dried over magnesium sulfate, filtered, and concentrated in vacuo; silica gel chromatography (Eluents: ethyl acetate, then 5% methanol in ethyl acetate) afforded $C_{21}$ as a colorless foam. Yield: 404 mg, 0.986 mmol, 75%. LCMS m/z 410.4 $[M+H]^+$. $^1H$ NMR (400 MHz, DMSO-$d_6$) δ 8.31 (br s, 1H), 8.15 (s, 1H), 7.91-7.89 (m, 1H), 7.76-7.72 (m, 1H), 7.65 (dd, J=8.6, 0.9 Hz, 1H), 7.25 (dd, J=8.7, 1.4 Hz, 1H), 6.90 (br t, J=5.9 Hz, 1H), 4.47-4.34 (m, 1H), 3.87 (s, 3H), 2.85 (dd, J=6, 6 Hz, 2H), 2.18-2.07 (m, 2H), 1.94-1.78 (m, 4H), 1.54-1.42 (m, 1H), 1.39 (s, 9H), 1.20-1.05 (m, 2H).

Step 2. Synthesis of 1-{(1r,4r)-4-[6-(1-methyl-1H-pyrazol-4-yl)-2H-indazol-2-yl]cyclohexyl}methanamine, hydrochloride salt (P13)

A solution of hydrogen chloride in 1,4-dioxane (4 M; 6 mL) was added to $C_{21}$ (404 mg, 0.986 mmol). Propan-2-ol (3 mL) was added to aid solubility and stirring, and the reaction mixture was allowed to stir overnight, whereupon it was diluted with diethyl ether (50 mL). Solids were collected via filtration and washed with diethyl ether to provide P13 as a solid. Yield: 362 mg, assumed quantitative. LCMS m/z 310.3 $[M+H]^+$. $^1H$ NMR (400 MHz, DMSO-$d_6$) δ 8.37 (br s, 1H), 8.17 (s, 1H), 7.92 (s, 1H), 7.74 (br s, 1H), 7.66 (br d, J=8.6 Hz, 1H), 7.27 (dd, J=8.7, 1.4 Hz, 1H), 4.50-4.39 (m, 1H), 3.87 (s, 3H), 2.78-2.68 (m, 2H), 2.22-2.12 (m, 2H), 2.01-1.84 (m, 4H), 1.78-1.65 (m, 1H), 1.29-1.15 (m, 2H).

Preparation P14: 3,5-Difluoro-4-[(4-methoxyphenyl)methoxy]-N-({(1r,4r)-4-[6-(4,4,5,5-tetramethyl-1,3,2-dioxaborolan-2-yl)-2H-indazol-2-yl]cyclohexyl}methyl)benzamide (P14)

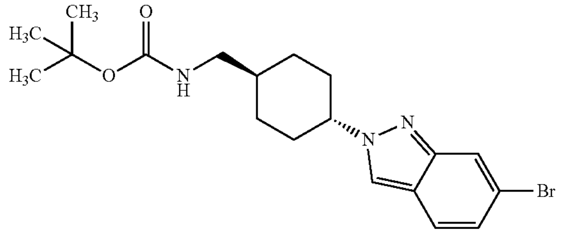

C20

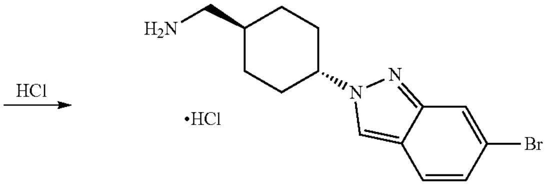

C22

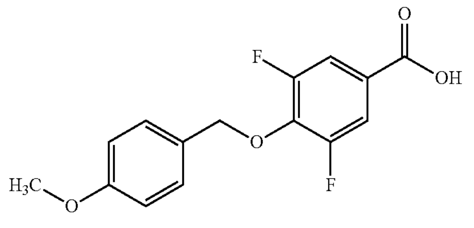

P1

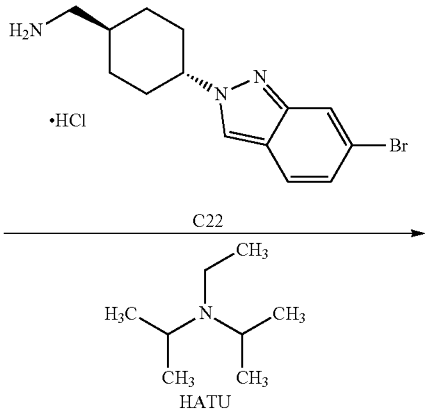

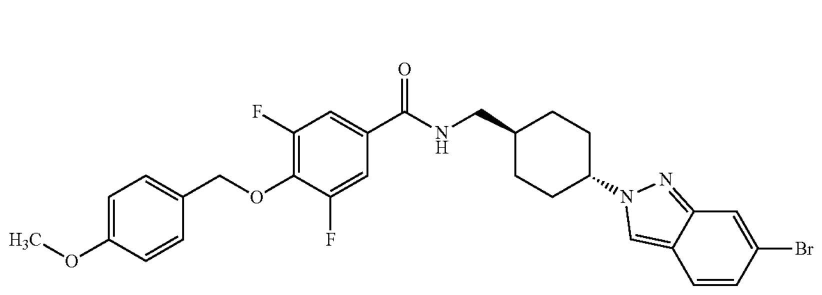

C23

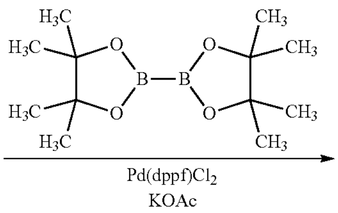

-continued

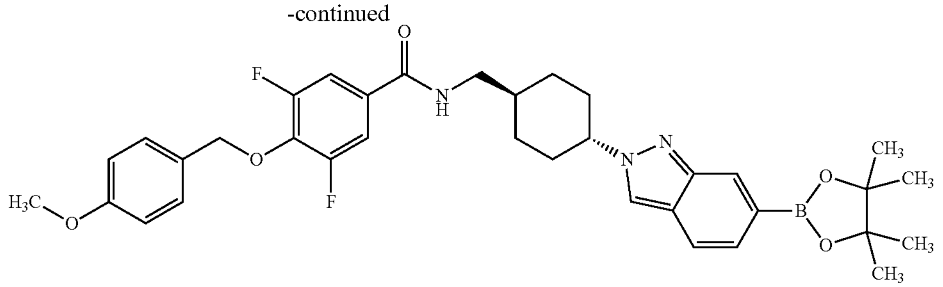

P14

Step 1. Synthesis of 1-[(1r,4r)-4-(6-bromo-2H-indazol-2-yl)cyclohexyl]methanamine, hydrochloride salt (C22)

A solution of hydrogen chloride in 1,4-dioxane (4 M; 25 mL, 100 mmol) was added to a solution of C20 (7.35 g, 18.0 mmol) in 1,4-dioxane (30 mL); the reaction mixture was stirred at room temperature for 3 hours, followed by overnight at 50° C. After the reaction mixture had cooled, it was diluted with diethyl ether (100 mL). Solids were collected via filtration and washed with diethyl ether, affording C22 as a solid. Yield: 6.20 g, 18.0 mmol, quantitative. LCMS m/z 308.5 (bromine isotope pattern observed) $[M+H]^+$. $^1H$ NMR (400 MHz, DMSO-$d_6$) δ 8.49 (br s, 1H), 8.06 (br s, 3H), 7.86-7.83 (m, 1H), 7.68 (d, J=8.8 Hz, 1H), 7.12 (dd, J=8.8, 1.7 Hz, 1H), 4.47 (tt, J=11.7, 3.9 Hz, 1H), 2.78-2.66 (m, 2H), 2.21-2.11 (m, 2H), 2.01-1.82 (m, 4H), 1.78-1.65 (m, 1H), 1.29-1.14 (m, 2H).

Step 2. Synthesis of N-{[(1r,4r)-4-(6-bromo-2H-indazol-2-yl)cyclohexyl]methyl}-3,5-difluoro-4-[(4-methoxyphenyl)methoxy]benzamide (C23)

To a suspension of C22 (6.20 g, 18.0 mmol) and P1 (5.92 g, 20.1 mmol) in N,N-dimethylformamide (15 mL) was added N,N-diisopropylethylamine (14 mL, 80.4 mmol), followed by O-(7-azabenzotriazol-1-yl)-N,N,N',N'-tetramethyluronium hexafluorophosphate (HATU, 95%; 9.66 g, 24.1 mmol). The reaction mixture was stirred at room temperature for 3 days, whereupon it was poured into water (450 mL) with stirring. The resulting solid was isolated via filtration and washed with water, providing C23 as a solid. Yield: 10.0 g, 17.1 mmol, 95%. LCMS m/z 584.2 (bromine isotope pattern observed) $[M+H]^+$. $^1H$ NMR (400 MHz, DMSO-$d_6$) δ 8.57 (br t, J=5.8 Hz, 1H), 8.45 (br s, 1H), 7.86-7.83 (m, 1H), 7.67 (d, J=8.8 Hz, 1H), 7.65-7.56 (m, 2H), 7.34 (d, J=8.6 Hz, 2H), 7.12 (dd, J=8.8, 1.7 Hz, 1H), 6.92 (d, J=8.6 Hz, 2H), 5.17 (s, 2H), 4.53-4.41 (m, 1H), 3.74 (s, 3H), 3.17 (dd, J=6, 6 Hz, 2H), 2.21-2.09 (m, 2H), 1.96-1.80 (m, 4H), 1.73-1.59 (m, 1H), 1.28-1.13 (m, 2H).

Step 3. Synthesis of 3,5-difluoro-4-[(4-methoxyphenyl)methoxy]-N-({(1r,4r)-4-[6-(4,4,5,5-tetramethyl-1,3,2-dioxaborolan-2-yl)-2H-indazol-2-yl]cyclohexyl}methyl)benzamide (P14)

A mixture of C23 (10 g, 17.1 mmol), 4,4,4',4',5,5,5',5'-octamethyl-2,2'-bi-1,3,2-dioxaborolane (6.52 g, 25.7 mmol), and potassium acetate (95%, 5.30 g, 51.3 mmol), in 1,4-dioxane (250 mL) was degassed with nitrogen for 10 minutes. [1,1'-Bis(diphenylphosphino)ferrocene]dichloropalladium(II), dichloromethane complex (700 mg, 0.857 mmol) was added and the reaction mixture was purged with nitrogen for an additional 5 minutes, whereupon it was heated at 100° C. for 2 hours. After the reaction mixture had cooled, it was filtered through diatomaceous earth and the filter pad was rinsed with ethyl acetate. The combined filtrates were concentrated in vacuo, and the residue was purified via silica gel chromatography (Gradient: 2% to 10% methanol in dichloromethane; loaded as a solution in dichloromethane) to afford P14 as a tan solid. Yield: 7.32 g, 11.6 mmol, 68%. LCMS m/z 632.3 $[M+H]^+$. $^1H$ NMR (400 MHz, DMSO-$d_6$) δ 8.57 (br t, J=5.8 Hz, 1H), 8.40 (br s, 1H), 7.96-7.94 (m, 1H), 7.65 (dd, J=8.4, 1 Hz, 1H), 7.66-7.56 (m, 2H), 7.34 (d, J=8.6 Hz, 2H), 7.25 (br d, J=8.4 Hz, 1H), 6.92 (d, J=8.7 Hz, 2H), 5.17 (s, 2H), 4.55-4.43 (m, 1H), 3.74 (s, 3H), 3.18 (dd, J=6, 6 Hz, 2H), 2.21-2.10 (m, 2H), 1.96-1.81 (m, 4H), 1.75-1.60 (m, 1H), 1.31 (s, 12H), 1.28-1.14 (m, 2H).

Preparation P15: N-{[(1r,4r)-4-(6-Chloro-2H-pyrazolo[4,3-c]pyridin-2-yl)cyclohexyl]methyl}-3,5-difluoro-4-[(4-methoxyphenyl)methoxy]benzamide (P15)

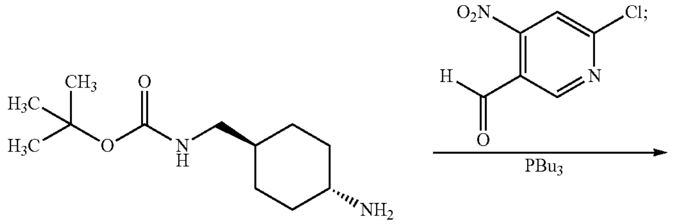

-continued

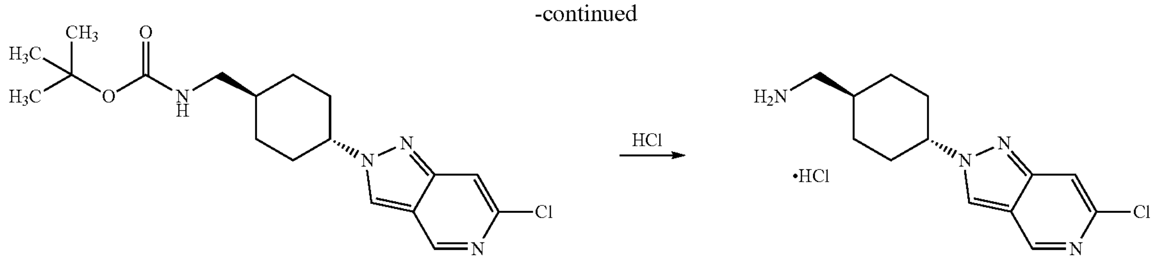

C24

C25

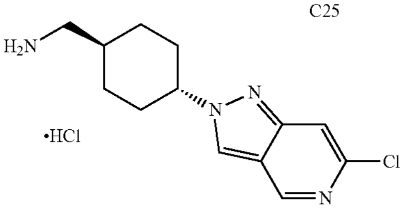

C25

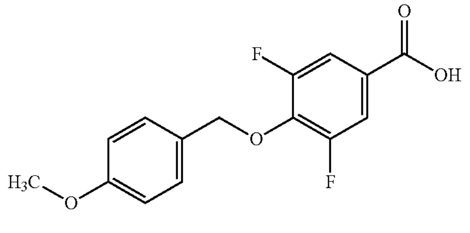

P1

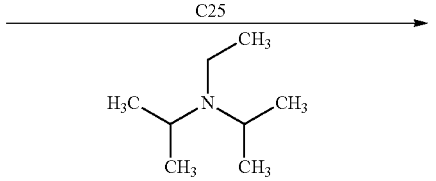

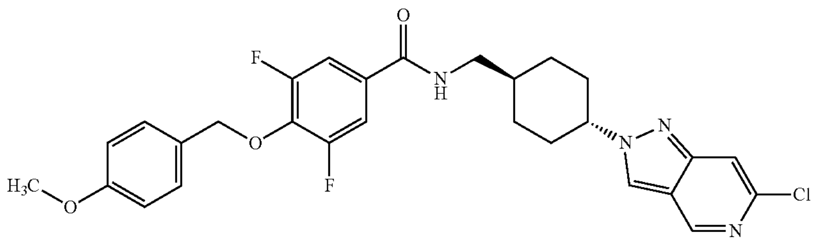

P15

Step 1. Synthesis of tert-butyl {[(1r,4r)-4-(6-chloro-2H-pyrazolo[4,3-c]pyridin-2-yl)cyclohexyl]methyl}carbamate (C24)

A mixture of 6-chloro-4-nitropyridine-3-carbaldehyde (2.00 g, 10.7 mmol) and tert-butyl {[(1r,4r)-4-aminocyclohexyl]methyl}carbamate (2.45 g, 10.7 mmol) in propan-2-ol (50 mL) was heated at 80° C. for 4 hours, whereupon the reaction mixture was cooled to room temperature. Tributylphosphine (6.51 g, 32.2 mmol) was then added, and the reaction mixture was heated at 80° C. for an additional 6 hours. After removal of solvent in vacuo, the residue was purified via reversed-phase HPLC (Column: Waters XBridge C18, 30×150 mm, 5 μm; Mobile phase A: water containing 0.05% formic acid; Mobile phase B: acetonitrile; Gradient: 50% to 60% B; Flow rate: 20 mL/minute) to provide C24 as a white solid. Yield: 260 mg, 0.713 mmol, 7%. LCMS m/z 365.2 (chlorine isotope pattern observed) $[M+H]^+$. $^1H$ NMR (400 MHz, DMSO-$d_6$) δ 9.01 (d, J=1.2 Hz, 1H), 8.81 (br s, 1H), 7.68 (br s, 1H), 6.91 (br t, J=5.9 Hz, 1H), 4.59-4.47 (m, 1H), 2.85 (dd, J=6, 6 Hz, 2H), 2.20-2.08 (m, 2H), 1.95-1.78 (m, 4H), 1.54-1.40 (m, 1H), 1.38 (s, 9H), 1.20-1.04 (m, 2H).

Step 2. Synthesis of 1-[(1r,4r)-4-(6-chloro-2H-pyrazolo[4,3-c]pyridin-2-yl)cyclohexyl]methanamine, hydrochloride salt (C25)

To a solution of C24 (260 mg, 0.713 mmol) in dichloromethane (4 mL) was added a solution of hydrogen chloride in 1,4-dioxane (4 M; 1 mL, 4 mmol). After the reaction mixture had been stirred at 15° C. for 4 hours, it was concentrated in vacuo to afford C25 as a yellow oil. Yield: 170 mg, 0.564 mmol, 79%. LCMS m/z 265.1 (chlorine isotope pattern observed) $[M+H]^+$.

Step 3. Synthesis of N-{[(1r,4r)-4-(6-chloro-2H-pyrazolo[4,3-c]pyridin-2-yl)cyclohexyl]methyl}-3,5-difluoro-4-[(4-methoxyphenyl)methoxy]benzamide (P15)

To a solution of P1 (186 mg, 0.632 mmol), N,N-diisopropylethylamine (163 mg, 1.26 mmol), and O-(7-azabenzotriazol-1-yl)-N,N,N'N'-tetramethyluronium hexafluorophosphate (HATU; 288 mg, 0.757 mmol) in dichloromethane (10 mL) was added C25 (167 mg, 0.554 mmol), whereupon the reaction mixture was stirred at 15° C. for 1 hour. It was then extracted with dichloromethane (3×30 mL), and the combined organic layers were washed with saturated aqueous sodium chloride solution, dried over sodium sulfate, filtered, and concentrated in vacuo. Purification using silica gel chromatography (Eluent: 4% methanol in dichloromethane) provided P15 as a yellow oil. Yield: 250 mg, 0.462 mmol, 83%. LCMS m/z 541.1 (chlorine isotope pattern observed) $[M+H]^+$. $^1H$ NMR (400 MHz, DMSO-$d_6$), characteristic peaks: d 9.01 (d, J=1.2 Hz, 1H), 8.80 (br s, 1H), 8.58 (br t, J=5.8 Hz, 1H), 7.68 (br s, 1H), 7.66-7.56 (m, 2H), 7.34 (d, J=8.6 Hz, 2H), 6.92 (d, J=8.7 Hz, 2H), 5.17 (s, 2H), 4.63-4.49 (m, 1H), 3.74 (s, 3H), 2.21-2.10 (m, 2H).

Preparation P16: N-{[4-(6-Bromo-2H-indazol-2-yl)bicyclo[2.2.2]octan-1-yl]methyl}-2,3,5-trifluoro-4-[(4-methoxyphenyl)methoxy]benzamide (P16)

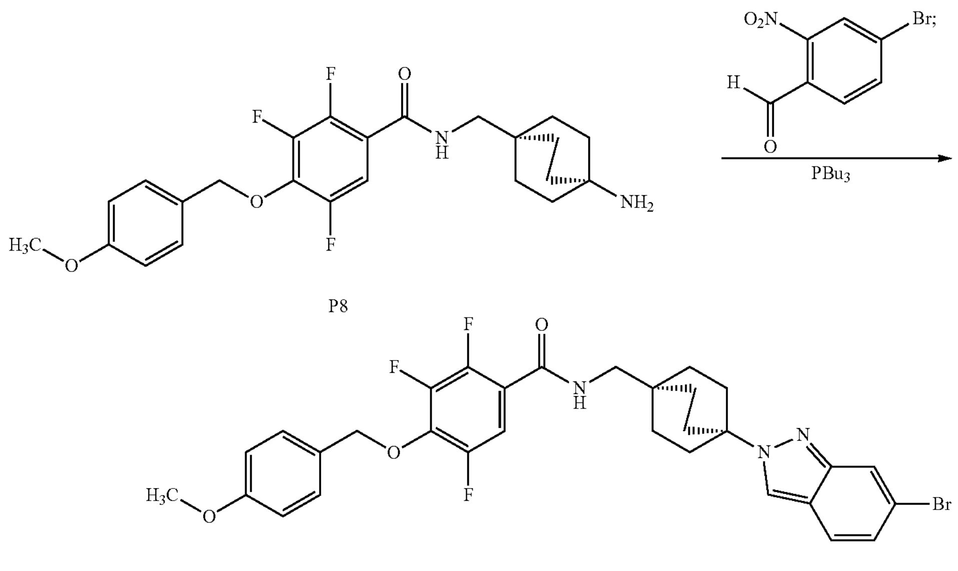

P8

P16

A solution of P8 (200 mg, 0.446 mmol) and 4-bromo-2-nitrobenzaldehyde (123 mg, 0.535 mmol) in propan-2-ol (10 mL) was stirred at 85° C. for 4 hours, whereupon it was cooled to room temperature and treated with tributylphosphine (2 mL, 8 mmol). After the reaction mixture had been stirred at 85° C. overnight, it was diluted with water (15 mL) and extracted with dichloromethane (3×10 mL). The combined organic layers were washed with saturated aqueous sodium chloride solution (100 mL), dried over sodium sulfate, filtered, concentrated in vacuo, and subjected to chromatography on silica gel (Gradient: 0% to 10% methanol in dichloromethane), affording P16 as a yellow solid. $^1H$ NMR data was obtained from a reaction carried out in a similar manner. Yield: 170 mg, 0.270 mmol, 61%. LCMS m/z 626.1 (bromine isotope pattern observed) $[M-H]^-$. $^1H$ NMR (400 MHz, DMSO-$d_6$) δ 8.46 (d, J=1.0 Hz, 1H), 8.40 (br t, J=6.3 Hz, 1H), 7.86-7.83 (m, 1H), 7.66 (br d, J=8.8 Hz, 1H), 7.38-7.32 (m, 1H), 7.36 (d, J=8.7 Hz, 2H), 7.11 (dd, J=8.8, 1.7 Hz, 1H), 6.94 (d, J=8.7 Hz, 2H), 5.22 (s, 2H), 3.75 (s, 3H), 3.10 (d, J=6.2 Hz, 2H), 2.20-2.10 (m, 6H), 1.71-1.60 (m, 6H).

Example 1: N-{[(1r,4r)-4-(1,3-Benzoxazol-2-yl)cyclohexyl]methyl}-3,5-difluoro-4-hydroxybenzamide (1)

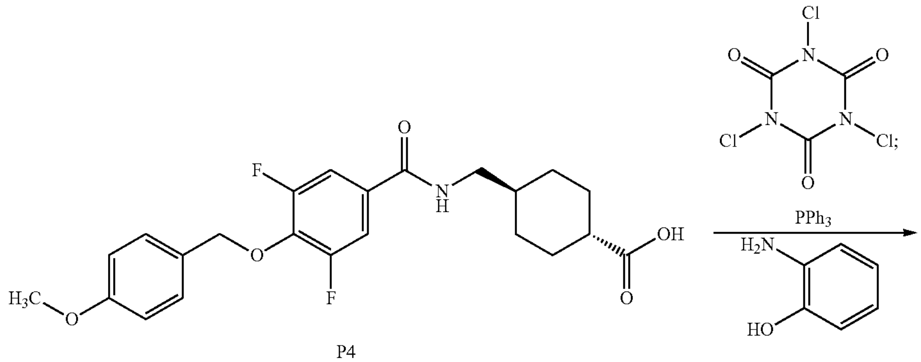

P4

-continued

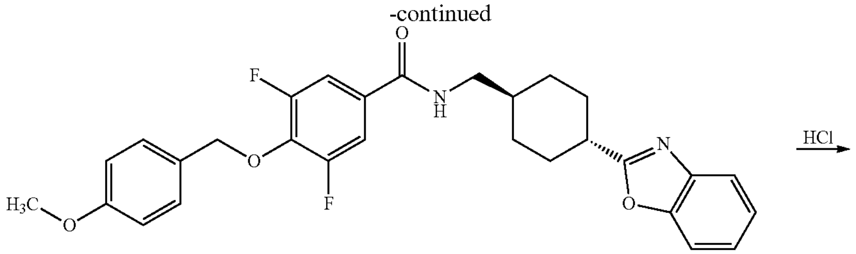

C26

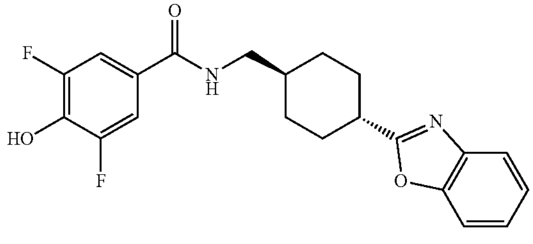

1

Step 1. Synthesis of N-{[(1r,4r)-4-(1,3-benzoxazol-2-yl)cyclohexyl]methyl}-3,5-difluoro-4-[(4-methoxyphenyl)methoxy]benzamide (C26)

1,3,5-Trichloro-1,3,5-triazinane-2,4,6-trione (161 mg, 0.693 mmol) and P4 (1.00 g, 2.31 mmol) were added to a 0° C. mixture of triphenylphosphine (95%, 637 mg, 2.31 mmol) in 1,4-dioxane (40 mL). After the reaction mixture had been stirred for 30 minutes, it was warmed to room temperature, 2-aminophenol (378 mg, 3.46 mmol) was added, and the reaction mixture was stirred overnight at 105° C. Once it had cooled, the reaction mixture was filtered through a pad of diatomaceous earth, and the pad was rinsed sequentially with 1,4-dioxane, ethyl acetate, and dichloromethane. The combined filtrates were concentrated in vacuo to afford C26 as an orange oil, which was progressed directly to the following step. LCMS m/z 507.3 $[M+H]^+$.

Step 2. Synthesis of N-{[(1r,4r)-4-(1,3-benzoxazol-2-yl)cyclohexyl]methyl}-3,5-difluoro-4-hydroxybenzamide (1)

A 0° C. suspension of C26 (from the previous step; 52.31 mmol) in 1,4-dioxane (20 mL) was treated with a solution of hydrogen chloride in 1,4-dioxane (4 M; 20 mL). After the reaction mixture had been allowed to stir at room temperature for 2 hours, it was concentrated in vacuo and purified via silica gel chromatography (Gradient: 0% to 100% ethyl acetate in heptane; the sample was loaded in dichloromethane containing a minimal quantity of methanol). The resulting material was partitioned between saturated aqueous sodium bicarbonate solution and ethyl acetate, whereupon the organic layer was washed with water, dried over sodium sulfate, filtered, and concentrated in vacuo. The residue was subjected to chromatography on silica gel (Gradient: 0% to 100% ethyl acetate in heptane, followed by 0% to 10% methanol in dichloromethane; the sample was loaded in dichloromethane containing a minimal quantity of methanol), providing N-{[(1r,4r)-4-(1,3-benzoxazol-2-yl)cyclohexyl]methyl}-3,5-difluoro-4-hydroxybenzamide (1) as a white solid. Yield: 46 mg, 0.12 mmol, 5% over 2 steps. LCMS m/z 387.3 $[M+H]^+$. $^1$H NMR (400 MHz, methanol-$d_4$) δ 7.65-7.60 (m, 1H), 7.58-7.53 (m, 1H), 7.52-7.42 (m, 2H), 7.38-7.31 (m, 2H), 3.27 (d, J=7.0 Hz, 2H), 2.98 (tt, J=12.2, 3.6 Hz, 1H), 2.32-2.22 (m, 2H), 2.04-1.94 (m, 2H), 1.80-1.62 (m, 3H), 1.31-1.16 (m, 2H).

Example 2: 3,5-Difluoro-4-hydroxy-N-{[(1r,4r)-4-{3-[5-(trifluoromethyl)pyridin-2-yl]-1,2,4-oxadiazol-5-yl}cyclohexyl]methyl}benzamide (2)

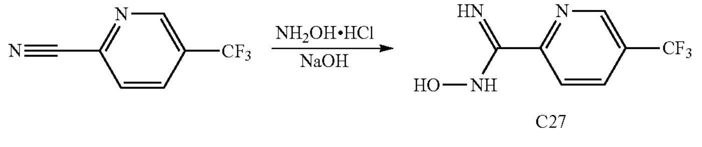

C27

-continued

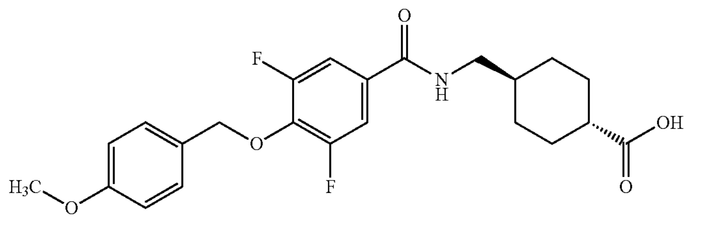

P4

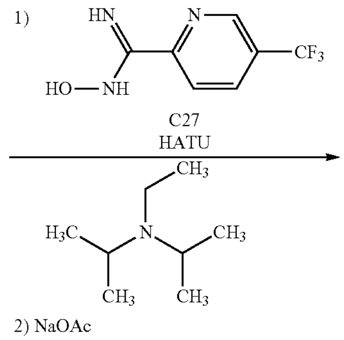

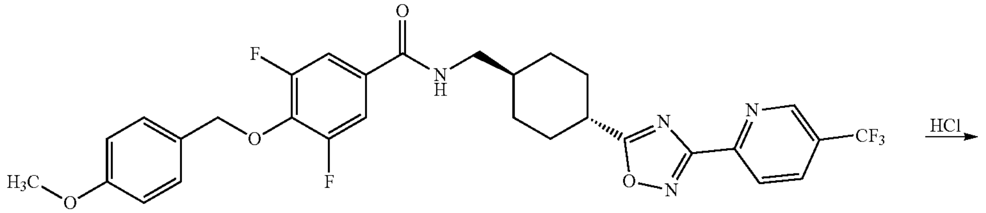

C28

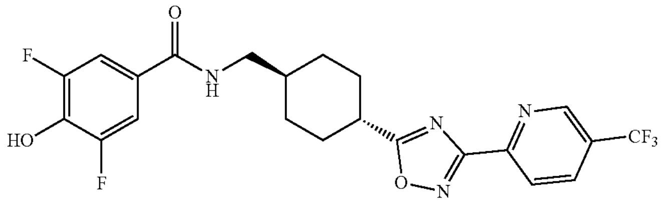

2

Step 1. Synthesis of N-hydroxy-5-(trifluoromethyl) pyridine-2-carboximidamide (C27)

To a mixture of 5-(trifluoromethyl)pyridine-2-carbonitrile (200 mg, 1.16 mmol) and hydroxylamine hydrochloride (242 mg, 3.48 mmol) in ethanol (20 mL) was added sodium hydroxide (139 mg, 3.48 mmol). After the reaction mixture had been stirred at room temperature for 3 hours, it was concentrated in vacuo to provide C27 as a white solid. Yield: 200 mg, 0.975 mmol, 84%. LCMS m/z 206.1 $[M+H]^+$.

Step 2. Synthesis of 3,5-difluoro-4-[(4-methoxyphenyl)methoxy]-N-{[(1r,4r)-4-{3-[5-(trifluoromethyl) pyridin-2-yl]-1,2,4-oxadiazol-5-yl}cyclohexyl] methyl}benzamide (C28)

To a 0° C. mixture of P4 (400 mg, 0.923 mmol), N,N-diisopropylethylamine (358 mg, 2.77 mmol), and O-(7-azabenzotriazol-1-yl)-N,N,N',N'-tetramethyluronium hexafluorophosphate (HATU; 526 mg, 1.38 mmol) in dichloromethane (20 mL) was added C27 (227 mg, 1.11 mmol). The reaction mixture was stirred at room temperature for 6 hours, whereupon it was diluted with water (20 mL) and extracted with dichloromethane (2×20 mL); the combined organic layers were washed with saturated aqueous sodium chloride solution (2×20 mL), dried over sodium sulfate, filtered, and concentrated in vacuo. Silica gel chromatography (Gradient: 0% to 7% methanol in dichloromethane) provided the acylated intermediate (100 mg, 0.161 mmol, 17%), LCMS m/z 621.3 $[M+H]^+$, as a white solid.

This material was dissolved in a mixture of ethanol (4 mL) and water (1 mL), treated with sodium acetate (39.6 mg, 0.483 mmol), and stirred at 100° C. for 1 hour under microwave irradiation. After the reaction mixture had been concentrated in vacuo, it was purified using chromatography on silica gel (Gradient: 0% to 5% methanol in dichloromethane) to provide C28 as a white solid. Yield: 60 mg, 0.10 mmol, 11% from P4. LCMS m/z 603.3 $[M+H]^+$.

Step 3. Synthesis of 3,5-difluoro-4-hydroxy-N-{[(1r,4r)-4-{3-[5-(trifluoromethyl)pyridin-2-yl]-1,2,4-oxadiazol-5-yl}cyclohexyl]methyl}benzamide (2)

To a solution of C28 (60 mg, 0.10 mmol) in dichloromethane (5 mL) was added a solution of hydrogen chloride in 1,4-dioxane (4 M; 1 mL). After the reaction mixture had been stirred at room temperature for 2 hours, it was concentrated in vacuo, diluted with dichloromethane (10 mL), treated with sodium bicarbonate (10 mg, 0.12 mmol), and concentrated under reduced pressure. Chromatography on silica gel (Gradient: 0% to 5% methanol in dichloromethane) afforded 3,5-difluoro-4-hydroxy-N-{[(1r,4r)-4-{3-[5-(trifluoromethyl)pyridin-2-yl]-1,2,4-oxadiazol-5-yl}cyclohexyl]methyl}benzamide (2) as a white solid. Yield: 11.6 mg, 24.0 μmol, 24%. LCMS m/z 483.2 $[M+H]^+$. $^1H$ NMR (400 MHz, DMSO-$d_6$) δ 9.19-9.14 (m, 1H), 8.48-8.39 (m, 2H), 8.27 (d, J=8.2 Hz, 1H), 7.60-7.54 (m, 2H), 3.19-3.05 (m, 3H), 2.25-2.13 (m, 2H), 1.93-1.81 (m, 2H), 1.67-1.51 (m, 3H), 1.22-1.07 (m, 2H).

Example 3: 2,3,5-Trifluoro-4-hydroxy-N-[(4-{3-[5-(trifluoromethyl)pyrimidin-2-yl]-1,2,4-oxadiazol-5-yl}bicyclo[2.2.2]octan-1-yl)methyl]benzamide (3)
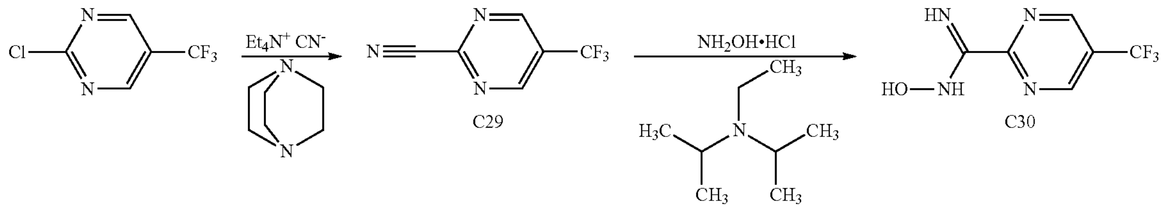
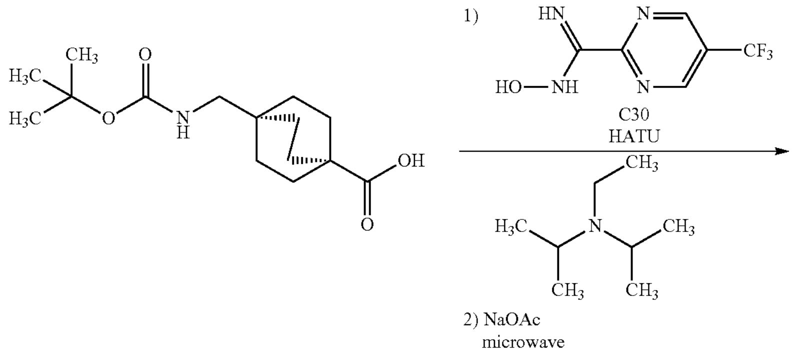
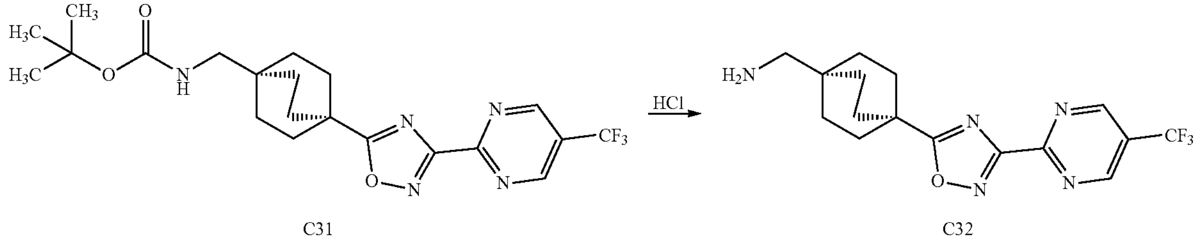
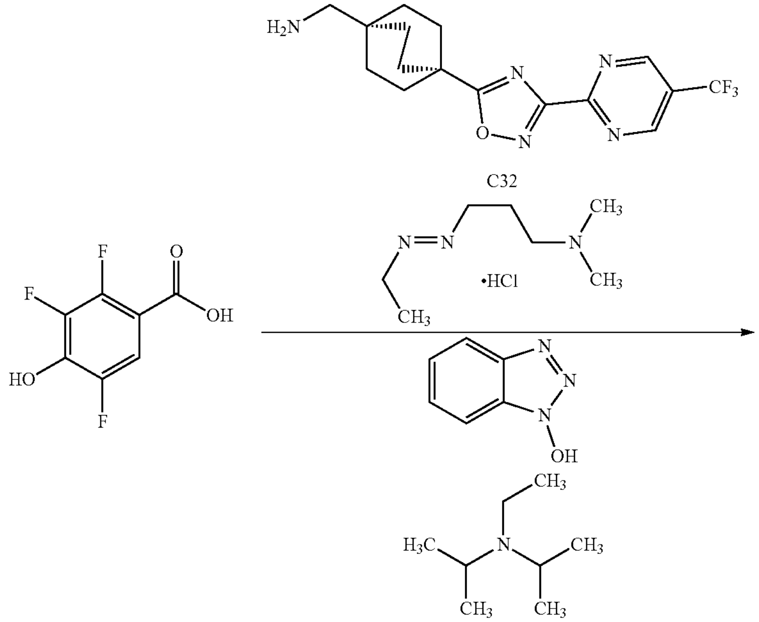

-continued

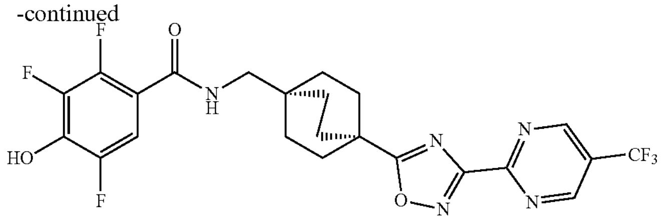

3

Step 1. Synthesis of 5-(trifluoromethyl)pyrimidine-2-carbonitrile (C29)

A solution of tetraethylammonium cyanide (1.88 g, 12.0 mmol) and 1,4-diazabicyclo[2.2.2]octane (1.47 g, 13.1 mmol) in acetonitrile (8 mL) was added to a mixture of 2-chloro-5-(trifluoromethyl)pyrimidine (2.00 g, 11.0 mmol) in acetonitrile (8 mL), whereupon the reaction mixture was stirred at room temperature for 3 hours. Removal of solvent in vacuo provided a residue containing $C_{29}$; this material, a light-yellow solid, was progressed directly to the following step.

Step 2. Synthesis of N-hydroxy-5-(trifluoromethyl) pyrimidine-2-carboximidamide (C30)

A mixture of C29 (from the previous step; ≤11.0 mmol), hydroxylamine hydrochloride (1.52 g, 21.9 mmol), and N,N-diisopropylethylamine (4.26 g, 33.0 mmol) in methanol (20 mL) was stirred at 70° C. for 12 hours. Concentration of the reaction mixture in vacuo afforded C30 (1.70 g), which was taken directly into the following step. LCMS m/z 207.1 $[M+H]^+$.

Step 3. Synthesis of tert-butyl [(4-{3-[5-(trifluoromethyl)pyrimidin-2-yl]-1,2,4-oxadiazol-5-yl}bicyclo [2.2.2]octan-1-yl)methyl]carbamate (C31)

To a solution of C30 (from the previous step; 1.70 g, 58.25 mmol) and 4-{[(tert-butoxycarbonyl)amino]methyl}bicyclo [2.2.2]octane-1-carboxylic acid (2.57 g, 9.07 mmol) in N,N-dimethylformamide (10 mL) were added O-(7-azabenzotriazol-1-yl)-N,N,N',N'-tetramethyluronium hexafluorophosphate (HATU; 4.70 g, 12.4 mmol) and N,N-diisopropylethylamine (3.20 g, 24.8 mmol). After the reaction mixture had been stirred at 25° C. for 2 hours, it was diluted with water and filtered; the filtrate was concentrated in vacuo to provide the acyl intermediate as a yellow solid. Yield: 1.90 g, 4.03 mmol, 37% over 3 steps. LCMS m/z 472.2 $[M+H]^+$.

To a solution of the acyl intermediate (2.00 g, 4.24 mmol) in a mixture of ethanol (6 mL) and water (3 mL) was added sodium acetate (1.04 g, 12.7 mmol). After the reaction mixture had been stirred at 100° C. for 1 hour under microwave irradiation, it was concentrated in vacuo. Purification via silica gel chromatography (Gradient: 0% to 6% methanol in dichloromethane) provided $C_{31}$ as a white solid. Yield: 1.00 g, 2.21 mmol, 52% from the acyl intermediate. LCMS m/z 454.2 $[M+H]^+$. $^1H$ NMR (400 MHz, methanol-$d_4$) δ 9.35-9.33 (m, 2H), 2.87 (s, 2H), 2.15-2.03 (m, 6H), 1.64-1.53 (m, 6H), 1.45 (s, 9H).

Step 4. Synthesis of 1-(4-{3-[5-(trifluoromethyl) pyrimidin-2-yl]-1,2,4-oxadiazol-5-yl}bicyclo[2.2.2] octan-1-yl)methanamine (C32)

A solution of hydrogen chloride in 1,4-dioxane (4 M; 5 mL, 20 mmol) was added to a solution of C31 (1.00 g, 2.21 mmol) in dichloromethane (15 mL), whereupon the reaction mixture was stirred at room temperature for 2 hours. It was then concentrated in vacuo, diluted with dichloromethane (10 mL), treated with sodium bicarbonate, and again concentrated under reduced pressure. Chromatography on silica gel (Gradient: 0% to 7% methanol in dichloromethane) afforded C32 as a white solid. Yield: 800 mg, quantitative. LCMS m/z 354.2 $[M+H]^+$. $^1H$ NMR (400 MHz, methanol-$d_4$) δ 9.35 (br s, 2H), 2.80 (s, 2H), 2.22-2.10 (m, 6H), 1.75-1.65 (m, 6H).

Step 5. Synthesis of 2,3,5-trifluoro-4-hydroxy-N-[(4-{3-[5-(trifluoromethyl)pyrimidin-2-yl]-1,2,4-oxadiazol-5-yl}bicyclo[2.2.2]octan-1-yl)methyl] benzamide (3)

To a solution of C32 (100 mg, 0.283 mmol) and 2,3,5-trifluoro-4-hydroxybenzoic acid (65.2 mg, 0.339 mmol) in N,N-dimethylformamide (5 mL) were added 1H-benzotriazol-1-ol (57.4 mg, 0.425 mmol), 1-[3-(dimethylamino) propyl]-3-ethylcarbodiimide hydrochloride (81.4 mg, 0.425 mmol), and N,N-diisopropylethylamine (110 mg, 0.851 mmol). After the reaction mixture had been stirred at 25° C. for 4 hours, it was diluted with water (15 mL) and extracted with dichloromethane (3×10 mL). The combined organic layers were washed with saturated aqueous sodium chloride solution (100 mL), dried over sodium sulfate, filtered, concentrated in vacuo, and purified via reversed-phase HPLC (Column: Waters XBridge C18, 19×150 mm, 5 µm; Mobile phase A: water containing 0.1% formic acid; Mobile phase B: acetonitrile; Gradient: 65% to 75% B; Flow rate: 20 mL/minute), affording 2,3,5-trifluoro-4-hydroxy-N-[(4-{3-[5-(trifluoromethyl)pyrimidin-2-yl]-1,2,4-oxadiazol-5-yl}bicyclo[2.2.2]octan-1-yl)methyl]benzamide (3) as a white solid. Yield: 105 mg, 0.199 mmol, 70%. LCMS m/z 528.0 $[M+H]^+$. $^1H$ NMR (400 MHz, DMSO-$d_6$) δ 11.36 (br s, 1H), 9.49 (s, 2H), 8.20 (br t, J=6 Hz, 1H), 7.28 (ddd, J=11.0, 6.2, 2.3 Hz, 1H), 3.09 (d, J=6.3 Hz, 2H), 2.06-1.93 (m, 6H), 1.61-1.50 (m, 6H).

Example 4: 3,5-Difluoro-4-hydroxy-N-{[(1r,4r)-4-{3-[5-(trifluoromethyl)pyrimidin-2-yl]-1,2,4-oxadiazol-5-yl}cyclohexyl]methyl}benzamide (4)

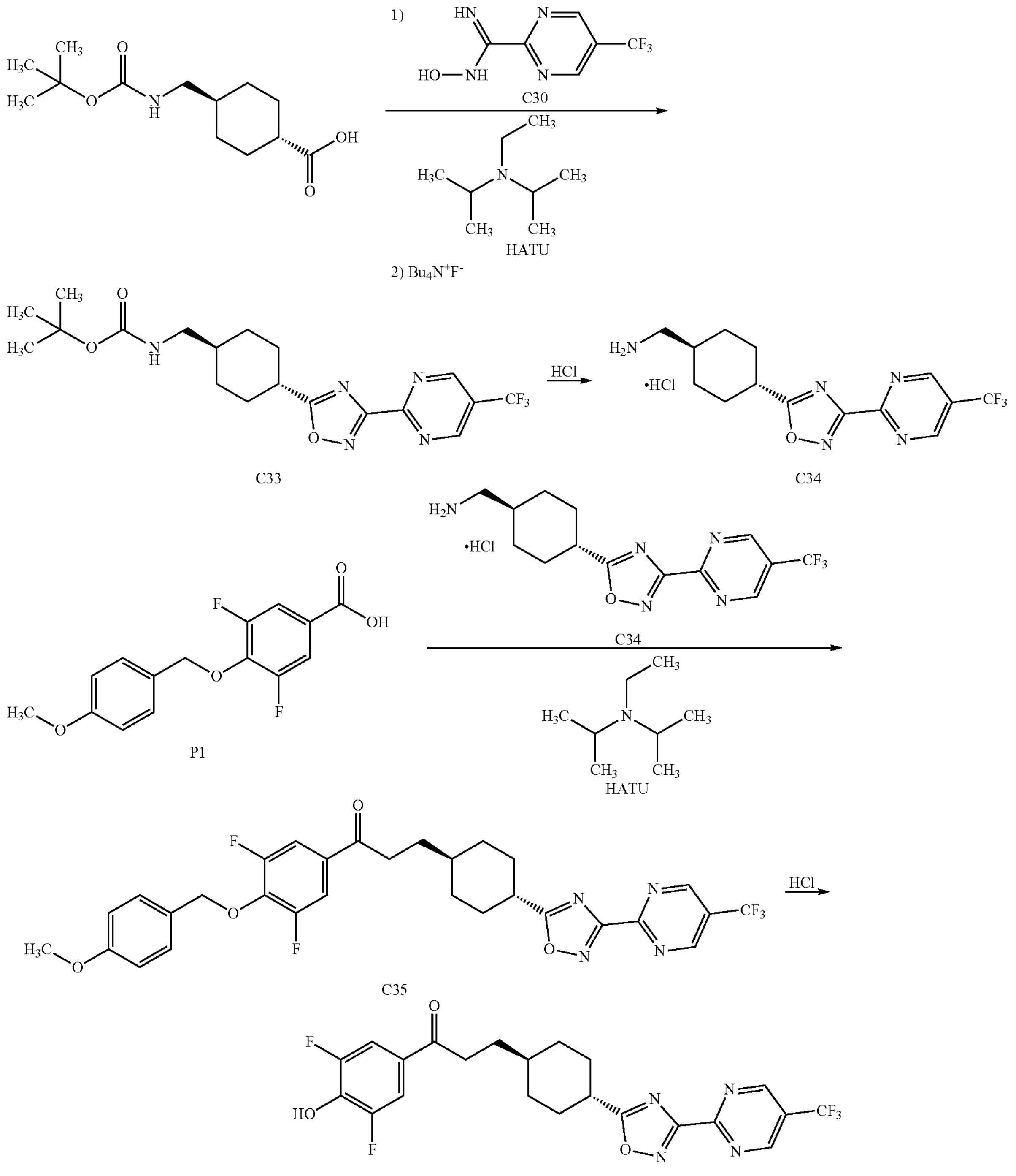

C33 C34 P1 C35 4

Step 1. Synthesis of tert-butyl {[(1r,4r)-4-{3-[5-(trifluoromethyl)pyrimidin-2-yl]-1,2,4-oxadiazol-5-yl}cyclohexyl]methyl}carbamate (C33)

To a solution of C30 (453 mg, 2.20 mmol) in N,N-dimethylformamide (8 mL) were added (1r,4r)-4-{[(tert-butoxycarbonyl)amino]methyl}cyclohexane-1-carboxylic acid (679 mg, 2.64 mmol), 0-(7-azabenzotriazol-1-yl)-N,N,N',N'-tetramethyluronium hexafluorophosphate (HATU; 1.25 g, 3.29 mmol), and N,N-diisopropylethylamine (852 mg, 6.59 mmol). The reaction was stirred at 25° C. for 2 hours, whereupon it was diluted with ice water (30 mL) and the solid was collected via filtration, providing the acyl intermediate as a brown solid. Yield: 510 mg, 1.14 mmol, 52%. LCMS m/z 446.1 $[M+H]^+$. $^1$H NMR (400 MHz, chloroform-d), characteristic peaks, integrations are approximate: d 9.08 (br s, 2H), 3.05-2.96 (m, 2H), 2.48 (tt, J=12.3, 3.6 Hz, 1H), 2.16-2.06 (m, 2H), 1.92-1.82 (m, 2H), 1.66-1.53 (m, 2H), 1.09-0.94 (m, 2H).

To a solution of the acyl intermediate (700 mg, 1.57 mmol) in dichloromethane (5 mL) was added a solution of tetrabutylammonium fluoride in tetrahydrofuran (1 M; 5 mL, 5 mmol), whereupon the reaction mixture was stirred at 25° C. for 4 hours. It was then concentrated in vacuo and subjected to chromatography on silica gel (Gradient: 0% to 50% ethyl acetate in petroleum ether), affording C33 as a white solid. Yield: 340 mg, 0.795 mmol, 51%. LCMS m/z 450.1 $[M+Na^+]$. $^1$H NMR (400 MHz, chloroform-d) δ 9.20-9.18 (m, 2H), 4.60 (br s, 1H), 3.11-2.99 (m, 3H), 2.34-2.24 (m, 2H), 2.00-1.91 (m, 2H), 1.84-1.69 (m, 2H), 1.6-1.50 (m, 1H, assumed; largely obscured by water peak), 1.45 (s, 9H), 1.20-1.06 (m, 2H).

Step 2. Synthesis of 1-[(1r,4r)-4-{3-[5-(trifluoromethyl)pyrimidin-2-yl]-1,2,4-oxadiazol-5-yl}cyclohexyl]methanamine, hydrochloride salt (C34)

A solution of hydrogen chloride in 1,4-dioxane (4 M; 2 mL, 8 mmol) was added to a solution of C33 (340 mg, 0.795 mmol) in dichloromethane (5 mL). After the reaction mixture had been stirred at 25° C. for 2 hours, it was concentrated in vacuo to provide C34 as a white solid. Yield: 200 mg, 0.550 mmol, 69%. LCMS m/z 328.1 $[M+H]^+$. $^1$H NMR (400 MHz, DMSO-$d_6$) δ 9.51-9.49 (m, 2H), 8.00 (br s, 3H), 3.14 (tt, J=12.1, 3.6 Hz, 1H), 2.75-2.65 (m, 2H), 2.27-2.17 (m, 2H), 1.97-1.87 (m, 2H), 1.73-1.53 (m, 3H), 1.23-1.09 (m, 2H).

Step 3. Synthesis of 3,5-difluoro-4-[(4-methoxyphenyl)methoxy]-N-{[(1r,4r)-4-{3-[5-(trifluoromethyl)pyrimidin-2-yl]-1,2,4-oxadiazol-5-yl}cyclohexyl]methyl}benzamide (C35)

To a 0° C. solution of P1 (27 mg, 91.8 μmol), C34 (30 mg, 82 μmol), and O-(7-azabenzotriazol-1-yl)-N,N,N',N'-tetramethyluronium hexafluorophosphate (HATU; 52.3 mg, 0.138 mmol) in N,N-dimethylformamide (3 mL) was added N,N-diisopropylethylamine (35.5 mg, 0.275 mmol), whereupon the reaction mixture was stirred at 25° C. for 2 hours. It was then treated with ice water (30 mL) and the resulting solid was collected via filtration to provide C35 as a white solid (60 mg). This material was taken directly to the following step. LCMS m/z 626.2 $[M+Na^+]$. $^1$H NMR (400 MHz, DMSO-$d_6$) δ 9.49 (s, 2H), 8.56 (br t, J=5.8 Hz, 1H), 7.66-7.56 (m, 2H), 7.34 (d, J=8.5 Hz, 2H), 6.92 (d, J=8.4 Hz, 2H), 5.17 (s, 2H), 3.74 (s, 3H), 3.19-3.08 (m, 3H), 2.24-2.15 (m, 2H), 1.91-1.82 (m, 2H), 1.67-1.51 (m, 3H), 1.22-1.08 (m, 2H).

Step 4. Synthesis of 3,5-difluoro-4-hydroxy-N-{[(1r,4r)-4-{3-[5-(trifluoromethyl)pyrimidin-2-yl]-1,2,4-oxadiazol-5-yl}cyclohexyl]methyl}benzamide (4)

A solution of $C_{35}$ (from the previous step; 60 mg, ≤82 μmol) in dichloromethane (4 mL) was treated with a solution of hydrogen chloride in 1,4-dioxane (4 M; 2 mL), and the reaction mixture was stirred at 25° C. for 2 hours. After removal of volatiles in vacuo, the residue was purified using silica gel chromatography (Gradient: 0% to 10% methanol in dichloromethane) to afford 3,5-difluoro-4-hydroxy-N-{[(1r,4r)-4-{3-[5-(trifluoromethyl)pyrimidin-2-yl]-1,2,4-oxadiazol-5-yl}cyclohexyl]methyl}benzamide (4) as a white solid. Yield: 14.3 mg, 29.6 μmol, 36% over 2 steps. LCMS m/z 484.1 $[M+H]^+$. $^1$H NMR (400 MHz, DMSO-$d_6$) δ 10.84 (br s, 1H), 9.49 (s, 2H), 8.44 (br t, J=5.8 Hz, 1H), 7.64-7.52 (m, 2H), 3.20-3.07 (m, 3H), 2.25-2.15 (m, 2H), 1.93-1.82 (m, 2H), 1.67-1.51 (m, 3H), 1.22-1.08 (m, 2H).

Example 5: 2,3,5-Trifluoro-4-hydroxy-N-({(1r,4r)-4-[6-(1-methyl-1H-pyrazol-4-yl)-2H-indazol-2-yl]cyclohexyl}methyl)benzamide, trifluoroacetate salt (5)

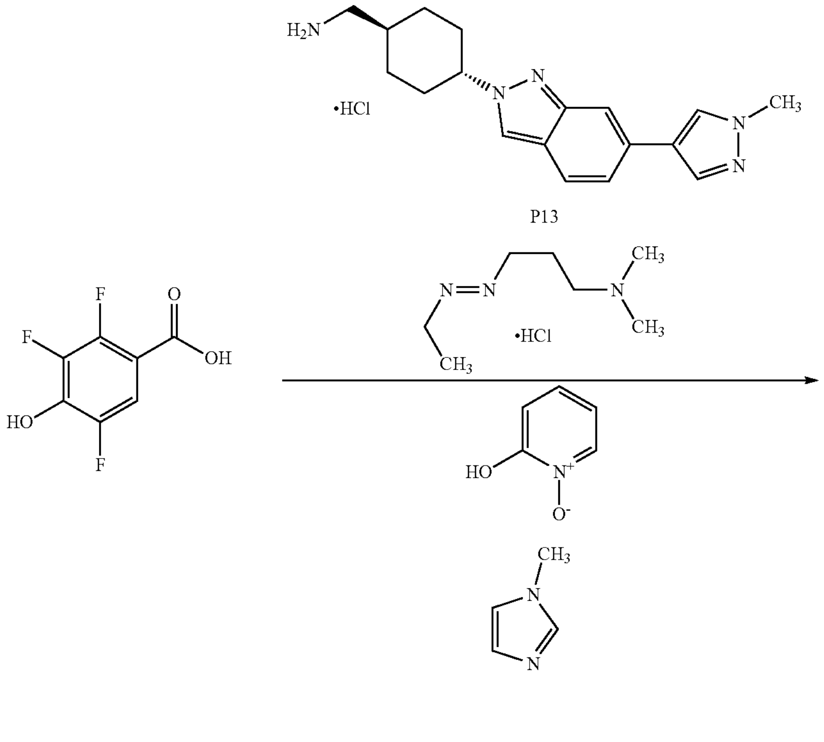

-continued

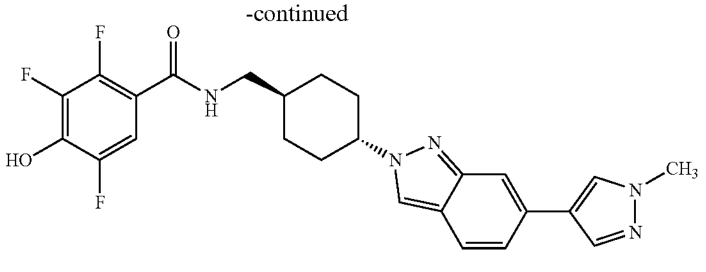

•$CF_3COOH$

5

A mixture of 2,3,5-trifluoro-4-hydroxybenzoic acid (50 mg, 0.26 mmol), P13 (75 mg, 0.22 mmol), 2-hydroxypyridine 1-oxide (26.5 mg, 0.239 mmol), and 1-methyl-1H-imidazole (52 µL, 0.65 mmol) in a mixture of water (0.32 mL) and N,N-dimethylformamide (1.3 mL) was allowed to stir at room temperature for 5 minutes, whereupon 1-[3-(dimethylamino)propyl]-3-ethylcarbodiimide hydrochloride (45.7 mg, 0.238 mmol) was added in one portion, and the reaction mixture was stirred at room temperature overnight. After dilution with water, the reaction mixture was acidified by addition of 1 M hydrochloric acid, and extracted with ethyl acetate. The organic layer was washed with water, dried over magnesium sulfate, filtered, and concentrated in vacuo to afford a solid, which was purified via reversed-phase HPLC (Column: Waters Sunfire C18, 19×100 mm, 5 µm; Mobile phase A: 0.05% trifluoroacetic acid in water (v/v); Mobile phase B: 0.05% trifluoroacetic acid in acetonitrile (v/v); Gradient: 5% to 95% B over 8.54 minutes, followed by 95% B for 1.46 minutes; Flow rate: 25 mL/minute) to provide 2,3,5-trifluoro-4-hydroxy-N-({(1r,4r)-4-[6-(1-methyl-1H-pyrazol-4-yl)-2H-indazol-2-yl]cyclohexyl}methyl)benzamide, trifluoroacetate salt (5). Yield: 46.3 mg, 95.8 µmol, 44%. LCMS m/z 484.6 $[M+H]^+$. Retention time: 2.51 minutes (Analytical conditions. Column: Waters Atlantis dC18, 4.6×50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 6: 3,5-Difluoro-4-hydroxy-N-{[(1r,4r)-4-(5-methoxy-2H-pyrazolo[3,4-c]pyridin-2-yl)cyclohexyl]methyl}benzamide (6)

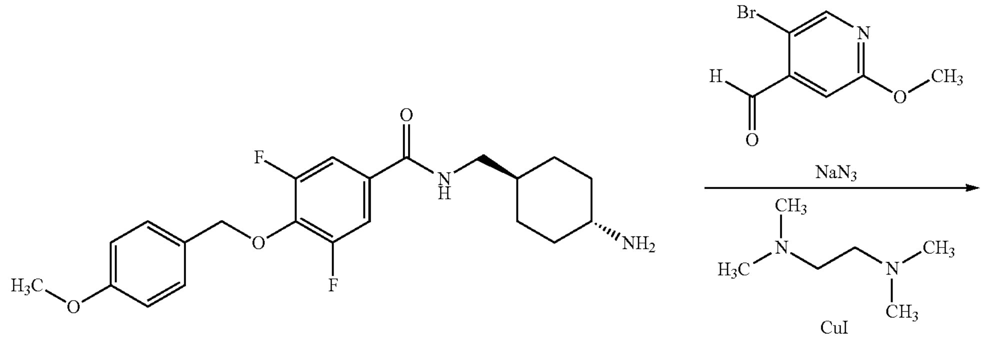

P3

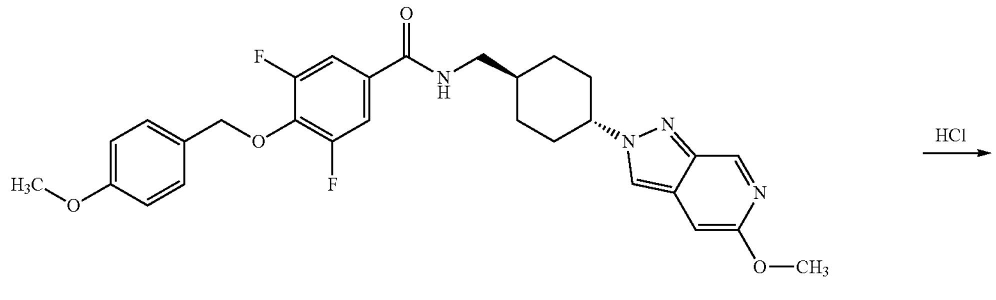

C36

-continued

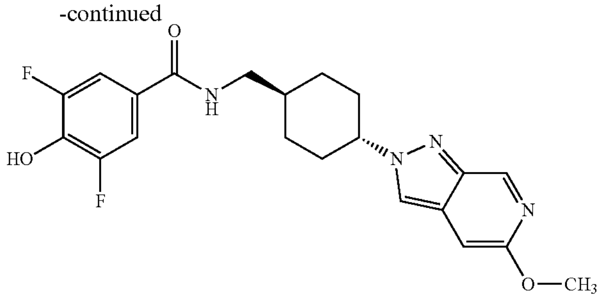

6

Step 1. Synthesis of 3,5-difluoro-4-[(4-methoxyphenyl)methoxy]-N-{[(1r,4r)-4-(5-methoxy-2H-pyrazolo[3,4-c]pyridin-2-yl)cyclohexyl]methyl}benzamide (C36)

A mixture of P3 (134 mg, 0.331 mmol) and 5-bromo-2-methoxypyridine-4-carbaldehyde (65 mg, 0.30 mmol) in toluene (8 mL) was stirred at 90° C. for 8 hours. The reaction mixture was then concentrated under reduced pressure and diluted with dimethyl sulfoxide (8 mL); to this were added copper(I) iodide (5.71 mg, 30.0 μmol), $N^1,N^1,N^2,N^2$-tetramethylethane-1,2-diamine (3.49 mg, 30.0 μmol), and sodium azide (39.1 mg, 0.601 mmol). After this reaction mixture had been stirred at 100° C. for 8 hours, it was treated with water (20 mL) and extracted with ethyl acetate (2×20 mL). The combined organic layers were washed with saturated aqueous sodium chloride solution (2×20 mL), dried over sodium sulfate, filtered, concentrated in vacuo, and purified via silica gel chromatography (Gradient: 0% to 8% methanol in dichloromethane) to provide C36 as a brown solid. Yield: 50 mg, 93 μmol, 31%. LCMS m/z 537.3 $[M+H]^+$.

Step 2. Synthesis of 3,5-difluoro-4-hydroxy-N-{[(1r,4r)-4-(5-methoxy-2H-pyrazolo[3,4-c]pyridin-2-yl)cyclohexyl]methyl}benzamide (6)

To a solution of C36 (50 mg, 93 μmol) in dichloromethane (5 mL) was added a solution of hydrogen chloride in 1,4-dioxane (4 M; 1 mL). The reaction mixture was stirred at room temperature for 2 hours, whereupon it was concentrated under reduced pressure, treated with dichloromethane (10 mL) and sodium bicarbonate (10 mg), and again concentrated in vacuo. Silica gel chromatography (Gradient: 0% to 7% methanol in dichloromethane) provided 3,5-difluoro-4-hydroxy-N-{[(1r,4r)-4-(5-methoxy-2H-pyrazolo[3,4-c]pyridin-2-yl)cyclohexyl]methyl}benzamide (6) as a white solid. Yield: 5.1 mg, 12 μmol, 13%. LCMS m/z 417.2 $[M+H]^+$. $^1H$ NMR (400 MHz, DMSO-$d_6$) δ 10.84 (s, 1H), 8.92-8.87 (m, 1H), 8.47 (br t, J=5.8 Hz, 1H), 8.37 (s, 1H), 7.64-7.53 (m, 2H), 6.88 (d, J=1.2 Hz, 1H), 4.59-4.49 (m, 1H), 3.84 (s, 3H), 3.17 (dd, J=6, 6 Hz, 2H), 2.21-2.10 (m, 2H), 1.99-1.83 (m, 4H), 1.74-1.60 (m, 1H), 1.29-1.14 (m, 2H).

Example 7: 2,3,5-Trifluoro-4-hydroxy-N-({4-[6-(pyrimidin-2-yl)-2H-indazol-2-yl]bicyclo[2.2.2]octan-1-yl}methyl)benzamide (7)

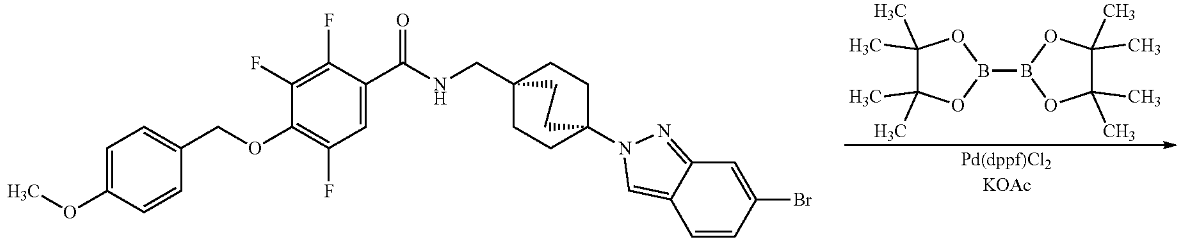

P16

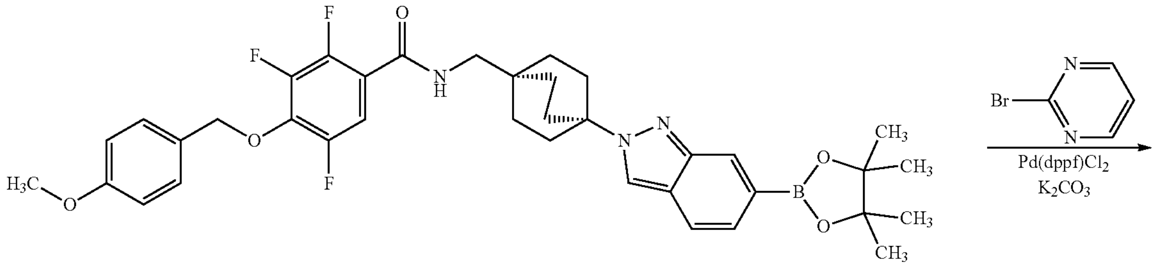

C37

-continued

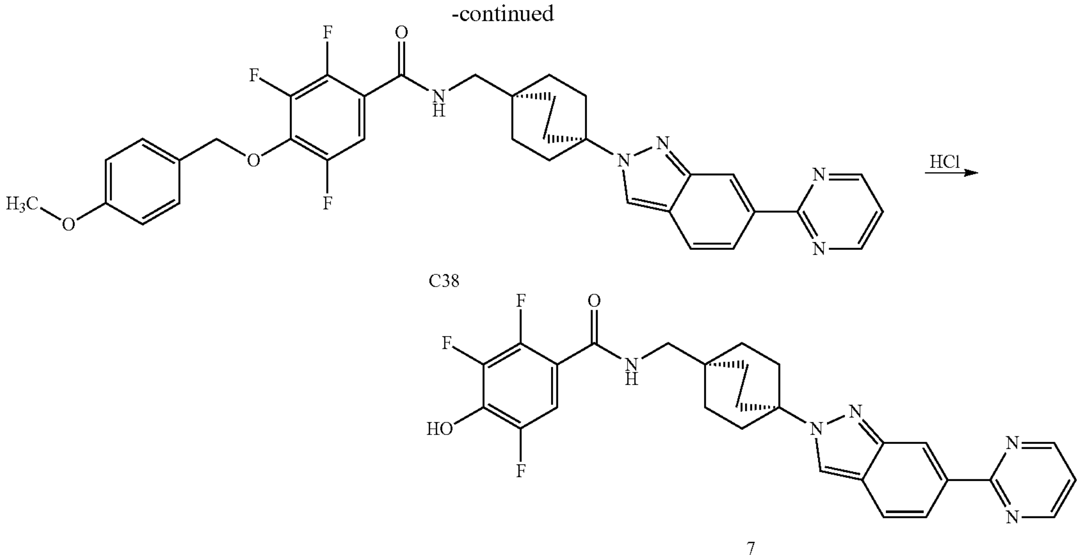

C38

7

Step 1. Synthesis of 2,3,5-trifluoro-4-[(4-methoxyphenyl)methoxy]-N-({4-[6-(4,4,5,5-tetramethyl-1,3,2-dioxaborolan-2-yl)-2H-indazol-2-yl]bicyclo[2.2.2]octan-1-yl}methyl)benzamide (C37)

To a solution of P16 (100 mg, 0.159 mmol) and 4,4,4',4',5,5,5',5'-octamethyl-2,2'-bi-1,3,2-dioxaborolane (48.5 mg, 0.191 mmol) in 1,4-dioxane (5 mL) were added [1,1'-bis(diphenylphosphino)ferrocene]dichloropalladium(II) (11.6 mg, 15.9 μmol) and potassium acetate (46.8 mg, 0.477 mmol), whereupon the reaction mixture was stirred at 90° C. for 12 hours. Concentration in vacuo provided C37, which was progressed directly to the following step.

Step 2. Synthesis of 2,3,5-trifluoro-4-[(4-methoxyphenyl)methoxy]-N-({4-[6-(pyrimidin-2-yl)-2H-indazol-2-yl]bicyclo[2.2.2]octan-1-yl}methyl)benzamide (C38)

To a solution of C37 (from the previous step; 50.159 mmol) and 2-bromopyrimidine (28.2 mg, 0.177 mmol) in 1,4-dioxane (5 mL) were added [1,1'-bis(diphenylphosphino)ferrocene]dichloropalladium(II) (10.8 mg, 14.8 μmol) and potassium carbonate (61.4 mg, 0.444 mmol). After the reaction mixture had been stirred at 90° C. for 12 hours, it was concentrated in vacuo and purified via silica gel chromatography (Gradient: 0% to 60% ethyl acetate in petroleum ether), affording C38 as a white solid. Yield: 40 mg, 64 μmol, 40% over 2 steps. LCMS m/z 628.2 $[M+H]^+$.

Step 3. Synthesis of 2,3,5-trifluoro-4-hydroxy-N-({4-[6-(pyrimidin-2-yl)-2H-indazol-2-yl]bicyclo[2.2.2]octan-1-yl}methyl)benzamide (7)

To a solution of C38 (40 mg, 64 μmol) in dichloromethane (10 mL) was added a solution of hydrogen chloride in 1,4-dioxane (4 M; 2 mL, 8 mmol), and the reaction mixture was stirred at 25° C. for 2 hours. It was then concentrated in vacuo, treated with dichloromethane (10 mL) and sodium bicarbonate (1 g), and concentrated under reduced pressure. Chromatography on silica gel (Gradient: 0% to 7% methanol in dichloromethane) provided 2,3,5-trifluoro-4-hydroxy-N-({4-[6-(pyrimidin-2-yl)-2H-indazol-2-yl]bicyclo[2.2.2]octan-1-yl}methyl)benzamide (7) as a white solid. Yield: 6.0 mg, 12 μmol, 19%. LCMS m/z 508.1 $[M+H]^+$. $^1H$ NMR (400 MHz, DMSO-$d_6$) δ 11.38 (br s, 1H), 8.91 (d, J=4.8 Hz, 2H), 8.67-8.65 (m, 1H), 8.47 (d, J=1.0 Hz, 1H), 8.21 (br t, J=6 Hz, 1H), 8.08 (dd, J=8.8, 1.4 Hz, 1H), 7.79 (dd, J=8.8, 0.9 Hz, 1H), 7.43 (t, J=4.8 Hz, 1H), 7.29 (ddd, J=11.1, 6.2, 2.3 Hz, 1H), 3.12 (d, J=6.3 Hz, 2H), 2.25-2.15 (m, 6H), 1.74-1.63 (m, 6H).

Example 8: 3,5-Difluoro-4-hydroxy-N-({(1r,4r)-4-[6-(2-methoxypyrimidin-5-yl)-2H-pyrazolo[4,3-c]pyridin-2-yl]cyclohexyl}methyl)benzamide (8)

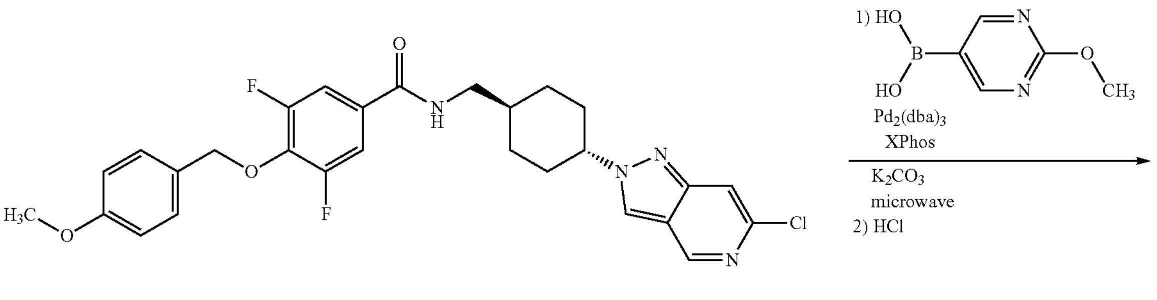

P15

-continued

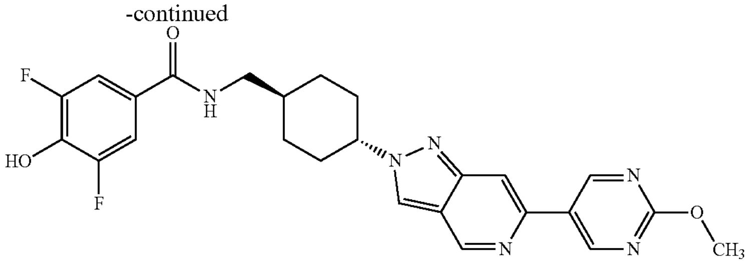

8

To a solution of P15 (60 mg, 0.11 mmol), (2-methoxypyrimidin-5-yl)boronic acid (25.6 mg, 0.166 mmol), 2-dicyclohexylphosphino-2',4',6'-triisopropylbiphenyl (XPhos; 21.1 mg, 44.3 μmol), and potassium carbonate (46.0 mg, 0.333 mmol) in a mixture of 1,4-dioxane (2 mL) and water (0.4 mL) was added tris(dibenzylideneacetone)dipalladium (0) (20.3 mg, 22.2 μmol). The reaction mixture was stirred at 100° C. for 1 hour under microwave irradiation, whereupon it was concentrated under reduced pressure. The residue was dissolved in dichloromethane (4 mL), treated with a solution of hydrogen chloride in 1,4-dioxane (4 M; 1 mL, 4 mmol), and stirred at 15° C. for 1 hour. After solvents had been removed in vacuo, purification via reversed-phase HPLC (Column: Welch Xtimate C18, 30×250 mm, 10 μm; Mobile phase A: water containing 0.05% formic acid; Mobile phase B: acetonitrile; Gradient: 43% to 95% B; Flow rate: 50 mL/minute) afforded 3,5-difluoro-4-hydroxy-N-({(1r,4r)-4-[6-(2-methoxypyrimidin-5-yl)-2H-pyrazolo[4,3-c]pyridin-2-yl]cyclohexyl}methyl)benzamide (8) as a solid. Yield: 5.2 mg, 10 μmol, 9%. LCMS m/z 495.1 $[M+H]^+$. $^1H$ NMR (400 MHz, DMSO-$d_6$) δ 9.30 (s, 2H), 9.25 (d, J=1.3 Hz, 1H), 8.76 (br s, 1H), 8.43 (br s, 1H), 8.23-8.20 (m, 1H), 7.62-7.49 (m, 2H), 4.64-4.50 (m, 1H), 3.98 (s, 3H), 3.18 (dd, J=6, 6 Hz, 2H), 2.24-2.12 (m, 2H), 2.01-1.84 (m, 4H), 1.75-1.60 (m, 1H), 1.33-1.12 (m, 2H).

Example 9: 2,3,5-Trifluoro-4-hydroxy-N-({(1r,4r)-4-[6-(pyrimidin-5-yl)-2H-indazol-2-yl]cyclohexyl}methyl)benzamide (9)

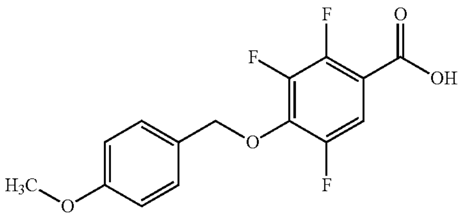

P2

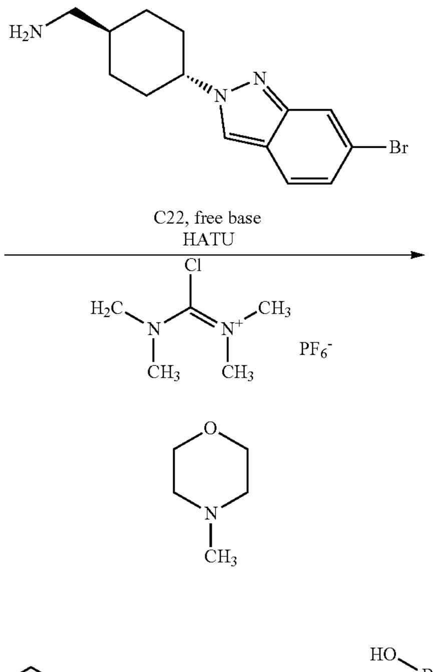

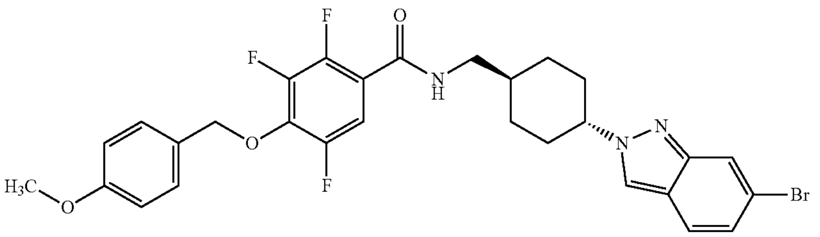

C39

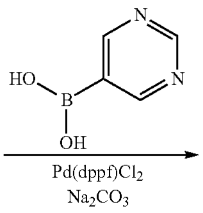

-continued

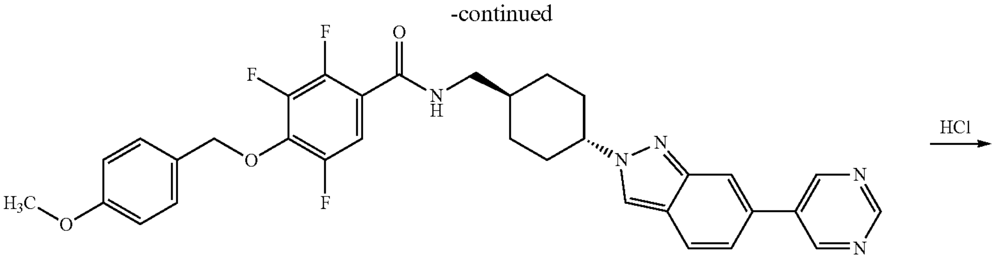

C40

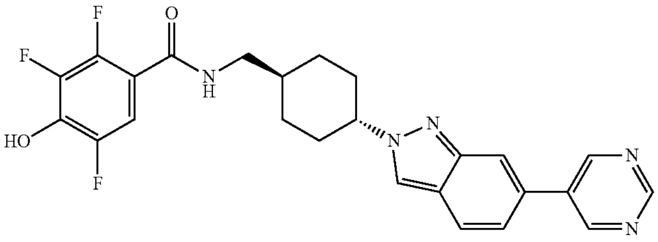

9

Step 1. Synthesis of N-{[(1r,4r)-4-(6-bromo-2H-indazol-2-yl)cyclohexyl]methyl}-2,3,5-trifluoro-4-[(4-methoxyphenyl)methoxy]benzamide (C39)

To a solution of C22, free base (4.67 g, 15.2 mmol) and P2 (4.97 g, 15.9 mmol) in N,N-dimethylformamide (30 mL) was added 4-methylmorpholine (9.99 mL, 90.9 mmol). The suspension was then treated portion-wise with chloro(dimethylamino)-N,N-dimethylmethaniminium hexafluorophosphate (4.25 g, 15.1 mmol, divided into 4 equal portions), and the reaction mixture was stirred at room temperature for 5 hours, whereupon it was added drop-wise to ice-cold water (300 mL). The resulting suspension was stirred for 20 minutes and filtered; the filter cake was washed three times with water to afford C39 as a light-brown solid. Yield: 9.20 g, quantitative. LCMS m/z 602.3 (bromine isotope pattern observed) $[M+H]^+$. $^1H$ NMR (400 MHz, DMSO-$d_6$) δ 8.53-8.43 (m, 2H), 7.85 (s, 1H), 7.67 (d, J=8.8 Hz, 1H), 7.40-7.30 (m, 3H), 7.12 (dd, J=8.8, 1.7 Hz, 1H), 6.94 (d, J=8.6 Hz, 2H), 5.22 (s, 2H), 4.53-4.40 (m, 1H), 3.75 (s, 3H), 3.17 (dd, J=6, 6 Hz, 2H), 2.20-2.09 (m, 2H), 1.97-1.81 (m, 4H), 1.72-1.58 (m, 1H), 1.29-1.13 (m, 2H).

Step 2. Synthesis of 2,3,5-trifluoro-4-[(4-methoxyphenyl)methoxy]-N-({(1r,4r)-4-[6-(pyrimidin-5-yl)-2H-indazol-2-yl]cyclohexyl}methyl)benzamide (C40)

A mixture of C39 (700 mg, 1.16 mmol), pyrimidin-5-ylboronic acid (144 mg, 1.16 mmol), sodium carbonate (369 mg, 3.48 mmol), and [1,1'-bis(diphenylphosphino)ferrocene]dichloropalladium(II), dichloromethane complex (94.2 mg, 0.115 mmol) in a mixture of 1,4-dioxane (20 mL) and water (5 mL) was stirred at 90° C. for 16 hours. The reaction mixture was then concentrated in vacuo and purified via silica gel chromatography (Gradient: 0% to 100% ethyl acetate in petroleum ether), providing C40 as a white solid. Yield: 300 mg, 0.499 mmol, 43%. LCMS m/z 602.2 $[M+H]^+$. $^1H$ NMR (400 MHz, DMSO-$d_6$) δ 9.20 (s, 2H), 9.18 (s, 1H), 8.53-8.46 (m, 2H), 8.08 (br s, 1H), 7.85 (d, J=8.7 Hz, 1H), 7.45 (dd, J=8.7, 1.6 Hz, 1H), 7.41-7.34 (m, 1H), 7.35 (d, J=8.6 Hz, 2H), 6.94 (d, J=8.6 Hz, 2H), 5.22 (s, 2H), 4.59-4.45 (m, 1H), 3.75 (s, 3H), 3.18 (dd, J=6, 6 Hz, 2H), 2.23-2.13 (m, 2H), 2.01-1.86 (m, 4H), 1.74-1.60 (m, 1H), 1.32-1.16 (m, 2H).

Step 3. Synthesis of 2,3,5-trifluoro-4-hydroxy-N-({(1r,4r)-4-[6-(pyrimidin-5-yl)-2H-indazol-2-yl]cyclohexyl}methyl)benzamide (9)

To a suspension of C40 (300 mg, 0.499 mmol) in dichloromethane (4.0 mL) was added a solution of hydrogen chloride in 1,4-dioxane (4 M; 1 mL, 4 mmol). The reaction mixture was stirred at 25° C. for 2 hours, whereupon it was concentrated in vacuo and purified using silica gel chromatography (Gradient: 0% to 100% ethyl acetate in petroleum ether) to afford 2,3,5-trifluoro-4-hydroxy-N-({(1r,4r)-4-[6-(pyrimidin-5-yl)-2H-indazol-2-yl]cyclohexyl}methyl)benzamide (9) as a white solid. Yield: 200 mg, 0.415 mmol, 83%. LCMS m/z 482.2 $[M+H]^+$. $^1H$ NMR (400 MHz, DMSO-$d_6$) δ 11.41 (br s, 1H), 9.21 (s, 2H), 9.18 (s, 1H), 8.49 (s, 1H), 8.37-8.30 (m, 1H), 8.09 (br s, 1H), 7.85 (d, J=8.7 Hz, 1H), 7.45 (dd, J=8.7, 1.6 Hz, 1H), 7.30 (ddd, J=11.1, 6.3, 2.2 Hz, 1H), 4.58-4.46 (m, 1H), 3.21-3.14 (m, 2H), 2.23-2.13 (m, 2H), 2.02-1.86 (m, 4H), 1.75-1.61 (m, 1H), 1.33-1.16 (m, 2H).

Example 10: N-{[(1r,4r)-4-{6-[1-(2,2-Difluoroethyl)-1H-pyrazol-4-yl]-2H-indazol-2-yl}cyclohexyl]methyl}-3,5-difluoro-4-hydroxybenzamide, trifluoroacetate salt (10)
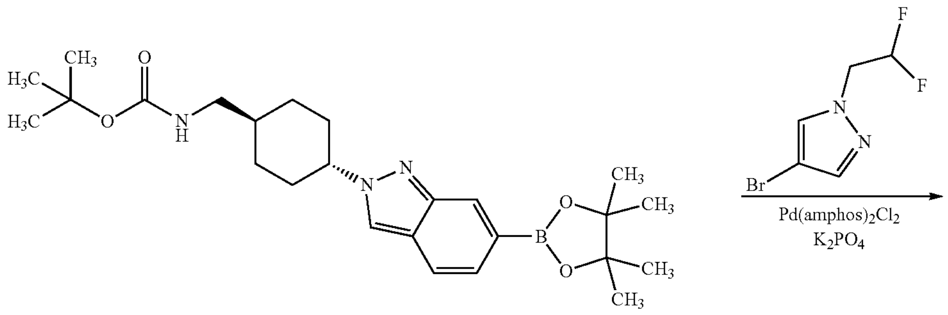
P12
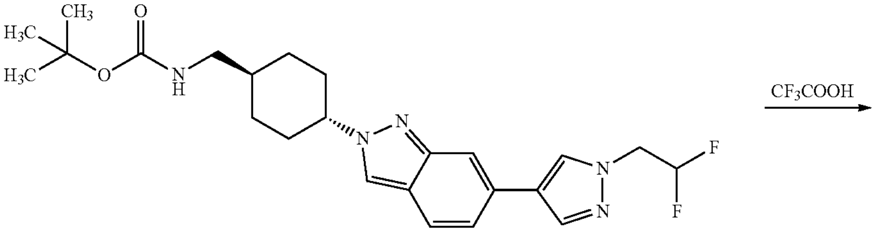
C41
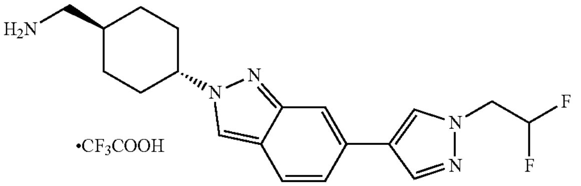
C42
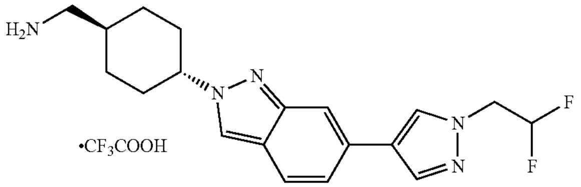
C42
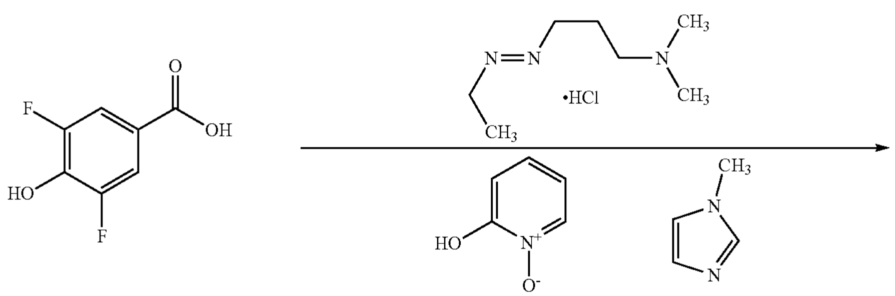

-continued

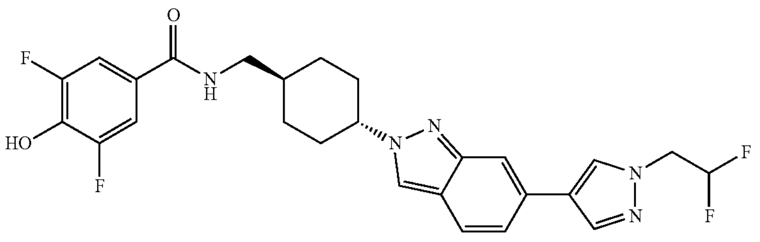

•$CF_3COOH$

10

Step 1. Synthesis of tert-butyl {[(1r,4r)-4-{6-[1-(2,2-difluoroethyl)-1H-pyrazol-4-yl]-2H-indazol-2-yl}cyclohexyl]methyl}carbamate (C41)

To a mixture of 4-bromo-1-(2,2-difluoroethyl)-1H-pyrazole (46.1 mg, 0.218 mmol) and P12 (100 mg, 0.220 mmol) were added 1,4-dioxane (1.8 mL) and water (0.6 mL), followed by tripotassium phosphate (140 mg, 0.660 mmol) and bis[di-tert-butyl(4-dimethylaminophenyl)phosphine]dichloropalladium(II) [$Pd(amphos)_2Cl_2$; 15.5 mg, 21.9 μmol]. The reaction mixture was heated at 85° C. for 18 hours, whereupon it was partitioned between water and ethyl acetate. After the aqueous layer had been extracted twice with ethyl acetate, the combined organic layers were dried over magnesium sulfate, filtered, and concentrated in vacuo. Silica gel chromatography (Gradient: 0% to 7.5% methanol in dichloromethane) provided C41 as an oil. Yield: 80 mg, 0.17 mmol, 78%. LCMS m/z 460.3 $[M+H]^+$. $^1H$ NMR (400 MHz, chloroform-d), characteristic peaks: d 7.91 (br s, 1H), 7.89 (s, 1H), 7.79 (br s, 1H), 7.74 (s, 1H), 7.65 (d, J=8.7 Hz, 1H), 7.22 (dd, J=8.7, 1.4 Hz, 1H), 6.13 (tt, J=55.4, 4.3 Hz, 1H), 4.68-4.58 (m, 1H), 4.51 (td, J=13.5, 4.3 Hz, 2H), 4.43-4.32 (m, 1H), 3.06 (dd, J=6, 6 Hz, 2H), 2.39-2.28 (m, 2H), 1.46 (s, 9H).

Step 2. Synthesis of 1-[(1r,4r)-4-{6-[1-(2,2-difluoroethyl)-1H-pyrazol-4-yl]-2H-indazol-2-yl}cyclohexyl]methanamine, trifluoroacetate salt (C42)

Trifluoroacetic acid (0.5 mL, 6 mmol) was added dropwise to a solution of C41 (80 mg, 0.17 mmol) in dichloromethane (2 mL). The reaction mixture was stirred for 30 minutes at room temperature, whereupon it was concentrated in vacuo to dryness; the residue was azeotroped twice with dichloromethane, providing C42 as a colorless oil (84 mg), most of which was taken directly to the following step. LCMS m/z 360.3 $[M+H]^+$. $^1H$ NMR (400 MHz, methanol-$d_4$), characteristic peaks: d 8.28-8.26 (m, 1H), 8.13 (s, 1H), 7.98 (s, 1H), 7.75 (br s, 1H), 7.72 (d, J=8.7 Hz, 1H), 7.38-7.33 (m, 1H), 6.22 (tt, J=55.2, 3.9 Hz, 1H), 4.61 (td, J=14.4, 3.9 Hz, 2H), 4.56-4.44 (m, 1H), 2.90 (d, J=7.0 Hz, 2H), 2.37-2.27 (m, 2H), 2.13-2.00 (m, 4H), 1.89-1.75 (m, 1H).

Step 3. Synthesis of N-{[(1r,4r)-4-{6-[1-(2,2-difluoroethyl)-1H-pyrazol-4-yl]-2H-indazol-2-yl}cyclohexyl]methyl}-3,5-difluoro-4-hydroxybenzamide, trifluoroacetate salt (10)

A solution of C42 (from the previous step; 82 mg, 50.17 mmol) in N,N-dimethylformamide (1.8 mL) was treated with water (0.4 mL). 3,5-Difluoro-4-hydroxybenzoic acid (36.2 mg, 0.208 mmol), 1-methyl-1H-imidazole (41.4 μL, 0.520 mmol), and 2-hydroxypyridine 1-oxide (64 mg, 5.76 mmol) were sequentially added, and the reaction mixture was stirred for 20 minutes at room temperature. 1-[3-(Dimethylamino)propyl]-3-ethylcarbodiimide hydrochloride (98%, 33.9 mg, 0.173 mmol) was then added, and stirring was continued for 18 hours at room temperature. The reaction mixture was diluted with water (10 mL), and acidified to pH 4 by addition of 1 M hydrochloric acid, whereupon it was extracted 3 times with ethyl acetate. The combined organic layers were washed 5 times with water, dried over magnesium sulfate, filtered, and concentrated in vacuo; reversed-phase HPLC (Column: Waters Sunfire C18, 19×100 mm, 5 μm; Mobile phase A: 0.05% trifluoroacetic acid in water (v/v); Mobile phase B: 0.05% trifluoroacetic acid in acetonitrile (v/v); Gradient: 20% to 60% B over 8.5 minutes, then 60% to 95% B over 0.5 minutes; Flow rate: 25 mL/minute) afforded N-{[(1r,4r)-4-{6-[1-(2,2-difluoroethyl)-1H-pyrazol-4-yl]-2H-indazol-2-yl}cyclohexyl]methyl}-3,5-difluoro-4-hydroxybenzamide, trifluoroacetate salt (10). Yield: 29.3 mg, 46.5 μmol, 27% over 2 steps. LCMS m/z 516.5 $[M+H]^+$. Retention time: 2.59 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 11: 2,3,5-Trifluoro-4-hydroxy-N-{[(1r,4r)-4-{6-[4-(trifluoromethyl)-1H-pyrazol-1-yl]-2H-indazol-2-yl}cyclohexyl]methyl}benzamide, trifluoroacetate salt (11)
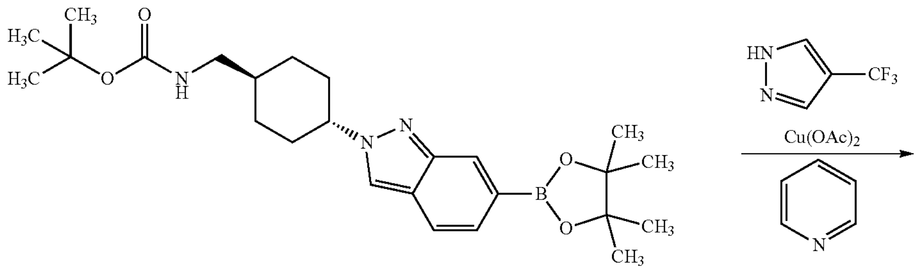
P12
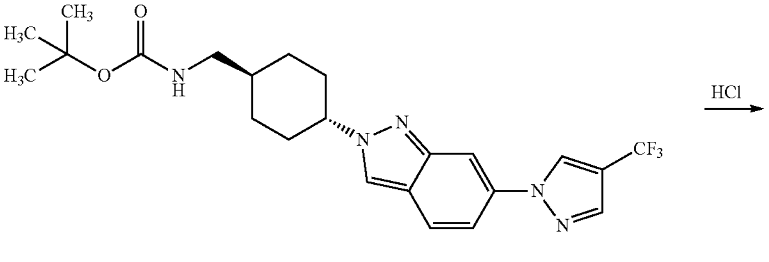
C43
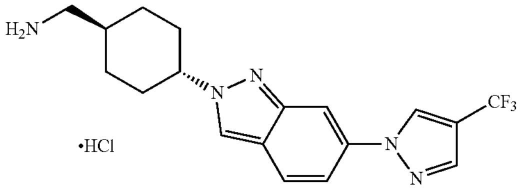
C44
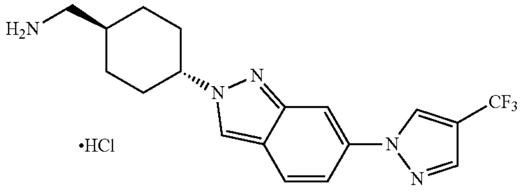
C44
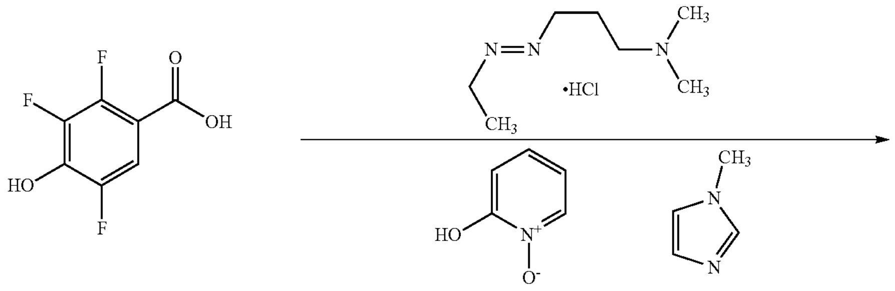

-continued

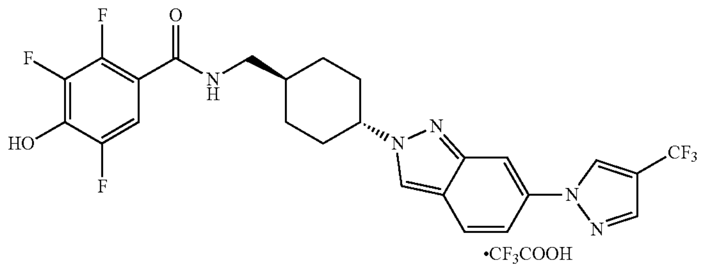

11

Step 1. Synthesis of tert-butyl {[(1r,4r)-4-{6-[4-(trifluoromethyl)-1H-pyrazol-1-yl]-2H-indazol-2-yl}cyclohexyl]methyl}carbamate (C43)

A mixture of P12 (100 mg, 0.220 mmol), 4-(trifluoromethyl)-1H-pyrazole (120 mg, 0.882 mmol), and copper(II) acetate (53 mg, 0.29 mmol) in pyridine (1.3 mL) was heated at 90° C. for 18 hours. For the first hour, the reaction mixture was left open to the air; it was subsequently capped, a needle was inserted through the cap to the atmosphere, and heating was continued for an additional 17 hours. The reaction mixture was concentrated in vacuo to dryness and the residue was partitioned between dichloromethane and water. The organic layer was subjected to silica gel chromatography (Gradient: 0% to 7.5% methanol in dichloromethane), affording C43 as a colorless oil. Yield: 80.0 mg, 0.173 mmol, 79%. LCMS m/z 464.3 $[M+H]^+$. $^1H$ NMR (400 MHz, chloroform-d), characteristic peaks: d 8.21 (br s, 1H), 8.00 (br s, 1H), 7.92 (s, 1H), 7.91-7.89 (m, 1H), 7.77 (br d, J=9.0 Hz, 1H), 7.49 (dd, J=9.0, 1.9 Hz, 1H), 4.64 (br s, 1H), 4.42 (tt, J=11.9, 3.7 Hz, 1H), 3.08 (dd, J=6, 6 Hz, 2H), 2.40-2.28 (m, 2H), 2.07-1.89 (m, 4H), 1.70-1.55 (m, 1H), 1.46 (s, 9H).

Step 2. Synthesis of 1-[(1r,4r)-4-{6-[4-(trifluoromethyl)-1H-pyrazol-1-yl]-2H-indazol-2-yl}cyclohexyl]methanamine, hydrochloride salt (C44)

To a solution of C43 (80.0 mg, 0.173 mmol) in 1,4-dioxane (2 mL) was added a solution of hydrogen chloride in 1,4-dioxane (4 M; 1 mL, 4 mmol), whereupon the reaction mixture was stirred for 2 hours. Removal of solvent in vacuo provided a residue that was azeotroped twice with dichloromethane to afford $C_{44}$ as a white solid (75 mg); most of this material was taken directly to the following step. LCMS m/z 364.3 $[M+H]^+$.

Step 3. Synthesis of 2,3,5-trifluoro-4-hydroxy-N-{[(1r,4r)-4-{6-[4-(trifluoromethyl)-1H-pyrazol-1-yl]-2H-indazol-2-yl}cyclohexyl]methyl}benzamide, trifluoroacetate salt (11)

A solution of C44 (from the previous step; 69 mg, 50.16 mmol) in N,N-dimethylformamide (1.8 mL) was treated with water (0.4 mL), whereupon the following reagents were sequentially added: 2,3,5-trifluoro-4-hydroxybenzoic acid (39.8 mg, 0.207 mmol), 1-methyl-1H-imidazole (55.0 μL, 0.690 mmol), and 2-hydroxypyridine 1-oxide (26.8 mg, 0.241 mmol). After the reaction mixture had been stirred for 20 minutes at room temperature, 1-[3-(dimethylamino)propyl]-3-ethylcarbodiimide hydrochloride (98%, 33.8 mg, 0.173 mmol) was added and stirring was continued for 18 hours. The reaction mixture was then diluted with water (10 mL), acidified to pH 4 by addition of 1 M hydrochloric acid, and extracted three times with ethyl acetate. The combined organic layers were washed five times with water, dried over magnesium sulfate, filtered, concentrated in vacuo, and purified using reversed-phase HPLC (Column: Waters Sunfire C18, 19×100 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 8.54 minutes, followed by 95% B for 1.46 minutes; Flow rate: 25 mL/minute) to provide 2,3,5-trifluoro-4-hydroxy-N-{[(1r,4r)-4-{6-[4-(trifluoromethyl)-1H-pyrazol-1-yl]-2H-indazol-2-yl}cyclohexyl] methyl}benzamide, trifluoroacetate salt (11). Yield: 41.1 mg, 63.1 μmol, 39% over 2 steps. LCMS m/z 538.5 $[M+H]^+$. Retention time: 3.11 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 12: 3,5-Difluoro-4-hydroxy-N-{[(1r,4r)-4-{6-[1-(oxan-4-yl)-1H-pyrazol-4-yl]-2H-indazol-2-yl}cyclohexyl]methyl}benzamide (12)

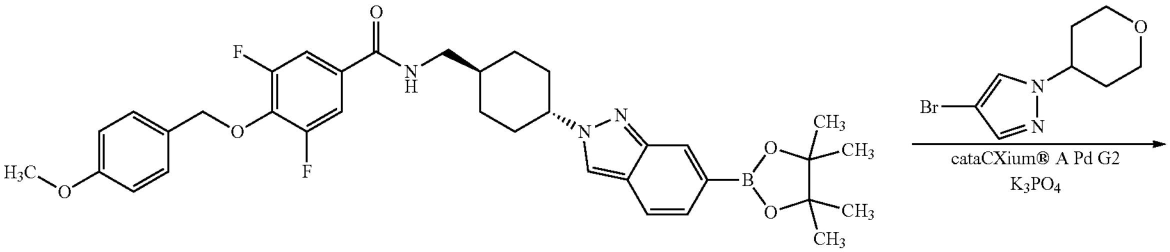

P14

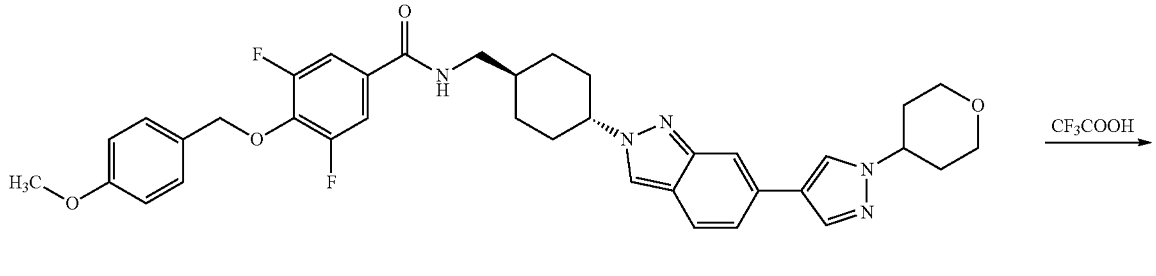

C45

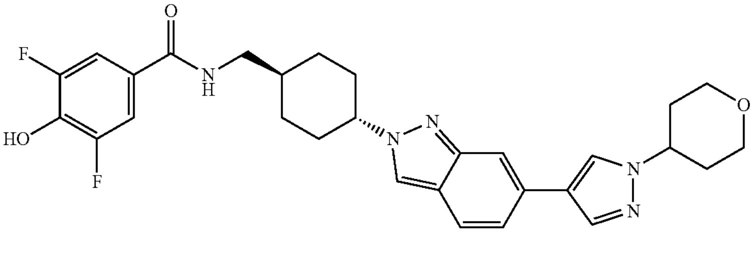

12

Step 1. Synthesis of 3,5-difluoro-4-[(4-methoxyphenyl)methoxy]-N-{[(1r,4r)-4-{6-[1-(oxan-4-yl)-1H-pyrazol-4-yl]-2H-indazol-2-yl}cyclohexyl]methyl}benzamide (C45)

This experiment was carried out in library format.

A solution of P14 (60 mg, 100 μmol) in 1,4-dioxane (1 mL) was added to 4-bromo-1-(oxan-4-yl)-1H-pyrazole (150 μmol). Aqueous tripotassium phosphate solution (1.5 M; 0.20 mL, 300 μmol) was then added, followed by chloro [(di(1-adamantyl)-N-butylphosphine)-2-(2-aminobiphenyl)] palladium(II) (cataCXium® A Pd G2; 5 μmol), whereupon the reaction vial was capped and shaken at 100° C. for 16 hours. After removal of solvent using a Speedvac® concentrator, the residue was mixed with water (1 mL), extracted with ethyl acetate (3×1.5 mL), and concentrated again, providing C45; this material was progressed directly to the following step.

Step 2. Synthesis of 3,5-difluoro-4-hydroxy-N-{[(1r,4r)-4-{6-[1-(oxan-4-yl)-1H-pyrazol-4-yl]-2H-indazol-2-yl}cyclohexyl]methyl}benzamide (12)

This experiment was carried out in library format.

A solution of trifluoroacetic acid (0.2 mL) in dichloromethane (0.8 mL) was added to C45 (from the previous step; 5100 μmol), whereupon the reaction vial was capped and shaken at 30° C. for 16 hours. After removal of solvent using a Speedvac® concentrator, reversed-phase HPLC (Column: YMC-Actus Triart C18, 30×150 mm, 5 μm; Mobile phase A: water containing 0.225% formic acid; Mobile phase B: acetonitrile; Gradient: 35% to 75% B; Flow rate: 35 mL/minute) afforded 3,5-difluoro-4-hydroxy-N-{[(1r,4r)-4-{6-[1-(oxan-4-yl)-1H-pyrazol-4-yl]-2H-indazol-2-yl}cyclohexyl]methyl}benzamide (12). Yield: 13.7 mg, 22.2 μmol, 22% over 2 steps. LCMS m/z 536 $[M+H]^+$. Retention time: 2.77 minutes (Column: Waters XBridge C18, 2.1×50 mm, 5 μm; Mobile phase A: water containing 0.0375% trifluoroacetic acid; Mobile phase B: acetonitrile containing 0.01875% trifluoroacetic acid; Gradient: 1% to 5% B over 0.6 minutes; 5% to 100% B over 3.4 minutes; Flow rate: 0.8 mL/minute).

Example 13: 3,5-Difluoro-4-hydroxy-N-{[(1r,4r)-4-{5-[5-(trifluoromethyl)pyridin-2-yl]-1,2,4-oxadiazol-3-yl}cyclohexyl]methyl}benzamide (13)

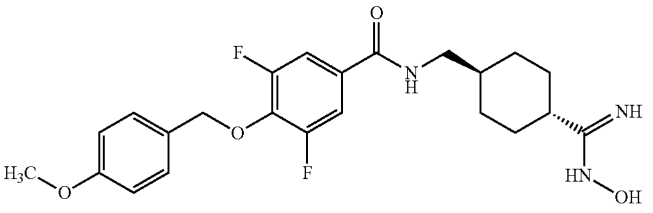

P5

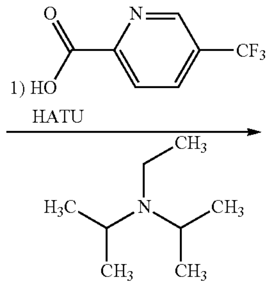

2) NaOAc
microwave

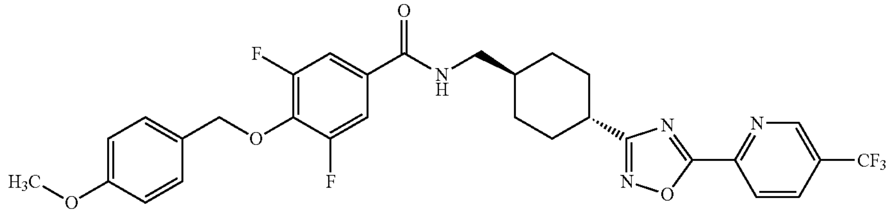

HCl

C46

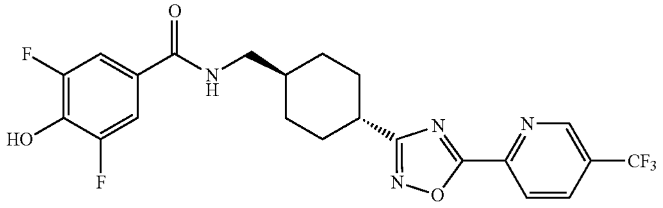

13

Step 1. Synthesis of 3,5-difluoro-4-[(4-methoxyphenyl)methoxy]-N-{[(1r,4r)-4-{5-[5-(trifluoromethyl)pyridin-2-yl]-1,2,4-oxadiazol-3-yl}cyclohexyl]methyl}benzamide (C46)

To a 0° C. mixture of 5-(trifluoromethyl)pyridine-2-carboxylic acid (47.0 mg, 0.246 mmol), N,N-diisopropylethylamine (86.6 mg, 0.670 mmol), and O-(7-azabenzotriazol-1-yl)-N,N,N',N'-tetramethyluronium hexafluorophosphate (HATU; 127 mg, 0.334 mmol) in dichloromethane (20 mL) was added P5 (100 mg, 0.223 mmol), whereupon the reaction mixture was stirred at room temperature for 1 hour. It was then diluted with water (20 mL) and extracted with dichloromethane (2×20 mL); the combined organic layers were washed with saturated aqueous sodium chloride solution (2×20 mL), dried over sodium sulfate, filtered, and concentrated in vacuo. Silica gel chromatography (Gradient: 0% to 5% methanol in dichloromethane) afforded the acyl intermediate as a white solid. Yield: 80 mg, 0.13 mmol, 58%. LCMS m/z 621.3 $[M+H]^+$.

Sodium acetate (31.7 mg, 0.386 mmol) was added to a solution of the acyl intermediate (80 mg, 0.13 mmol) in a mixture of ethanol (4 mL) and water (1 mL). After the reaction mixture had been stirred at 100° C. for 1 hour under microwave irradiation, it was concentrated in vacuo. Silica gel chromatography (Gradient: 0% to 7% methanol in dichloromethane) provided C46 as a white solid. Yield: 40 mg, 66 μmol, 51% from the acyl intermediate. LCMS m/z 625.3 $[M+Na^+]$.

Step 2. Synthesis of 3,5-difluoro-4-hydroxy-N-{[(1r,4r)-4-{5-[5-(trifluoromethyl)pyridin-2-yl]-1,2,4-oxadiazol-3-yl}cyclohexyl]methyl}benzamide (13)

A solution of hydrogen chloride in 1,4-dioxane (4 M; 1 mL) was added to a solution of C46 (40 mg, 66 μmol) in dichloromethane (5 mL). The reaction mixture was stirred at room temperature for 2 hours, whereupon it was concentrated in vacuo, diluted with dichloromethane (10 mL), and treated with sodium bicarbonate (10 mg, 0.12 mmol). After removal of solvents under reduced pressure, the residue was subjected to silica gel chromatography (Gradient: 0% to 6% methanol in dichloromethane), followed by reversed-phase HPLC (Column: Waters XBridge C18, 19×100 mm, 5 μm; Mobile phase A: water containing 0.1% formic acid; Mobile phase B: acetonitrile; Gradient: 50% to 60% B; Flow rate: 20 mL/minute), to afford 3,5-difluoro-4-hydroxy-N-{[(1r,4r)-4-{5-[5-(trifluoromethyl)pyridin-2-yl]-1,2,4-oxadiazol-3-yl}cyclohexyl]methyl}benzamide (13) as a white solid. Yield: 9.0 mg, 19 μmol, 29%. LCMS m/z 483.2 $[M+H]^+$. $^1H$ NMR (400 MHz, methanol-$d_4$) δ 9.09 (br s, 1H), 8.45 (d, half of AB quartet, J=8.3 Hz, 1H), 8.40 (dd, component of ABX system, J=8.4, 2.3 Hz, 1H), 7.51-7.41 (m, 2H), 3.27 (d, J=6.9 Hz, 2H), 2.91 (tt, J=12.2, 3.4 Hz, 1H), 2.24-2.14 (m, 2H), 2.03-1.92 (m, 2H), 1.80-1.59 (m, 3H), 1.29-1.15 (m, 2H).

Example 14: N-[(4-{5-[5-(Difluoromethyl)pyrazin-2-yl]-1,2,4-oxadiazol-3-yl}bicyclo[2.2.2]octan-1-yl)methyl]-3,5-difluoro-4-hydroxybenzamide, ammonium salt (14)

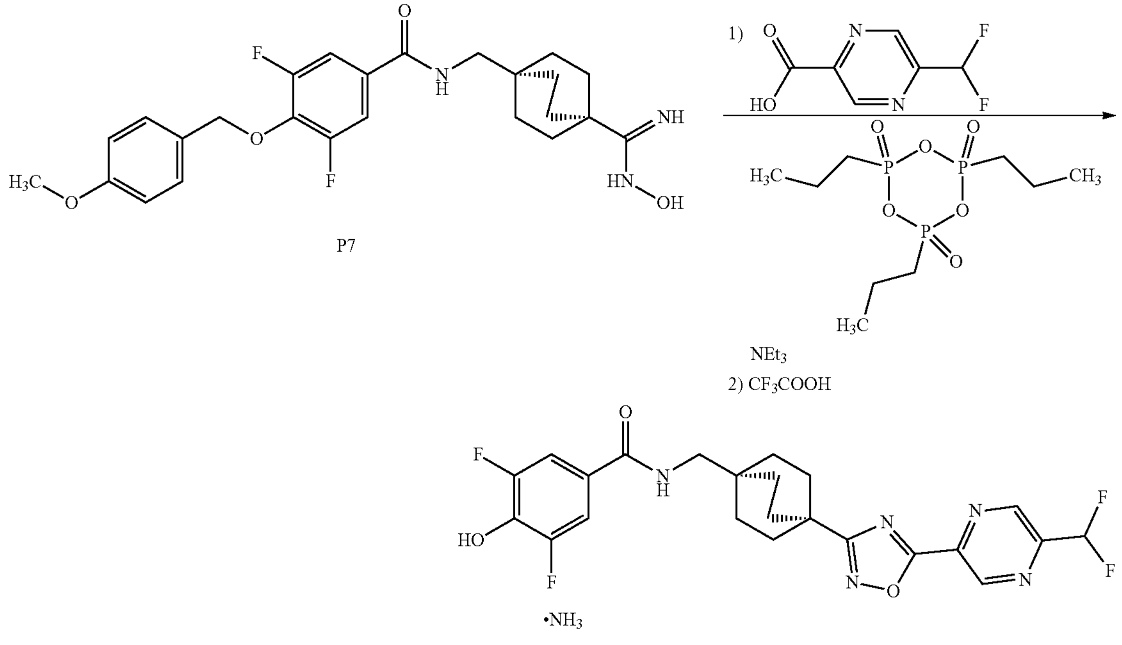

P7

14

This reaction was carried out in library format.

A stock solution of P7 (300 mg, 0.634 mmol) in ethyl acetate (6 mL) was employed; 1 mL of this solution (0.106 mmol of P7) was treated with 5-(difluoromethyl)pyrazine-2-carboxylic acid (18.3 mg, 0.105 mmol), followed by triethylamine (42.2 μL, 0.303 mmol) and 2,4,6-tripropyl-1,3,5,2,4,6-trioxatriphosphinane 2,4,6-trioxide (50% solution by weight in ethyl acetate; 0.15 mL, 0.25 mmol) The reaction vial was heated at 100° C. until oxadiazole formation had occurred, whereupon it was cooled to room temperature, diluted with ethyl acetate (3 mL) and washed sequentially with water (2×3 mL) and saturated aqueous sodium chloride solution (3 mL). The organic layer was concentrated in vacuo, and the residue was dissolved in 1,1,1,3,3,3-hexafluoropropan-2-ol, treated with 1 equivalent of trifluoroacetic acid, and stirred until phenol deprotection was complete. Removal of solvent under reduced pressure was followed by reversed-phase HPLC (Column: Waters XBridge C18, 19×100 mm, 5 μm; Mobile phase A: water containing 0.03% ammonium hydroxide; Mobile phase B: acetonitrile containing 0.03% ammonium hydroxide; Gradient: 5% to 95% B; Flow rate: 25 mL/minute), affording N-[(4-{5-[5-(difluoromethyl)pyrazin-2-yl]-1,2,4-oxadiazol-3-yl}bicyclo[2.2.2]octan-1-yl)methyl]-3,5-difluoro-4-hydroxybenzamide, ammonium salt (14). Yield: 13.8 mg, 27.1 μmol, 26%. LCMS m/z 492.4 $[M+H]^+$. Retention time: 2.54 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 15: 2,3,5-Trifluoro-4-hydroxy-N-({4-[3-(6-methoxypyridazin-3-yl)-1,2,4-oxadiazol-5-yl]bicyclo[2.2.2]octan-1-yl}methyl)benzamide (15)

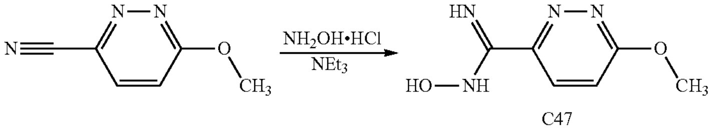

C47

-continued
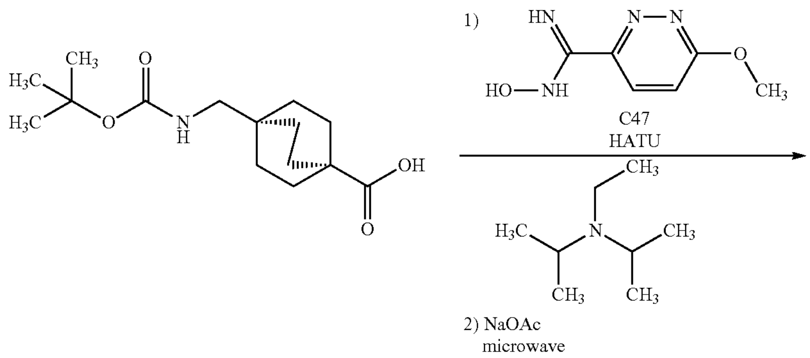
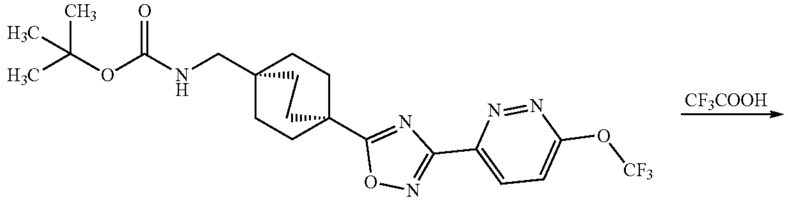
C48
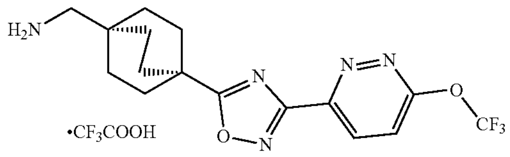
C49
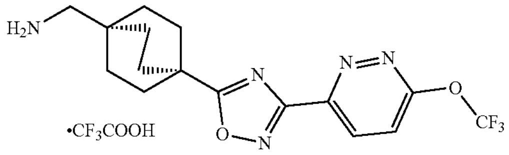
C49
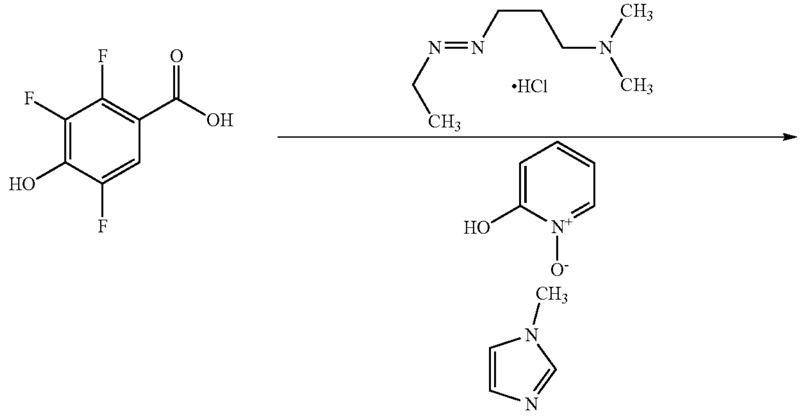
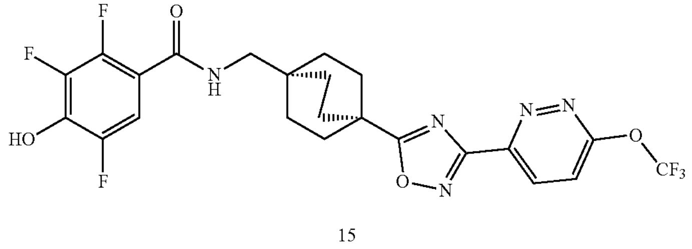
15

Step 1. Synthesis of N-hydroxy-6-methoxypyridazine-3-carboximidamide (C47)

To a solution of 6-methoxypyridazine-3-carbonitrile (745 mg, 5.51 mmol) in methanol (3.7 mL) was added hydroxylamine hydrochloride (383 mg, 5.51 mmol), followed by triethylamine (0.776 mL, 5.57 mmol). The reaction mixture was stirred at room temperature for 4 days, whereupon it was cooled in an ice bath for 15 minutes; the precipitated solid was collected via filtration to provide $C_{47}$ as a purple solid. Yield: 690 mg, 4.10 mmol, 74%. LCMS m/z 169.1 $[M+H]^+$. $^1H$ NMR (400 MHz, DMSO-$d_6$) δ 10.13 (s, 1H), 7.94 (d, J=9.3 Hz, 1H), 7.22 (d, J=9.3 Hz, 1H), 5.98 (br s, 2H), 4.05 (s, 3H).

Step 2. Synthesis of tert-butyl ({4-[3-(6-methoxypyridazin-3-yl)-1,2,4-oxadiazol-5-yl]bicyclo[2.2.2]octan-1-yl}methyl)carbamate (C48)

O-(7-Azabenzotriazol-1-yl)-N,N,N',N'-tetramethyluronium hexafluorophosphate (HATU; 312 mg, 0.821 mmol) was added to a solution of C47 (155 mg, 0.547 mmol) in N,N-dimethylformamide (3 mL). After the reaction mixture had been stirred for 20 minutes, 4-{[(tert-butoxycarbonyl)amino]methyl}bicyclo[2.2.2]octane-1-carboxylic acid (101 mg, 0.601 mmol) and N,N-diisopropylethylamine (0.286 mL, 1.64 mmol) were added, and stirring was continued at room temperature for 18 hours. The reaction mixture was then diluted with water; the solid was collected via filtration and washed with water, affording the acyl intermediate as a white solid. Yield: 134 mg, 0.309 mmol, 56%. LCMS m/z 434.4 $[M+H]^+$. $^1H$ NMR (400 MHz, methanol-$d_4$) δ 8.22 (d, J=9.3 Hz, 1H), 7.21 (d, J=9.3 Hz, 1H), 6.61-6.52 (m, 1H; assumed to be the amide proton, slow to exchange), 4.14 (s, 3H), 2.83 (d, J=6.5 Hz, 2H), 2.00-1.91 (m, 6H), 1.54-1.45 (m, 6H), 1.44 (s, 9H).

The acyl intermediate (134 mg, 0.309 mmol) and sodium acetate (51.2 mg, 0.624 mmol) were taken up in a mixture of water (0.1 mL) and ethanol (1 mL), and the reaction vial was heated at 120° C. for 2.5 hours under microwave irradiation. The reaction mixture was then diluted with water (approximately 0.5 mL) and filtered; the filter cake was washed with ethanol to afford C48 as an off-white solid. Yield: 75 mg, 0.18 mmol, 58% from the acyl intermediate. LCMS m/z 416.4 $[M+H]^+$. $^1H$ NMR (400 MHz, methanol-$d_4$) δ 8.20 (d, J=9.2 Hz, 1H), 7.33 (d, J=9.2 Hz, 1H), 6.68-6.58 (m, 1H), 4.19 (s, 3H), 2.88 (d, J=6.4 Hz, 2H), 2.13-2.02 (m, 6H), 1.63-1.53 (m, 6H), 1.45 (s, 9H).

Step 3. Synthesis of 1-{4-[3-(6-methoxypyridazin-3-yl)-1,2,4-oxadiazol-5-yl]bicyclo[2.2.2]octan-1-yl}methanamine, trifluoroacetate salt (C49)

Trifluoroacetic acid (0.15 mL, 1.9 mmol) was added drop-wise to a 0° C. solution of C48 (75 mg, 0.18 mmol) in dichloromethane (2 mL). After the reaction mixture had been stirred for 30 minutes, trifluoroacetic acid (0.15 mL, 1.9 mmol) was again added; 30 minutes later, the reaction mixture was treated once more with trifluoroacetic acid (20 μL, 0.26 mmol) and stirred for an additional 5 minutes. It was then concentrated in vacuo, and the residue was azeotroped once with toluene and once with dichloromethane, affording C49 as an oil (84 mg). Most of this material was used in the following step. LCMS m/z 316.2 $[M+H]^+$.

Step 4. Synthesis of 2,3,5-trifluoro-4-hydroxy-N-({4-[3-(6-methoxypyridazin-3-yl)-1,2,4-oxadiazol-5-yl]bicyclo[2.2.2]octan-1-yl}methyl)benzamide (15)

A solution of C49 (from the previous step; 84 mg, 50.18 mmol) in a mixture of N,N-dimethylformamide (1.8 mL) and water (0.41 mL) was treated sequentially with 2,3,5-trifluoro-4-hydroxybenzoic acid (41.9 mg, 0.218 mmol), 1-methyl-1H-imidazole (43.4 μL, 0.544 mmol), and 2-hydroxypyridine 1-oxide (20.2 mg, 0.182 mmol). After the reaction mixture had been stirred for 20 minutes at room temperature, 1-[3-(dimethylamino)propyl]-3-ethylcarbodiimide hydrochloride (35.5 mg, 0.185 mmol) was added; stirring was continued at room temperature for 18 hours, whereupon the reaction mixture was diluted with water (10 mL), acidified to pH 4 by addition of methanesulfonic acid, and extracted 3 times with ethyl acetate. The combined organic layers were washed 5 times with water, dried over magnesium sulfate, filtered, and concentrated in vacuo. Purification via reversed-phase HPLC (Column: Waters Sunfire C18, 19×100 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 8.54 minutes, followed by 95% B for 1.46 minutes; Flow rate: 25 mL/minute) provided 2,3,5-trifluoro-4-hydroxy-N-({4-[3-(6-methoxypyridazin-3-yl)-1,2,4-oxadiazol-5-yl]bicyclo[2.2.2]octan-1-yl}methyl)benzamide (15). Yield: 26.6 mg, 54.3 μmol, 30% over 2 steps. LCMS m/z 490.4 $[M+H]^+$. Retention time: 2.57 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 16: 3,5-Difluoro-N-{[(1r,4r)-4-(6-fluoro-2H-indazol-2-yl)cyclohexyl]methyl}-4-hydroxybenzamide, ammonium salt (16)

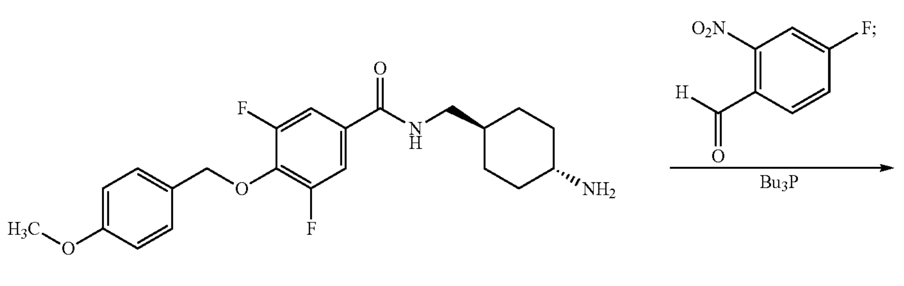

P3

-continued

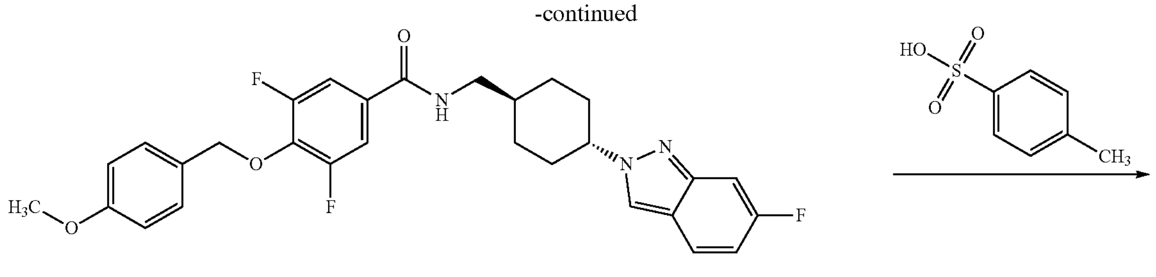

C50

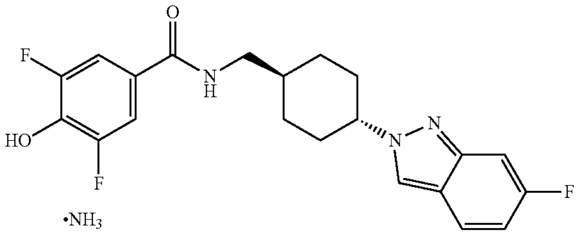

16

Step 1. Synthesis of 3,5-difluoro-N-{[(1r,4r)-4-(6-fluoro-2H-indazol-2-yl)cyclohexyl]methyl}-4-[(4-methoxyphenyl)methoxy]benzamide (C50)

This reaction was carried out in library format.

A solution of P3 (60.7 mg, 0.150 mmol) in propan-2-ol (0.6 mL) was added to 4-fluoro-2-nitrobenzaldehyde (0.15 mmol). The reaction vial was capped, then evacuated and charged with nitrogen. This evacuation cycle was repeated twice, whereupon the reaction mixture was shaken at 80° C. for 4 hours before being cooled to room temperature. After addition of tributylphosphine (0.1 mL, 0.4 mmol), the reaction mixture was shaken at 80° C. for 18 hours. It was then partitioned between half-saturated aqueous sodium bicarbonate solution (1.5 mL) and ethyl acetate (2.4 mL) and subjected to vortexing. The organic layer was eluted through a solid-phase extraction cartridge (6 mL) charged with sodium sulfate (~1 g); this extraction procedure was repeated twice, and the combined eluents were concentrated in vacuo to provide C50, which was taken directly to the following step.

Step 2. Synthesis of 3,5-difluoro-N-{[(1r,4r)-4-(6-fluoro-2H-indazol-2-yl)cyclohexyl]methyl}-4-hydroxybenzamide, ammonium salt (16)

This reaction was carried out in library format.

A solution of p-toluenesulfonic acid (57.1 mg, 0.300 mmol) in 1,1,1,3,3,3-hexafluoropropan-2-ol (0.6 mL) was added to C50 (from the previous step; 50.150 mmol), and the reaction mixture was shaken at room temperature for 3 days. After removal of solvent using a Genevac concentrator, purification was carried out via reversed-phase HPLC (Column: Waters XBridge C18, 19×100 mm, 5 μm; Mobile phase A: water containing 0.03% ammonium hydroxide; Mobile phase B: acetonitrile containing 0.03% ammonium hydroxide; Gradient: 5% to 95% B over 8.54 minutes, then 95% B for 1.46 minutes; Flow rate: 25 mL/minute) to afford 3,5-difluoro-N-{[(1r,4r)-4-(6-fluoro-2H-indazol-2-yl)cyclohexyl]methyl}-4-hydroxybenzamide, ammonium salt (16). Yield: 11.4 mg, 27.1 μmol, 18% over 2 steps. LCMS m/z 404.4 $[M+H]^+$. Retention time: 2.61 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 17: N-{[(1r,4r)-4-{3-[6-(2,2-Dimethylpropanamido)pyridazin-3-yl]-1,2,4-oxadiazol-5-yl}cyclohexyl]methyl}-3,5-difluoro-4-hydroxybenzamide, ammonium salt (17)

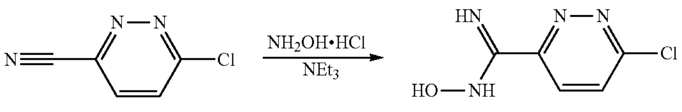

C51

-continued

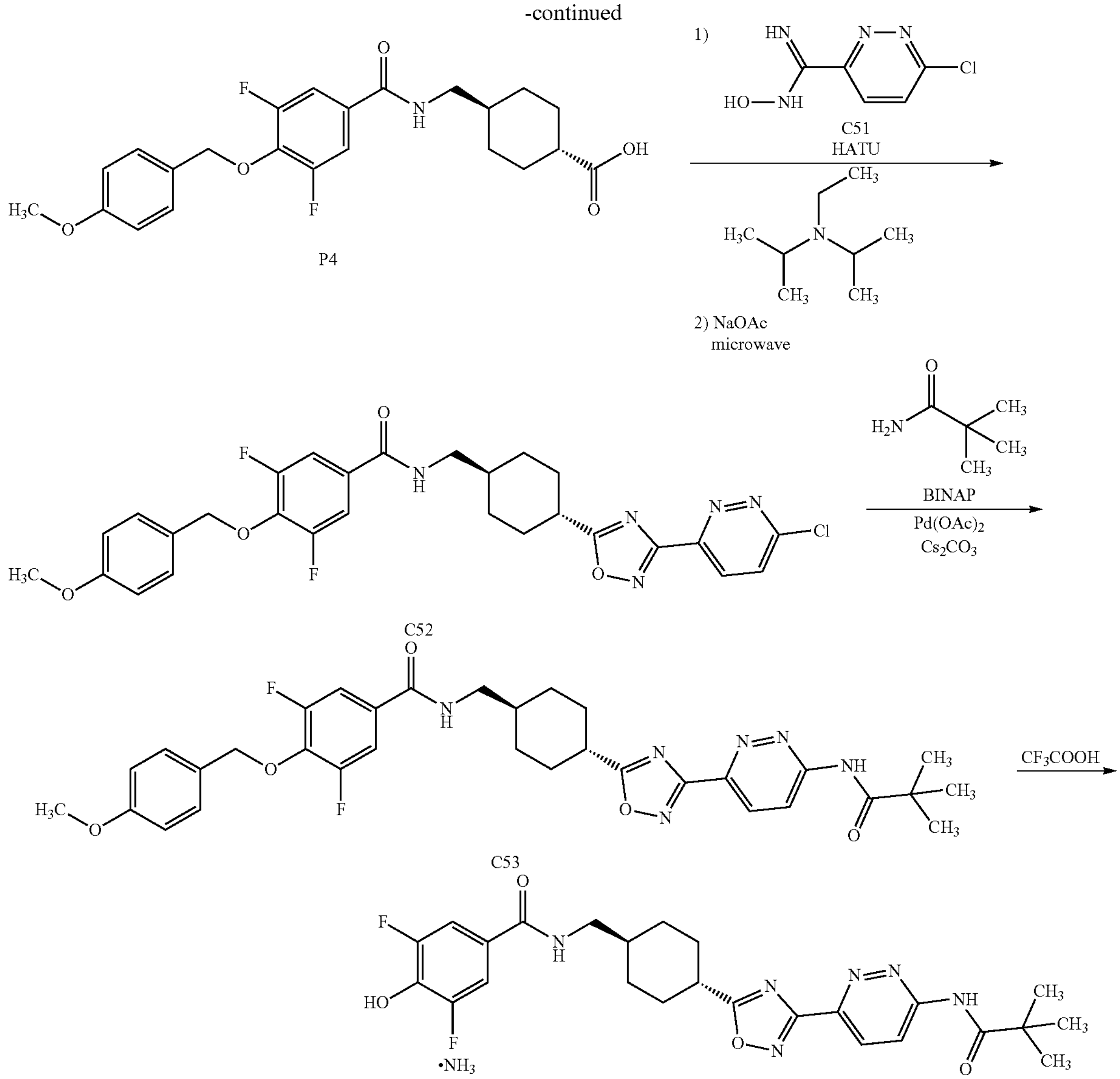

P4

C52

C53

17

Step 1. Synthesis of 6-chloro-N-hydroxypyridazine-3-carboximidamide (C51)

To a solution of 6-chloropyridazine-3-carbonitrile (698 mg, 5.00 mmol) in methanol (15 mL) was added hydroxylamine hydrochloride (382 mg, 5.50 mmol), followed by triethylamine (0.775 mL, 5.56 mmol). The reaction mixture was stirred for 2 hours, whereupon the solids were collected via filtration, providing C51 as a brown solid. Yield: 465 mg, 2.69 mmol, 54%. LCMS m/z 173.1 $[M+H]^+$. $^1H$ NMR (400 MHz, DMSO-$d_6$) δ 10.43 (s, 1H), 8.08 (d, J=9.1 Hz, 1H), 7.88 (d, J=9.0 Hz, 1H), 6.15 (br s, 2H).

Step 2. Synthesis of N-({(1r,4r)-4-[3-(6-chloropyridazin-3-yl)-1,2,4-oxadiazol-5-yl]cyclohexyl}methyl)-3,5-difluoro-4-[(4-methoxyphenyl)methoxy]benzamide (C52)

A solution of P4 (595 mg, 1.37 mmol) in N,N-dimethylformamide (9 mL) was treated with 0-(7-azabenzotriazol-1-yl)-N,N,N',N'-tetramethyluronium hexafluorophosphate (HATU; 783 mg, 2.06 mmol). After 30 minutes, C51 (261 mg, 1.51 mmol) and N,N-diisopropylethylamine (0.717 mL, 4.12 mmol) were added, whereupon the reaction mixture was stirred for 18 hours at room temperature. The precipitate was collected by filtration and washed with dichloromethane to afford the acyl intermediate as an off-white solid. Yield: 358 mg, 0.609 mmol, 44%. LCMS m/z 588.3 $[M+H]^+$. $^1H$ NMR (400 MHz, DMSO-$d_6$) δ 8.52 (br t, J=5.8 Hz, 1H), 8.15 (d, J=9.0 Hz, 1H), 8.01 (d, J=9.0 Hz, 1H), 7.64-7.55 (m, 2H), 7.34 (d, J=8.6 Hz, 2H), 7.29 (br s, 2H), 6.92 (d, J=8.6 Hz, 2H), 5.17 (s, 2H), 3.74 (s, 3H), 3.12 (dd, J=6, 6 Hz, 2H), 2.57-2.44 (m, 1H, assumed; almost entirely obscured by solvent peak), 2.05-1.96 (m, 2H), 1.85-1.75 (m, 2H), 1.61-1.48 (m, 1H), 1.47-1.32 (m, 2H), 1.06-0.92 (m, 2H).

A portion of the acyl intermediate (219 mg, 0.372 mmol) and sodium acetate (61.7 mg, 0.752 mmol), in a mixture of ethanol (4.5 mL) and water (0.45 mL), was heated at 120° C. for 1 hour under microwave irradiation. The resulting solid was isolated via filtration and washed with a 10:1 mixture of ethanol and water, providing $C_{52}$ as a white solid. Yield: 172 mg, 0.302 mmol, 81% from the acyl intermediate. LCMS m/z 570.3 (chlorine isotope pattern observed) $[M+H]^+$. $^1$H NMR (400 MHz, DMSO-$d_6$) δ 8.55 (br t, J=5.8 Hz, 1H), 8.32 (d, J=9.0 Hz, 1H), 8.14 (d, J=8.9 Hz, 1H), 7.65-7.56 (m, 2H), 7.34 (d, J=8.6 Hz, 2H), 6.92 (d, J=8.6 Hz, 2H), 5.17 (s, 2H), 3.74 (s, 3H), 3.20-3.09 (m, 3H), 2.25-2.14 (m, 2H), 1.92-1.83 (m, 2H), 1.69-1.51 (m, 3H), 1.23-1.08 (m, 2H).

Step 3. Synthesis of N-{[(1r,4r)-4-{3-[6-(2,2-dimethylpropanamido)pyridazin-3-yl]-1,2,4-oxadiazol-5-yl}cyclohexyl]methyl}-3,5-difluoro-4-[(4-methoxyphenyl)methoxy]benzamide (C53)

A mixture of C52 (46 mg, 81 μmol), 2,2-dimethylpropanamide (9.8 mg, 97 μmol), palladium(II) acetate (0.906 mg, 4.04 μmol), ([1,1'-binaphthalene]-2,2'-diyl)bis(diphenylphosphane) (BINAP; 5.03 mg, 8.08 μmol), and cesium carbonate (65.7 mg, 0.202 mmol) in 1,4-dioxane (1 mL) was degassed under vacuum and charged with nitrogen. This evacuation cycle was repeated twice, whereupon the reaction vial was heated at 100° C. for 18 hours. After the reaction mixture had been partitioned between water and ethyl acetate, the aqueous layer was extracted twice with ethyl acetate, and the combined organic layers were dried over magnesium sulfate, filtered, and concentrated in vacuo to provide C53 as a brown oil (64 mg). This material was taken directly to the following step. LCMS m/z 635.4 $[M+H]^+$.

Step 4. Synthesis of N-{[(1r,4r)-4-{3-[6-(2,2-dimethylpropanamido)pyridazin-3-yl]-1,2,4-oxadiazol-5-yl}cyclohexyl]methyl}-3,5-difluoro-4-hydroxybenzamide, ammonium salt (17)

Trifluoroacetic acid (0.3 mL, 4 mmol) was added to a solution of C53 (from the previous step; 64 mg, ≤81 μmol) in dichloromethane (1 mL). The reaction mixture was stirred at room temperature for 1 hour, whereupon it was concentrated in vacuo and azeotroped twice with dichloromethane. Reversed-phase HPLC (Column: Waters XBridge C18, 19×100 mm, 5 μm; Mobile phase A: water containing 0.03% ammonium hydroxide; Mobile phase B: acetonitrile containing 0.03% ammonium hydroxide; Gradient: 5% to 50% B over 8.5 minutes, then 50% to 95% B over 0.5 minutes, then 95% B for 1.0 minute; Flow rate: 25 mL/minute) afforded N-{[(1r,4r)-4-{3-[6-(2,2-dimethylpropanamido)pyridazin-3-yl]-1,2,4-oxadiazol-5-yl}cyclohexyl]methyl}-3,5-difluoro-4-hydroxybenzamide, ammonium salt (17). Yield: 4.2 mg, 7.9 μmol, 10% over 2 steps. LCMS m/z 515.3 $[M+H]^+$. Retention time: 2.83 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 18: 3,5-Difluoro-4-hydroxy-N-({(1r,4r)-4-[4-(quinoxalin-6-yl)-1H-1,2,3-triazol-1-yl]cyclohexyl}methyl)benzamide (18)

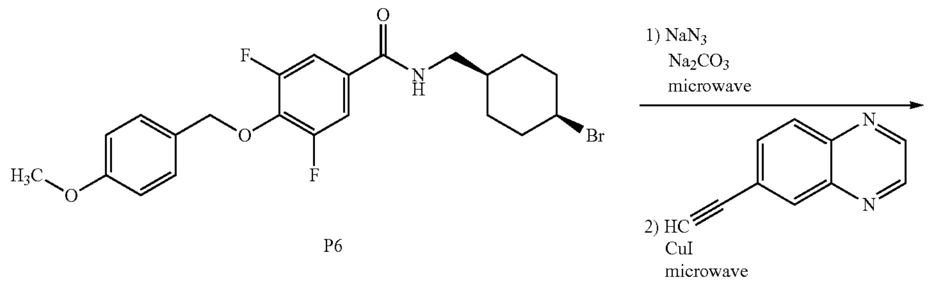

P6

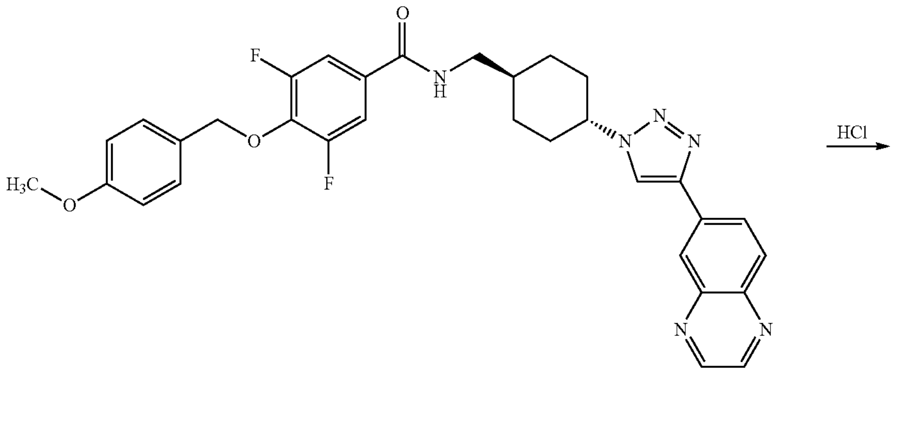

C54

-continued

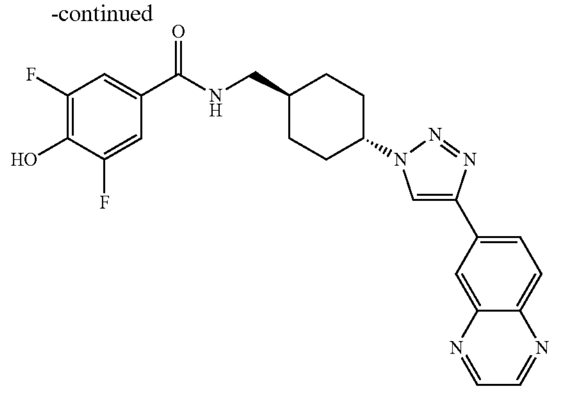

18

Step 1. Synthesis of 3,5-difluoro-4-[(4-methoxyphenyhmethoxy]-N-({(1r,4r)-4-[4-(quinoxalin-6-yl)-1H-1,2,3-triazol-1-yl]cyclohexyl}methyl)benzamide (C54)

This reaction was carried out in library format.

A solution of P6 (100 μmol) in N,N-dimethylformamide (0.50 mL) was treated with a solution of sodium azide in water (2.0 M; 0.20 mL, 400 μmol), followed by a solution of sodium carbonate in water (0.2 M; 0.10 mL, 20 μmol). The reaction vial was capped, and the reaction mixture was heated at 125° C. for 10 minutes under microwave irradiation. After the reaction mixture had cooled to room temperature, 6-ethynylquinoxaline (100 μmol) and copper(I) iodide (2.0 mg, 10 μmol) were added, and microwave irradiation was continued for 40 minutes at 125° C. When the reaction mixture had returned to room temperature, it was treated with an aqueous solution of sodium hypochlorite (8% to 10%; 1.0 mL) and the vial was shaken at 30° C. for 5 minutes; solvents were removed using a Speedvac® concentrator to provide C54. This material was progressed directly to the following step.

Step 2. Synthesis of 3,5-difluoro-4-hydroxy-N-({(1r,4r)-4-[4-(quinoxalin-6-yl)-1H-1,2,3-triazol-1-yl]cyclohexyl}methyl)benzamide (18)

This reaction was carried out in library format.

To a solution of C54 (from the previous step; 5100 μmol) in dichloromethane (0.8 mL) was added a solution of hydrogen chloride in 1,4-dioxane (4 M; 0.2 mL, 800 μmol), whereupon the reaction vial was capped and shaken at 30° C. for 16 hours. After solvents had been removed using a Speedvac® concentrator, the residue was purified via reversed-phase HPLC (Column: YMC-Actus Triart C18, 30×150 mm, 5 μm; Mobile phase A: water containing ammonium hydroxide (pH 10); Mobile phase B: acetonitrile; Gradient: 10% to 50% B; Flow rate: 35 mL/minute) to afford 3,5-difluoro-4-hydroxy-N-({(1r,4r)-4-[4-(quinoxalin-6-yl)-1H-1,2,3-triazol-1-yl]cyclohexyl}methyl)benzamide (18). Yield: 9.1 mg, 20 μmol, 20%. LCMS m/z 465 $[M+H]^+$. Retention time: 2.46 minutes (Analytical conditions. Column: Waters XBridge C18, 2.1×50 mm, 5 μm; Mobile phase A: water containing 0.0375% trifluoroacetic acid; Mobile phase B: acetonitrile containing 0.01875% trifluoroacetic acid; Gradient: 1% to 5% B over 0.6 minutes; 5% to 100% B over 3.4 minutes; Flow rate: 0.8 mL/minute).

Example 19: 2,3,5-Trifluoro-4-hydroxy-N-({(1r,4r)-4-[6-(4-methylpiperazin-1-yl)-2H-indazol-2-yl]cyclohexyl}methyl)benzamide, trifluoroacetate salt (19)

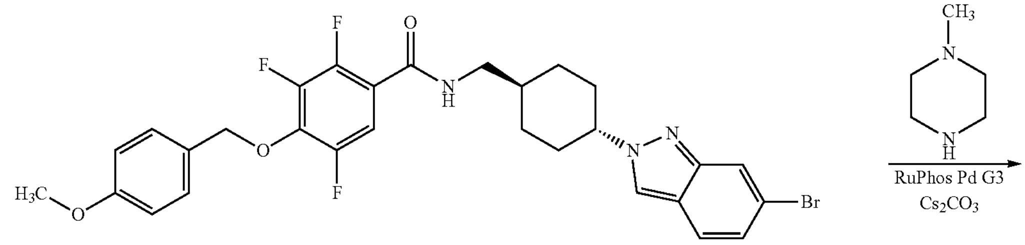

C39

-continued

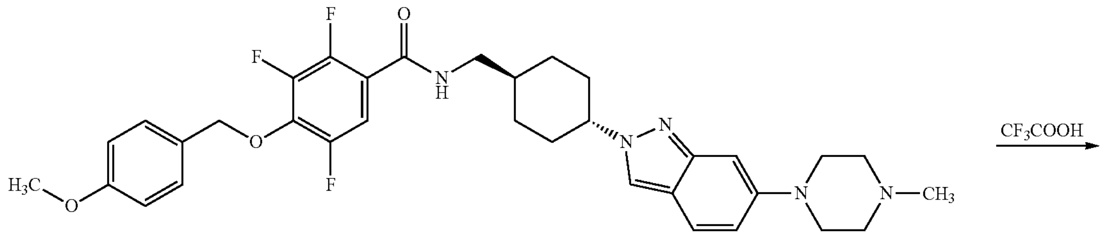

C55

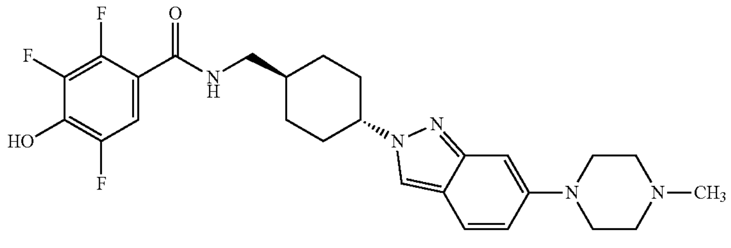

•$CF_3COOH$

19

Step 1. Synthesis of 2,3,5-trifluoro-4-[(4-methoxyphenyl)methoxy]-N-({(1r,4r)-4-[6-(4-methylpiperazin-1-yl)-2H-indazol-2-yl]cyclohexyl}methyl)benzamide (C55)

In a glove box under nitrogen, a scintillation vial was charged with C39 (100 mg, 0.166 mmol), cesium carbonate (162 mg, 0.497 mmol), and (2-dicyclohexylphosphino-2',6'-diisopropoxy-1,1'-biphenyl)[2-(2'-amino-1,1'-biphenyl)] palladium(II) methanesulfonate (RuPhos Pd G3; 13.9 mg, 16.6 µmol). The contents of the vial were stirred for 2 minutes, whereupon toluene (1.7 mL) was added; to the resulting solution was added 1-methylpiperazine (27.6 µL, 0.249 mmol), and the vial was transferred to a heating block. After the reaction mixture had been slowly heated to 90° C. under vigorous stirring, it was held at 90° C. overnight. It was then allowed to cool to room temperature, concentrated in vacuo, taken up in ethyl acetate (50 mL) and washed sequentially with water (3x50 mL) and saturated aqueous sodium chloride solution (25 mL). The organic layer was concentrated under reduced pressure to afford an oil (106 mg). LCMS analysis indicated that both C55 and 19 were present in this material, the bulk of which was taken directly to the following step. LCMS m/z 622.5 and 502.4 $[M+H]^+$.

Step 2. Synthesis of 2,3,5-trifluoro-4-hydroxy-N-({(1r,4r)-4-[6-(4-methylpiperazin-1-yl)-2H-indazol-2-yl]cyclohexyl}methyl)benzamide, trifluoroacetate salt (19)

Trifluoroacetic acid (50 µL, 0.65 mmol) was added to a solution of C55 and 19 (from the previous step; 103 mg, 50.161 mmol) in 1,1,1,3,3,3-hexafluoropropan-2-ol (1.5 mL). After the reaction mixture had been stirred overnight at room temperature, it was concentrated in vacuo and purified via reversed-phase HPLC [Column: Waters Sunfire C18, 19x100 mm, 5 µm; Mobile phase A: 0.05% trifluoroacetic acid in water (v/v); Mobile phase B: 0.05% trifluoroacetic acid in acetonitrile (v/v); Gradient: 5% to 35% B over 8.5 minutes, then 35% to 95% B over 0.5 minutes; Flow rate: 25 mL/minute], affording 2,3,5-trifluoro-4-hydroxy-N-({(1r,4r)-4-[6-(4-methylpiperazin-1-yl)-2H-indazol-2-yl]cyclohexyl}methyl)benzamide, trifluoroacetate salt (19). Yield: 40 mg, 65 µmol, 40% over 2 steps. LCMS m/z 502.3 $[M+H]^+$. Retention time: 1.91 minutes (Analytical conditions. Column: Waters Atlantis dC18, 4.6x50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 20: 3,5-Difluoro-4-hydroxy-N-({(1r,4r)-4-[5-(1-methyl-1H-pyrazol-3-yl)-1-oxo-1,3-dihydro-2H-isoindol-2-yl]cyclohexyl}methyl)benzamide (20)
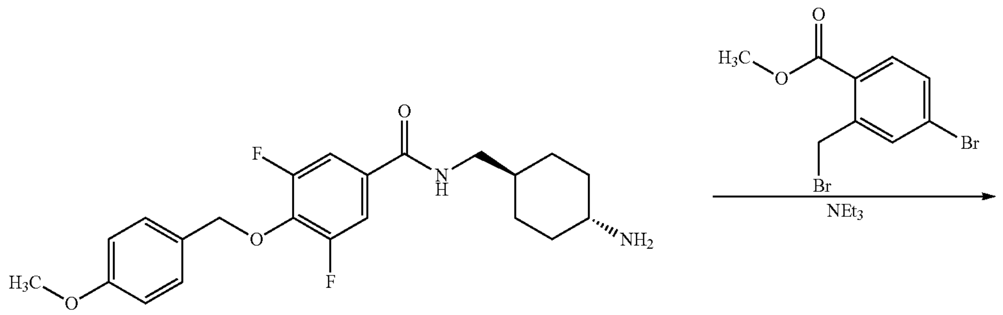
P3
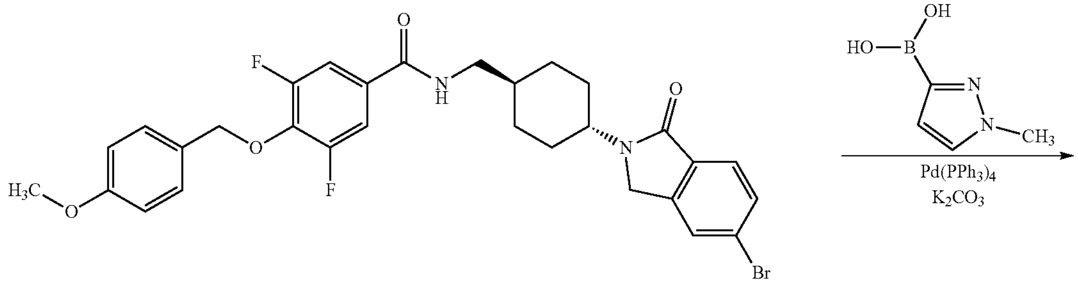
C56
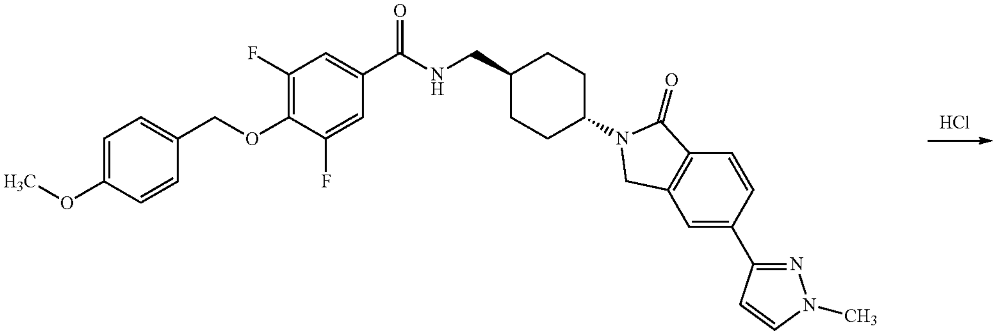
C57
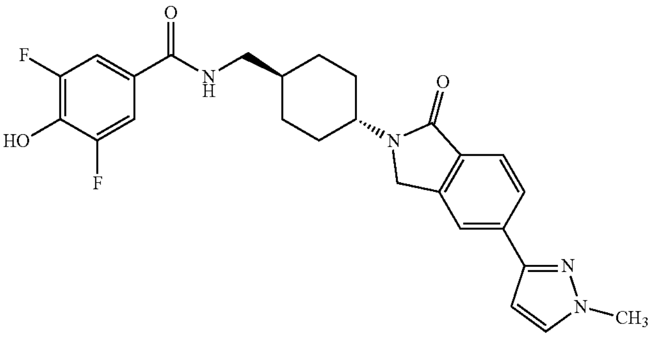
20

Step 1. Synthesis of N-{[(1r,4r)-4-(5-bromo-1-oxo-1,3-dihydro-2H-isoindol-2-yl)cyclohexyl]methyl}-3,5-difluoro-4-[(4-methoxyphenyl)methoxy]benzamide (C56)

To a solution of P3 (400 mg, 0.989 mmol) and triethylamine (150 mg, 1.48 mmol) in toluene (10 mL) was added methyl 4-bromo-2-(bromomethyl)benzoate (305 mg, 0.990 mmol). After the reaction mixture had been stirred at 100° C. for 16 hours, it was concentrated in vacuo; silica gel chromatography (Eluent: 5% methanol in dichloromethane) afforded C56 as a white solid. Yield: 332 mg, 0.554 mmol, 56%. LCMS m/z 599.0 (bromine isotope pattern observed) $[M+H]^+$. $^1H$ NMR (400 MHz, DMSO-$d_6$) δ 8.55 (br t, J=5.6 Hz, 1H), 7.84 (s, 1H), 7.69-7.55 (m, 4H), 7.33 (d, J=8.5 Hz, 2H), 6.92 (d, J=8.4 Hz, 2H), 5.17 (s, 2H), 4.43 (s, 2H), 4.04-3.92 (m, 1H), 3.74 (s, 3H), 3.12 (dd, J=6, 6 Hz, 2H), 1.89-1.70 (m, 4H), 1.63-1.46 (m, 3H), 1.19-1.04 (m, 2H).

Step 2. Synthesis of 3,5-difluoro-4-[(4-methoxyphenyl)methoxy]-N-({(1r,4r)-4-[5-(1-methyl-1H-pyrazol-3-yl)-1-oxo-1,3-dihydro-2H-isoindol-2-yl]cyclohexyl}methyl)benzamide (C57)

To a mixture of C56 (100 mg, 0.167 mmol), (1-methyl-1H-pyrazol-3-yl)boronic acid (25.2 mg, 0.200 mmol), and potassium carbonate (69.2 mg, 0.501 mmol) in 1,4-dioxane (10 mL) was added tetrakis(triphenylphosphine)palladium (0) (19.3 mg, 16.7 μmol), whereupon the reaction mixture was stirred at 100° C. for 16 hours. After solvents had been removed via concentration in vacuo, silica gel chromatography (Eluent: 5% methanol in dichloromethane) provided C57 as an oil. Yield: 42 mg, 70 μmol, 42%. LCMS m/z 601.2 $[M+H]^+$.

Step 3. Synthesis of 3,5-difluoro-4-hydroxy-N-({(1r,4r)-4-[5-(1-methyl-1H-pyrazol-3-yl)-1-oxo-1,3-dihydro-2H-isoindol-2-yl]cyclohexyl}methyl)benzamide (20)

To a solution of C57 (37 mg, 62 μmol) in dichloromethane (5 mL) was added a solution of hydrogen chloride in 1,4-dioxane (4 M; 1 mL). The reaction mixture was stirred at 25° C. for 1 hour, whereupon it was concentrated in vacuo; purification via reversed-phase HPLC (Column: Waters XBridge C18, 19×100 mm, 5 μm; Mobile phase A: water containing 0.1% formic acid; Mobile phase B: acetonitrile; Gradient: 25% to 45% B; Flow rate: 20 mL/minute), provided 3,5-difluoro-4-hydroxy-N-({(1r,4r)-4-[5-(1-methyl-1H-pyrazol-3-yl)-1-oxo-1,3-dihydro-2H-isoindol-2-yl]cyclohexyl}methyl)benzamide (20). Yield: 15.8 mg, 32.9 μmol, 53%. LCMS m/z 481.2 $[M+H]^+$. $^1H$ NMR (400 MHz, DMSO-$d_6$) δ 8.37 (br t, J=5.8 Hz, 1H), 7.97 (br s, 1H), 7.89 (dd, J=7.9, 1.4 Hz, 1H), 7.77 (d, J=2.3 Hz, 1H), 7.66 (d, J=7.9 Hz, 1H), 7.59-7.47 (m, 2H), 6.79 (d, J=2.3 Hz, 1H), 4.46 (s, 2H), 4.00 (tt, J=12.2, 3.8 Hz, 1H), 3.90 (s, 3H), 3.12 (dd, J=6, 6 Hz, 2H), 1.90-1.73 (m, 4H), 1.65-1.49 (m, 3H), 1.20-1.05 (m, 2H).

Example 21: 2,3,5-Trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide, hydrochloride salt (21)

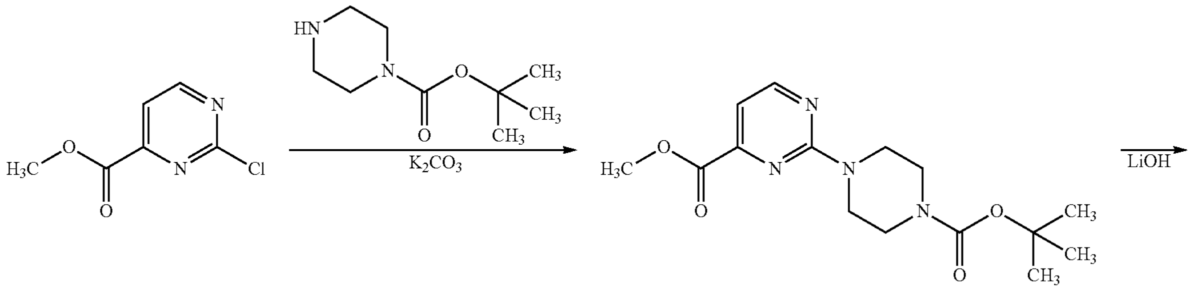

C58

-continued
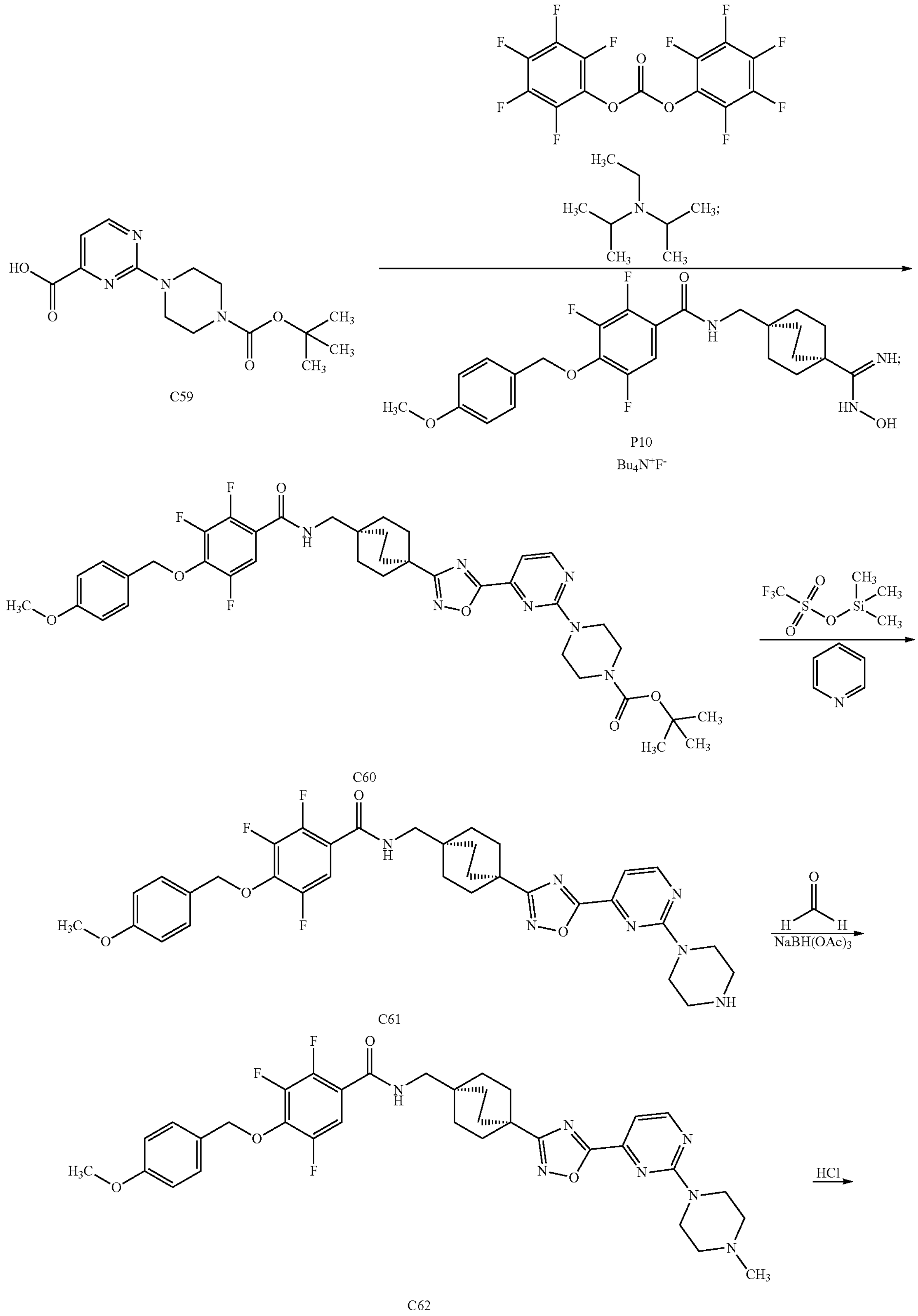
C59
P10
C60
C61
C62

-continued

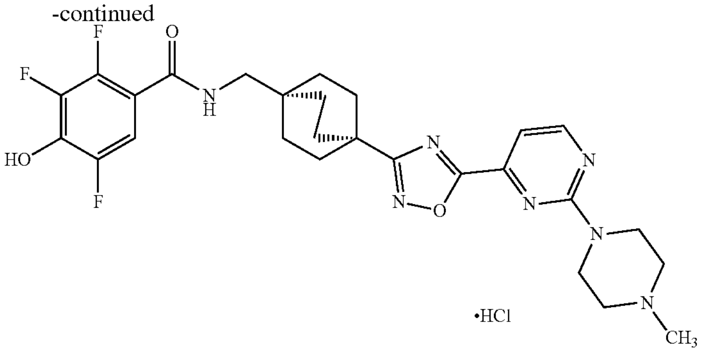

21

Step 1. Synthesis of methyl 2-[4-(tert-butoxycarbonyl)piperazin-1-yl]pyrimidine-4-carboxylate (C58)

Potassium carbonate (2.18 g, 15.8 mmol) was added to a solution of methyl 2-chloropyrimidine-4-carboxylate (95%, 956 mg, 5.26 mmol) and tert-butyl piperazine-1-carboxylate (1.00 g, 5.37 mmol) in acetonitrile (26 mL), whereupon the reaction mixture was stirred at 65° C. After 1.5 hours, LCMS analysis indicated the presence of C58: LCMS m/z 267.2 [(M-2-methylprop-1-ene)+H]$^+$. The reaction mixture was allowed to stir at 65° C. for an additional hour, and was then diluted with water and extracted three times with dichloromethane. The combined organic layers were concentrated in vacuo to afford C58 as a yellow solid (1.75 g), the bulk of which was progressed to the following step. $^1$H NMR (400 MHz, chloroform-d) b 8.51 (d, J=4.8 Hz, 1H), 7.14 (d, J=4.8 Hz, 1H), 3.96 (s, 3H), 3.92-3.84 (m, 4H), 3.55-3.47 (m, 4H), 1.49 (s, 9H).

Step 2. Synthesis of 2-[4-(tert-butoxycarbonyl)piperazin-1-yl]pyrimidine-4-carboxylic acid (C59)

A solution of lithium hydroxide (1.26 g, 52.6 mmol) in a mixture of tetrahydrofuran (10 mL), water (10 mL), and methanol (5 mL) was added to C58 (from the previous step; 1.70 g, 55.11 mmol). The reaction mixture was heated at 50° C. for 1 hour, allowed to cool to room temperature, and concentrated in vacuo to remove most of the solvent. After acidification of the residue to pH 2 to 3 by addition of 1 M hydrochloric acid, the mixture was extracted three times with ethyl acetate. At this point, the aqueous layer was acidified again to bring the pH to 2, and extracted twice with ethyl acetate. All of the organic layers were combined, dried over magnesium sulfate, filtered, and concentrated under reduced pressure to provide C59 as a pale-yellow solid. Yield: 1.42 g, 4.60 mmol, 90% over 2 steps. LCMS m/z 307.2 [M−H]$^-$. $^1$H NMR (400 MHz, chloroform-d) δ 8.62 (d, J=4.7 Hz, 1H), 7.31 (d, J=4.7 Hz, 1H), 3.90-3.82 (m, 4H), 3.58-3.51 (m, 4H), 1.50 (s, 9H).

Step 3. Synthesis of tert-butyl 4-(4-{3-[4-({2,3,5-trifluoro-4-[(4-methoxyphenyl)methoxy]benzamido}methyl)bicyclo[2.2.2]octan-1-yl]-1,2,4-oxadiazol-5-yl}pyrimidin-2-yl)piperazine-1-carboxylate (C60)

N,N-Diisopropylethylamine (0.532 mL, 3.05 mmol) was added drop-wise to a solution of C59 (345 mg, 1.12 mmol) and bis(pentafluorophenyl) carbonate (98%, 450 mg, 1.12 mmol) in tetrahydrofuran (5 mL). After the reaction mixture had been stirred at room temperature for 30 minutes, additional bis(pentafluorophenyl) carbonate (98%, 20 mg, 51 μmol) was added and stirring was continued for 10 minutes, whereupon P10 (500 mg, 1.02 mmol) was added, followed by another 30 minutes of stirring at room temperature. The reaction mixture was then treated with a solution of tetrabutylammonium fluoride in tetrahydrofuran (1.0 M; 5.09 mL, 5.09 mmol) and heated at 50° C. overnight. After cooling to room temperature, the reaction mixture was treated with a small amount of aqueous sodium bicarbonate solution, diluted with water, and extracted three times with ethyl acetate. The combined organic layers were dried over magnesium sulfate, filtered, concentrated in vacuo, and purified via chromatography on silica gel (Gradient: 30% to 100% ethyl acetate in heptane), affording C60 as a yellow solid. Yield: 474 mg (corrected for residual dichloromethane), 0.621 mmol, 61%. LCMS m/z 764.5 [M+H]$^+$. $^1$H NMR (400 MHz, DMSO-$d_6$) δ 8.67 (d, J=4.8 Hz, 1H), 8.35 (br t, J=6.3 Hz, 1H), 7.38-7.31 (m, 1H), 7.36 (br d, J=8.6 Hz, 2H), 7.30 (d, J=4.8 Hz, 1H), 6.94 (br d, J=8.7 Hz, 2H), 5.22 (s, 2H), 3.83-3.77 (m, 4H), 3.75 (s, 3H), 3.47-3.40 (m, 4H), 3.07 (d, J=6.2 Hz, 2H), 1.94-1.84 (m, 6H), 1.57-1.48 (m, 6H), 1.43 (s, 9H).

Step 4. Synthesis of 2,3,5-trifluoro-4-[(4-methoxyphenyl)methoxy]-N-[(4-{5-[2-(piperazin-1-yl)pyrimidin-4-yl]-1,2,4-oxadiazol-3-yl}bicyclo[2.2.2]octan-1-yl)methyl]benzamide (C61)

A solution of C60 (840 mg, 1.10 mmol) and pyridine (0.711 mL, 8.79 mmol) in dichloromethane (36 mL) was cooled to approximately −15° C. and treated drop-wise with trimethylsilyl trifluoromethanesulfonate (0.796 mL, 4.40 mmol). The reaction mixture was stirred overnight at −15° C., although by morning the temperature of the cooling bath had reached 12° C. The reaction mixture was then cooled in an ice bath, whereupon aqueous sodium bicarbonate solution (20 mL) was slowly added and the resulting mixture was stirred for 10 minutes. The aqueous layer was adjusted to pH 10 and extracted three times with dichloromethane; the combined organic layers were washed sequentially with saturated aqueous sodium bicarbonate solution and saturated aqueous sodium chloride solution, dried over magnesium sulfate, filtered, and concentrated under reduced pressure. The residue was co-evaporated three times with dichloromethane, providing C61 as a yellow solid. Yield: 673 mg, 1.01 mmol, 92%. LCMS m/z 664.4 [M+H]$^+$. $^1$H NMR (400 MHz, chloroform-d) b 8.51 (d, J=4.8 Hz, 1H), 7.59 (ddd, J=11.7, 6.8, 2.3 Hz, 1H), 7.34 (d, J=8.6 Hz, 2H), 7.22 (d, J=4.8 Hz, 1H), 6.88 (d, J=8.6 Hz, 2H), 6.62-6.50 (m, 1H), 5.24 (s, 2H), 3.96-3.86 (m, 4H), 3.80 (s, 3H), 3.30 (br d, J=6 Hz, 2H), 3.04-2.91 (m, 4H), 2.07-1.96 (m, 6H), 1.66-1.56 (m, 6H).

Step 5. Synthesis of 2,3,5-trifluoro-4-[(4-methoxyphenyl)methoxy]-N-[(4-{5-[2-(4-methylpiperazin-1-yl)pyrimidin-4-yl]-1,2,4-oxadiazol-3-yl}bicyclo[2.2.2]octan-1-yl)methyl]benzamide (C62)

To a solution of C61 (100 mg, 0.151 mmol) and formaldehyde (43 mg, 1.43 mmol) in 1,2-dichloroethane (8 mL) was added sodium triacetoxyborohydride (91 mg, 0.43 mmol). After the reaction mixture had been stirred at 25° C. for 1 hour, it was subjected to an aqueous workup and extracted with dichloromethane (2×30 mL); the combined organic layers were washed with saturated aqueous sodium chloride solution, dried over sodium sulfate, filtered, and concentrated in vacuo. Silica gel chromatography (Eluent: 5% methanol in dichloromethane) provided C62 as a yellow solid. Yield: 72.0 mg, 0.106 mmol, 70%. LCMS m/z 678.2 $[M+H]^+$. $^1H$ NMR (400 MHz, DMSO-$d_6$) b 8.65 (d, J=4.9 Hz, 1H), 8.36 (br t, J=6.2 Hz, 1H), 7.37-7.30 (m, 1H), 7.36 (d, J=8.5 Hz, 2H), 7.27 (d, J=4.8 Hz, 1H), 6.94 (d, J=8.4 Hz, 2H), 5.22 (s, 2H), 3.84-3.76 (m, 4H), 3.75 (s, 3H), 3.06 (d, J=6.2 Hz, 2H), 2.45-2.34 (m, 4H), 2.23 (s, 3H), 1.92-1.84 (m, 6H), 1.58-1.47 (m, 6H).

Step 6. Synthesis of 2,3,5-trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide, hydrochloride salt (21)

A solution of hydrogen chloride in 1,4-dioxane (4 M: 1 mL, 4 mmol) was added to a solution of C62 (72.0 mg, 0.106 mmol) in dichloromethane (4 mL). After the reaction mixture had been stirred at 25° C. for 1 hour, it was concentrated in vacuo and purified via reversed-phase HPLC (Column: Waters XBridge C18, 19×150 mm, 5 μm, Mobile phase A: water containing 0.05% formic acid; Mobile phase B: acetonitrile; Gradient: 15% to 45% B; Flow rate: 20 mL/minute) to provide 2,3,5-trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide, hydrochloride salt (21) as a white solid. Yield: 30.0 mg, 50.5 μmol, 48%. LCMS m/z 558.3 $[M+H]^+$. $^1H$ NMR (400 MHz, DMSO-$d_6$), characteristic peaks: δ 8.75 (d, J=4.9 Hz, 1H), 8.19 (br t, J=6 Hz, 1H), 7.42 (d, J=4.9 Hz, 1H), 7.27 (ddd, J=11.0, 6.2, 2.4 Hz, 1H), 3.66-3.2 (m, 8H, assumed; entirely obscured by water peak), 3.07 (d, J=6.2 Hz, 2H), 2.84 (s, 3H), 1.96-1.83 (m, 6H), 1.60-1.47 (m, 6H).

Using analogous procedures, compounds of Examples 22-214 were synthesized as described in Tables 1 and 2.

TABLE 1

Structure and IUPAC Name for Examples 1-214.

| Example | Structure | IUPAC Name |
|---|---|---|
| 1 | 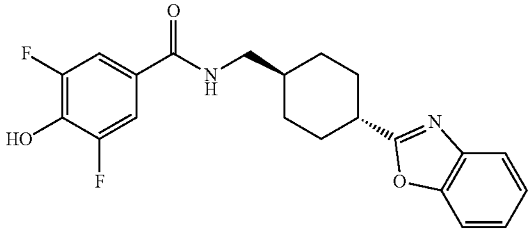 [SMILES: O=C(NC[C@H]1CC[C@H](c2nc3ccccc3o2)CC1)c1cc(F)c(O)c(F)c1] | N-{[(1r,4r)-4-(1,3-benzoxazol-2-yl)cyclohexyl]methyl}-3,5-difluoro-4-hydroxy-benzamide |
| 2 | 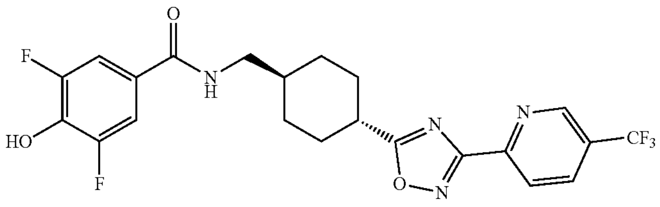 [SMILES: O=C(NC[C@H]1CC[C@H](c2nc(-c3ccc(C(F)(F)F)cn3)no2)CC1)c1cc(F)c(O)c(F)c1] | 3,5-difluoro-4-hydroxy-N-{[(1r,4r)-4-{3-[5-(trifluoromethyl)pyridin-2-yl]-1,2,4-oxadiazol-5-yl}cyclohexyl]methyl}benzamide |
| 3 | 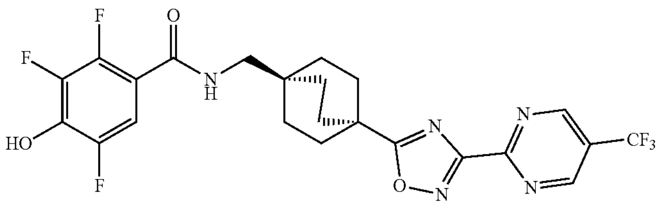 [SMILES: O=C(NC[C@]12CC[C@@](c3nc(-c4ncc(C(F)(F)F)cn4)no3)(CC1)CC2)c1cc(F)c(O)c(F)c1F] | 2,3,5-trifluoro-4-hydroxy-N-[(4-{3-[5-(trifluoromethyl)pyrimidin-2-yl]-1,2,4-oxadiazol-5-yl}bicyclo[2.2.2]octan-1-yl)methyl]benzamide |

TABLE 1-continued

| Example | Structure | IUPAC Name |
| --- | --- | --- |
| Structure and IUPAC Name for Examples 1-214. | | |
| 4 | 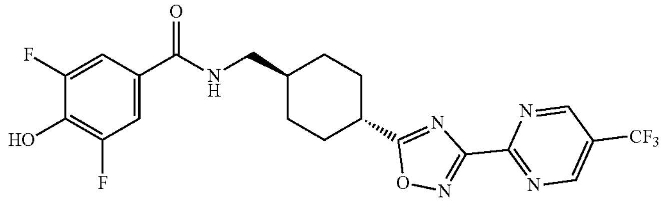 [SMILES: O=C(NC[C@H]1CC[C@H](c2nc(-c3ncc(C(F)(F)F)cn3)no2)CC1)c1cc(F)c(O)c(F)c1] | 3,5-difluoro-4-hydroxy-N-{[(1r,4r)-4-{3-[5-(trifluoromethyl)pyrimidin-2-yl]-1,2,4-oxadiazol-5-yl}cyclohexyl]methyl}benzamide |
| 5 | 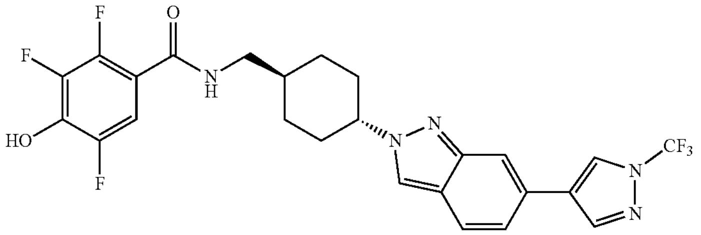 •$CF_3COOH$ | 2,3,5-trifluoro-4-hydroxy-N-({(1r,4r)-4-[6-(1-methyl-1H-pyrazol-4-yl)-2H-indazol-2-yl]cyclohexyl}methyl)benzamide, trifluoroacetate salt |
| 6 | 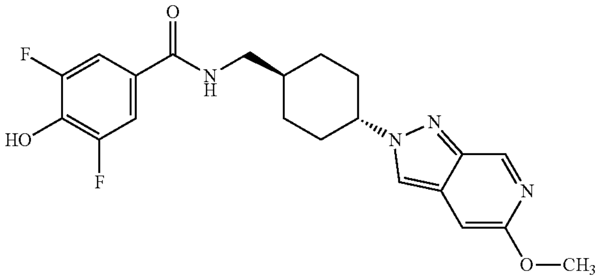 [SMILES: COc1cc2cn([C@H]3CC[C@H](CNC(=O)c4cc(F)c(O)c(F)c4)CC3)nc2cn1] | 3,5-difluoro-4-hydroxy-N-{[(1r,4r)-4-(5-methoxy-2H-pyrazolo[3,4-c]pyridin-2-yl)cyclohexyl]methyl}benzamide |
| 7 | 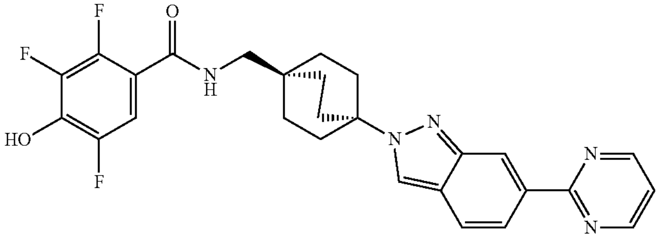 [SMILES: O=C(NC[C@]12CC[C@@](n3cc4ccc(-c5ncccn5)cc4n3)(CC1)CC2)c1cc(F)c(O)c(F)c1F] | 2,3,5-trifluoro-4-hydroxy-N-({4-[6-(pyrimidin-2-yl)-2H-indazol-2-yl]bicyclo[2.2.2]octan-1-yl}methyl)benzamide |
| 8 | 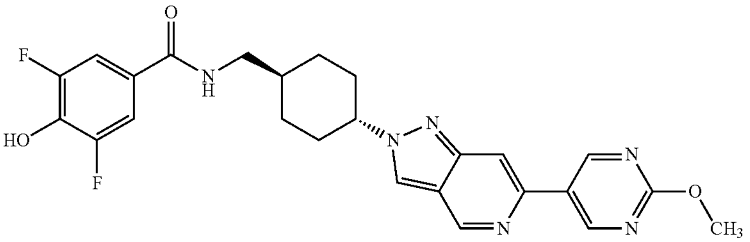 [SMILES: COc1ncc(-c2cc3nn([C@H]4CC[C@H](CNC(=O)c5cc(F)c(O)c(F)c5)CC4)cc3cn2)cn1] | 3,5-difluoro-4-hydroxy-N-({(1r,4r)-4-[6-(2-methoxypyrimidin-5-yl)-2H-pyrazolo[4,3-c]pyridin-2-yl]cyclohexyl}methyl)benzamide |
| 9 | 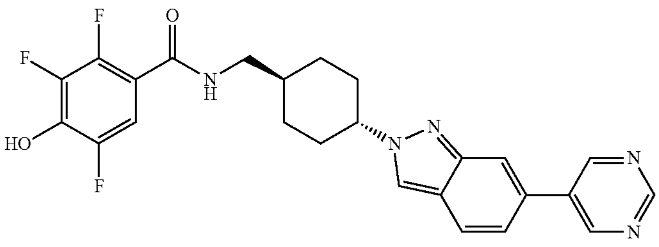 [SMILES: O=C(NC[C@H]1CC[C@H](n2cc3ccc(-c4cncnc4)cc3n2)CC1)c1cc(F)c(O)c(F)c1F] | 2,3,5-trifluoro-4-hydroxy-N-({(1r,4r)-4-[6-(pyrimidin-5-yl)-2H-indazol-2-yl]cyclohexyl}methyl)benzamide |

TABLE 1-continued

| Structure and IUPAC Name for Examples 1-214. | | |
|---|---|---|
| Example | Structure | IUPAC Name |
| 10 | 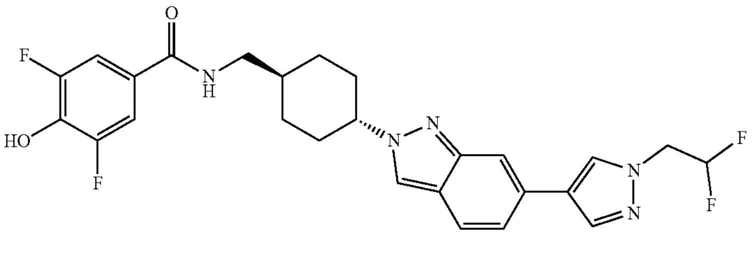 •$CF_3COOH$ | N-{[(1r,4r)-4-{6-[1-(2,2-difluoroethyl)-1H-pyrazol-4-yl]-2H-indazol-2-yl}cyclohexyl]methyl}-3,5-difluoro-4-hydroxybenzamide, trifluoroacetate salt |
| 11 | 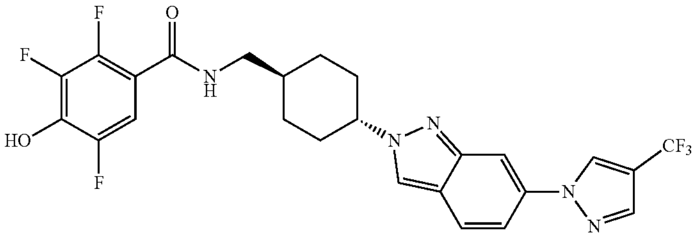 •$CF_3COOH$ | 2,3,5-trifluoro-4-hydroxy-N-{[(1r,4r)-4-{6-[4-(trifluoromethyl)-1H-pyrazol-1-yl]-2H-indazol-2-yl}cyclohexyl]methyl}benzamide, trifluoroacetate salt |
| 12 | 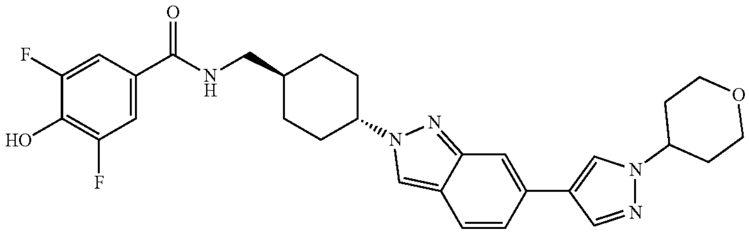 [SMILES: O=C(NC[C@H]1CC[C@H](n2cc3ccc(-c4cnn(C5CCOCC5)c4)cc3n2)CC1)c1cc(F)c(O)c(F)c1] | 3,5-difluoro-4-hydroxy-N-{[(1r,4r)-4-{6-[1-(oxan-4-yl)-1H-pyrazol-4-yl]-2H-indazol-2-yl}cyclohexyl]methyl}benzamide |
| 13 | 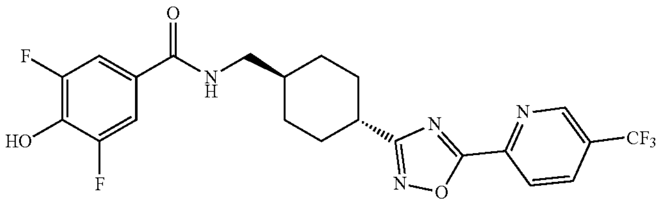 [SMILES: O=C(NC[C@H]1CC[C@H](c2noc(-c3ccc(C(F)(F)F)cn3)n2)CC1)c1cc(F)c(O)c(F)c1] | 3,5-difluoro-4-hydroxy-N-{[(1r,4r)-4-{5-[5-(trifluoromethyl)pyridin-2-yl]-1,2,4-oxadiazol-3-yl}cyclohexyl]methyl}benzamide |
| 14 | 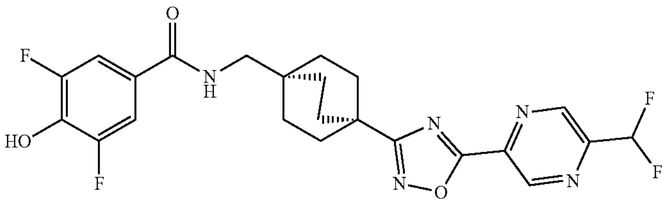 •$NH_3$ | N-[(4-{5-[5-(difluoromethyl)pyrazin-2-yl]-1,2,4-oxadiazol-3-yl}bicyclo[2.2.2]octan-1-yl)methyl]-3,5-difluoro-4-hydroxybenzamide, ammonium salt |
| 15 | 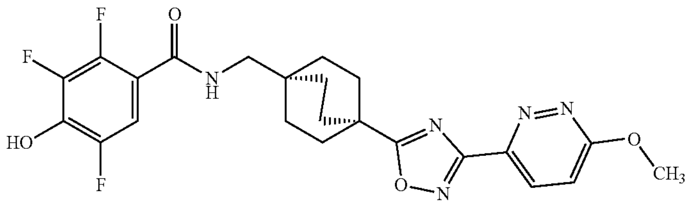 [SMILES: COc1ccc(-c2noc([C@]34CC[C@](CNC(=O)c5cc(F)c(O)c(F)c5F)(CC3)CC4)n2)nn1] | 2,3,5-trifluoro-4-hydroxy-N-({4-[3-(6-methoxypyridazin-3-yl)-1,2,4-oxadiazol-5-yl]bicyclo[2.2.2]octan-1-yl}methyl)benzamide |

TABLE 1-continued

Structure and IUPAC Name for Examples 1-214.

| Example | Structure | IUPAC Name |
|---|---|---|
| 16 | 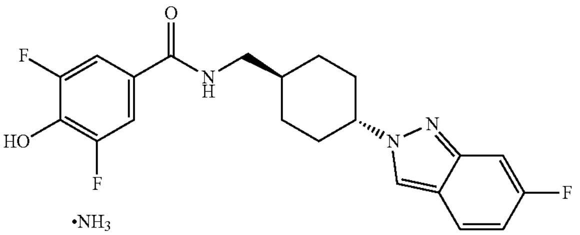 •$NH_3$ | 3,5-difluoro-N-{[(1r,4r)-4-(6-fluoro-2H-indazol-2-yl)cyclohexyl]methyl}-4-hydroxybenzamide, ammonium salt |
| 17 | 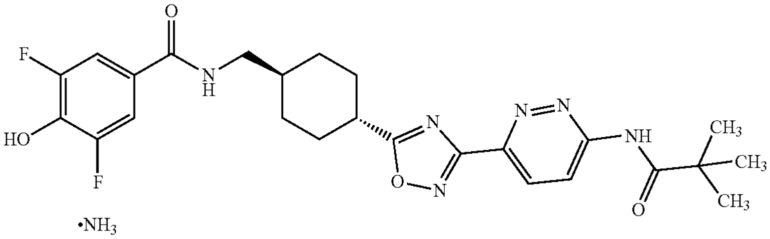 •$NH_3$ | N-{[(1r,4r)-4-{3-[6-(2,2-dimethylpropanamido)pyridazin-3-yl]-1,2,4-oxadiazol-5-yl}cyclohexyl]methyl}-3,5-difluoro-4-hydroxybenzamide, ammonium salt |
| 18 | 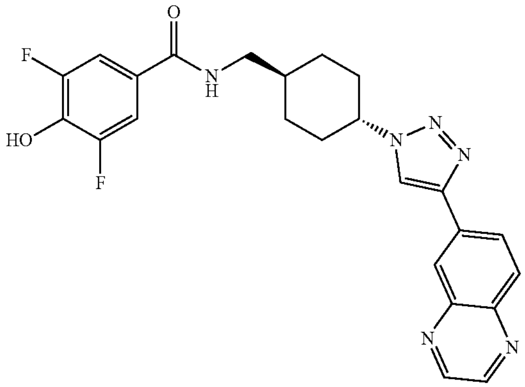 [SMILES: O=C(NC[C@H]1CC[C@H](n2cc(-c3ccc4nccnc4c3)nn2)CC1)c1cc(F)c(O)c(F)c1] | 3,5-difluoro-4-hydroxy-N-({(1r,4r)-4-[4-(quinoxalin-6-yl)-1H-1,2,3-triazol-1-yl]cyclohexyl}methyl)benzamide |
| 19 | 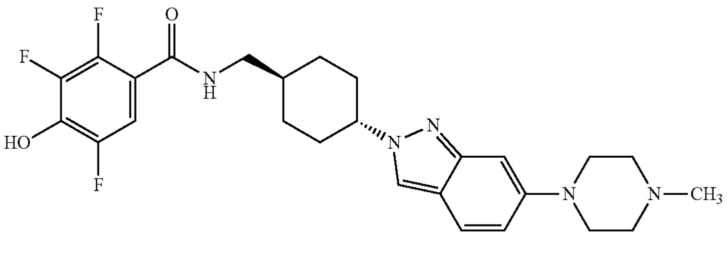 •$CF_3COOH$ | 2,3,5-trifluoro-4-hydroxy-N-({(1r,4r)-4-[6-(4-methylpiperazin-1-yl)-2H-indazol-2-yl]cyclohexyl}methyl)benzamide, trifluoroacetate salt |
| 20 | 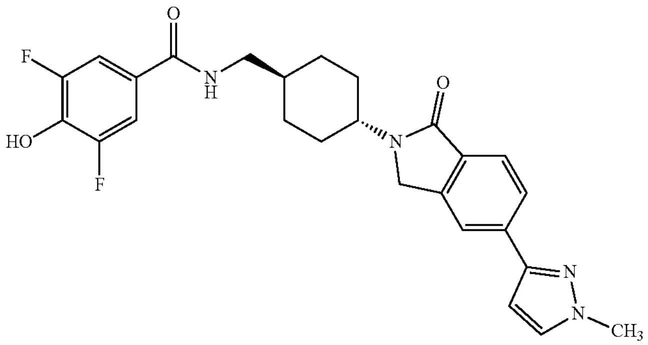 [SMILES: Cn1ccc(-c2ccc3c(c2)CN([C@H]2CC[C@H](CNC(=O)c4cc(F)c(O)c(F)c4)CC2)C3=O)n1] | 3,5-difluoro-4-hydroxy-N-({(1r,4r)-4-[5-(1-methyl-1H-pyrazol-3-yl)-1-oxo-1,3-dihydro-2H-isoindol-2-yl]cyclohexyl}methyl)benzamide |

TABLE 1-continued

Structure and IUPAC Name for Examples 1-214.

| Example | Structure | IUPAC Name |
|---|---|---|
| 21 | 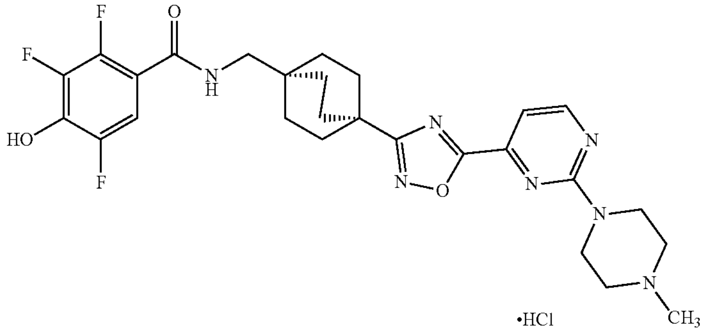 [SMILES: CN1CCN(c2nccc(-c3nc([C@]45CC[C@](CNC(=O)c6cc(F)c(O)c(F)c6F)(CC4)CC5)no3)n2)CC1 ; Cl] | 2,3,5-Trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide, hydrochloride salt |
| 22 | 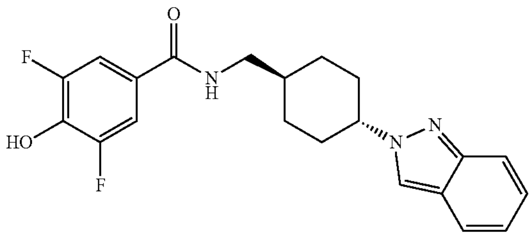 [SMILES: O=C(NC[C@H]1CC[C@H](n2cc3ccccc3n2)CC1)c1cc(F)c(O)c(F)c1] | 3,5-difluoro-4-hydroxy-N-{[(1r,4r)-4-(2H-indazol-2-yl)cyclohexyl]methyl}benzamide |
| 23 | 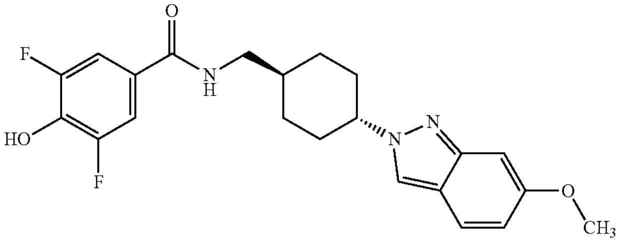 [SMILES: COc1ccc2cn([C@H]3CC[C@H](CNC(=O)c4cc(F)c(O)c(F)c4)CC3)nc2c1] | 3,5-difluoro-4-hydroxy-N-{[(1r,4r)-4-(6-methoxy-2H-indazol-2-yl)cyclohexyl]methyl}benzamide |
| 24 | 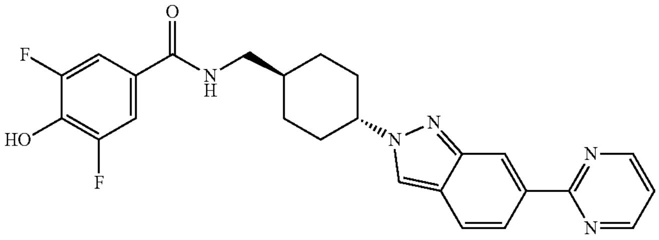 [SMILES: O=C(NC[C@H]1CC[C@H](n2cc3ccc(-c4ncccn4)cc3n2)CC1)c1cc(F)c(O)c(F)c1] | 3,5-difluoro-4-hydroxy-N-({(1r,4r)-4-[6-(pyrimidin-2-yl)-2H-indazol-2-yl]cyclohexyl}methyl)benzamide |
| 25 | 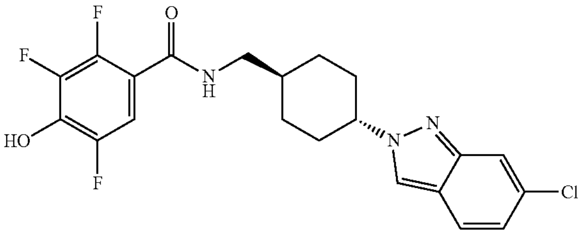 [SMILES: O=C(NC[C@H]1CC[C@H](n2cc3ccc(Cl)cc3n2)CC1)c1cc(F)c(O)c(F)c1F] | N-{[(1r,4r)-4-(6-chloro-2H-indazol-2-yl)cylohexyl]methyl}-2,3,5-trifluoro-4-hydroxybenzamide |

TABLE 1-continued

| Structure and IUPAC Name for Examples 1-214. | | |
|---|---|---|
| Example | Structure | IUPAC Name |
| 26 | 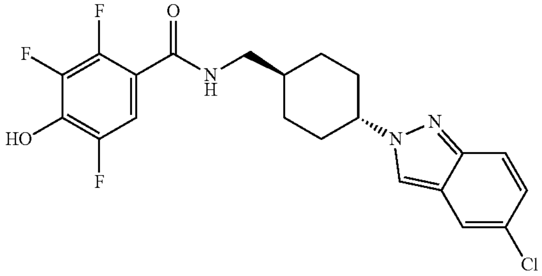 [SMILES: O=C(NC[C@H]1CC[C@H](n2cc3cc(Cl)ccc3n2)CC1)c1cc(F)c(O)c(F)c1F] | N-{[(1r,4r)-4-(5-chloro-2H-indazol-2-yl) cyclohexyl]methyl}-2,3,5-trifluoro-4-hydroxybenzamide |
| 27 | 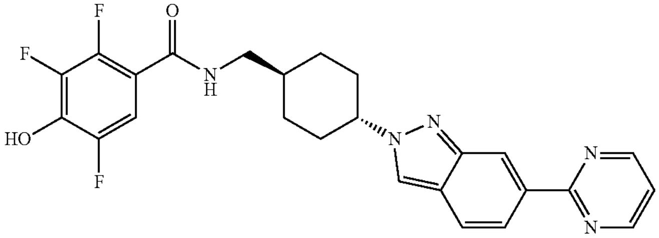 [SMILES: O=C(NC[C@H]1CC[C@H](n2cc3ccc(-c4ncccn4)cc3n2)CC1)c1cc(F)c(O)c(F)c1F] | 2,3,5-trifluoro-4-hydroxy-N-({(1r,4r)-4-[6-(pyrimidin-2-yl)-2H-indazol-2-yl] cyclohexyl}methyl) benzamide |
| 28 | 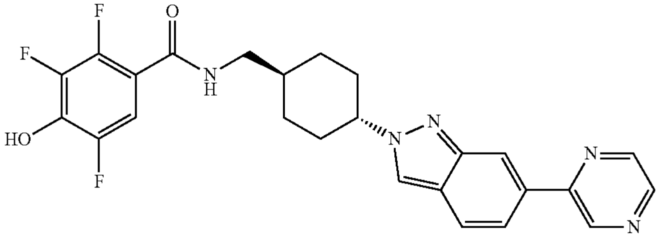 [SMILES: O=C(NC[C@H]1CC[C@H](n2cc3ccc(-c4cnccn4)cc3n2)CC1)c1cc(F)c(O)c(F)c1F] | 2,3,5-trifluoro-4-hydroxy-N-({(1r,4r)-4-[6-(pyrazin-2-yl)-2H-indazol-2-yl]cyclohexyl} methyl)benzamide |
| 29 | 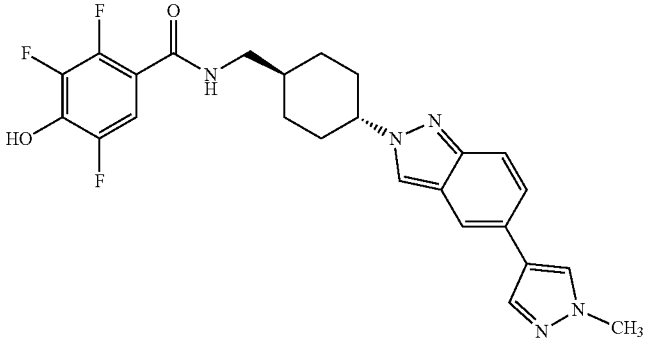 [SMILES: Cn1cc(-c2ccc3nn([C@H]4CC[C@H](CNC(=O)c5cc(F)c(O)c(F)c5F)CC4)cc3c2)cn1] | 2,3,5-trifluoro-4-hydroxy-N-({(1r,4r)-4-[6-(1-methyl-1H-pyrazol-4-yl)imidazo[1,2-a] pyridin-2-yl] cyclohexyl}methyl)benzamide |
| 30 | 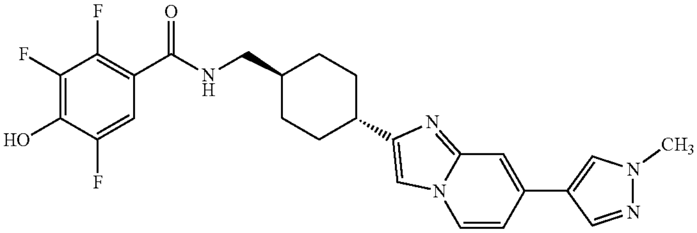 [SMILES: Cn1cc(-c2ccn3cc([C@H]4CC[C@H](CNC(=O)c5cc(F)c(O)c(F)c5F)CC4)nc3c2)cn1] | 2,3,5-trifluoro-4-hydroxy-N-({(1r,4r)-4-[7-(1-methyl-1H-pyrazol-4-yl)imidazo[1,2-a]pyridin-2-yl]cyclohexyl}methyl) benzamide |

TABLE 1-continued

Structure and IUPAC Name for Examples 1-214.

| Example | Structure | IUPAC Name |
|---|---|---|
| 31 | 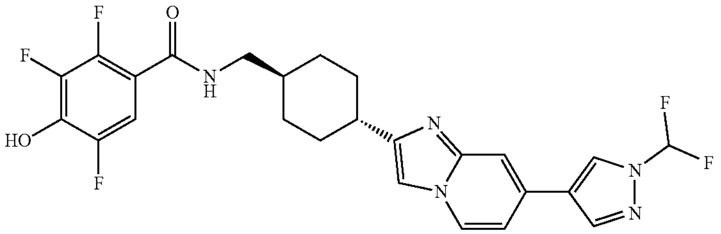 [SMILES: O=C(NC[C@H]1CC[C@H](c2cn3ccc(-c4cnn(C(F)F)c4)cc3n2)CC1)c1cc(F)c(O)c(F)c1F] | N-{[(1r,4r)-4-{7-[1-(difluoromethyl)-1H-pyrazol-4-yl]imidazo[1,2-a]pyridin-2-yl}cyclohexyl]methyl}-2,3,5-trifluoro-4-hydroxybenzamide |
| 32 | 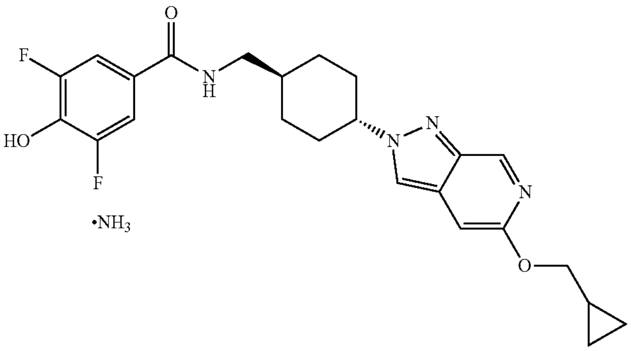 | N-({(1r,4r)-4-[5-(cyclopropyl-methoxy)-2H-pyrazolo[3,4-c]pyridin-2-yl]cyclohexyl}methyl)-3,5-difluoro-4-hydroxybenzamide, ammonium salt |
| 33 | 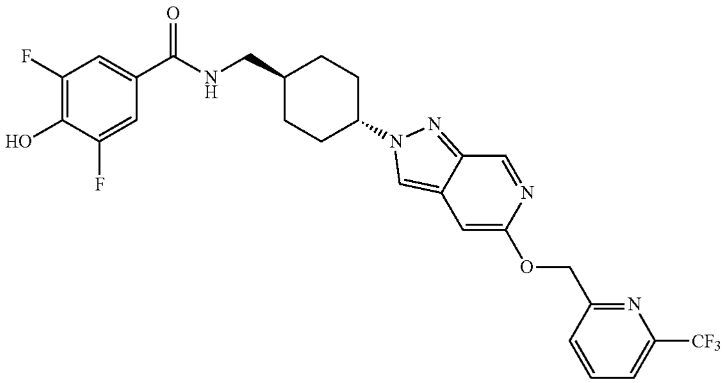 [SMILES: O=C(NC[C@H]1CC[C@H](n2cc3cc(OCc4cccc(C(F)(F)F)n4)ncc3n2)CC1)c1cc(F)c(O)c(F)c1] | 3,5-difluoro-4-hydroxy-N-{[(1r,4r)-4-(5-{[6-(trifluoromethyl)pyridin-2-yl]methoxy}-2H-pyrazolo[3,4-c]pyridin-2-yl)cyclohexyl]methyl}benzamide |
| 34 | 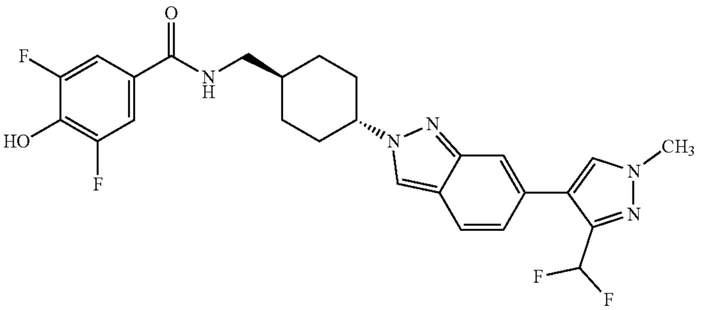 [SMILES: Cn1cc(-c2ccc3cn([C@H]4CC[C@H](CNC(=O)c5cc(F)c(O)c(F)c5)CC4)nc3c2)c(C(F)F)n1] | N-{[(1r,4r)-4-{6-[3-(difluoromethyl)-1-methyl-1H-pyrazol-4-yl]-2H-indazol-2-yl}cyclohexyl]methyl}-3,5-difluoro-4-hydroxybenzamide |

TABLE 1-continued

| Structure and IUPAC Name for Examples 1-214. | | |
|---|---|---|
| Example | Structure | IUPAC Name |
| 35 | 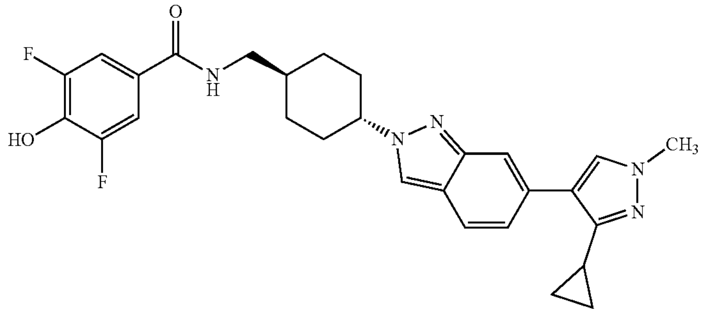 [SMILES: Cn1cc(-c2ccc3cn([C@H]4CC[C@H](CNC(=O)c5cc(F)c(O)c(F)c5)CC4)nc3c2)c(C2CC2)n1] | N-({(1r,4r)-4-[6-(3-cyclopropyl-1-methyl-1H-pyrazol-4-yl)-2H-indazol-2-yl]cyclohexyl}methyl)-3,5-difluoro-4-hydroxybenzamide |
| 36 | 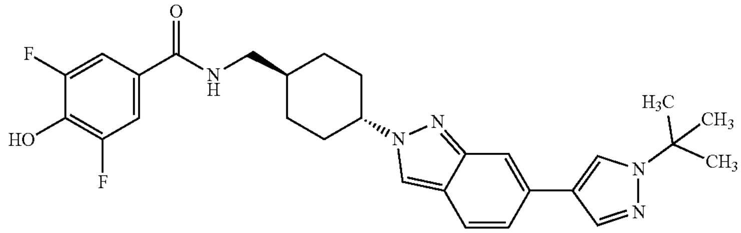 [SMILES: CC(C)(C)n1cc(-c2ccc3cn([C@H]4CC[C@H](CNC(=O)c5cc(F)c(O)c(F)c5)CC4)nc3c2)cn1] | N-({(1r,4r)-4-[6-(1-tert-butyl-1H-pyrazol-4-yl)-2H-indazol-2-yl]cyclohexyl}methyl)-3,5-difluoro-4-hydroxybenzamide |
| 37 | 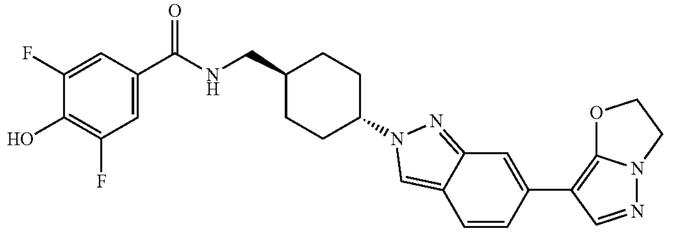 [SMILES: O=C(NC[C@H]1CC[C@H](n2cc3ccc(-c4cnn5c4OCC5)cc3n2)CC1)c1cc(F)c(O)c(F)c1] | N-({(1r,4r)-4-[6-(2,3-dihydropyrazolo[5,1-b][1,3]oxazol-7-yl)-2H-indazol-2-yl]cyclohexyl}methyl)-3,5-difluoro-4-hydroxybenzamide |
| 38 | 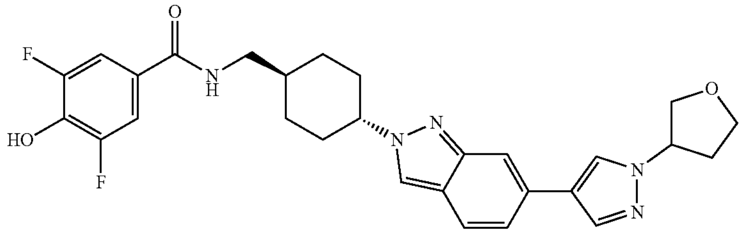 [SMILES: O=C(NC[C@H]1CC[C@H](n2cc3ccc(-c4cnn(C5CCOC5)c4)cc3n2)CC1)c1cc(F)c(O)c(F)c1] | 3,5-difluoro-4-hydroxy-N-{[(1r,4r)-4-{6-[1-(oxolan-3-yl)-1H-pyrazol-4-yl]-2H-indazol-2-yl}cyclohexyl]methyl}benzamide |
| 39 | 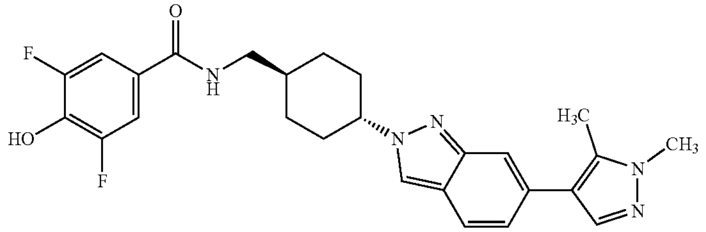 [SMILES: Cc1c(-c2ccc3cn([C@H]4CC[C@H](CNC(=O)c5cc(F)c(O)c(F)c5)CC4)nc3c2)cnn1C] | N-({(1r,4r)-4-[6-(1,5-dimethyl-1H-pyrazol-4-yl)-2H-indazol-2-yl]cyclohexyl}methyl)-3,5-difluoro-4-hydroxybenzamide |
| 40 | 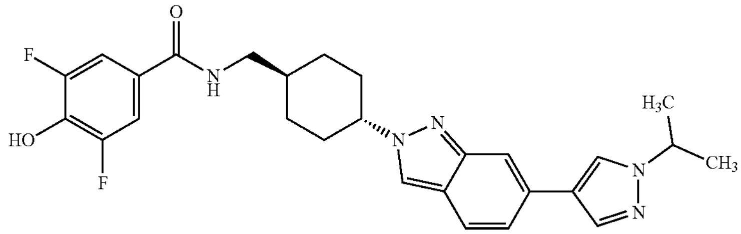 [SMILES: CC(C)n1cc(-c2ccc3cn([C@H]4CC[C@H](CNC(=O)c5cc(F)c(O)c(F)c5)CC4)nc3c2)cn1] | 3,5-difluoro-4-hydroxy-N-{[(1r,4r)-4-{6-[1-(propan-2-yl)-1H-pyrazol-4-yl]-2H-indazol-2-yl}cyclohexyl]methyl}benzamide |

TABLE 1-continued

Structure and IUPAC Name for Examples 1-214.

| Example | Structure | IUPAC Name |
|---|---|---|
| 41 | 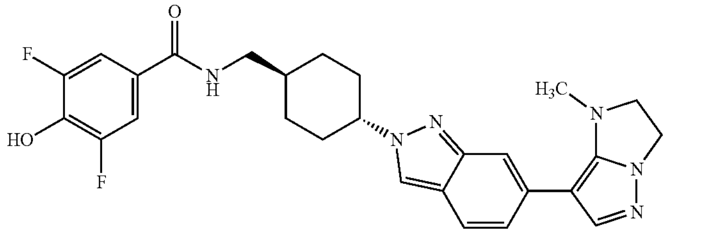 [SMILES: CN1CCn2ncc(-c3ccc4cn([C@H]5CC[C@H](CNC(=O)c6cc(F)c(O)c(F)c6)CC5)nc4c3)c21] | 3,5-difluoro-4-hydroxy-N-({(1r,4r)-4-[6-(1-methyl-2,3-dihydro-1H-imidazo[1,2-b]pyrazol-7-yl)-2H-indazol-2-yl]cyclohexyl}methyl)benzamide |
| 42 | 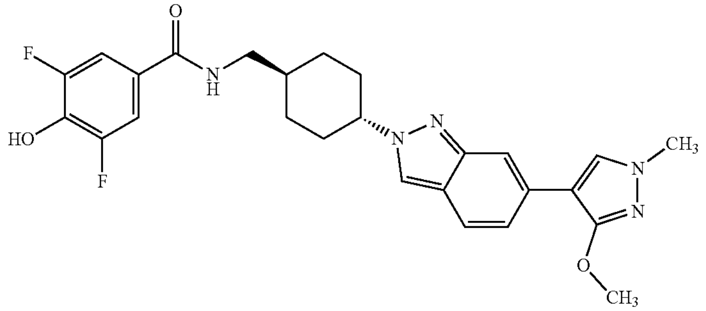 [SMILES: COc1nn(C)cc1-c1ccc2cn([C@H]3CC[C@H](CNC(=O)c4cc(F)c(O)c(F)c4)CC3)nc2c1] | 3,5-difluoro-4-hydroxy-N-({(1r,4r)-4-[6-(3-methoxy-1-methyl-1H-pyrazol-4-yl)-2H-indazol-2-yl]cyclohexyl}methyl)benzamide |
| 43 | 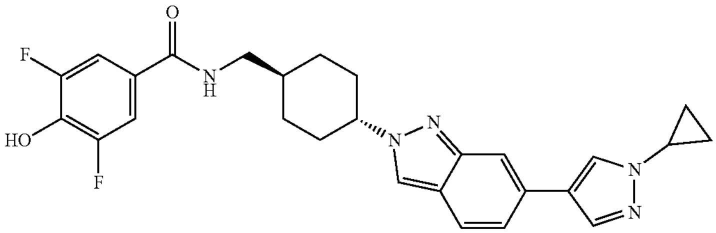 [SMILES: O=C(NC[C@H]1CC[C@H](n2cc3ccc(-c4cnn(C5CC5)c4)cc3n2)CC1)c1cc(F)c(O)c(F)c1] | N-({(1r,4r)-4-[6-(1-cyclopropyl-1H-pyrazol-4-yl)-2H-indazol-2-yl]cyclohexyl}methyl)-3,5-difluoro-4-hydroxybenzamide |
| 44 | 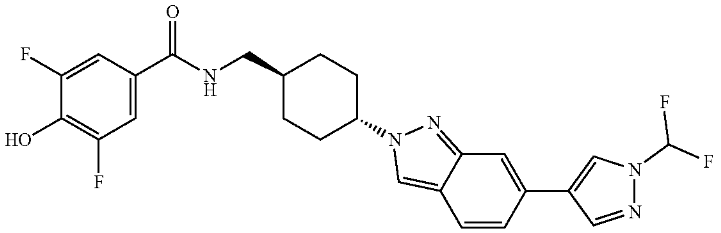 [SMILES: O=C(NC[C@H]1CC[C@H](n2cc3ccc(-c4cnn(C(F)F)c4)cc3n2)CC1)c1cc(F)c(O)c(F)c1] | N-{[(1r,4r)-4-{6-[1-(difluoromethyl)-1H-pyrazol-4-yl]-2H-indazol-2-yl}cyclohexyl]methyl}-3,5-difluoro-4-hydroxybenzamide |
| 45 | 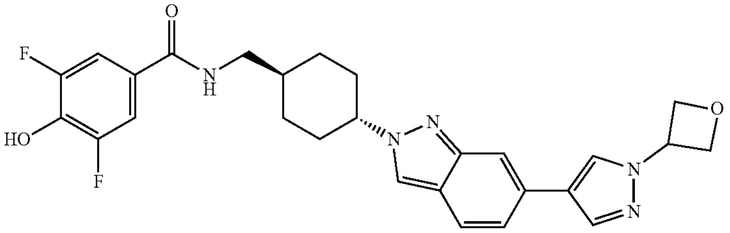 [SMILES: O=C(NC[C@H]1CC[C@H](n2cc3ccc(-c4cnn(C5COC5)c4)cc3n2)CC1)c1cc(F)c(O)c(F)c1] | 3,5-difluoro-4-hydroxy-N-{[(1r,4r)-4-{6-[1-(oxetan-3-yl)-1H-pyrazol-4-yl]-2H-indazol-2-yl}cyclohexyl]methyl}benzamide |
| 46 | 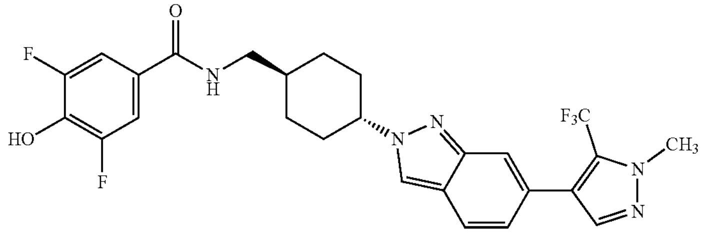 [SMILES: Cn1ncc(-c2ccc3cn([C@H]4CC[C@H](CNC(=O)c5cc(F)c(O)c(F)c5)CC4)nc3c2)c1C(F)(F)F] | 3,5-difluoro-4-hydroxy-N-{[(1r,4r)-4-{6-[1-methyl-5-(trifluoromethyl)-1H-pyrazol-4-yl]-2H-indazol-2-yl}cyclohexyl]methyl}benzamide |

TABLE 1-continued

Structure and IUPAC Name for Examples 1-214.

| Example | Structure | IUPAC Name |
| --- | --- | --- |
| 47 | 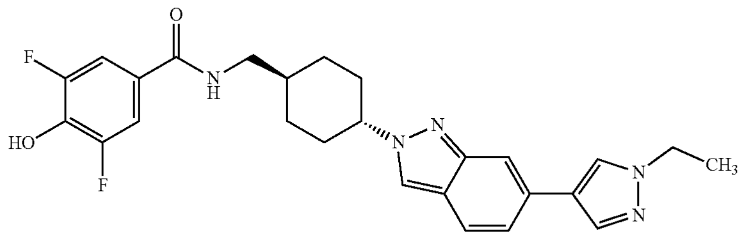 [SMILES: CCn1cc(-c2ccc3cn([C@H]4CC[C@H](CNC(=O)c5cc(F)c(O)c(F)c5)CC4)nc3c2)cn1] | N-({(1r,4r)-4-[6-(1-ethyl-1H-pyrazol-4-yl)-2H-indazol-2-yl]cyclohexyl}methyl)-3,5-difluoro-4-hydroxybenzamide |
| 48 | 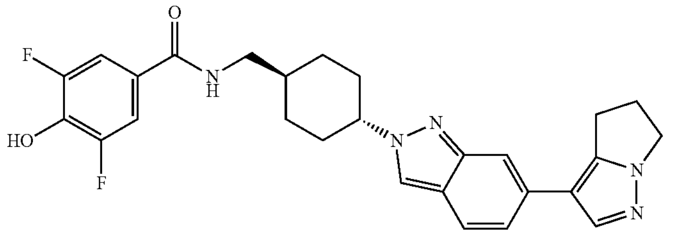 [SMILES: O=C(NC[C@H]1CC[C@H](n2cc3ccc(-c4cnn5c4CCC5)cc3n2)CC1)c1cc(F)c(O)c(F)c1] | N-({(1r,4r)-4-[6-(5,6-dihydro-4H-pyrrolo[1,2-b]pyrazol-3-yl)-2H-indazol-2-yl]cyclohexyl}methyl)-3,5-difluoro-4-hydroxybenzamide |
| 49 | 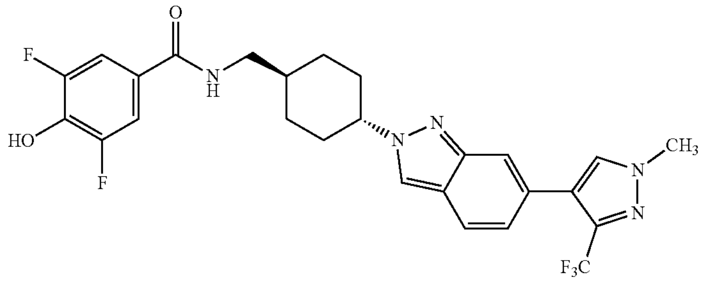 [SMILES: Cn1cc(-c2ccc3cn([C@H]4CC[C@H](CNC(=O)c5cc(F)c(O)c(F)c5)CC4)nc3c2)c(C(F)(F)F)n1] | 3,5-difluoro-4-hydroxy-N-{[(1r,4r)-4-{6-[1-methyl-3-(trifluoromethyl)-1H-pyrazol-4-yl]-2H-indazol-2-yl}cyclohexyl]methyl}benzamide |
| 50 | 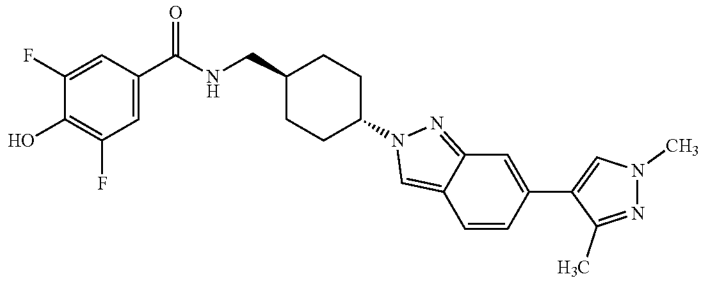 [SMILES: Cc1nn(C)cc1-c1ccc2cn([C@H]3CC[C@H](CNC(=O)c4cc(F)c(O)c(F)c4)CC3)nc2c1] | N-({(1r,4r)-4-[6-(1,3-dimethyl-1H-pyrazol-4-yl)-2H-indazol-2-yl]cyclohexyl}methyl)-3,5-difluoro-4-hydroxybenzamide |
| 51 | 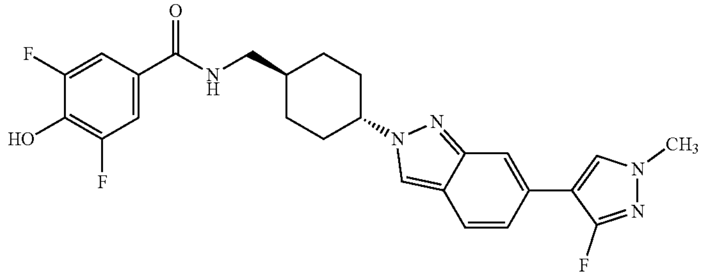 [SMILES: Cn1cc(-c2ccc3cn([C@H]4CC[C@H](CNC(=O)c5cc(F)c(O)c(F)c5)CC4)nc3c2)c(F)n1] | 3,5-difluoro-N-({(1r,4r)-4-[6-(3-fluoro-1-methyl-1H-pyrazol-4-yl)-2H-indazol-2-yl]cyclohexyl}methyl)-4-hydroxybenzamide |

TABLE 1-continued

| Structure and IUPAC Name for Examples 1-214. | | |
|---|---|---|
| Example | Structure | IUPAC Name |
| 52 | 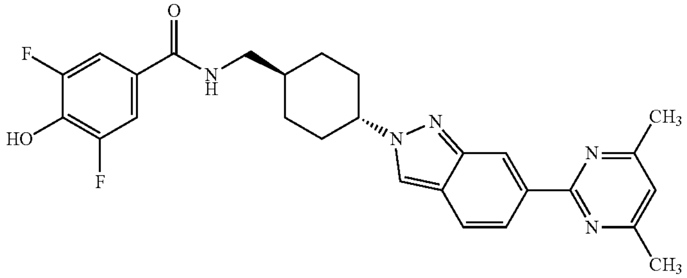 [SMILES: Cc1cc(C)nc(-c2ccc3cn([C@H]4CC[C@H](CNC(=O)c5cc(F)c(O)c(F)c5)CC4)nc3c2)n1] | N-({(1r,4r)-4-[6-(4,6-dimethylpyrimidin-2-yl)-2H-indazol-2-yl]cyclohexyl}methyl)-3,5-difluoro-4-hydroxybenzamide |
| 53 | 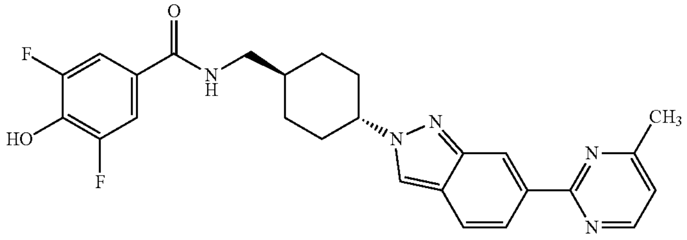 [SMILES: Cc1ccnc(-c2ccc3cn([C@H]4CC[C@H](CNC(=O)c5cc(F)c(O)c(F)c5)CC4)nc3c2)n1] | 3,5-difluoro-4-hydroxy-N-({(1r,4r)-4-[6-(4-methylpyrimidin-2-yl)-2H-indazol-2-yl]cyclohexyl}methyl)benzamide |
| 54 | 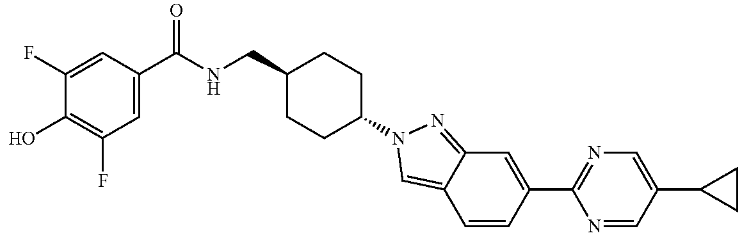 [SMILES: O=C(NC[C@H]1CC[C@H](n2cc3ccc(-c4ncc(C5CC5)cn4)cc3n2)CC1)c1cc(F)c(O)c(F)c1] | N-({(1r,4r)-4-[6-(5-cyclopropylpyrimidin-2-yl)-2H-indazol-2-yl]cyclohexyl}methyl)-3,5-difluoro-4-hydroxybenzamide |
| 55 | 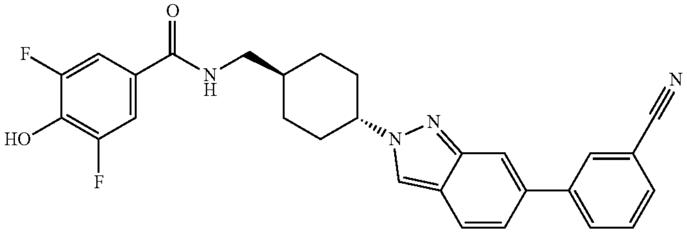 [SMILES: N#Cc1cccc(-c2ccc3cn([C@H]4CC[C@H](CNC(=O)c5cc(F)c(O)c(F)c5)CC4)nc3c2)c1] | N-({(1r,4r)-4-[6-(3-cyanophenyl)-2H-indazol-2-yl]cyclohexyl}methyl)-3,5-difluoro-4-hydroxybenzamide |
| 56 | 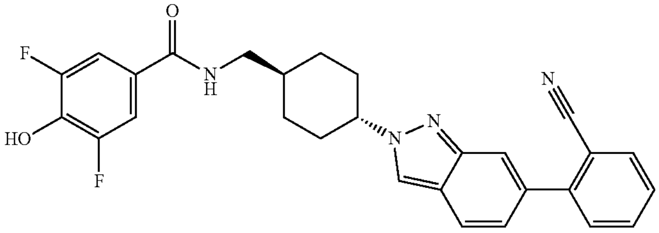 [SMILES: N#Cc1ccccc1-c1ccc2cn([C@H]3CC[C@H](CNC(=O)c4cc(F)c(O)c(F)c4)CC3)nc2c1] | N-({(1r,4r)-4-[6-(2-cyanophenyl)-2H-indazol-2-yl]cyclohexyl}methyl)-3,5-difluoro-4-hydroxybenzamide |
| 57 | 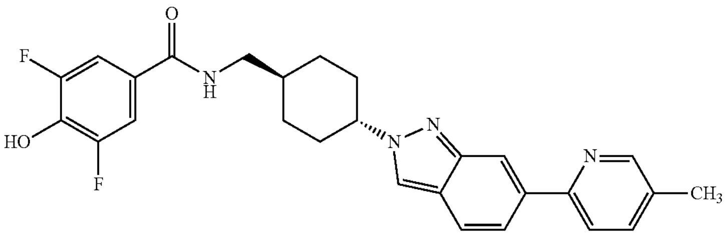 [SMILES: Cc1ccc(-c2ccc3cn([C@H]4CC[C@H](CNC(=O)c5cc(F)c(O)c(F)c5)CC4)nc3c2)nc1] | 3,5-difluoro-4-hydroxy-N-({(1r,4r)-4-[6-(5-methylpyridin-2-yl)-2H-indazol-2-yl]cyclohexyl}methyl)benzamide |

TABLE 1-continued

| Example | Structure | IUPAC Name |
|---|---|---|
| | Structure and IUPAC Name for Examples 1-214. | |
| 58 | 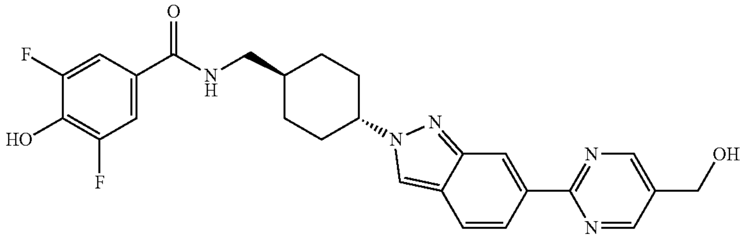 [SMILES: O=C(NC[C@H]1CC[C@H](n2cc3ccc(-c4ncc(CO)cn4)cc3n2)CC1)c1cc(F)c(O)c(F)c1] | 3,5-difluoro-4-hydroxy-N-{[(1r,4r)-4-{6-[5-(hydroxymethyl)pyrimidin-2-yl]-2H-indazol-2-yl}cyclohexyl]methyl}benzamide |
| 59 | 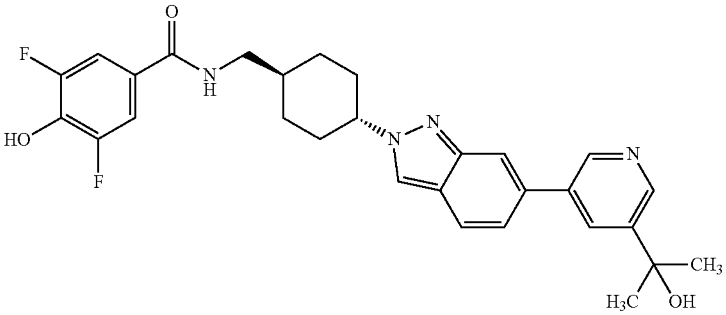 [SMILES: CC(C)(O)c1cncc(-c2ccc3cn([C@H]4CC[C@H](CNC(=O)c5cc(F)c(O)c(F)c5)CC4)nc3c2)c1] | 3,5-difluoro-4-hydroxy-N-{[(1r,4r)-4-{6-[5-(2-hydroxypropan-2-yl)pyridin-3-yl]-2H-indazol-2-yl}cyclohexyl]methyl}benzamide |
| 60 | 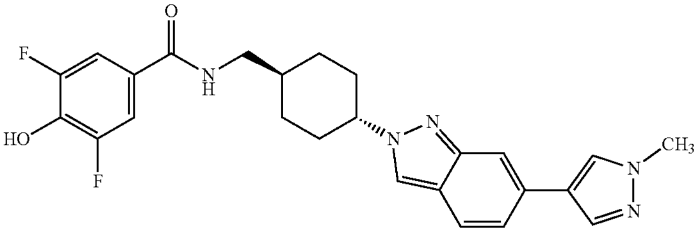 [SMILES: Cn1cc(-c2ccc3cn([C@H]4CC[C@H](CNC(=O)c5cc(F)c(O)c(F)c5)CC4)nc3c2)cn1] | 3,5-difluoro-4-hydroxy-N-({(1r,4r)-4-[6-(1-methyl-1H-pyrazol-4-yl)-2H-indazol-2-yl]cyclohexyl}methyl)benzamide |
| 61 | 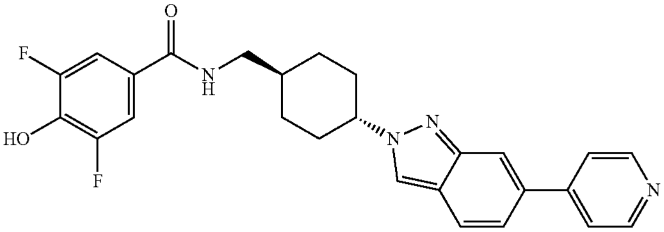 [SMILES: O=C(NC[C@H]1CC[C@H](n2cc3ccc(-c4ccncc4)cc3n2)CC1)c1cc(F)c(O)c(F)c1] | 3,5-difluoro-4-hydroxy-N-({(1r,4r)-4-[6-(pyridin-4-yl)-2H-indazol-2-yl]cyclohexyl}methyl)benzamide |
| 62 | 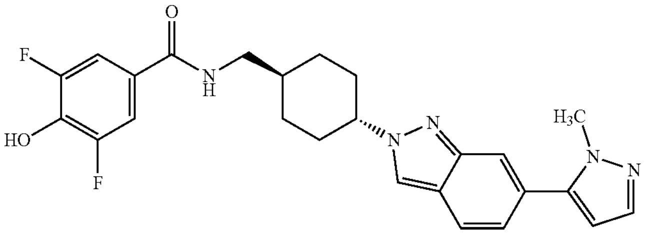 [SMILES: Cn1nccc1-c1ccc2cn([C@H]3CC[C@H](CNC(=O)c4cc(F)c(O)c(F)c4)CC3)nc2c1] | 3,5-difluoro-4-hydroxy-N-({(1r,4r)-4-[6-(1-methyl-1H-pyrazol-5-yl)-2H-indazol-2-yl]cyclohexyl}methyl)benzamide |
| 63 | 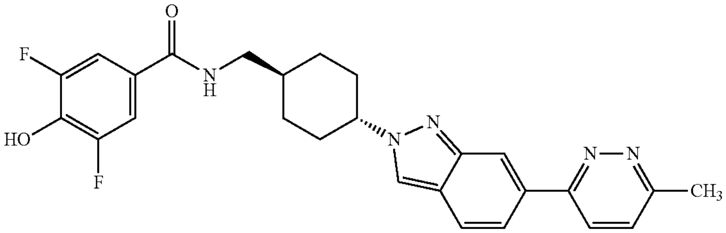 [SMILES: Cc1ccc(-c2ccc3cn([C@H]4CC[C@H](CNC(=O)c5cc(F)c(O)c(F)c5)CC4)nc3c2)nn1] | 3,5-difluoro-4-hydroxy-N-({(1r,4r)-4-[6-(6-methylpyridazin-3-yl)-2H-indazol-2-yl]cyclohexyl}methyl)benzamide |

TABLE 1-continued

| Example | Structure | IUPAC Name |
|---|---|---|
| 64 | 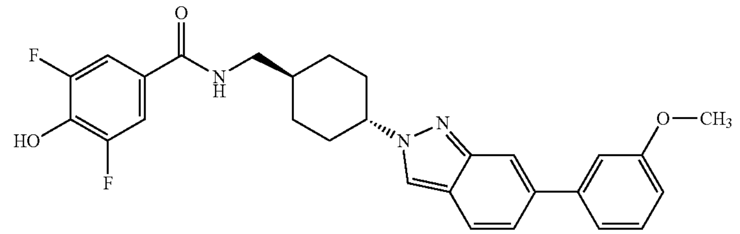 [SMILES: COc1cccc(-c2ccc3cn([C@H]4CC[C@H](CNC(=O)c5cc(F)c(O)c(F)c5)CC4)nc3c2)c1] | 3,5-difluoro-4-hydroxy-N-({(1r,4r)-4-[6-(3-methoxyphenyl)-2H-indazol-2-yl]cyclohexyl}methyl)benzamide |
| 65 | 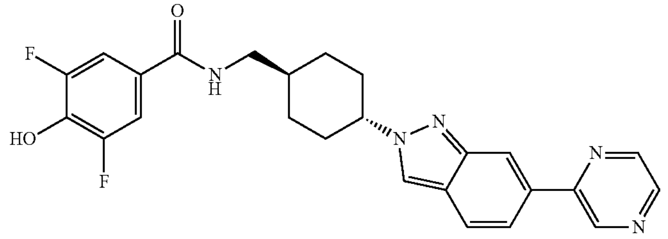 | 3,5-difluoro-4-hydroxy-N-({(1r,4r)-4-[6-(pyrazin-2-yl)-2H-indazol-2-yl]cyclohexyl}methyl)benzamide |
| 66 | 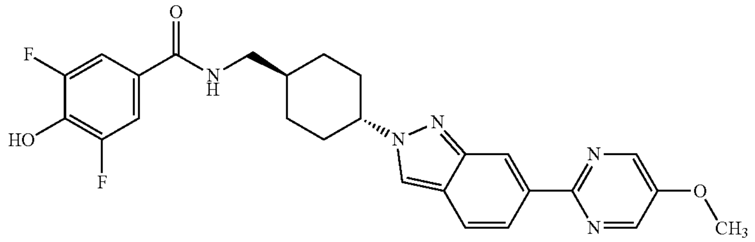 | 3,5-difluoro-4-hydroxy-N-({(1r,4r)-4-[6-(5-methoxypyrimidin-2-yl)-2H-indazol-2-yl]cyclohexyl}methyl)benzamide |
| 67 | 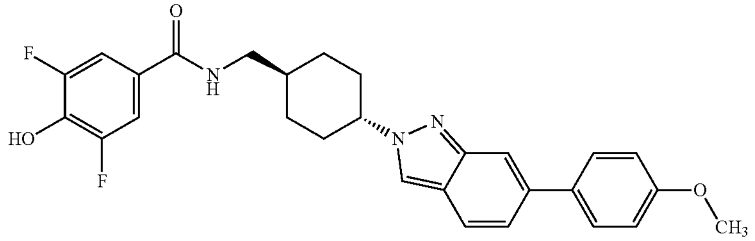 | 3,5-difluoro-4-hydroxy-N-({(1r,4r)-4-[6-(4-methoxyphenyl)-2H-indazol-2-yl]cyclohexyl}methyl)benzamide |
| 68 | 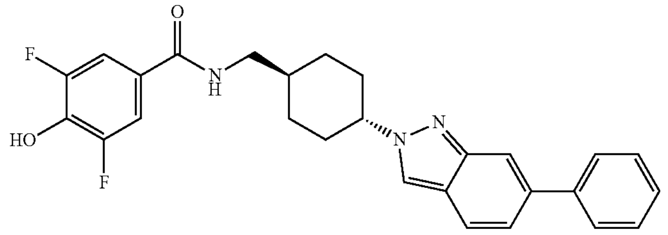 | 3,5-difluoro-4-hydroxy-N-{[(1r,4r)-4-(6-phenyl-2H-indazol-2-yl)cyclohexyl]methyl}benzamide |
| 69 | 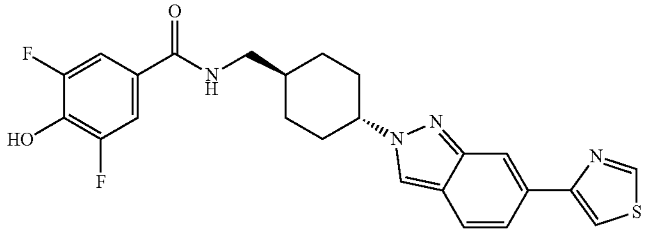 | 3,5-difluoro-4-hydroxy-N-({(1r,4r)-4-[6-(1,3-thiazol-4-yl)-2H-indazol-2-yl]cyclohexyl}methyl)benzamide |

Structure and IUPAC Name for Examples 1-214.

TABLE 1-continued

Structure and IUPAC Name for Examples 1-214.

| Example | Structure | IUPAC Name |
|---|---|---|
| 70 | 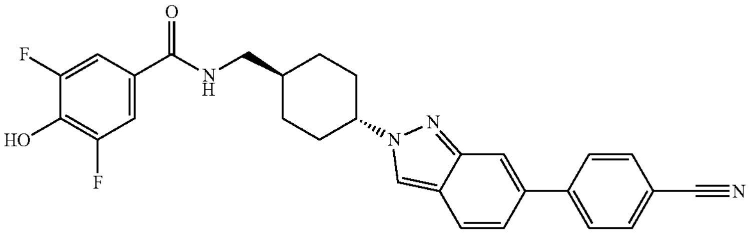 | N-({(1r,4r)-4-[6-(4-cyanophenyl)-2H-indazol-2-yl]cyclohexyl}methyl)-3,5-difluoro-4-hydroxybenzamide |
| 71 | 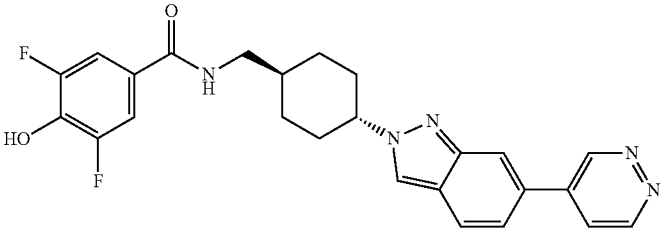 | 3,5-difluoro-4-hydroxy-N-({(1r,4r)-4-[6-(pyridazin-4-yl)-2H-indazol-2-yl]cyclohexyl}methyl)benzamide |
| 72 | 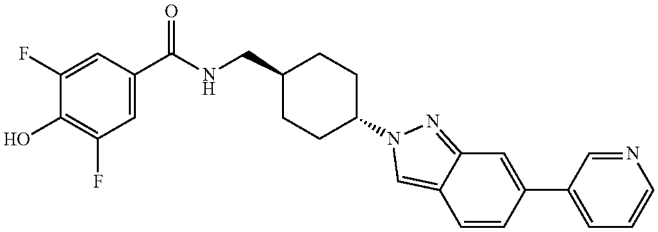 | 3,5-difluoro-4-hydroxy-N-({(1r,4r)-4-[6-(pyridin-3-yl)-2H-indazol-2-yl]cyclohexyl}methyl)benzamide |
| 73 | 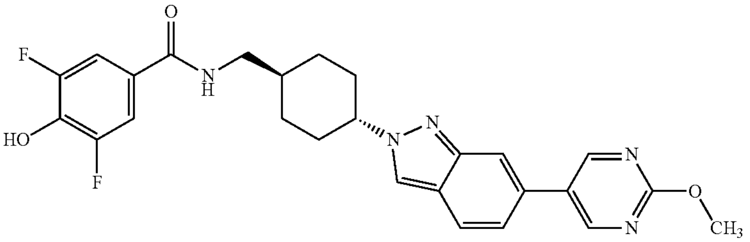 | 3,5-difluoro-4-hydroxy-N-({(1r,4r)-4-[6-(2-methoxypyrimidin-5-yl)-2H-indazol-2-yl]cyclohexyl}methyl)benzamide |
| 74 | 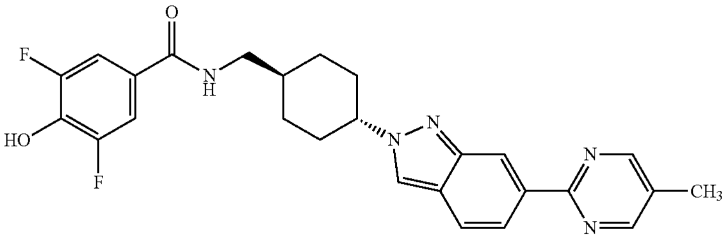 | 3,5-difluoro-4-hydroxy-N-({(1r,4r)-4-[6-(5-methylpyrimidin-2-yl)-2H-indazol-2-yl]cyclohexyl}methyl)benzamide |
| 75 | 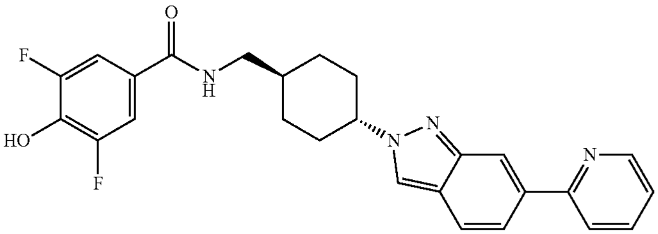 | 3,5-difluoro-4-hydroxy-N-({(1r,4r)-4-[6-(pyridin-2-yl)-2H-indazol-2-yl]cyclohexyl}methyl)benzamide |

TABLE 1-continued

| Structure and IUPAC Name for Examples 1-214. | | |
|---|---|---|
| Example | Structure | IUPAC Name |
| 76 | 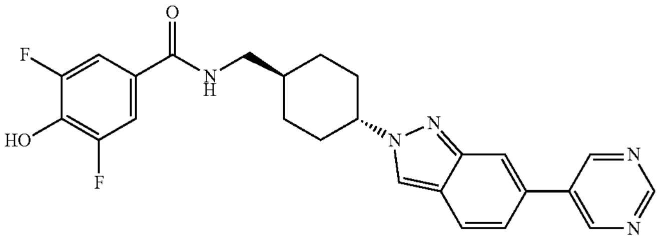 | 3,5-difluoro-4-hydroxy-N-({(1r,4r)-4-[6-(pyrimidin-5-yl)-2H-indazol-2-yl]cyclohexyl}methyl)benzamide |
| 77 | 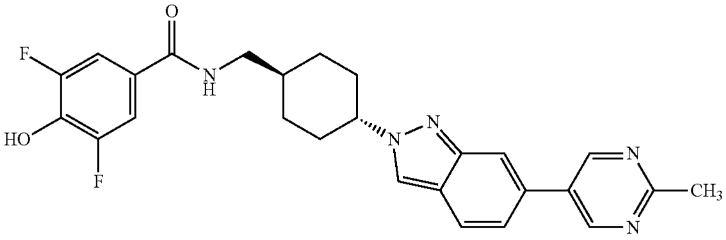 | 3,5-difluoro-4-hydroxy-N-({(1r,4r)-4-[6-(2-methylpyrimidin-5-yl)-2H-indazol-2-yl]cyclohexyl}methyl)benzamide |
| 78 | 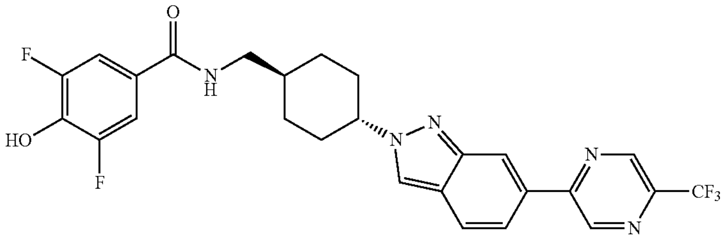 | 3,5-difluoro-4-hydroxy-N-{[(1r,4r)-4-{6-[5-(trifluoromethyl)pyrazin-2-yl]-2H-indazol-2-yl}cyclohexyl]methyl}benzamide |
| 79 | 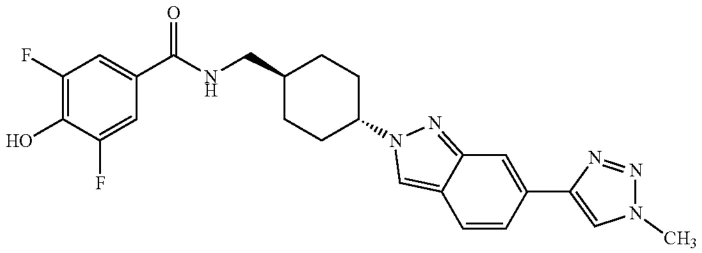 | 3,5-difluoro-4-hydroxy-N-({(1r,4r)-4-[6-(1-methyl-1H-1,2,3-triazol-4-yl)-2H-indazol-2-yl]cyclohexyl}methyl)benzamide |
| 80 | 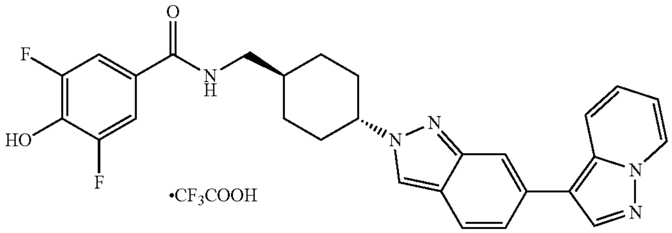 •$CF_3COOH$ | 3,5-difluoro-4-hydroxy-N-({(1r,4r)-4-[6-(pyrazolo[1,5-a]pyridin-3-yl)-2H-indazol-2-yl]cyclohexyl}methyl)benzamide, trifuoroacetate salt |
| 81 | 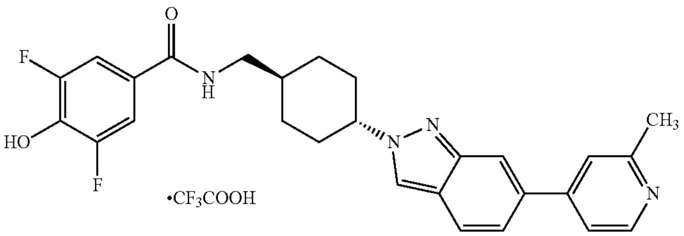 •$CF_3COOH$ | 3,5-difluoro-4-hydroxy-N-({(1r,4r)-4-[6-(2-methylpyridin-4-yl)-2H-indazol-2-yl]cyclohexyl}methyl)benzamide, trifluoroacetate salt |

TABLE 1-continued

Structure and IUPAC Name for Examples 1-214.

| Example | Structure | IUPAC Name |
|---|---|---|
| 82 | 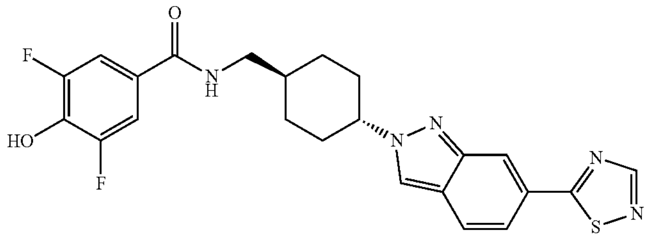 | 3,5-difluoro-4-hydroxy-N-({(1r,4r)-4-[6-(1,2,4-thiadiazol-5-yl)-2H-indazol-2-yl]cyclohexyl}methyl)benzamide |
| 83 | 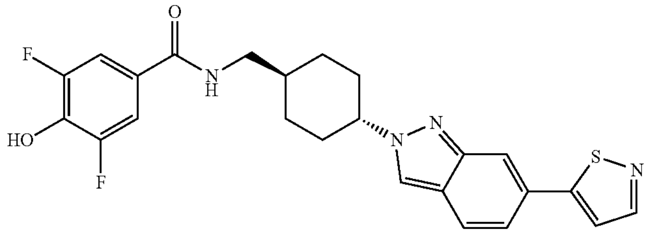 | 3,5-difluoro-4-hydroxy-N-({(1r,4r)-4-[6-(1,2-thiazol-5-yl)-2H-indazol-2-yl]cyclohexyl}methyl)benzamide |
| 84 | 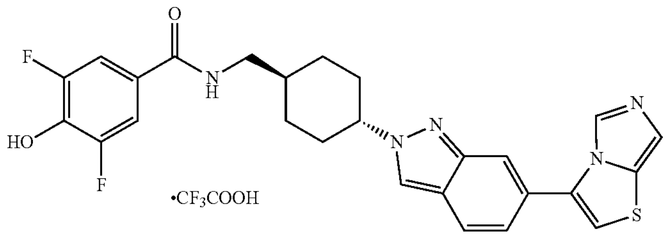 | 3,5-difluoro-4-hydroxy-N-({(1r,4r)-4-[6-(imidazo[5,1-b][1,3]thiazol-3-yl)-2H-indazol-2-yl]cyclohexyl}methyl)benzamide, trifluoroacetate salt |
| 85 | 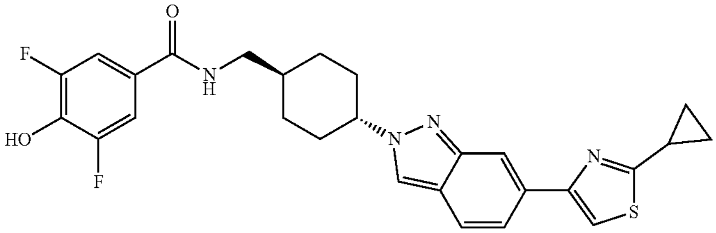 | N-({(1r,4r)-4-[6-(2-cyclopropyl-1,3-thiazol-4-yl)-2H-indazol-2-yl]cyclohexyl}methyl)-3,5-difluoro-4-hydroxybenzamide |
| 86 | 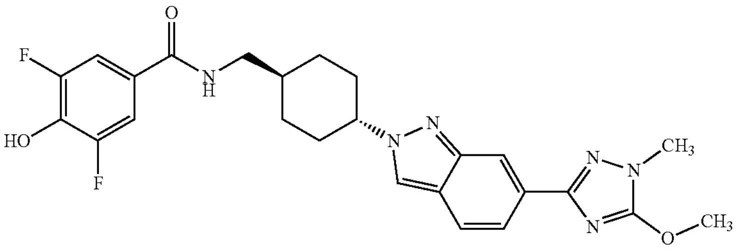 | 3,5-difluoro-4-hydroxy-N-({(1r,4r)-4-[6-(5-methoxy-1-methyl-1H-1,2,4-triazol-3-yl)-2H-indazol-2-yl]cyclohexyl}methyl)benzamide |
| 87 | 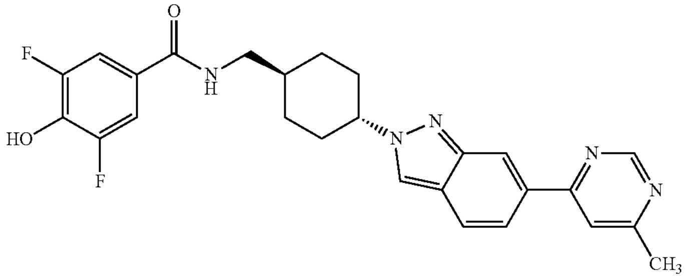 | 3,5-difluoro-4-hydroxy-N-({(1r,4r)-4-[6-(6-methylpyrimidin-4-yl)-2H-indazol-2-yl]cyclohexyl}methyl)benzamide |

TABLE 1-continued

Structure and IUPAC Name for Examples 1-214.

| Example | Structure | IUPAC Name |
|---|---|---|
| 88 | 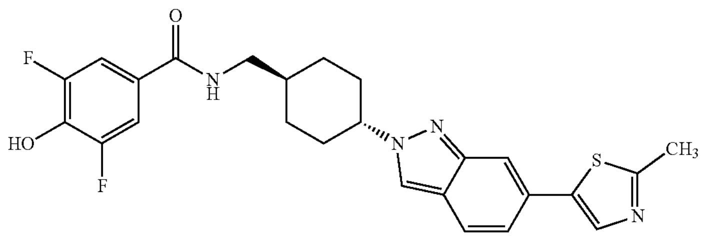 | 3,5-difluoro-4-hydroxy-N-({(1r,4r)-4-[6-(2-methyl-1,3-thiazol-5-yl)-2H-indazol-2-yl]cyclohexyl}methyl)benzamide |
| 89 | 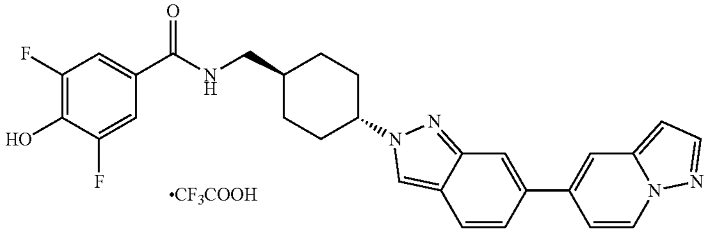 •$CF_3COOH$ | 3,5-difluoro-4-hydroxy-N-({(1r,4r)-4-[6-(pyrazolo[1,5-a]pyridin-5-yl)-2H-indazol-2-yl]cyclohexyl}methyl)benzamide, trifluoroacetate salt |
| 90 | 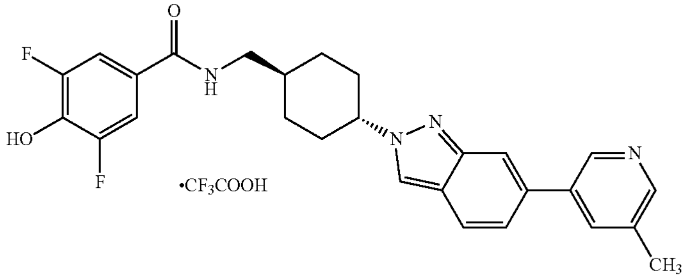 •$CF_3COOH$ | 3,5-difluoro-4-hydroxy-N-({(1r,4r)-4-[6-(5-methylpyridin-3-yl)-2H-indazol-2-yl]cyclohexyl}methyl)benzamide, trifluoroacetate salt |
| 91 | 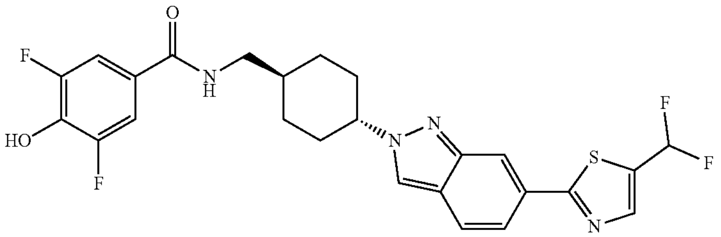 | N-{[(1r,4r)-4-{6-[5-(difluoromethyl)-1,3-thiazol-2-yl]-2H-indazol-2-yl}cyclohexyl]methyl}-3,5-difluoro-4-hydroxybenzamide |
| 92 | 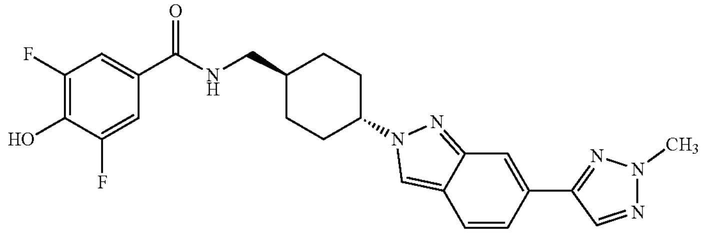 | 3,5-difluoro-4-hydroxy-N-({(1r,4r)-4-[6-(2-methyl-2H-1,2,3-triazol-4-yl)-2H-indazol-2-yl]cyclohexyl}methyl)benzamide |

TABLE 1-continued

| Structure and IUPAC Name for Examples 1-214. | | |
|---|---|---|
| Example | Structure | IUPAC Name |
| 93 | 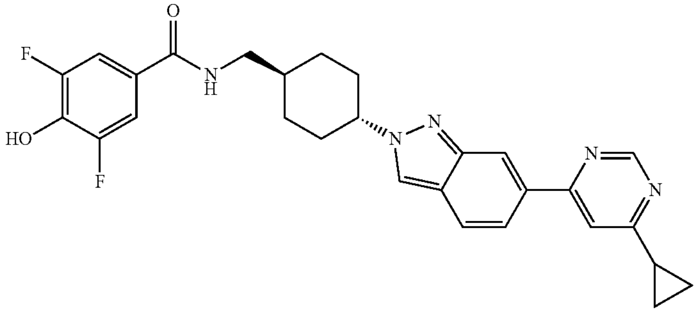 | N-({(1r,4r)-4-[6-(6-cyclopropylpyrimidin-4-yl)-2H-indazol-2-yl]cyclohexyl}methyl)-3,5-difluoro-4-hydroxybenzamide |
| 94 | 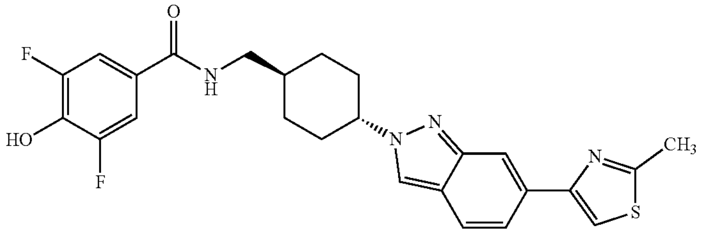 | 3,5-difluoro-4-hydroxy-N-({(1r,4r)-4-[6-(2-methyl-1,3-thiazol-4-yl)-2H-indazol-2-yl]cyclohexyl}methyl)benzamide |
| 95 | 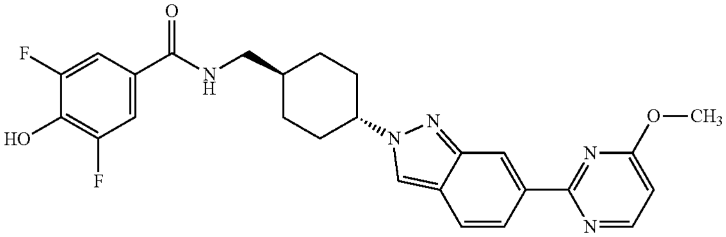 | 3,5-difluoro-4-hydroxy-N-({(1r,4r)-4-[6-(4-methoxypyrimidin-2-yl)-2H-indazol-2-yl]cyclohexyl}methyl)benzamide |
| 96 | 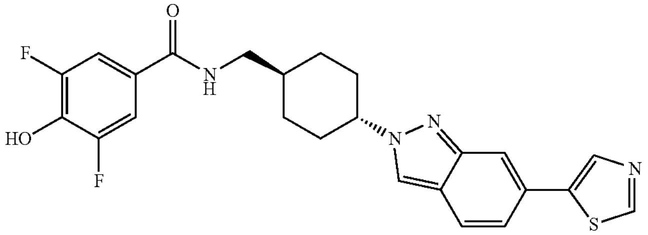 | 3,5-difluoro-4-hydroxy-N-({(1r,4r)-[6-(1,3-thiazol-5-yl)-2H-indazol-2-yl]cyclohexyl}methyl)benzamide |
| 97 | 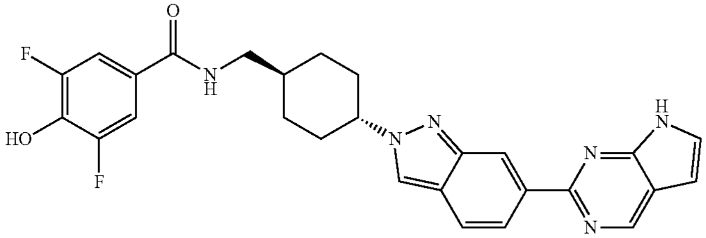 | 3,5-difluoro-4-hydroxy-N-({(1r,4r)-4-[6-(7H-pyrrolo[2,3-d]pyrimidin-2-yl)-2H-indazol-2-yl]cyclohexyl}methyl)benzamide |
| 98 | 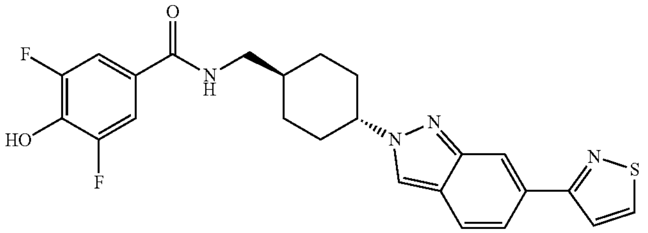 | 3,5-difluoro-4-hydroxy-N-({(1r,4r)-4-[6-(1,2-thiazol-3-yl)-2H-indazol-2-yl]cyclohexyl}methyl)benzamide |

TABLE 1-continued

| Structure and IUPAC Name for Examples 1-214. | | |
|---|---|---|
| Example | Structure | IUPAC Name |
| 99 | 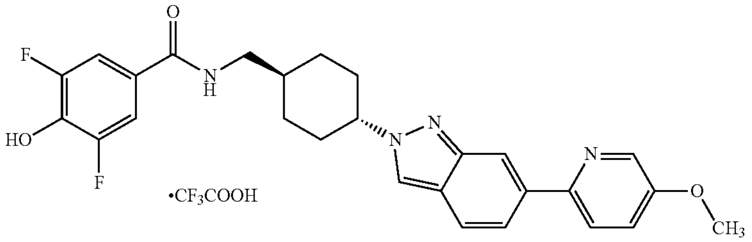 | 3,5-difluoro-4-hydroxy-N-({(1r,4r)-4-[6-(5-methoxy-pyridin-2-yl)-2H-indazol-2-yl] cyclohexyl}methyl) benzamide, trifluoroacetate salt |
| 100 | 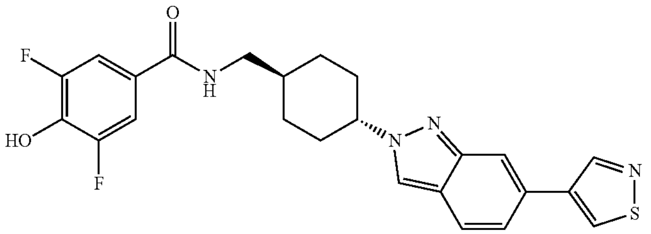 | 3,5-difluoro-4-hydroxy-N-({(1r,4r)-4-[6-(1,2-thiazol-4-yl)-2H-indazol-2-yl]cyclohexyl} methyl)benzamide |
| 101 | 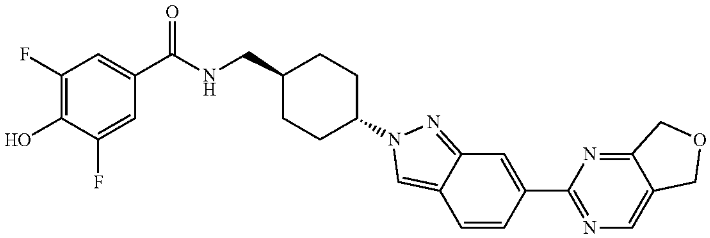 | N-({(1r,4r)-4-[6-(5,7-dihydrofuro[3,4-d] pyrimidin-2-yl)-2H-indazol-2-yl] cyclohexyl}methyl)-3,5-difluoro-4-hydroxybenzamide |
| 102 | 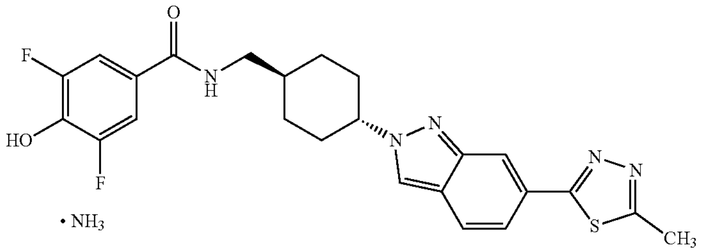 | 3,5-difluoro-4-hydroxy-N-({(1r,4r)-4-[6-(5-methyl-1,3,4-thiadiazol-2-yl)-2H-indazol-2-yl] cyclohexyl}methyl) benzamide, ammonium salt |
| 103 | 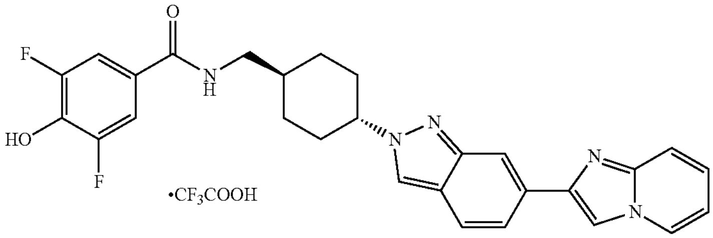 | 3,5-difluoro-4-hydroxy-N-({(1r,4r)-4-[6-(imidazo[1,2-a] pyridin-2-yl)-2H-indazol-2-yl] cyclohexyl}methyl) benzamide, trifluoroacetate salt |
| 104 | 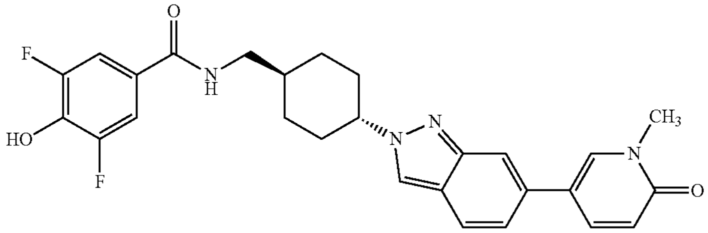 | 3,5-difluoro-4-hydroxy-N-({(1r,4r)-4-[6-(1-methyl-6-oxo-1,6-dihydropyridin-3-yl)-2H-indazol-2-yl]cyclohexyl}methyl) benzamide |

TABLE 1-continued

| Structure and IUPAC Name for Examples 1-214. | | |
|---|---|---|
| Example | Structure | IUPAC Name |
| 105 | 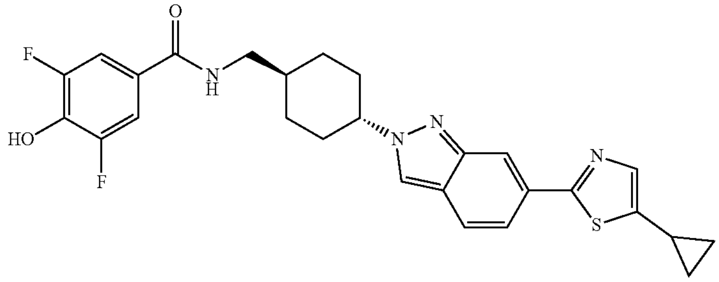 | N-({(1r,4r)-4-[6-(5-cyclopropyl-1,3-thiazol-2-yl)-2H-indazol-2-yl]cyclohexyl}methyl)-3,5-difluoro-4-hydroxybenzamide |
| 106 | 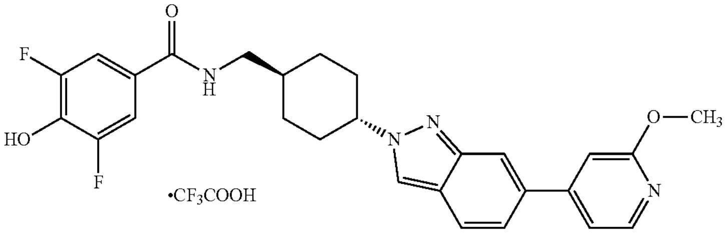 •CF₃COOH | 3,5-difluoro-4-hydroxy-N-({(1r,4r)-4-[6-(2-methoxypyridin-4-yl)-2H-indazol-2-yl]cyclohexyl}methyl)benzamide, trifluoroacetate salt |
| 107 | 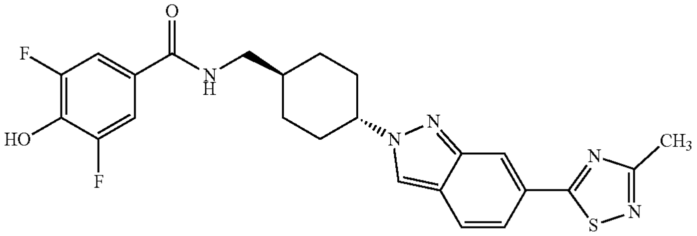 | 3,5-difluoro-4-hydroxy-N-({(1r,4r)-4-[6-(3-methyl-1,2,4-thiadiazol-5-yl)-2H-indazol-2-yl]cyclohexyl}methyl)benzamide |
| 108 | 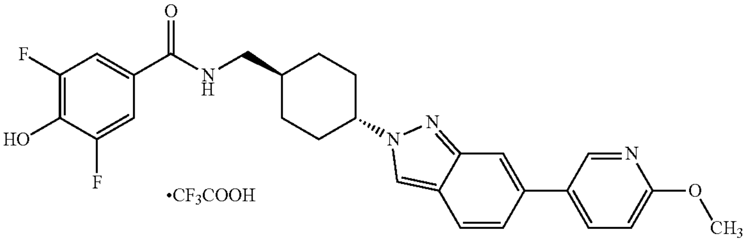 •CF₃COOH | 3,5-difluoro-4-hydroxy-N-({(1r,4r)-4-[6-(6-methoxy-pyridin-3-yl)-2H-indazol-2-yl]cyclohexyl}methyl)benzamide, trifluoroacetate salt |
| 109 | 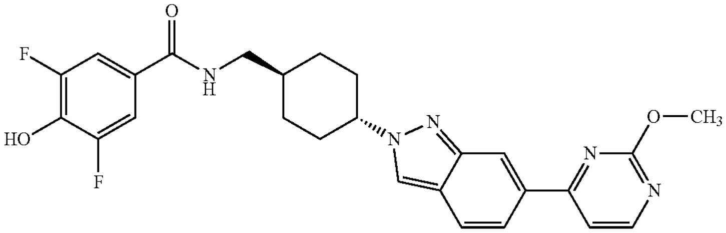 | 3,5-difluoro-4-hydroxy-N-({(1r,4r)-4-[6-(2-methoxy-pyrimidin-4-yl)-2H-indazol-2-yl]cyclohexyl}methyl)benzamide |
| 110 | 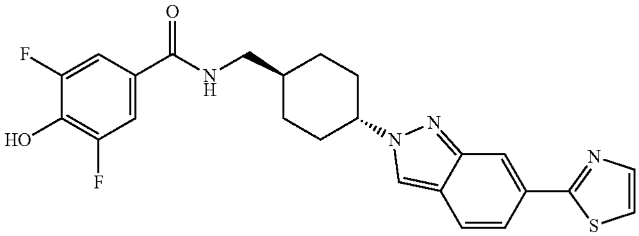 | 3,5-difluoro-4-hydroxy-N-({(1r,4r)-4-[6-(1,3-thiazol-2-yl)-2H-indazol-2-yl]cyclohexyl}methyl)benzamide |

TABLE 1-continued

| Structure and IUPAC Name for Examples 1-214. | | |
|---|---|---|
| Example | Structure | IUPAC Name |
| 111 | 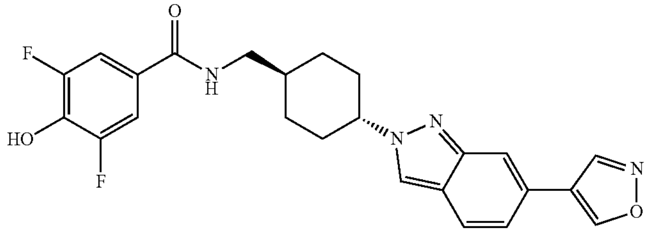 | 3,5-difluoro-4-hydroxy-N-({(1r,4r)-4-[6-(1,2-oxazol-4-yl)-2H-indazol-2-yl]cyclohexyl}methyl) benzamide |
| 112 | 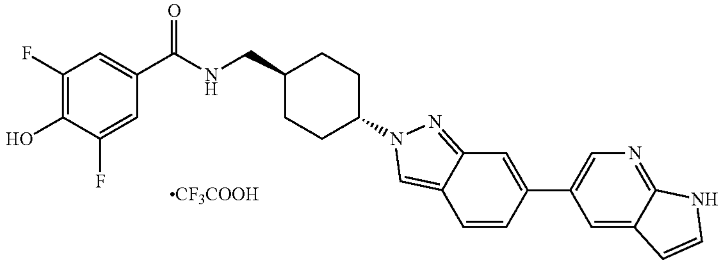 •$CF_3COOH$ | 3,5-difluoro-4-hydroxy-N-({(1r,4r)-4-[6-(1H-pyrrolo[2,3-b] pyridin-5-yl)-2H-indazol-2-yl] cyclohexyl}methyl) benzamide, trifluoroacetate salt |
| 113 | 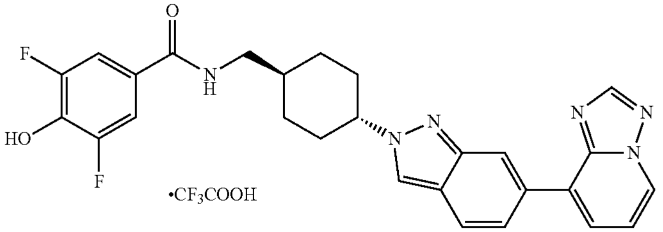 •$CF_3COOH$ | 3,5-difluoro-4-hydroxy-N-({(1r,4r)-4-[6-([1,2,4]triazolo[1,5-a] pyridin-8-yl)-2H-indazol-2-yl] cyclohexyl}methyl) benzamide, trifluoroacetate salt |
| 114 | 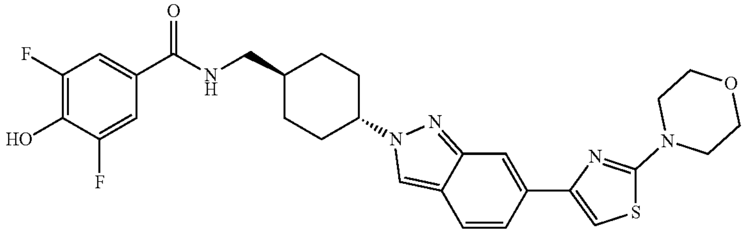 | 3,5-difluoro-4-hydroxy-N-{[(1r,4r)-4-{6-[2-(morpholin-4-yl)-1,3-thiazol-4-yl]-2H-indazol-2-yl}cyclohexyl]methyl} benzamide |
| 115 | 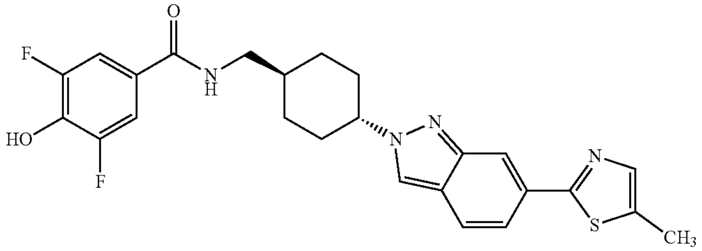 | 3,5-difluoro-4-hydroxy-N-({(1r,4r)-4-[6-(5-methyl-1,3-thiazol-2-yl)-2H-indazol-2-yl]cyclohexyl}methyl) benzamide |
| 116 | 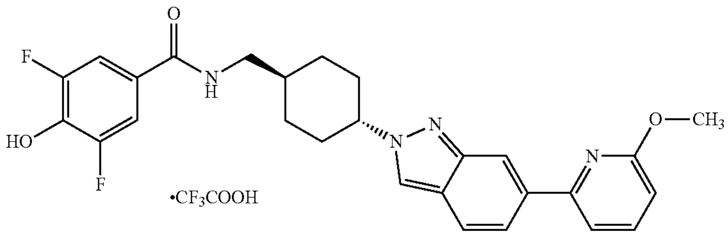 •$CF_3COOH$ | 3,5-difluoro-4-hydroxy-N-({(1r,4r)-4-[6-(6-methoxy-pyridin-2-yl)-2H-indazol-2-yl] cyclohexyl}methyl) benzamide, trifluoroacetate salt |

TABLE 1-continued

Structure and IUPAC Name for Examples 1-214.

| Example | Structure | IUPAC Name |
| --- | --- | --- |
| 117 | 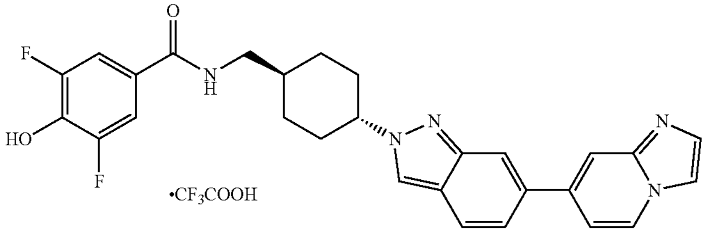 $\cdot CF_3COOH$ | 3,5-difluoro-4-hydroxy-N-({(1r,4r)-4-[6-(imidazo[1,2-a]pyridin-7-yl)-2H-indazol-2-yl]cyclohexyl}methyl)benzamide, trifluoroacetate salt |
| 118 | 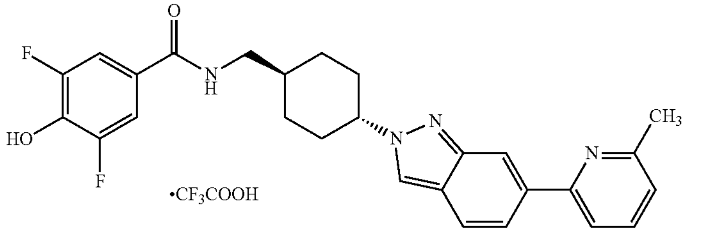 $\cdot CF_3COOH$ | 3,5-difluoro-4-hydroxy-N-({(1r,4r)-4-[6-(6-methylpyridin-2-yl)-2H-indazol-2-yl]cyclohexyl}methyl)benzamide, trifluoroacetate salt |
| 119 | 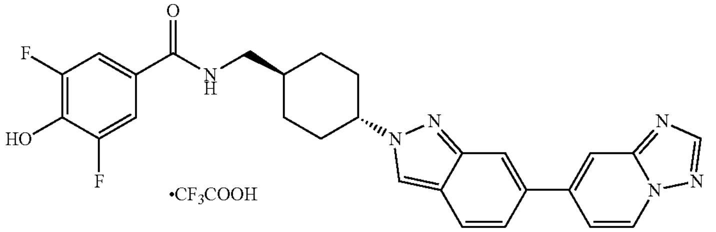 $\cdot CF_3COOH$ | 3,5-difluoro-4-hydroxy-N-({(1r,4r)-4-[6-([1,2,4]triazolo[1,5-a]pyridin-7-yl)-2H-indazol-2-yl]cyclohexyl}methyl)benzamide, trifluoroacetate salt |
| 120 | 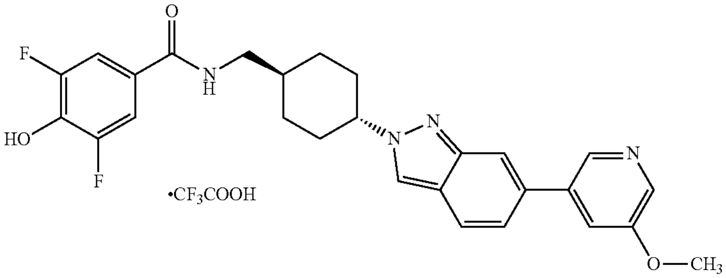 $\cdot CF_3COOH$ | 3,5-difluoro-4-hydroxy-N-({(1r,4r)-4-[6-(5-methoxypyridin-3-yl)-2H-indazol-2-yl]cyclohexyl}methyl)benzamide, trifluoroacetate salt |
| 121 | 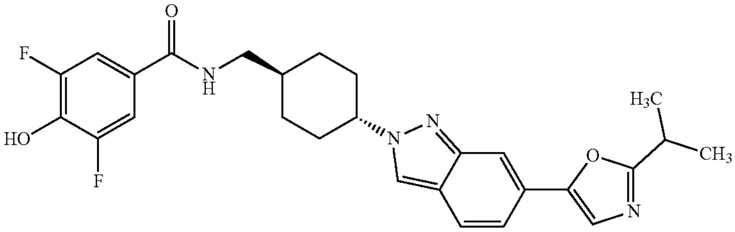 | 3,5-difluoro-4-hydroxy-N-{[(1r,4r)-4-{6-[2-(propan-2-yl)-1,3-oxazol-5-yl]-2H-indazol-2-yl}cyclohexyl]methyl}benzamide |
| 122 | 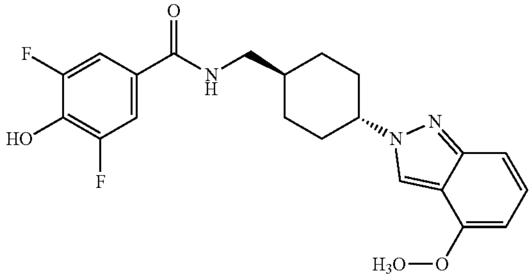 | 3,5-difluoro-4-hydroxy-N-{[(1r,4r)-4-(4-methoxy-2H-indazol-2-yl)cyclohexyl]methyl}benzamide |

TABLE 1-continued

Structure and IUPAC Name for Examples 1-214.

| Example | Structure | IUPAC Name |
| --- | --- | --- |
| 123 | 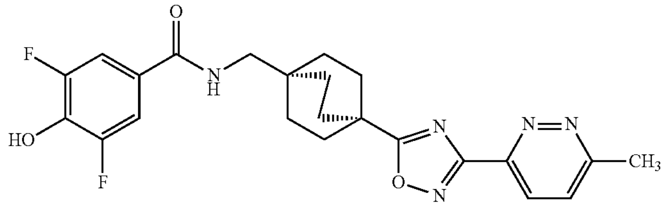 | 3,5-difluoro-4-hydroxy-N-({4-[3-(6-methylpyridazin-3-yl)-1,2,4-oxadiazol-5-yl]bicyclo[2.2.2]octan-1-yl}methyl)benzamide |
| 124 | 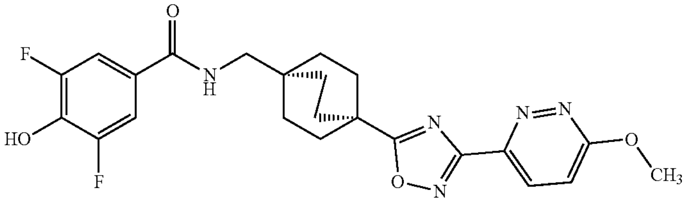 | 3,5-difluoro-4-hydroxy-N-({4-[3-(6-methoxypyridazin-3-yl)-1,2,4-oxadiazol-5-yl]bicyclo[2.2.2]octan-1-yl}methyl)benzamide |
| 125 | 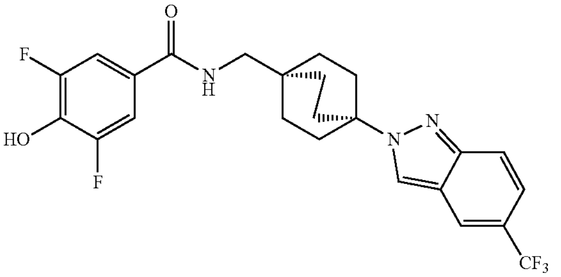 | 3,5-difluoro-4-hydroxy-N-({4-[5-(trifluoromethyl)-2H-indazol-2-yl]bicyclo[2.2.2]octan-1-yl}methyl)benzamide |
| 126 | 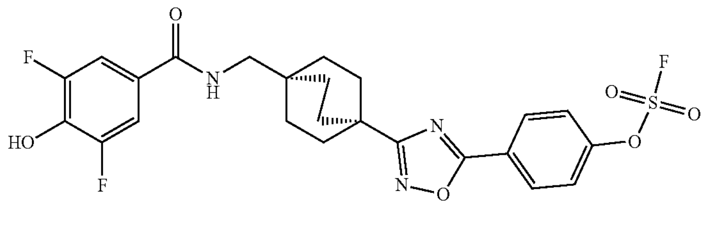 | 4-(3-{4-[(3,5-difluoro-4-hydroxybenzamido)methyl]bicyclo[2.2.2]octan-1-yl}-1,2,4-oxadiazol-5-yl)phenyl sulfurofluoridate |
| 127 | 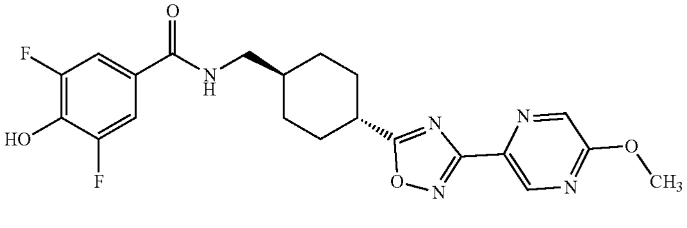 | 3,5-difluoro-4-hydroxy-N-({(1r,4r)-4-[3-(5-methoxy-pyrazin-2-yl)-1,2,4-oxadiazol-5-yl]cyclohexyl}methyl)benzamide |
| 128 | 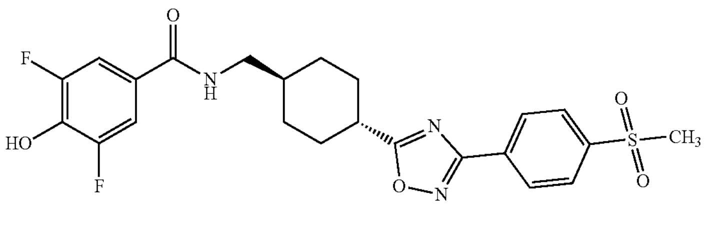 | 3,5-difluoro-4-hydroxy-N-{[(1r,4r)-4-{3-[4-(methanesulfonyl)phenyl]-1,2,4-oxadiazol-5-yl}cyclohexyl]methyl}benzamide |

TABLE 1-continued

| Structure and IUPAC Name for Examples 1-214. | | |
|---|---|---|
| Example | Structure | IUPAC Name |
| 129 | 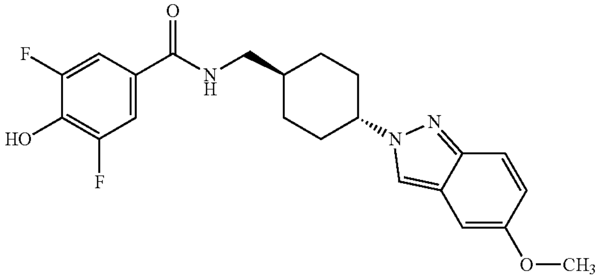 | 3,5-difluoro-4-hydroxy-N-{[(1r,4r)-4-(5-methoxy-2H-indazol-2-yl)cyclohexyl]methyl}benzamide |
| 130 | 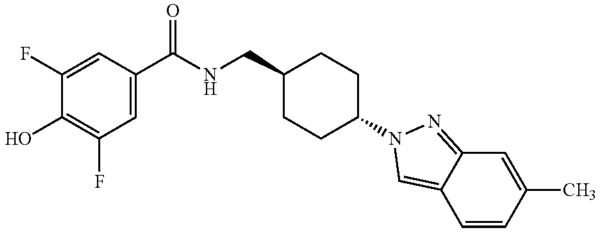 | 3,5-difluoro-4-hydroxy-N-{[(1r,4r)-4-(6-methyl-2H-indazol-2-yl)cyclohexyl]methyl}benzamide |
| 131 | 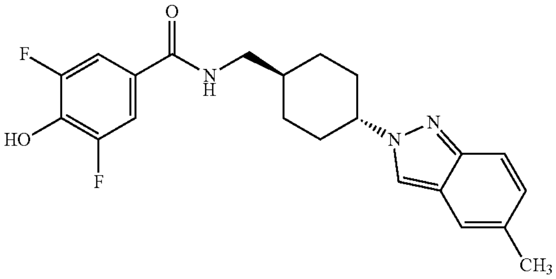 | 3,5-difluoro-4-hydroxy-N-{[(1r,4r)-4-(5-methyl-2H-indazol-2-yl)cyclohexyl]methyl}benzamide |
| 132 | 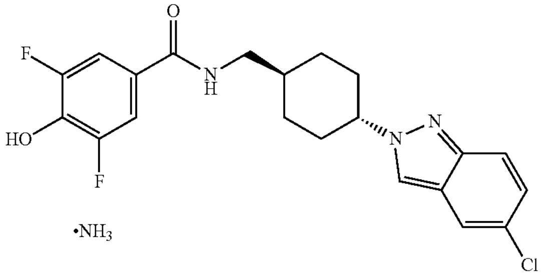 | N-{[(1r,4r)-4-(5-chloro-2H-indazol-2-yl)cyclohexyl]methyl}-3,5-difluoro-4-hydroxybenzamide, ammonium salt |
| 133 | 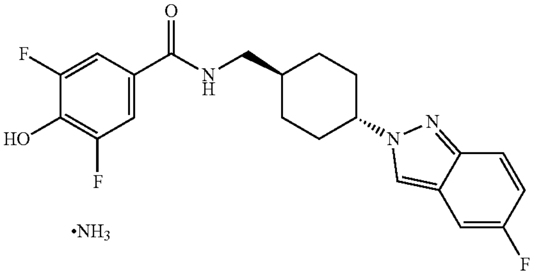 | 3,5-difluoro-N-{[(1r,4r)-4-(5-fluoro-2H-indazol-2-yl)cyclohexyl]methyl}-4-hydroxybenzamide, ammonium salt |

TABLE 1-continued

Structure and IUPAC Name for Examples 1-214.

| Example | Structure | IUPAC Name |
|---|---|---|
| 134 | 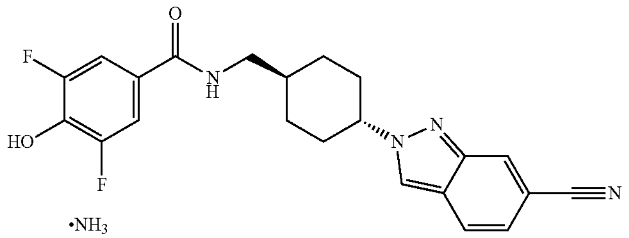 | N-{[(1r,4r)-4-(6-cyano-2H-indazol-2-yl)cyclohexyl]methyl}-3,5-difluoro-4-hydroxybenzamide, ammonium salt |
| 135 | 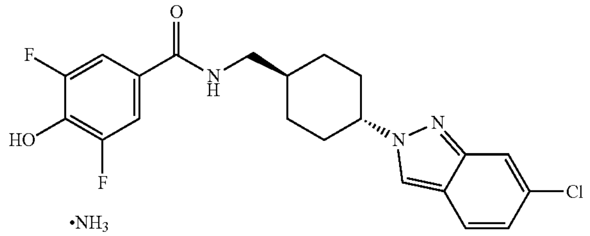 | N-{[(1r,4r)-4-(6-chloro-2H-indazol-2-yl)cyclohexyl]methyl}-3,5-difluoro-4-hydroxybenzamide, ammonium salt |
| 136 | 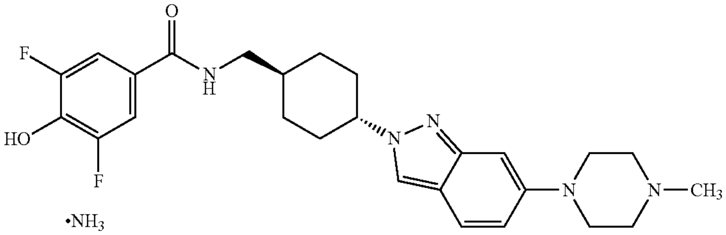 | 3,5-difluoro-4-hydroxy-N-({(1r,4r)-4-[6-(4-methyl-piperazin-1-yl)-2H-indazol-2-yl] cyclohexyl}methyl) benzamide, ammonium salt |
| 137 | 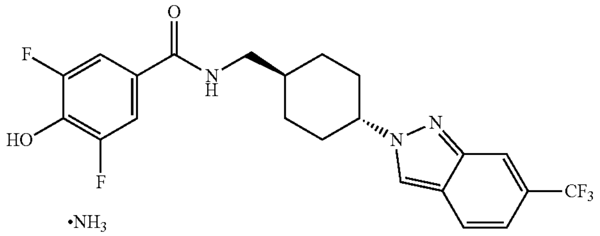 | 3,5-difluoro-4-hydroxy-N-({(1r,4r)-4-[6-(trifluoromethyl)-2H-indazol-2-yl]cyclohexyl}methyl) benzamide, ammonium salt |
| 138 | 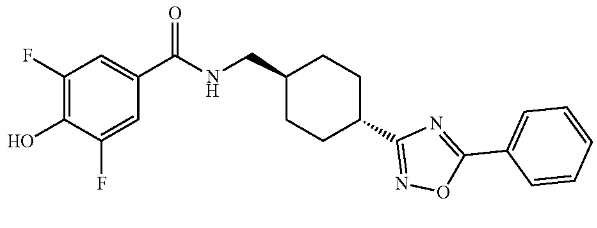 | 3,5-difluoro-4-hydroxy-N-{[(1r,4r)-4-(5-phenyl-1,2,4-oxadiazol-3-yl)cyclohexyl] methyl}benzamide |
| 139 | 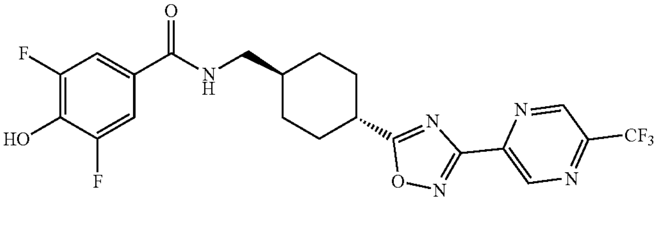 | 3,5-difluoro-4-hydroxy-N-{[(1r,4r)-4-{3-[5-(trifluoromethyl) pyrazin-2-yl]-1,2,4-oxadiazol-5-yl}cyclohexyl]methyl} benzamide |

TABLE 1-continued

| Example | Structure | IUPAC Name |
|---|---|---|
| 140 | 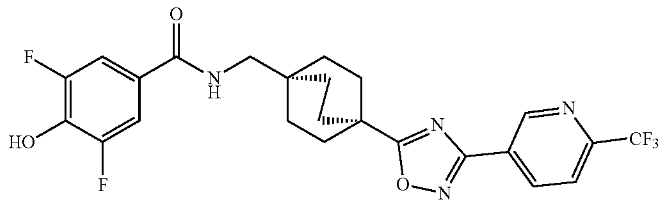 [SMILES: O=C(NC[C@]12CC[C@](c3nc(-c4ccc(C(F)(F)F)nc4)no3)(CC1)CC2)c1cc(F)c(O)c(F)c1] | 3,5-difluoro-4-hydroxy-N-[(4-{3-[6-(trifluoromethyl) pyridin-3-yl]-1,2,4-oxadiazol-5-yl}bicyclo[2.2.2] octan-1-yl)methyl] benzamide |
| 141 | 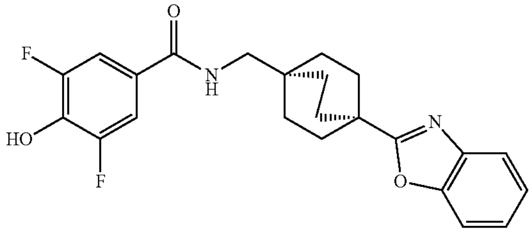 [SMILES: O=C(NC[C@]12CC[C@](c3nc4ccccc4o3)(CC1)CC2)c1cc(F)c(O)c(F)c1] | N-{[4-(1,3-benzoxazol-2-yl) bicyclo[2.2.2]octan-1-yl]methyl}-3,5-difluoro-4-hydroxybenzamide |
| 142 | 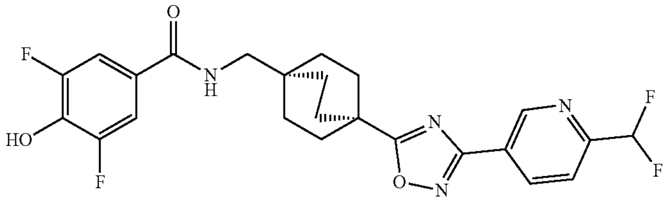 [SMILES: O=C(NC[C@]12CC[C@](c3nc(-c4ccc(C(F)F)nc4)no3)(CC1)CC2)c1cc(F)c(O)c(F)c1] | N-[(4-{3-[6-(difluoromethyl) pyridin-3-yl]-1,2,4-oxadiazol-5-yl} bicyclo[2.2.2]octan-1-yl)methyl]-3,5-difluoro-4-hydroxybenzamide |
| 143 | 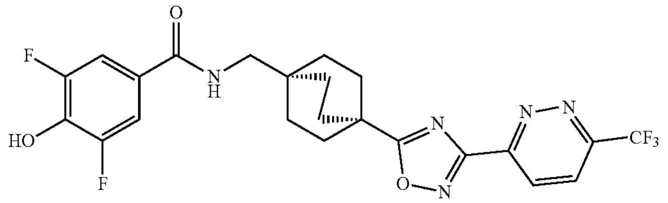 [SMILES: O=C(NC[C@]12CC[C@](c3nc(-c4ccc(C(F)(F)F)nn4)no3)(CC1)CC2)c1cc(F)c(O)c(F)c1] | 3,5-difluoro-4-hydroxy-[(4-{3-[6-(trifluoromethyl) pyridazin-3-yl]-1,2,4-oxadiazol-5-yl} bicyclo[2.2.2]octan-1-yl)methyl]benzamide |
| 144 | 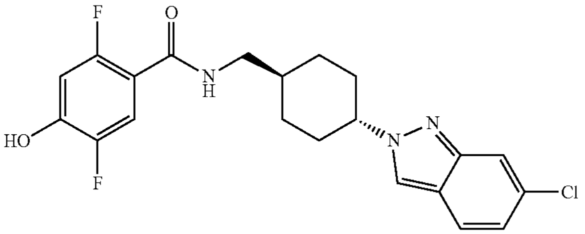 •$CF_3COOH$ | N-{[(1r,4r)-4-(6-chloro-2H-indazol-2-yl)cyclohexyl] methyl}-2,5-difluoro-4-hydroxybenzamide, trifluoroacetate salt |
| 145 | 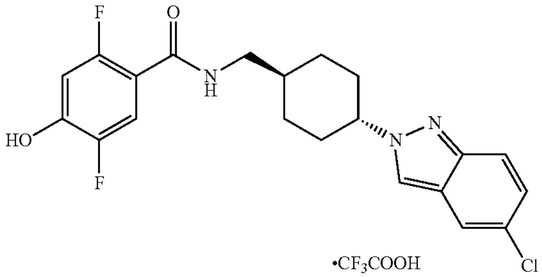 [SMILES: O=C(NC[C@H]1CC[C@H](n2cc3cc(Cl)ccc3n2)CC1)c1cc(F)c(O)cc1F ; "·CF3COOH"] •$CF_3COOH$ | N-{[(1r,4r)-4-(5-chloro-2H-indazol-2-yl)cyclohexyl]methyl}-2,5-difluoro-4-hydroxybenzamide, trifluoroacetate salt |

TABLE 1-continued

Structure and IUPAC Name for Examples 1-214.

| Example | Structure | IUPAC Name |
|---|---|---|
| 146 | 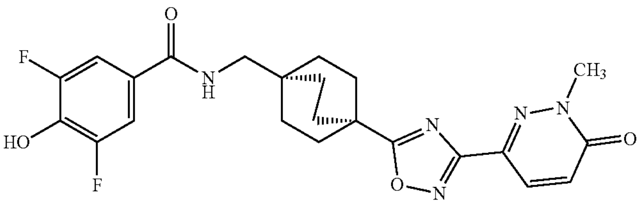 [SMILES: Cn1nc(-c2noc([C@]34CC[C@](CNC(=O)c5cc(F)c(O)c(F)c5)(CC3)CC4)n2)ccc1=O] | 3,5-difluoro-4-hydroxy-N-({4-[3-(1-methyl-6-oxo-1,6-dihydro-pyridazin-3-yl)-1,2,4-oxadiazol-5-yl]bicyclo[2.2.2] octan-1-yl}methyl) benzamide |
| 147 | 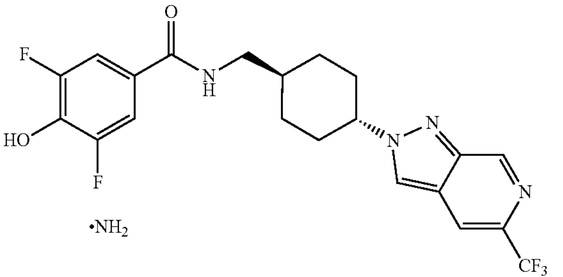 •$NH_2$ | 3,5-difluoro-4-hydroxy-N-({(1r,4r)-4-[5-(trifluoromethyl)-2H-pyrazolo[3,4-c] pyridin-2-yl] cyclohexyl}methyl) benzamide, ammonium salt |
| 148 | 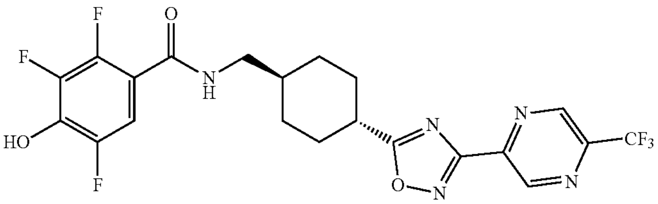 [SMILES: O=C(NC[C@H]1CC[C@H](c2nc(-c3cnc(C(F)(F)F)cn3)no2)CC1)c1cc(F)c(O)c(F)c1F] | 2,3,5-trifluoro-4-hydroxy-N-{[(1r,4r)-4-{3-[5-(trifluoromethyl) pyrazin-2-yl]-1,2,4-oxadiazol-5-yl} cyclohexyl]methyl} benzamide |
| 149 | 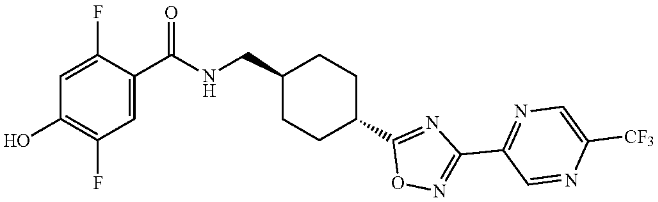 [SMILES: O=C(NC[C@H]1CC[C@H](c2nc(-c3cnc(C(F)(F)F)cn3)no2)CC1)c1cc(F)c(O)cc1F] | 2,5-difluoro-4-hydroxy-N-{[(1r,4r)-4-{3-[5-(trifluoromethyl) pyrazin-2-yl]-1,2,4-oxadiazol-5-yl} cyclohexyl]methyl} benzamide |
| 150 | 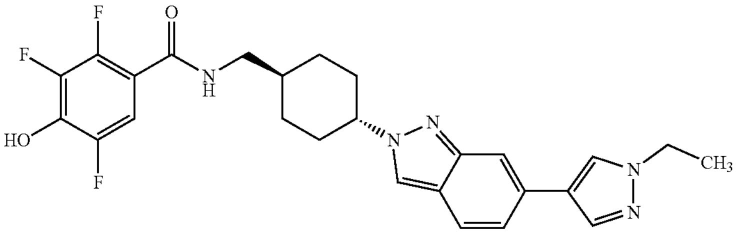 •$CF_3COOH$ | N-({(1r,4r)-4-[6-(1-ethyl-1H-pyrazol-4-yl)-2H-indazol-2-yl] cyclohexyl}methyl)-2,3,5-trifluoro-4-hydroxybenzamide, trifluoroacetate salt |
| 151 | 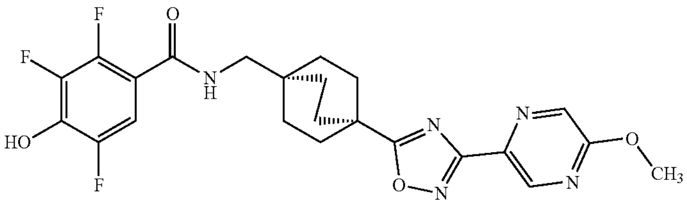 [SMILES: COc1cnc(-c2noc([C@]34CC[C@](CNC(=O)c5cc(F)c(O)c(F)c5F)(CC3)CC4)n2)cn1] | 2,3,5-trifluoro-4-hydroxy-N-({4-[3-(5-methoxypyrazin-2-yl)-1,2,4-oxadiazol-5-yl]bicyclo[2.2.2] octan-1-yl}methyl) benzamide |

TABLE 1-continued

Structure and IUPAC Name for Examples 1-214.

| Example | Structure | IUPAC Name |
|---|---|---|
| 152 | 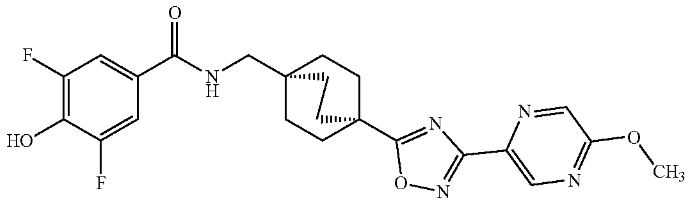 [SMILES: COc1cnc(-c2noc([C@]34CC[C@](CNC(=O)c5cc(F)c(O)c(F)c5)(CC3)CC4)n2)cn1] | 3,5-difluoro-4-hydroxy-N-({4-[3-(5-methoxypyrazin-2-yl)-1,2,4-oxadiazol-5-yl]bicyclo[2.2.2]octan-1-yl}methyl)benzamide |
| 153 | 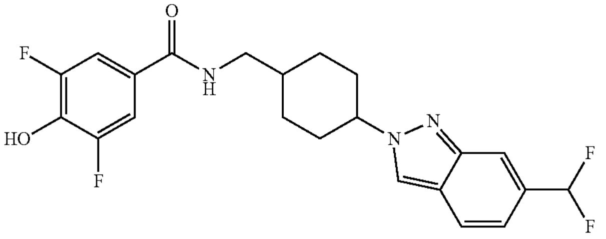 •$CF_3COOH$ | N-({(1r,4r)-4-[6-(difluoromethyl)-2H-indazol-2-yl]cyclohexyl}methyl)-2,3,5-trifluoro-4-hydroxybenzamide, trifluoroacetate salt |
| 154 | 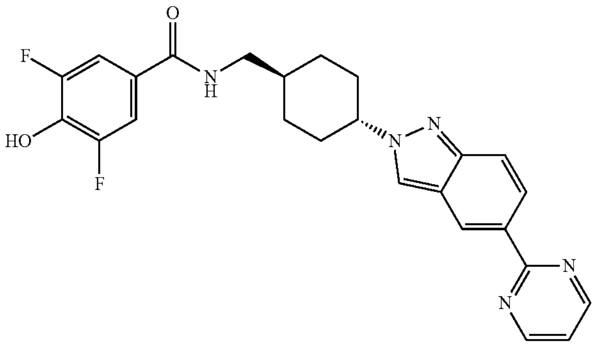 [SMILES: O=C(NC[C@H]1CC[C@H](n2cc3cc(-c4ncccn4)ccc3n2)CC1)c1cc(F)c(O)c(F)c1] | 3,5-difluoro-4-hydroxy-N-({(1r,4r)-4-[5-(pyrimidin-2-yl)-2H-indazol-2-yl]cyclohexyl}methyl)benzamide |
| 155 | 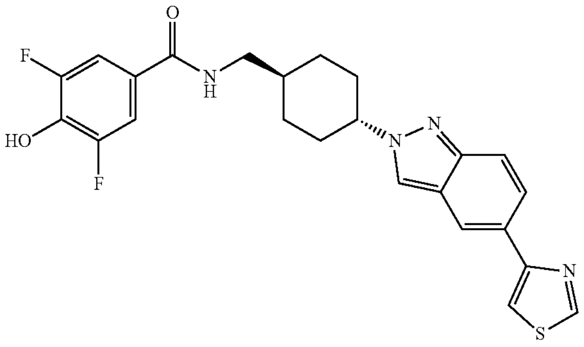 [SMILES: O=C(NC[C@H]1CC[C@H](n2cc3cc(-c4cscn4)ccc3n2)CC1)c1cc(F)c(O)c(F)c1] | 3,5-difluoro-4-hydroxy-N-({(1r,4r)-4-[5-(1,3-thiazol-4-yl)-2H-indazol-2-yl]cyclohexyl}methyl)benzamide |
| 156 | 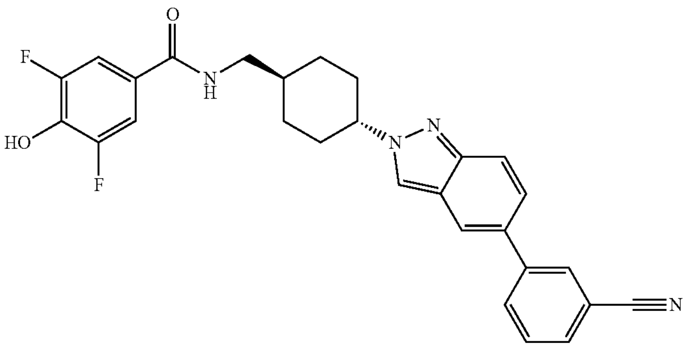 [SMILES: N#Cc1cccc(-c2ccc3nn([C@H]4CC[C@H](CNC(=O)c5cc(F)c(O)c(F)c5)CC4)cc3c2)c1] | N-({(1r,4r)-4-[5-(3-cyanophenyl)-2H-indazol-2-yl]cyclohexyl}methyl)-3,5-difluoro-4-hydroxybenzamide |

TABLE 1-continued

| Structure and IUPAC Name for Examples 1-214. | | |
|---|---|---|
| Example | Structure | IUPAC Name |
| 157 | 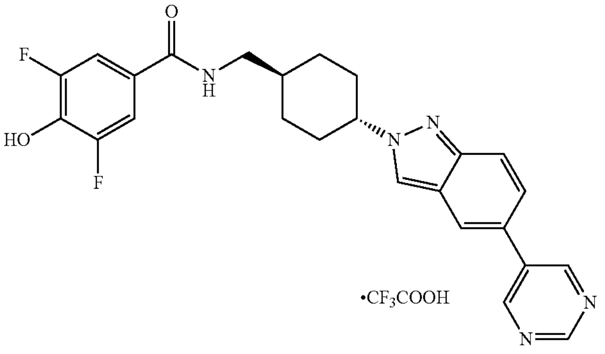 [SMILES: O=C(NC[C@H]1CC[C@H](n2cc3cc(-c4cncnc4)ccc3n2)CC1)c1cc(F)c(O)c(F)c1 ; "·CF3COOH"] •$CF_3COOH$ | 3,5-difluoro-4-hydroxy-N-({(1r,4r)-4-[5-(pyrimidin-5-yl)-2H-indazol-2-yl] cyclohexyl}methyl) benzamide, trifluoroacetate salt |
| 158 | 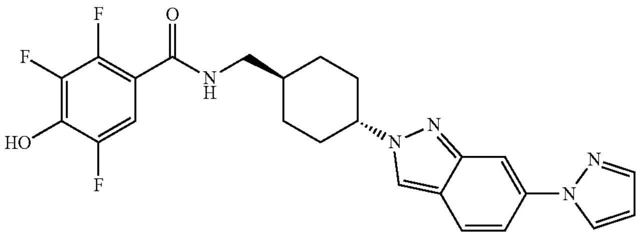 •$CF_3COOH$ | 2,3,5-trifluoro-4-hydroxy-N-({(1r,4r)-4-[6-(1H-pyrazol-1-yl)-2H-indazol-2-yl]cyclohexyl}methyl) benzamide, trifluoroacetate salt |
| 159 | 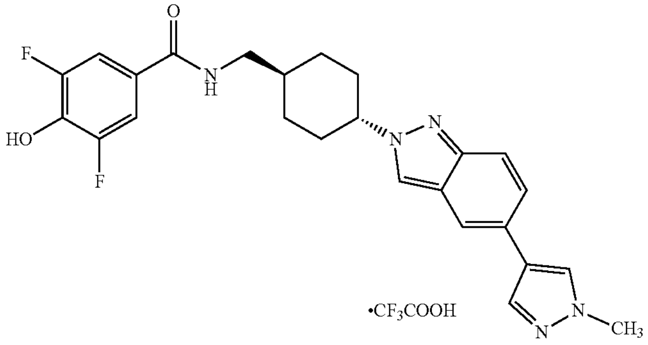 [SMILES: Cn1cc(-c2ccc3nn([C@H]4CC[C@H](CNC(=O)c5cc(F)c(O)c(F)c5)CC4)cc3c2)cn1 ; "·CF3COOH"] •$CF_3COOH$ | 3,5-difluoro-4-hydroxy-N-({(1r,4r)-4-[5-(1-methyl-1H-pyrazol-4-yl)-2H-indazol-2-yl] cyclohexyl}methyl) benzamide, trifluoroacetate salt |
| 160 | 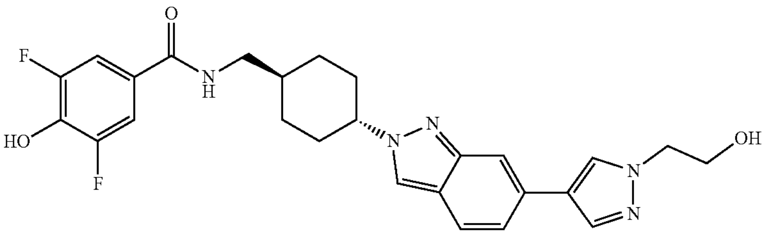 •$CF_3COOH$ | 3,5-difluoro-4-hydroxy-N-{[(1r,4r)-4-{6-[1-(2-hydroxyethyl)-1H-pyrazol-4-yl]-2H-indazol-2-yl}cyclo-hexyl]methyl} benzamide, trifluoroacetate salt |

TABLE 1-continued

Structure and IUPAC Name for Examples 1-214.

| Example | Structure | IUPAC Name |
|---|---|---|
| 161 | 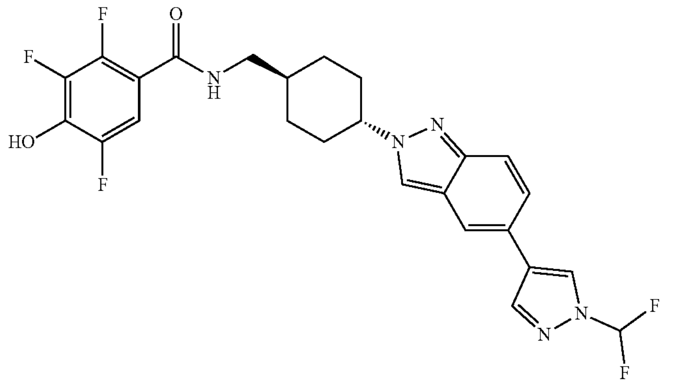 [SMILES: O=C(NC[C@H]1CC[C@H](n2cc3cc(-c4cnn(C(F)F)c4)ccc3n2)CC1)c1cc(F)c(O)c(F)c1F] | N-{[(1r,4r)-4-{5-[1-(difluoromethyl)-1H-pyrazol-4-yl]-2H-indazol-2-yl}cyclohexyl]methyl}-2,3,5-trifluoro-4-hydroxybenzamide |
| 162 | 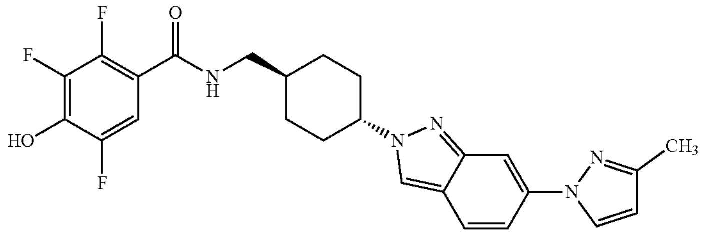 [SMILES: Cc1ccn(-c2ccc3cn([C@H]4CC[C@H](CNC(=O)c5cc(F)c(O)c(F)c5F)CC4)nc3c2)n1] | 2,3,5-trifluoro-4-hydroxy-N-({(1r,4r)-4-[6-(3-methyl-1H-pyrazol-1-yl)-2H-indazol-2-yl]cyclohexyl}methyl)benzamide |
| 163 | 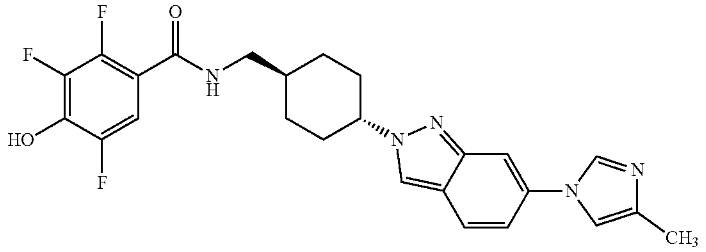 •$CF_3COOH$ | 2,3,5-trifluoro-4-hydroxy-N-({(1r,4r)-4-[6-(4-methyl-1H-imidazol-1-yl)-2H-indazol-2-yl]cyclohexyl}methyl)benzamide |
| 164 | 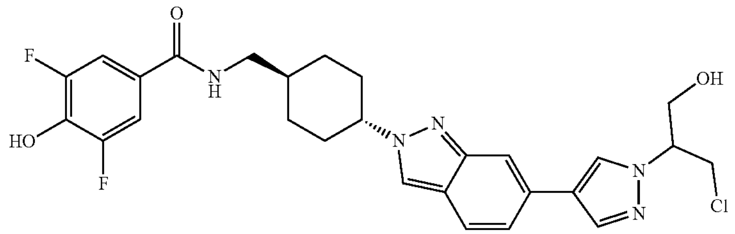 •$CF_3COOH$ | N-{[(1r,4r)-4-{6-[1-(1-chloro-3-hydroxypropan-2-yl)-1H-pyrazol-4-yl]-2H-indazol-2-yl}cyclohexyl]methyl}-3,5-difluoro-4-hydroxybenzamide, trifluoroacetate salt |
| 165 | 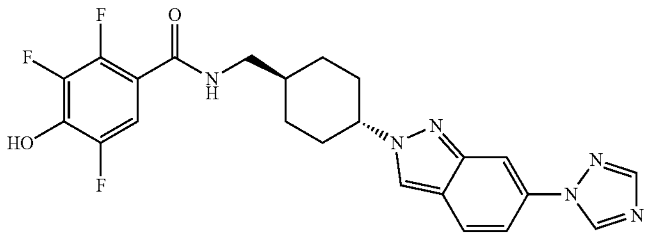 [SMILES: O=C(NC[C@H]1CC[C@H](n2cc3ccc(-n4cncn4)cc3n2)CC1)c1cc(F)c(O)c(F)c1F] | 2,3,5-trifluoro-4-hydroxy-N-({(1r,4r)-4-[6-(1H-1,2,4-triazol-1-yl)-2H-indazol-2-yl]cyclohexyl}methyl)benzamide |

TABLE 1-continued

Structure and IUPAC Name for Examples 1-214.

| Example | Structure | IUPAC Name |
|---|---|---|
| 166 | 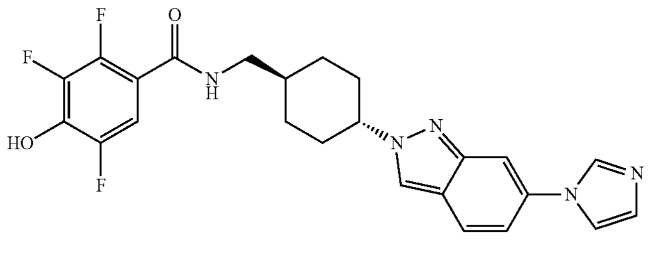 •$CF_3COOH$ | 2,3,5-trifluoro-4-hydroxy-N-({(1r,4r)-4-[6-(1H-imidazol-1-yl)-2H-indazol-2-yl]cyclohexyl}methyl) benzamide, trifluoroacetate salt |
| 167 | 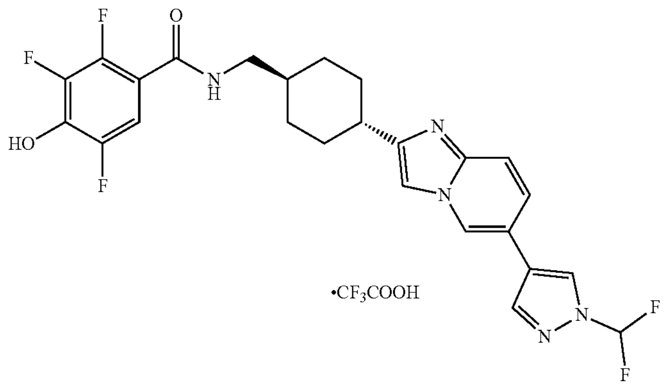 [SMILES: O=C(NC[C@H]1CC[C@H](c2cn3cc(-c4cnn(C(F)F)c4)ccc3n2)CC1)c1cc(F)c(O)c(F)c1F ; "·CF3COOH"] •$CF_3COOH$ | N-{[(1r,4r)-4-{6-[1-(difluoromethyl)-1H-pyrazol-4-yl]imidazo [1,2-a]pyridin-2-yl}cyclohexyl] methyl}-2,3,5-trifluoro-4-hydroxy-benzamide, trifluoroacetate salt |
| 168 | 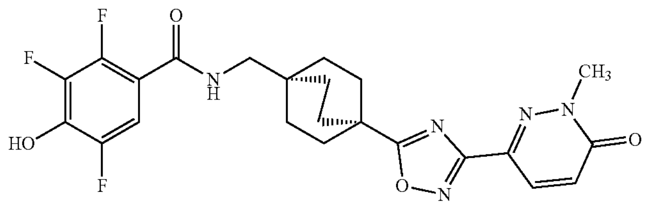 [SMILES: Cn1nc(-c2noc([C@]34CC[C@](CNC(=O)c5cc(F)c(O)c(F)c5F)(CC3)CC4)n2)ccc1=O] | 2,3,5-trifluoro-4-hydroxy-N-({4-[3-(1-methyl-6-oxo-1,6-dihydropyridazin-3-yl)-1,2,4-oxadiazol-5-yl]bicyclo[2.2.2] octan-1-yl}methyl) benzamide |
| 169 | 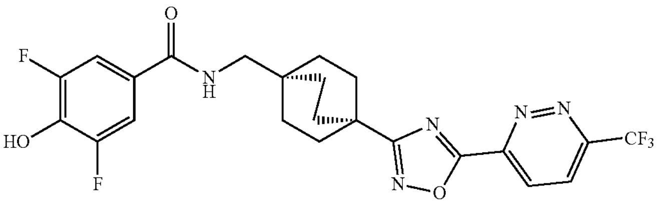 •$NH_3$ | 3,5-difluoro-4-hydroxy-N-[(4-{5-[6-(trifluoromethyl) pyridazin-3-yl]-1,2,4-oxadiazol-3-yl} bicyclo[2.2.2]octan-1-yl)methyl]benzamide, ammonium salt |
| 170 | 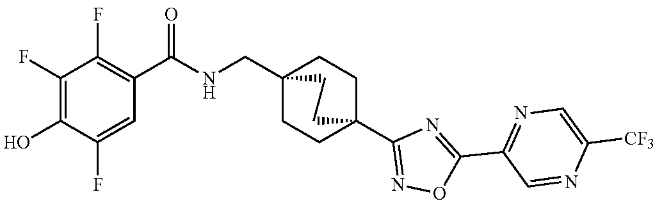 •$NH_3$ | 2,3,5-trifluoro-4-hydroxy-N-[(4-{5-[5-(trifluoromethyl) pyrazin-2-yl]-1,2,4-oxadiazol-3-yl} bicyclo[2.2.2]octan-1-yl)methyl] benzamide, ammonium salt |

TABLE 1-continued

Structure and IUPAC Name for Examples 1-214.

| Example | Structure | IUPAC Name |
|---|---|---|
| 171 | 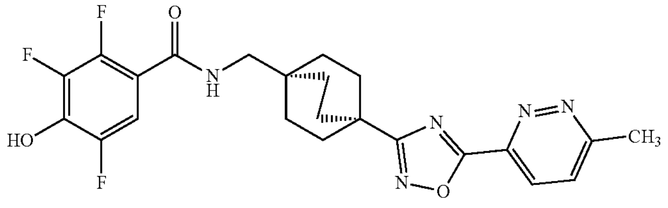 •$NH_3$ | 2,3,5-trifluoro-4-hydroxy-N-({4-[5-(6-methylpyridazin-3-yl)-1,2,4-oxadiazol-3-yl]bicyclo[2.2.2]octan-1-yl}methyl)benzamide, ammonium salt |
| 172 | 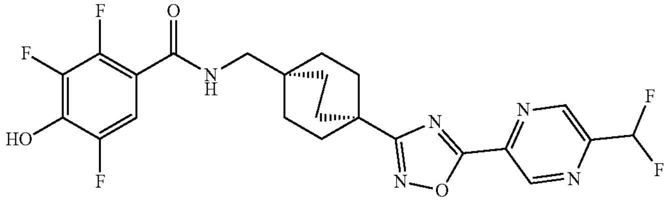 •$NH_3$ | N-[(4-{5-[5-(difluoromethyl)pyrazin-2-yl]-1,2,4-oxadiazol-3-yl}bicyclo[2.2.2]octan-1-yl)methyl]-2,3,5-trifluoro-4-hydroxybenzamide, ammonium salt |
| 173 | 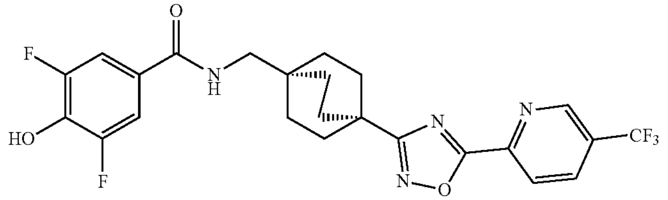 •$NH_3$ | 3,5-difluoro-4-hydroxy-N-[(4-{5-[5-(trifluoromethyl)pyridin-2-yl]-1,2,4-oxadiazol-3-yl}bicyclo[2.2.2]octan-1-yl)methyl]benzamide, ammonium salt |
| 174 | 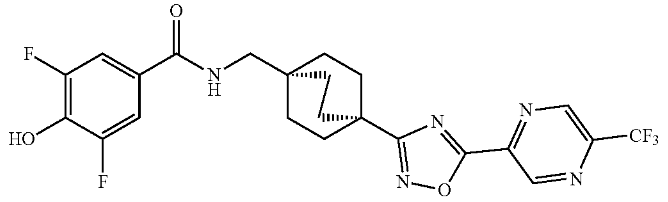 •$NH_3$ | 3,5-difluoro-4-hydroxy-N-[(4-{5-[5-(trifluoromethyl)pyrazin-2-yl]-1,2,4-oxadiazol-3-yl}bicyclo[2.2.2]octan-1-yl)methyl]benzamide, ammonium salt |
| 175 | 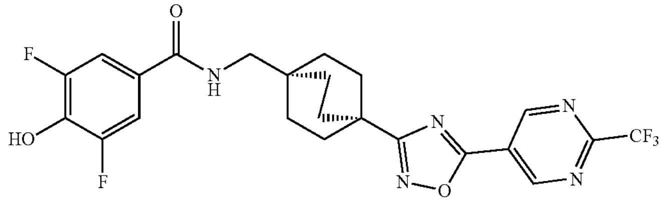 •$NH_3$ | 3,5-difluoro-4-hydroxy-N-[(4-{5-[2-(trifluoromethyl)pyrimidin-5-yl]-1,2,4-oxadiazol-3-yl}bicyclo[2.2.2]octan-1-yl)methyl]benzamide, ammonium salt |
| 176 | 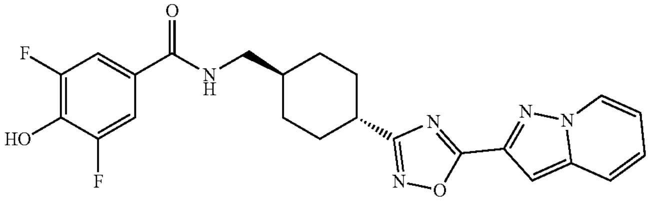 [SMILES: O=C(NC[C@H]1CC[C@H](c2noc(-c3cc4ccccn4n3)n2)CC1)c1cc(F)c(O)c(F)c1] | 3,5-difluoro-4-hydroxy-N-({(1r,4r)-4-[5-(pyrazolo[1,5-a]pyridin-2-yl)-1,2,4-oxadiazol-3-yl]cyclohexyl}methyl)benzamide |

TABLE 1-continued

| Structure and IUPAC Name for Examples 1-214. | | |
|---|---|---|
| Example | Structure | IUPAC Name |
| 177 | 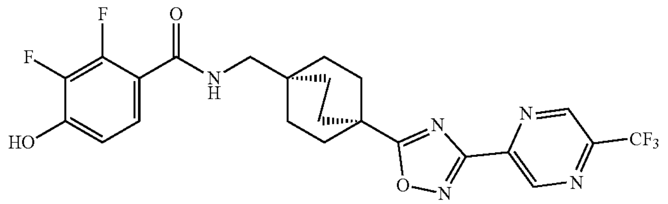 [SMILES: O=C(NC[C@]12CC[C@](c3nc(-c4cnc(C(F)(F)F)cn4)no3)(CC1)CC2)c1ccc(O)c(F)c1F] | 2,3-difluoro-4-hydroxy-N-[(4-{3-[5-(trifluoromethyl) pyrazin-2-yl]-1,2,4-oxadiazol-5-yl} bicyclo[2.2.2]octan-1-yl)methyl]benzamide |
| 178 | 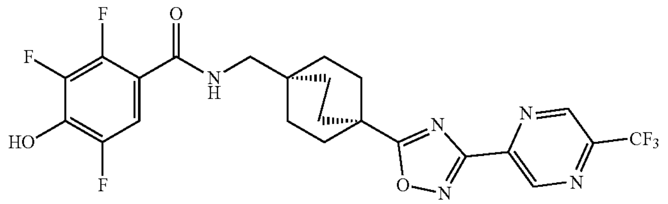 [SMILES: O=C(NC[C@]12CC[C@](c3nc(-c4cnc(C(F)(F)F)cn4)no3)(CC1)CC2)c1cc(F)c(O)c(F)c1F] | 2,3,5-trifluoro-4-hydroxy-N-[(4-{3-[5-(trifluoromethyl) pyrazin-2-yl]-1,2,4-oxadiazol-5-yl} bicyclo[2.2.2]octan-1-yl)methyl]benzamide |
| 179 | 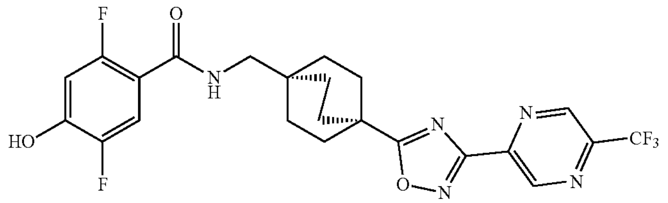 [SMILES: O=C(NC[C@]12CC[C@](c3nc(-c4cnc(C(F)(F)F)cn4)no3)(CC1)CC2)c1cc(F)c(O)cc1F] | 2,5-difluoro-4-hydroxy-N-[(4-{3-[5-(trifluoromethyl) pyrazin-2-yl]-1,2,4-oxadiazol-5-yl} bicyclo[2.2.2]octan-1-yl)methyl]benzamide |
| 180 | 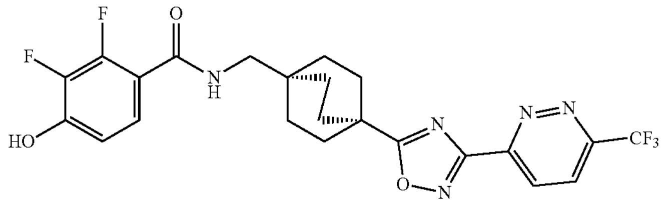 [SMILES: O=C(NC[C@]12CC[C@](c3nc(-c4ccc(C(F)(F)F)nn4)no3)(CC1)CC2)c1ccc(O)c(F)c1F] | 2,3-difluoro-4-hydroxy-N-[(4-{3-[6-(trifluoromethyl) pyridazin-3-yl]-1,2,4-oxadiazol-5-yl} bicyclo[2.2.2]octan-1-yl)methyl]benzamide |
| 181 | 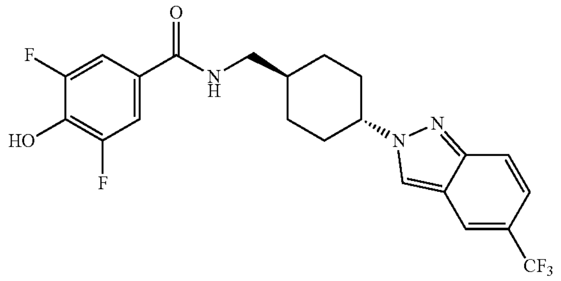 [SMILES: O=C(NC[C@H]1CC[C@H](n2cc3cc(C(F)(F)F)ccc3n2)CC1)c1cc(F)c(O)c(F)c1] | 3,5-difluoro-4-hydroxy-N-({(1r,4r)-4-[5-(trifluoromethyl)-2H-indazol-2-yl]cyclohexyl}methyl) benzamide |
| 182 | 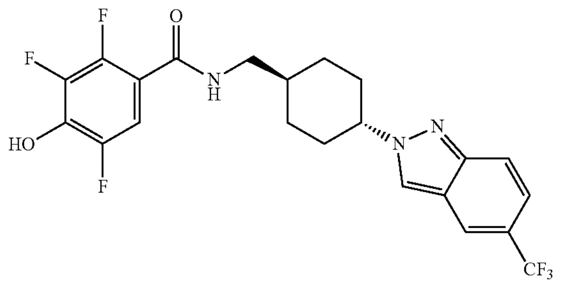 [SMILES: O=C(NC[C@H]1CC[C@H](n2cc3cc(C(F)(F)F)ccc3n2)CC1)c1cc(F)c(O)c(F)c1F] | 2,3,5-trifluoro-4-hydroxy-N-({(1r,4r)-4-[5-(trifluoromethyl)-2H-indazol-2-yl]cyclohexyl}methyl) benzamide |

TABLE 1-continued

| Structure and IUPAC Name for Examples 1-214. | | |
|---|---|---|
| Example | Structure | IUPAC Name |
| 183 | 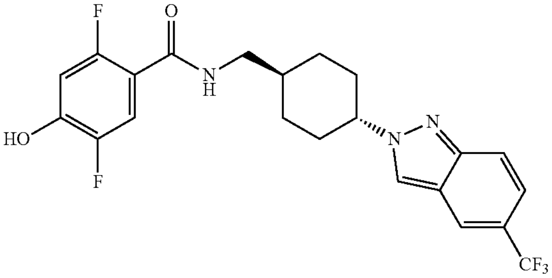 [SMILES: O=C(NC[C@H]1CC[C@H](n2cc3cc(C(F)(F)F)ccc3n2)CC1)c1cc(F)c(O)cc1F] | 2,5-difluoro-4-hydroxy-N-({(1r,4r)-4-[5-(trifluoromethyl)-2H-indazol-2-yl]cyclohexyl}methyl)benzamide |
| 184 | 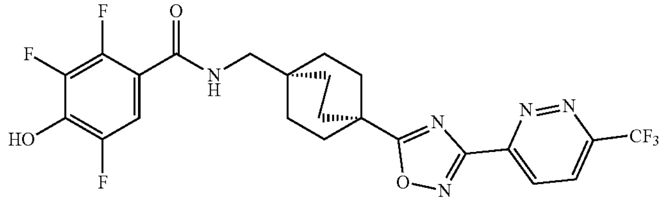 [SMILES: O=C(NC[C@]12CC[C@](c3nc(-c4ccc(C(F)(F)F)nn4)no3)(CC1)CC2)c1cc(F)c(O)c(F)c1F] | 2,3,5-trifluoro-4-hydroxy-N-[(4-{3-[6-(trifluoromethyl)pyridazin-3-yl]-1,2,4-oxadiazol-5-yl}bicyclo[2.2.2]octan-1-yl)methyl]benzamide |
| 185 | 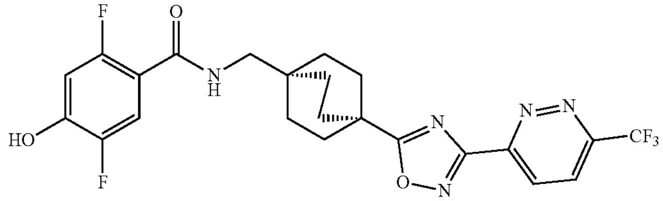 [SMILES: O=C(NC[C@]12CC[C@](c3nc(-c4ccc(C(F)(F)F)nn4)no3)(CC1)CC2)c1cc(F)c(O)cc1F] | 2,5-difluoro-4-hydroxy-N-[(4-{3-[6-(trifluoromethyl)pyridazin-3-yl]-1,2,4-oxadiazol-5-yl}bicyclo[2.2.2]octan-1-yl)methyl]benzamide |
| 186 | 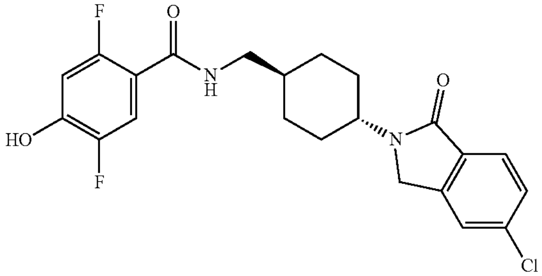 [SMILES: O=C(NC[C@H]1CC[C@H](N2Cc3cc(Cl)ccc3C2=O)CC1)c1cc(F)c(O)cc1F] | N-{[(1r,4r)-4-(5-chloro-1-oxo-1,3-dihydro-2H-isoindol-2-yl)cyclohexyl]methyl}-2,5-difluoro-4-hydroxybenzamide |
| 187 | 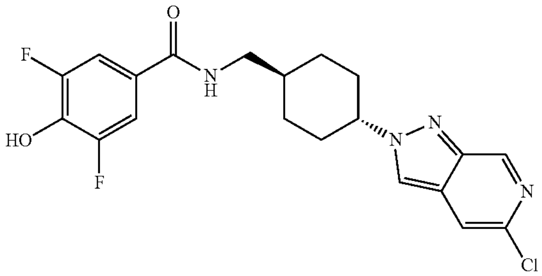 [SMILES: O=C(NC[C@H]1CC[C@H](n2cc3cc(Cl)ncc3n2)CC1)c1cc(F)c(O)c(F)c1] | N-{[(1r,4r)-4-(5-chloro-2H-pyrazolo[3,4-c]pyridin-2-yl)cyclohexyl]methyl}-3,5-difluoro-4-hydroxybenzamide |
| 188 | 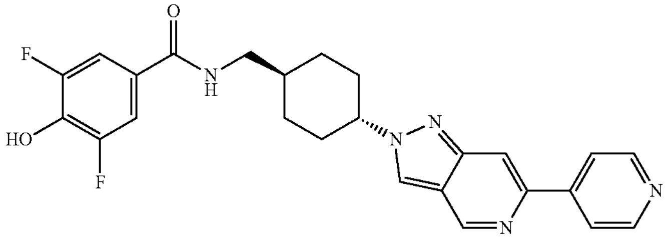 [SMILES: O=C(NC[C@H]1CC[C@H](n2cc3cnc(-c4ccncc4)cc3n2)CC1)c1cc(F)c(O)c(F)c1] | 3,5-difluoro-4-hydroxy-N-({(1r,4r)-4-[6-(pyridin-4-yl)-2H-pyrazolo[4,3-c]pyridin-2-yl]cyclohexyl}methyl)benzamide |

TABLE 1-continued

| Structure and IUPAC Name for Examples 1-214. | | |
|---|---|---|
| Example | Structure | IUPAC Name |
| 189 | 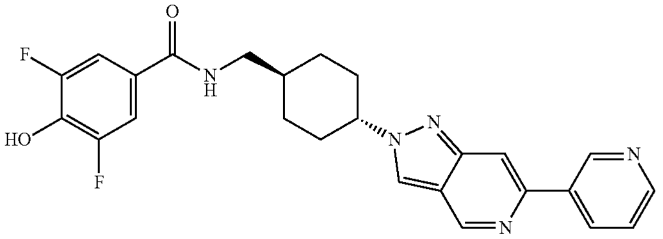 [SMILES: O=C(NC[C@H]1CC[C@H](n2cc3cnc(-c4cccnc4)cc3n2)CC1)c1cc(F)c(O)c(F)c1] | 3,5-difluoro-4-hydroxy-N-({(1r,4r)-4-[6-(pyridin-3-yl)-2H-pyrazolo[4,3-c]pyridin-2-yl]cyclohexyl}methyl)benzamide |
| 190 | 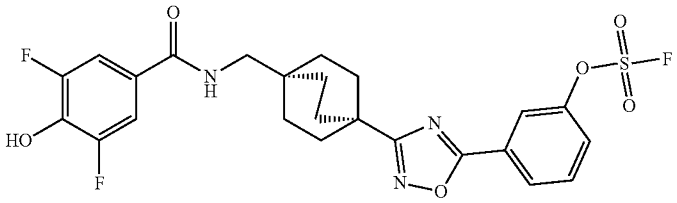 [SMILES: O=C(NC[C@]12CC[C@](c3noc(-c4cccc(OS(=O)(=O)F)c4)n3)(CC1)CC2)c1cc(F)c(O)c(F)c1] | 3-(3-{4-[(3,5-difluoro-4-hydroxybenzamido)methyl]bicyclo[2.2.2]octan-1-yl}-1,2,4-oxadiazol-5-yl)phenyl sulfurofluoridate |
| 191 | 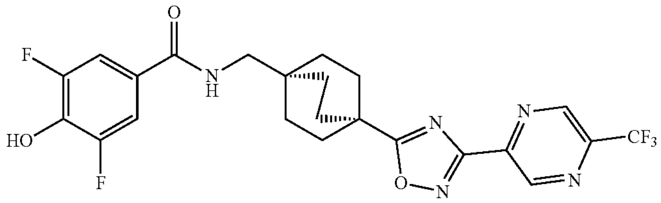 [SMILES: O=C(NC[C@]12CC[C@](c3nc(-c4cnc(C(F)(F)F)cn4)no3)(CC1)CC2)c1cc(F)c(O)c(F)c1] | 3,5-difluoro-4-hydroxy-N-[(4-{3-[5-(trifluoromethyl)pyrazin-2-yl]-1,2,4-oxadiazol-5-yl}bicyclo[2.2.2]octan-1-yl)methyl]benzamide |
| 192 | 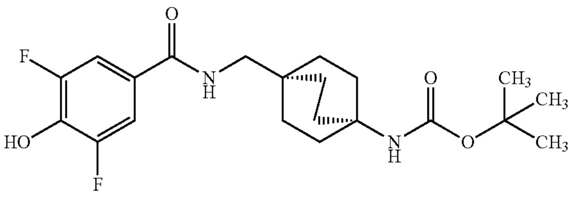 [SMILES: CC(C)(C)OC(=O)N[C@]12CC[C@](CNC(=O)c3cc(F)c(O)c(F)c3)(CC1)CC2] | tert-butyl {4-[(3,5-difluoro-4-hydroxybenzamido)methyl]bicyclo[2.2.2]octan-1-yl}carbamate |
| 193 | 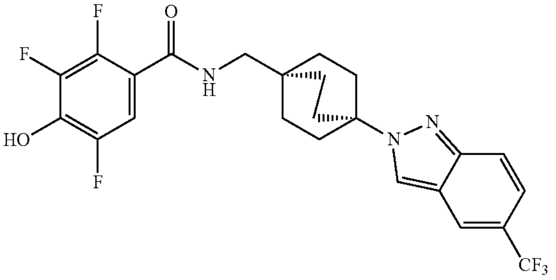 [SMILES: O=C(NC[C@]12CC[C@](n3cc4cc(C(F)(F)F)ccc4n3)(CC1)CC2)c1cc(F)c(O)c(F)c1F] | 2,3,5-trifluoro-4-hydroxy-N-({4-[5-(trifluoromethyl)-2H-indazol-2-yl]bicyclo[2.2.2]octan-1-yl}methyl)benzamide |
| 194 | 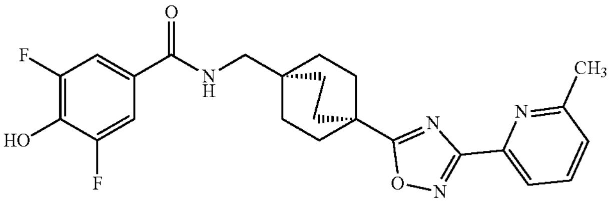 [SMILES: Cc1cccc(-c2noc([C@]34CC[C@](CNC(=O)c5cc(F)c(O)c(F)c5)(CC3)CC4)n2)n1] | 3,5-difluoro-4-hydroxy-N-({4-[3-(6-methylpyridin-2-yl)-1,2,4-oxadiazol-5-yl]bicyclo[2.2.2]octan-1-yl}methyl)benzamide |

TABLE 1-continued

| Structure and IUPAC Name for Examples 1-214. | | |
|---|---|---|
| Example | Structure | IUPAC Name |
| 195 | 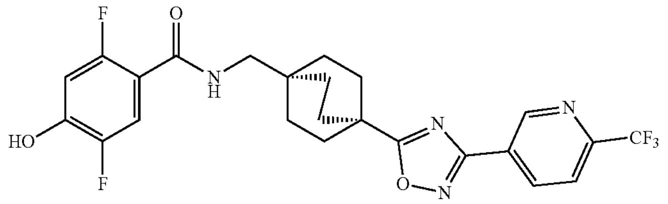 [SMILES: O=C(NC[C@]12CC[C@](c3nc(-c4ccc(C(F)(F)F)nc4)no3)(CC1)CC2)c1cc(F)c(O)cc1F] | 2,5-difluoro-4-hydroxy-N-[(4-{3-[6-(trifluoromethyl)pyridin-3-yl]-1,2,4-oxadiazol-5-yl}bicyclo[2.2.2]octan-1-yl)methyl]benzamide |
| 196 | 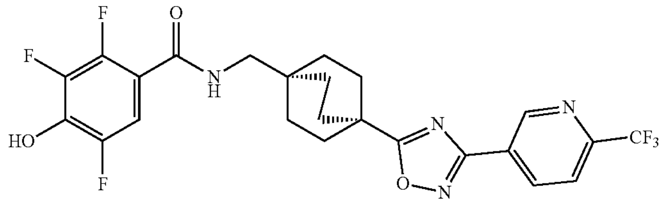 [SMILES: O=C(NC[C@]12CC[C@](c3nc(-c4ccc(C(F)(F)F)nc4)no3)(CC1)CC2)c1cc(F)c(O)c(F)c1F] | 2,3,5-trifluoro-4-hydroxy-N-[(4-{3-[6-(trifluoromethyl)pyridin-3-yl]-1,2,4-oxadiazol-5-yl}bicyclo[2.2.2]octan-1-yl)methyl]benzamide |
| 197 | 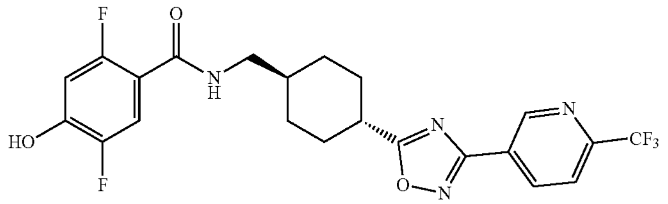 [SMILES: O=C(NC[C@H]1CC[C@H](c2nc(-c3ccc(C(F)(F)F)nc3)no2)CC1)c1cc(F)c(O)cc1F] | 2,5-difluoro-4-hydroxy-N-{[(1r,4r)-4-{3-[6-(trifluoromethyl)pyridin-3-yl]-1,2,4-oxadiazol-5-yl}cyclohexyl]methyl}benzamide |
| 198 | 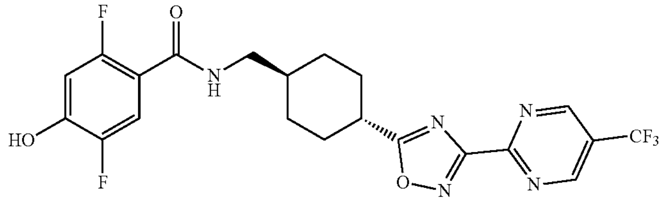 [SMILES: O=C(NC[C@H]1CC[C@H](c2nc(-c3ncc(C(F)(F)F)cn3)no2)CC1)c1cc(F)c(O)cc1F] | 2,5-difluoro-4-hydroxy-N-{[(1r,4r)-4-{3-[5-(trifluoromethyl)pyrimidin-2-yl]-1,2,4-oxadiazol-5-yl}cyclohexyl]methyl}benzamide |
| 199 | 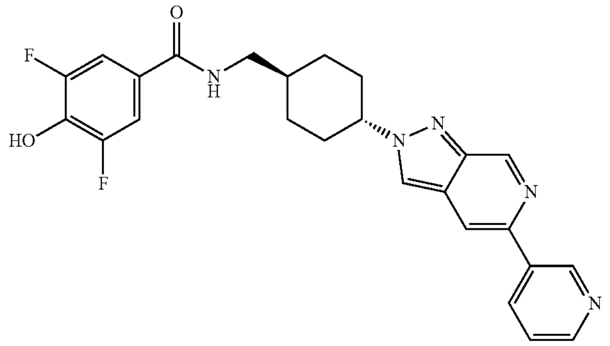 [SMILES: O=C(NC[C@H]1CC[C@H](n2cc3cc(-c4cccnc4)ncc3n2)CC1)c1cc(F)c(O)c(F)c1] | 3,5-difluoro-4-hydroxy-N-({(1r,4r)-4-[5-(pyridin-3-yl)-2H-pyrazolo[3,4-c]pyridin-2-yl]cyclohexyl}methyl)benzamide |
| 200 | 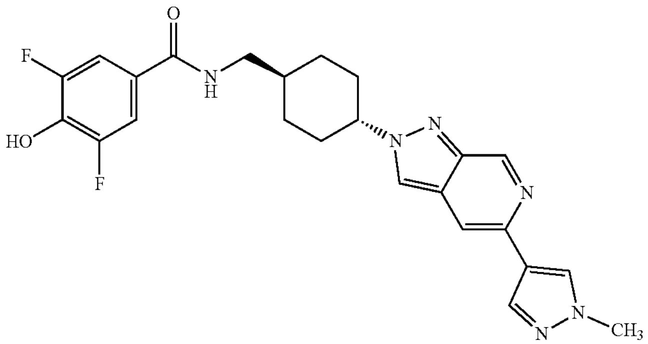 [SMILES: Cn1cc(-c2cc3cn([C@H]4CC[C@H](CNC(=O)c5cc(F)c(O)c(F)c5)CC4)nc3cn2)cn1] | 3,5-difluoro-4-hydroxy-N-({(1r,4r)-4-[5-(1-methyl-1H-pyrazol-4-yl)-2H-pyrazolo[3,4-c]pyridin-2-yl]cyclohexyl}methyl)benzamide |

TABLE 1-continued

Structure and IUPAC Name for Examples 1-214.

| Example | Structure | IUPAC Name |
| --- | --- | --- |
| 201 | 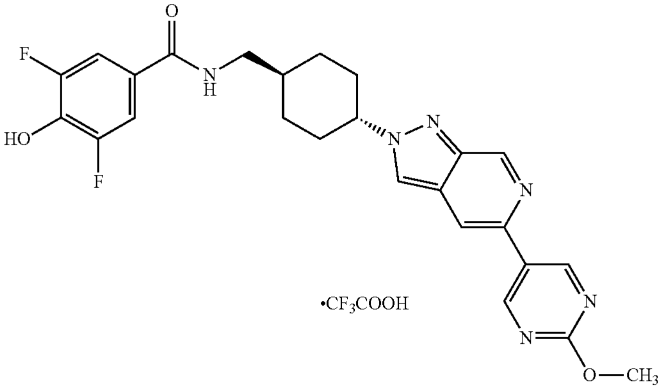 [SMILES: COc1ncc(-c2cc3cn([C@H]4CC[C@H](CNC(=O)c5cc(F)c(O)c(F)c5)CC4)nc3cn2)cn1 ; "·CF3COOH"] •$CF_3COOH$ | 3,5-difluoro-4-hydroxy-N-({(1r,4r)-4-[5-(2-methoxypyrimidin-5-yl)-2H-pyrazolo[3,4-c]pyridin-2-yl]cyclohexyl}methyl)benzamide, trifluoroacetate salt |
| 202 | 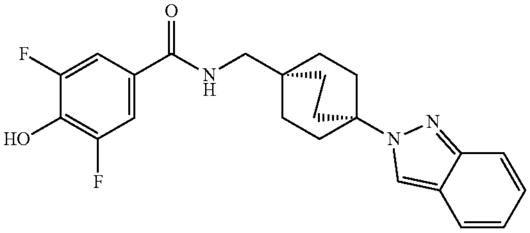 [SMILES: O=C(NC[C@]12CC[C@](n3cc4ccccc4n3)(CC1)CC2)c1cc(F)c(O)c(F)c1] | 3,5-difluoro-4-hydroxy-N-{[4-(2H-indazol-2-yl)bicyclo[2.2.2]octan-1-yl]methyl}benzamide |
| 203 | 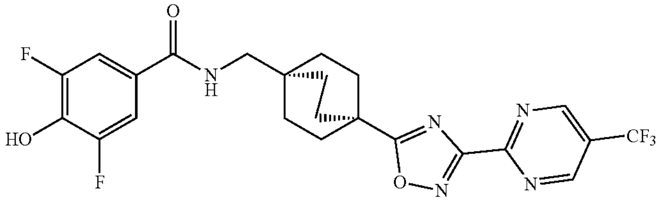 [SMILES: O=C(NC[C@]12CC[C@](c3nc(-c4ncc(C(F)(F)F)cn4)no3)(CC1)CC2)c1cc(F)c(O)c(F)c1] | 3,5-difluoro-4-hydroxy-N-[(4-{3-[5-(trifluoromethyl)pyrimidin-2-yl]-1,2,4-oxadiazol-5-yl}bicyclo[2.2.2]octan-1-yl)methyl]benzamide |
| 204 | 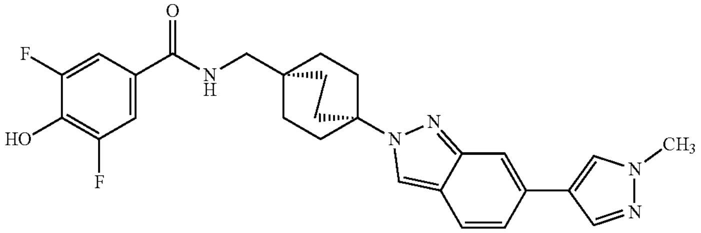 [SMILES: Cn1cc(-c2ccc3cn([C@]45CC[C@](CNC(=O)c6cc(F)c(O)c(F)c6)(CC4)CC5)nc3c2)cn1] | 3,5-difluoro-4-hydroxy-N-({4-[6-(1-methyl-1H-pyrazol-4-yl)-2H-indazol-2-yl]bicyclo[2.2.2]octan-1-yl}methyl)benzamide |
| 205 | 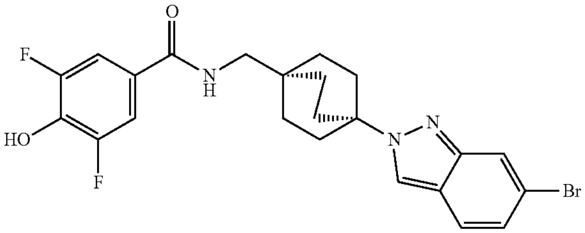 [SMILES: O=C(NC[C@]12CC[C@](n3cc4ccc(Br)cc4n3)(CC1)CC2)c1cc(F)c(O)c(F)c1] | N-{[4-(6-bromo-2H-indazol-2-yl)bicyclo[2.2.2]octan-1-yl]methyl}-3,5-difluoro-4-hydroxybenzamide |
| 206 | 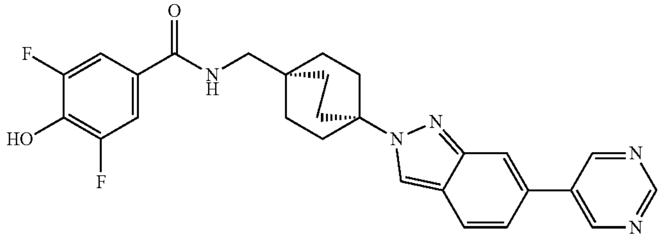 [SMILES: O=C(NC[C@]12CC[C@](n3cc4ccc(-c5cncnc5)cc4n3)(CC1)CC2)c1cc(F)c(O)c(F)c1] | 3,5-difluoro-4-hydroxy-N-({4-[6-(pyrimidin-5-yl)-2H-indazol-2-yl]bicyclo[2.2.2]octan-1-yl}methyl)benzamide |

TABLE 1-continued

| Structure and IUPAC Name for Examples 1-214. | | |
|---|---|---|
| Example | Structure | IUPAC Name |
| 207 | 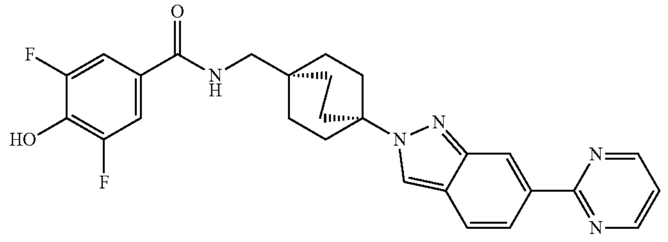 [SMILES: O=C(NC[C@]12CC[C@](n3cc4ccc(-c5ncccn5)cc4n3)(CC1)CC2)c1cc(F)c(O)c(F)c1] | 3,5-difluoro-4-hydroxy-N-({4-[6-(pyrimidin-2-yl)-2H-indazol-2-yl]bicyclo[2.2.2]octan-1-yl}methyl)benzamide |
| 208 | 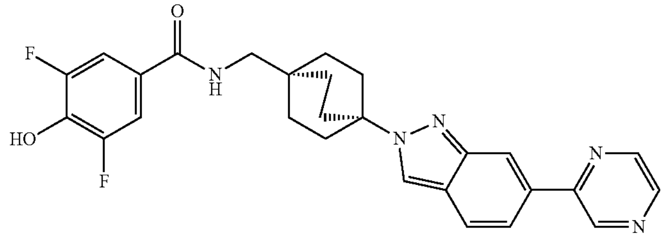 [SMILES: O=C(NC[C@]12CC[C@](n3cc4ccc(-c5cnccn5)cc4n3)(CC1)CC2)c1cc(F)c(O)c(F)c1] | 3,5-difluoro-4-hydroxy-N-({4-[6-(pyrazin-2-yl)-2H-indazol-2-yl]bicyclo[2.2.2]octan-1-yl}methyl)benzamide |
| 209 | 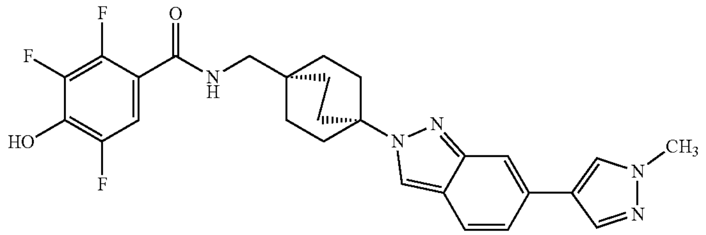 [SMILES: Cn1cc(-c2ccc3cn([C@]45CC[C@](CNC(=O)c6cc(F)c(O)c(F)c6F)(CC4)CC5)nc3c2)cn1] | 2,3,5-trifluoro-4-hydroxy-N-({4-[6-(1-methyl-1H-pyrazol-4-yl)-2H-indazol-2-yl]bicyclo[2.2.2]octan-1-yl}methyl)benzamide |
| 210 | 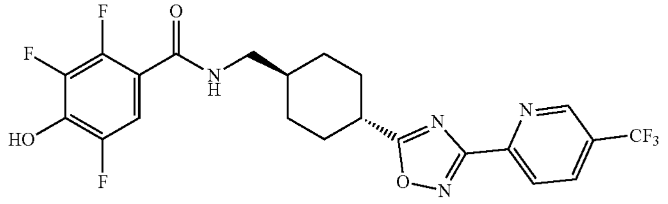 [SMILES: O=C(NC[C@H]1CC[C@H](c2nc(-c3ccc(C(F)(F)F)cn3)no2)CC1)c1cc(F)c(O)c(F)c1F] | 2,3,5-trifluoro-4-hydroxy-N-{[(1r,4r)-4-{3-[5-(trifluoromethyl)pyridin-2-yl]-1,2,4-oxadiazol-5-yl}cyclohexyl]methyl}benzamide |
| 211 | 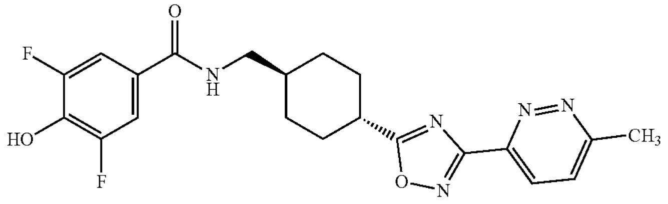 [SMILES: Cc1ccc(-c2noc([C@H]3CC[C@H](CNC(=O)c4cc(F)c(O)c(F)c4)CC3)n2)nn1] | 3,5-difluoro-4-hydroxy-N-({(1r,4r)-4-[3-(6-methyl-pyridazin-3-yl)-1,2,4-oxadiazol-5-yl]cyclohexyl}methyl)benzamide |
| 212 | 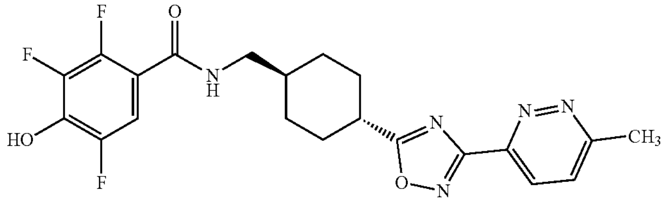 [SMILES: Cc1ccc(-c2noc([C@H]3CC[C@H](CNC(=O)c4cc(F)c(O)c(F)c4F)CC3)n2)nn1] | 2,3,5-trifluoro-4-hydroxy-N-({(1r,4r)-4-[3-(6-methylpyridazin-3-yl)-1,2,4-oxadiazol-5-yl]cyclohexyl}methyl)benzamide |

TABLE 1-continued

| Structure and IUPAC Name for Examples 1-214. | | |
|---|---|---|
| Example | Structure | IUPAC Name |
| 213 | 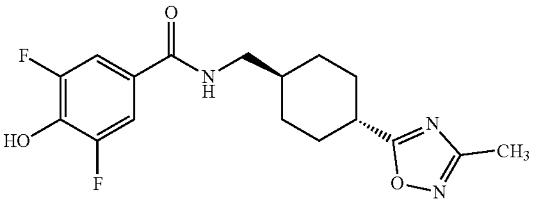 [SMILES: Cc1noc([C@H]2CC[C@H](CNC(=O)c3cc(F)c(O)c(F)c3)CC2)n1] | 3,5-difluoro-4-hydroxy-N-{[(1r,4r)-4-(3-methyl-1,2,4-oxadiazol-5-yl)cyclohexyl]methyl}benzamide |
| 214 | 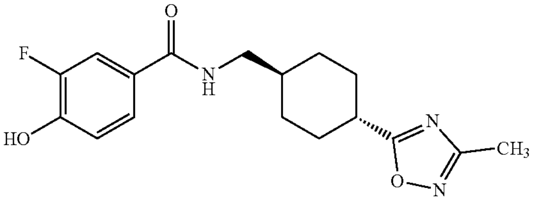 [SMILES: Cc1noc([C@H]2CC[C@H](CNC(=O)c3ccc(O)c(F)c3)CC2)n1] | 3-fluoro-4-hydroxy-N-{[(1r,4r)-4-(3-methyl-1,2,4-oxadiazol-5-yl)cyclohexyl]methyl}benzamide |

TABLE 2

| Method of synthesis and physicochemical data for Examples 22-214. | | |
|---|---|---|
| Example | Method of synthesis; Non-commercial starting materials | $^1$H NMR (400 MHz, DMSO-$d_6$) d; Mass spectrum, observed ion m/z $[M + H]^+$ or HPLC retention time; Mass spectrum m/z $[M + H]^+$ (unless otherwise indicated) |
| 22 | P3[1] | 10.87 (br s, 1H), 8.47 (br t, J = 6 Hz, 1H), 8.38 (s, 1H), 7.67 (d, J = 8.4 Hz, 1H), 7.64-7.53 (m, 3H), 7.20 (dd, J = 8.7, 6.5 Hz, 1H), 7.00 (dd, J = 8.4, 6.5 Hz, 1H), 4.53-4.40 (m, 1H), 3.17 (dd, J = 6, 6 Hz, 2H), 2.20-2.09 (m, 2H), 1.98-1.82 (m, 4H), 1.74-1.60 (m, 1H), 1.29-1.12 (m, 2H); 386.2 |
| 23 | Example 4[2,3]; P1 | 10.84 (br s, 1H), 8.46 (br t, J = 5.6 Hz, 1H), 8.24 (s, 1H), 7.64-7.54 (m, 2H), 7.53 (d, J = 9.0 Hz, 1H), 6.91 (br s, 1H), 6.67 (dd, J = 9.0, 2.2 Hz, 1H), 4.43-4.31 (m, 1H), 3.77 (s, 3H), 3.17 (dd, J = 6, 6 Hz, 2H), 2.18-2.07 (m, 2H), 1.95-1.78 (m, 4H), 1.72-1.59 (m, 1H), 1.27-1.12 (m, 2H); 416.3 |
| 24 | Example 7[4,2]; P14 | 10.84 (br s, 1H), 8.91 (d, J = 4.8 Hz, 2H), 8.67 (br s, 1H), 8.51-8.44 (m, 2H), 8.09 (dd, J = 8.8, 1.4 Hz, 1H), 7.80 (br d, J = 8.8 Hz, 1H), 7.64-7.54 (m, 2H), 7.43 (t, J = 4.8 Hz, 1H), 4.58-4.47 (m, 1H), 3.18 (dd, J = 6, 6 Hz, 2H), 2.24-2.14 (m, 2H), 2.00-1.86 (m, 4H), 1.76-1.63 (m, 1H), 1.31-1.16 (m, 2H); 464.4 |
| 25 | Example 5[5] | 11.36 (s, 1H), 8.47 (s, 1H), 8.33 (br t, J = 6 Hz, 1H), 7.73 (d, J = 8.8 Hz, 1H), 7.69-7.67 (m, 1H), 7.30 (ddd, J = 11.1, 6.3, 2.3 Hz, 1H), 7.01 (dd, J = 8.8, 1.8 Hz, 1H), 4.53-4.41 (m, 1H), 3.17 (dd, J = 6, 6 Hz, 2H), 2.20-2.10 (m, 2H), 1.96-1.82 (m, 4H), 1.73-1.59 (m, 1H), 1.29-1.18 (m, 2H); 438.3 (chlorine isotope pattern observed) |
| 26 | Example 5[5] | 11.36 (s, 1H), 8.40 (s, 1H), 8.36-8.29 (m, 1H), 7.77 (br d, J = 2 Hz, 1H), 7.64 (d, J = 9.1 Hz, 1H), 7.30 (ddd, J = 11.1, 6.3, 2.3 Hz, 1H), 7.19 (dd, J = 9.1, 2.1 Hz, 1H), 4.54-4.42 (m, 1H), 3.17 (dd, J = 6, 6 Hz, 2H), 2.20-2.10 (m, 2H), 1.97-1.82 (m, 4H), 1.73-1.59 (m, 1H), 1.28-1.14 (m, 2H); 438.3 (chlorine isotope pattern observed) |
| 27 | Example 5[6]; P12 | 11.37 (br s, 1H), 8.92 (d, J = 4.9 Hz, 2H), 8.68 (br s, 1H), 8.48 (br s, 1H), 8.37-8.30 (m, 1H), 8.10 (dd, J = 8.8, 1.4 Hz, 1H), 7.80 (d, J = 8.9 Hz, 1H), 7.43 (t, J = 4.8 Hz, 1H), 7.30 (ddd, J = 11.1, 6.3, 2.3 Hz, 1H), 4.58-4.47 (m, 1H), 3.18 (dd, J = 6, 6 Hz, 2H), 2.25-2.14 (m, 2H), 2.02-1.86 (m, 4H), 1.76-1.62 (m, 1H), 1.32-1.16 (m, 2H); 482.2 |
| 28 | Example 5[7]; P12 | 11.37 (br s, 1H), 9.34 (d, J = 1.6 Hz, 1H), 8.72 (dd, J = 2.5, 1.5 Hz, 1H), 8.60 (d, J = 2.5 Hz, 1H), 8.48 (br s, 1H), 8.44-8.41 (m, 1H), 8.37-8.30 (m, 1H), 7.83 (br s, 2H), 7.30 (ddd, J = 11.1, 6.3, 2.3 Hz, 1H), |

TABLE 2-continued

| Method of synthesis and physicochemical data for Examples 22-214. | | |
|---|---|---|
| Example | Method of synthesis; Non-commercial starting materials | $^1$H NMR (400 MHz, DMSO-$d_6$) d; Mass spectrum, observed ion m/z $[M + H]^+$ or HPLC retention time; Mass spectrum m/z $[M + H]^+$ (unless otherwise indicated) |
| | | 4.58-4.46 (m, 1H), 3.18 (dd, J = 6, 6 Hz, 2H), 2.25-2.14 (m, 2H), 2.01-1.86 (m, 4H), 1.76-1.62 (m, 1H), 1.32-1.16 (m, 2H); 482.3 |
| 29 | Example 5[8]; C19 | 11.49 (v br s, 1H), 8.71 (s, 1H), 8.30-8.24 (m, 1H), 8.12 (s, 1H), 7.84 (s, 1H), 7.60 (s, 1H), 7.44 (AB quartet, $J_{AB}$ = 9.2 Hz, $\Delta$□$_{AB}$ = 34.5 Hz, 2H), 7.32-7.24 (m, 1H), 3.87 (s, 3H), 3.14 (dd, J = 6, 6 Hz, 2H), 2.67-2.58 (m, 1H), 2.12-2.04 (m, 2H), 1.90-1.82 (m, 2H), 1.64-1.53 (m, 1H), 1.48-1.37 (m, 2H), 1.17-1.06 (m, 2H); 484.2 |
| 30 | Example 29; P11 | $^1$H NMR (400 MHz, DMSO-$d_6$), characteristic peaks: d 11.38 (br s, 1H), 8.76 (d, J = 7.0 Hz, 1H), 8.56 (s, 1H), 8.37-8.27 (m, 1H), 8.22 (s, 1H), 7.99 (s, 1H), 7.86 (s, 1H), 7.71 (d, J = 7.2 Hz, 1H), 7.36-7.22 (m, 1H), 3.92 (s, 3H), 3.24-3.08 (m, 2H), 2.90-2.76 (m, 1H), 1.96-1.82 (m, 2H), 1.70-1.39 (m, 3H), 1.24-1.05 (m, 2H); 484.3 |
| 31 | Example 29; P11 | 8.85 (s, 1H), 8.47 (d, J = 7.0 Hz, 1H), 8.41 (s, 1H), 8.30-8.22 (m, 1H), 8.03-7.68 (m, 2H), 7.63 (s, 1H), 7.28 (ddd, J = 11.1, 6.3, 2.3 Hz, 1H), 7.20 (dd, J = 7.1, 1.8 Hz, 1H), 3.15 (dd, J = 6, 6 Hz, 2H), 2.63 (tt, J = 11.9, 3.6 Hz, 1H), 2.15-2.04 (m, 2H), 1.92-1.81 (m, 2H), 1.65-1.51 (m, 1H), 1.50-1.34 (m, 2H), 1.20-1.04 (m, 2H); 520.3 |
| 32 | P1[9,10] | 2.33 minutes[11]; 457 |
| 33 | P1[9,12] | 2.95 minutes[11]; 562 |
| 34 | Example 12; P14 | 2.72 minutes[11]; 516 |
| 35 | Example 12; P14 | 2.68 minutes[11]; 506 |
| 36 | Example 12; P14 | 2.87 minutes[11]; 508 |
| 37 | Example 12; P14 | 2.46 minutes[11]; 494 |
| 38 | Example 12; P14 | 2.73 minutes[13]; 522 |
| 39 | Example 12; P14 | 2.52 minutes[11]; 480 |
| 40 | Example 12; P14 | 2.72 minutes[11]; 494 |
| 41 | Example 12; P14 | 2.43 minutes[11]; 507 |
| 42 | Example 12; P14 | 2.80 minutes[13]; 496 |
| 43 | Example 12; P14 | 2.66 minutes[11]; 492 |
| 44 | Example 12; P14 | 2.77 minutes[11]; 502 |
| 45 | Example 12; P14 | 2.67 minutes[13]; 508 |
| 46 | Example 12; P14 | 2.96 minutes[11]; 534 |
| 47 | Example 12; P14 | 2.59 minutes[11]; 480 |
| 48 | Example 12; P14 | 2.55 minutes[11]; 492 |
| 49 | Example 12; P14 | 2.89 minutes[11]; 534 |
| 50 | Example 12; P14 | 2.50 minutes[11]; 480 |
| 51 | Example 12; P14 | 2.68 minutes[11]; 484 |
| 52 | Example 12; P14 | 2.73 minutes[11]; 492 |
| 53 | Example 12; P14 | 2.68 minutes[11]; 478 |
| 54 | Example 12; P14 | 2.92 minutes[11]; 504 |
| 55 | Example 12; P14 | 2.99 minutes[11]; 487 |
| 56 | Example 12; P14 | 2.96 minutes[11]; 487 |
| 57 | Example 12; P14 | 2.20 minutes[11]; 477 |
| 58 | Example 12; P14 | 2.57 minutes[13]; 494 |
| 59 | Example 12; P14 | 2.17 minutes[11]; 521 |
| 60 | Example 5; P13 | 10.83 (s, 1H), 8.47 (br t, J = 5.8 Hz, 1H), 8.32 (br s, 1H), 8.15 (s, 1H), 7.90 (br s, 1H), 7.75 (br s, 1H), 7.65 (d, J = 8.7 Hz, 1H), 7.64-7.54 (m, 2H), 7.25 (dd, J = 8.7, 1.4 Hz, 1H), 4.49-4.38 (m, 1H), 3.87 (s, 3H), 3.18 (dd, J = 6, 6 Hz, 2H), 2.21-2.09 (m, 2H), 1.97-1.81 (m, 4H), 1.74-1.60 (m, 1H), 1.29-1.13 (m, 2H); 466.2 |
| 61 | Example 12; P14 | 2.10 minutes[11]; 463 |
| 62 | Example 12; P14 | 2.56 minutes[11]; 466 |
| 63 | Example 12; P14 | 2.47 minutes[13]; 478 |
| 64 | P14[14] | 2.95 minutes[15]; 492.3 |
| 65 | Example 12; P14 | 2.74 minutes[13]; 464 |
| 66 | Example 12; P14 | 2.72 minutes[11]; 494 |
| 67 | Example 12; P14 | 3.06 minutes[11]; 492 |
| 68 | Example 12; P14 | 3.13 minutes[11]; 462 |
| 69 | Example 12; P14 | 2.66 minutes[11]; 469 |
| 70 | P14[14] | 2.88 minutes[15]; 487.3 |
| 71 | Example 12; P14 | 2.50 minutes[13]; 464 |
| 72 | Example 12; P14 | 2.10 minutes[11]; 463 |
| 73 | Example 12; P14 | 2.62 minutes[11]; 494 |
| 74 | Example 12; P14 | 2.70 minutes[11]; 478 |

TABLE 2-continued

Method of synthesis and physicochemical data for Examples 22-214.

| Example | Method of synthesis; Non-commercial starting materials | $^1$H NMR (400 MHz, DMSO-$d_6$) d; Mass spectrum, observed ion m/z $[M + H]^+$ or HPLC retention time; Mass spectrum m/z $[M + H]^+$ (unless otherwise indicated) |
|---|---|---|
| 75 | Example 12; P14 | 2.13 minutes[11]; 463 |
| 76 | Example 12; P14 | 2.63 minutes[13]; 464 |
| 77 | Example 12; P14 | 2.44 minutes[11]; 478 |
| 78 | Example 12[16]; P14 | 3.22 minutes[11]; 532 |
| 79 | P14[17] | 2.68 minutes[13]; 467 |
| 80 | P14[17] | 2.86 minutes[11]; 502 |
| 81 | Example 12[16]; P14 | 2.27 minutes[11]; 477 |
| 82 | P14[17] | 3.03 minutes[13]; 470 |
| 83 | P14[17] | 2.90 minutes[11]; 469 |
| 84 | P14[17] | 2.30 minutes[11]; 508 |
| 85 | P14[17] | 3.15 minutes[11]; 509 |
| 86 | P14[17] | 2.67 minutes[11]; 497 |
| 87 | Example 12[16]; P14 | 2.58 minutes[11]; 478 |
| 88 | P14[17] | 2.75 minutes[11]; 483 |
| 89 | Example 12[16]; P14 | 2.91 minutes[11]; 502 |
| 90 | Example 12[16]; P14 | 2.30 minutes[11]; 477 |
| 91 | P14[17] | 3.09 minutes[11]; 519 |
| 92 | P14[17] | 2.71 minutes[11]; 467 |
| 93 | Example 12[16]; P14 | 2.88 minutes[11]; 504 |
| 94 | P14[17] | 2.86 minutes[11]; 483 |
| 95 | Example 12[16]; P14 | 2.81 minutes[11]; 494 |
| 96 | P14[17] | 2.72 minutes[11]; 469 |
| 97 | Example 12[18]; P14 | 2.29 minutes[11]; 503 |
| 98 | P14[17] | 2.91 minutes[11]; 469 |
| 99 | Example 12[16]; P14 | 2.45 minutes[11]; 493 |
| 100 | P14[17] | 2.83 minutes[11]; 469 |
| 101 | Example 12[16,18]; P14 | 2.89 minutes[13]; 506 |
| 102 | P14[17] | 2.61 minutes[13]; 484 |
| 103 | P14[17] | 2.29 minutes[11]; 502 |
| 104 | Example 12[16]; P14 | 2.69 minutes[13]; 493 |
| 105 | P14[17] | 3.17 minutes[11]; 509 |
| 106 | Example 12[16]; P14 | 2.77 minutes[11]; 493 |
| 107 | P14[17] | 2.91 minutes[11]; 484 |
| 108 | Example 12[16]; P14 | 2.92 minutes[11]; 493 |
| 109 | Example 12[16]; P14 | 2.78 minutes[11]; 494 |
| 110 | P14[17] | 2.83 minutes[11]; 469 |
| 111 | P14[17] | 2.94 minutes[13]; 453 |
| 112 | Example 12[19,16]; P14 | 2.52 minutes[11]; 502 |
| 113 | Example 12[16]; P14 | 2.63 minutes[11]; 503 |
| 114 | P14[17] | 2.87 minutes[11]; 554 |
| 115 | P14[17] | 2.95 minutes[11]; 483 |
| 116 | Example 12[16]; P14 | 3.15 minutes[11]; 493 |
| 117 | Example 12[16]; P14 | 2.30 minutes[11]; 502 |
| 118 | Example 12[16]; P14 | 2.26 minutes[11]; 477 |
| 119 | Example 12[16]; P14 | 2.56 minutes[11]; 503 |
| 120 | Example 12[16]; P14 | 2.38 minutes[11]; 493 |

TABLE 2-continued

| Method of synthesis and physicochemical data for Examples 22-214. | | |
|---|---|---|
| Example | Method of synthesis; Non-commercial starting materials | $^1$H NMR (400 MHz, DMSO-$d_6$) d; Mass spectrum, observed ion m/z $[M + H]^+$ or HPLC retention time; Mass spectrum m/z $[M + H]^+$ (unless otherwise indicated) |
| 121 | P14[17] | 2.99 minutes[11]; 495 |
| 122 | Example 6; P3 | $^1$H NMR (400 MHz, methanol-$d_4$), characteristic peaks: d 8.23 (s, 1H), 7.53-7.41 (m, 2H), 7.23-7.10 (m, 2H), 6.39 (d, J = 7.2 Hz, 1H), 4.49-4.36 (m, 1H), 3.92 (s, 3H), 2.31-2.18 (m, 2H), 2.09-1.91 (m, 4H), 1.87-1.72 (m, 1H), 1.39-1.22 (m, 2H); 416.2 |
| 123 | Example 4[20] | 10.84 (s, 1H), 8.30 (br t, J = 6.3 Hz, 1H), 8.13 (d, J = 8.7 Hz, 1H), 7.78 (d, J = 8.7 Hz, 1H), 7.65-7.55 (m, 2H), 3.10 (d, J = 6.2 Hz, 2H), 2.72 (s, 3H), 2.04-1.93 (m, 6H), 1.60-1.50 (m, 6H); 456.1 |
| 124 | Example 2[21,22]; P1 | 10.82 (s, 1H), 8.29 (t, J = 6.3 Hz, 1H), 8.13 (d, J = 9.2 Hz, 1H), 7.66-7.54 (m, 2H), 7.41 (d, J = 9.2 Hz, 1H), 4.12 (s, 3H), 3.10 (d, J = 6.2 Hz, 2H), 2.05-1.90 (m, 6H), 1.62-1.48 (m, 6H); 472.6 |
| 125 | P1[23] | $^1$H NMR (400 MHz, methanol-$d_4$) d 8.50 (br s, 1H), 8.11-8.08 (m, 1H), 7.74 (br d, J = 9.1 Hz, 1H), 7.52-7.42 (m, 2H), 7.44 (dd, J = 9.1, 1.8 Hz, 1H), 3.24 (s, 2H), 2.36-2.22 (m, 6H), 1.86-1.73 (m, 6H); 480.1 |
| 126 | P7[24] | $^1$H NMR (400 MHz, methanol-$d_4$) d 8.31 (br d, J = 8.9 Hz, 2H), 7.70 (br d, J = 8.9 Hz, 2H), 7.52-7.41 (m, 2H), 3.19 (s, 2H), 2.07-1.94 (m, 6H), 1.70-1.57 (m, 6H); 538.2 |
| 127 | Example 2[25]; P4 | 2.67 minutes[15]; 446.4 |
| 128 | Example 2[26,2]; P4 | 10.83 (s, 1H), 8.44 (br t, J = 5.8 Hz, 1H), 8.18 (AB quartet, $J_{AB}$ = 8.4 Hz, $\Delta\square_{AB}$ = 44.4 Hz, 4H), 7.64-7.52 (m, 2H), 3.29 (s, 3H), 3.20-3.04 (m, 3H), 2.25-2.13 (m, 2H), 1.93-1.81 (m, 2H), 1.69-1.50 (m, 3H), 1.22-1.07 (m, 2H); 492.2 |
| 129 | Example 6[25]; P3 | 2.48 minutes[15]; 416.5 |
| 130 | Example 6[25]; P3 | 2.54 minutes[15]; 400.5 |
| 131 | Example 6[25]; P3 | 2.61 minutes[15]; 400.5 |
| 132 | Example 16; P3 | 2.83 minutes[15]; 420.3 (chlorine isotope pattern observed) |
| 133 | Example 16; P3 | 2.63 minutes[15]; 404.4 |
| 134 | Example 16; P3 | 2.57 minutes[15]; 411.4 |
| 135 | Example 16; P3 | 2.83 minutes[15]; 420.3 (chlorine isotope pattern observed) |
| 136 | Example 16; P3 | 1.78 minutes[15]; 484.5 |
| 137 | Example 16; P3 | 2.94 minutes[15]; 454.4 |
| 138 | Example 13[25]; P5 | 3.11 minutes[15]; 414.2 |
| 139 | Example 22; P4 | 2.80 minutes[15]; 484.4 |
| 140 | Example 22[1,2]; P4 | 3.30 minutes[15]; 509.6 |
| 141 | Example 4[27]; P1 | 2.93 minutes[15]; 413.5 |
| 142 | Example 2[21,2] | 3.04 minutes[15]; 491.4 |
| 143 | Example 4[28]; P1 | 8.51 (AB quartet, $J_{AB}$ = 8.8 Hz, $\Delta\square_{AB}$ = 27.5 Hz, 2H), 8.28 (br t, J = 6.3 Hz, 1H), 7.65-7.53 (m, 2H), 3.10 (d, J = 6.2 Hz, 2H), 2.06-1.95 (m, 6H), 1.62-1.50 (m, 6H); 510.1 |
| 144 | Example 5[29] | 2.76 minutes[15]; 420.4 (chlorine isotope pattern observed); |
| 145 | Example 5[29] | 2.95 minutes[15]; 420.4 (chlorine isotope pattern observed) |
| 146 | C49, P1[30] | 10.83 (s, 1H), 8.28 (br t, J = 6.2 Hz, 1H), 7.91 (d, J = 9.7 Hz, 1H), 7.65-7.54 (m, 2H), 7.09 (d, J = 9.7 Hz, 1H), 3.75 (s, 3H), 3.09 (d, J = 6.2 Hz, 2H), 2.00-1.89 (m, 6H), 1.58-1.48 (m, 6H); 472.5 |
| 147 | Example 5[31] | 2.50 minutes[15]; 455.4 |
| 148 | Example 15 | 2.83 minutes[15]; 502.3 |
| 149 | Example 15 | 2.78 minutes[15]; 484.3 |
| 150 | Example 5[32]; P12 | 2.66 minutes[15]; 498.5 |
| 151 | Example 15 | 2.83 minutes[15]; 490.4 |
| 152 | Example 15 | 2.72 minutes[15]; 472.4 |
| 153 | Example 15[33]; C20 | 2.86 minutes[15]; 454.4 |
| 154 | Example 5[34] | 2.52 minutes[15]; 464.4 |
| 155 | Example 154 | 2.62 minutes[15]; 469.4 |
| 156 | Example 154 | 3.03 minutes[15]; 487.5 |
| 157 | Example 154 | 2.37 minutes[15]; 464.5 |
| 158 | Example 11; P12 | 2.68 minutes[15]; 470.4 |
| 159 | Example 5[35] | 2.43 minutes[15]; 466.5 |
| 160 | Example 5[36]; P12 | 2.19 minutes[15]; 496.5 |

TABLE 2-continued

Method of synthesis and physicochemical data for Examples 22-214.

| Example | Method of synthesis; Non-commercial starting materials | $^1H$ NMR (400 MHz, DMSO-$d_6$) d; Mass spectrum, observed ion m/z $[M + H]^+$ or HPLC retention time; Mass spectrum m/z $[M + H]^+$ (unless otherwise indicated) |
|---|---|---|
| 161 | Example 159 | 2.81 minutes[15]; 520.5 |
| 162 | Example 11; P12 | 2.76 minutes[15]; 484.5 |
| 163 | Example 11; P12 | 1.90 minutes[15]; 484.4 |
| 164 | Example 5[37]; P12 | 1.44 minutes[15]; 544.5 (chlorine isotope pattern observed) |
| 165 | Example 11; P12 | 2.42 minutes[15]; 471.4 |
| 166 | Example 11; P12 | 1.88 minutes[15]; 470.4 |
| 167 | Example 5[38] | 2.13 minutes[15]; 520.4 |
| 168 | Example 146; C48, P2 | 2.50 minutes[15]; 490.6 |
| 169 | Example 14; P7 | 2.70 minutes[15]; 510.4 |
| 170 | Example 14; P10 | 2.97 minutes[15]; 528.3 |
| 171 | Example 14; P10 | 2.42 minutes[15]; 474.4 |
| 172 | Example 14; P10 | 2.78 minutes[15]; 510.4 |
| 173 | Example 14; P7 | 2.91 minutes[15]; 509.4 |
| 174 | Example 14; P7 | 2.89 minutes[15]; 510.4 |
| 175 | Example 14; P7 | 2.91 minutes[15]; 510.4 |
| 176 | Example 13; P5 | 8.85 (dd, J = 7.0, 1.2 Hz, 1H), 8.48-8.36 (m, 1H), 7.85 (br d, J = 8.9 Hz, 1H), 7.63-7.51 (m, 2H), 7.38 (ddd, J = 8.9, 6.8, 1 Hz, 1H), 7.33 (br s, 1H), 7.13 (ddd, J = 6.9, 6.9, 1.3 Hz, 1H), 3.15 (dd, J = 6, 6 Hz, 2H), 2.86 (tt, J = 12.1, 3.6 Hz, 1H), 2.15-2.04 (m, 2H), 1.93-1.81 (m, 2H), 1.69-1.43 (m, 3H), 1.21-1.05 (m, 2H); 454.2 |
| 177 | Example 4[20,39] | 10.85 (s, 1H), 9.42 (br s, 1H), 9.39 (br s, 1H), 8.09 (br t, J = 6 Hz, 1H), 7.26 (ddd, J = 8, 8, 2.1 Hz, 1H), 6.83 (ddd, J = 8, 8, 2 Hz, 1H), 3.09 (d, J = 6.2 Hz, 2H), 2.06-1.95 (m, 6H), 1.62-1.51 (m, 6H); 510.2 |
| 178 | Example 5[40] | 11.34 (s, 1H), 9.42 (br s, 1H), 9.39 (br s, 1H), 8.20 (br t, J = 6 Hz, 1H), 7.28 (ddd, J = 11.1, 6.2, 2.3 Hz, 1H), 3.09 (d, J = 6.3 Hz, 2H), 2.06-1.96 (m, 6H), 1.62-1.51 (m, 6H); 528.2 |
| 179 | Example 15[41] | 9.41 (br s, 1H), 9.39 (br s, 1H), 8.03-7.94 (m, 1H), 7.40 (dd, J = 11.3, 6.9 Hz, 1H), 6.79 (dd, J = 11.6, 7.1 Hz, 1H), 3.09 (d, J = 6.2 Hz, 2H), 2.05-1.95 (m, 6H), 1.61-1.50 (m, 6H); 510.2 |
| 180 | Example 3 | 8.51 (AB quartet, $J_{AB}$ = 8.8 Hz, $\Delta\square_{AB}$ = 27.2 Hz, 2H), 8.13-8.03 (m, 1H), 7.26 (ddd, J = 8, 8, 2.2 Hz, 1H), 6.86-6.78 (m, 1H), 3.09 (d, J = 6.3 Hz, 2H), 2.08-1.96 (m, 6H), 1.63-1.52 (m, 6H); 510.2 |
| 181 | Example 4[42]; P1 | 10.84 (s, 1H), 8.64 (s, 1H), 8.47 (br t, J = 5.8 Hz, 1H), 8.21-8.17 (m, 1H), 7.80 (d, J = 9.0 Hz, 1H), 7.64-7.54 (m, 2H), 7.43 (dd, J = 9.1, 1.8 Hz, 1H), 4.62-4.50 (m, 1H), 3.18 (dd, J = 6, 6 Hz, 2H), 2.21-2.11 (m, 2H), 1.99-1.83 (m, 4H), 1.75-1.61 (m, 1H), 1.31-1.14 (m, 2H); 454.1 |
| 182 | Example 3[42] | 11.38 (br s, 1H), 8.65 (s, 1H), 8.37-8.31 (m, 1H), 8.19 (br s, 1H), 7.80 (d, J = 9.0 Hz, 1H), 7.43 (dd, J = 9.1, 1.8 Hz, 1H), 7.30 (ddd, J = 11.1, 6.3, 2.3 Hz, 1H), 4.62-4.49 (m, 1H), 3.18 (dd, J = 6, 6 Hz, 2H), 2.22-2.12 (m, 2H), 2.00-1.85 (m, 4H), 1.75-1.60 (m, 1H), 1.31-1.15 (m, 2H); 472.2 |
| 183 | Example 3[42] | 10.90 (s, 1H), 8.64 (s, 1H), 8.21-8.17 (m, 1H), 8.17-8.11 (m, 1H), 7.80 (d, J = 9.0 Hz, 1H), 7.47-7.39 (m, 2H), 6.80 (dd, J = 11.6, 7.1 Hz, 1H), 4.61-4.49 (m, 1H), 3.17 (dd, J = 6, 6 Hz, 2H), 2.22-2.11 (m, 2H), 1.99-1.84 (m, 4H), 1.75-1.60 (m, 1H), 1.31-1.14 (m, 2H); 454.1 |
| 184 | Example 15[43] | 11.35 (br s, 1H), 8.51 (AB quartet, $J_{AB}$ = 8.9 Hz, $\Delta\square_{AB}$ = 26.9 Hz, 2H), 8.20 (br t, J = 6 Hz, 1H), 7.28 (ddd, J = 11.0, 6.2, 2.3 Hz, 1H), 3.09 (d, J = 6.2 Hz, 2H), 2.08-1.96 (m, 6H), 1.63-1.51 (m, 6H); 528.2 |
| 185 | Example 3 | 8.51 (AB quartet, $J_{AB}$ = 8.9 Hz, $\Delta\square_{AB}$ = 27.2 Hz, 2H), 8.03-7.92 (m, 1H), 7.40 (dd, J = 11.3, 6.9 Hz, 1H), 6.79 (dd, J = 11.6, 7.0 Hz, 1H), 3.09 (d, J = 6.3 Hz, 2H), 2.07-1.95 (m, 6H), 1.61-1.51 (m, 6H); 510.1 |
| 186 | Example 3[44] | 8.12-8.04 (m, 1H), 7.71-7.69 (m, 1H), 7.67 (d, half of AB quartet, J = 8.1 Hz, 1H), 7.53 (dd, component of ABX system, J = 8.1, 1.9 Hz, 1H), 7.40 (dd, J = 11.4, 6.9 Hz, 1H), 6.77 (dd, J = 11.7, 7.1 Hz, 1H), 4.44 (s, 2H), 3.98 (tt, J = 12.1, 3.9 Hz, |

TABLE 2-continued

| Method of synthesis and physicochemical data for Examples 22-214. | | |
|---|---|---|
| Example | Method of synthesis; Non-commercial starting materials | $^1$H NMR (400 MHz, DMSO-$d_6$) d; Mass spectrum, observed ion m/z $[M + H]^+$ or HPLC retention time; Mass spectrum m/z $[M + H]^+$ (unless otherwise indicated) |
| | | 1H), 3.12 (dd, J = 6, 6 Hz, 2H), 1.90-1.71 (m, 4H), 1.63-1.47 (m, 3H), 1.19-1.04 (m, 2H); 435.1 (chlorine isotope pattern observed) |
| 187 | Example 4[45] | 9.04-9.01 (m, 1H), 8.56 (s, 1H), 8.47-8.40 (m, 1H), 7.79 (d, J = 1.2 Hz, 1H), 7.62-7.51 (m, 2H), 4.68-4.56 (m, 1H), 3.17 (dd, J = 6, 6 Hz, 2H), 2.22-2.12 (m, 2H), 1.99-1.84 (m, 4H), 1.74-1.60 (m, 1H), 1.30-1.14 (m, 2H); 421.1 (chlorine isotope pattern observed) |
| 188 | Example 8; P15 | 10.86 (br s, 1H), 9.35 (d, J = 1.3 Hz, 1H), 8.84 (s, 1H), 8.83-8.79 (m, 2H), 8.58 (br s, 1H), 8.49 (br t, J = 5.8 Hz, 1H), 8.45 (br d, J = 6 Hz, 2H), 7.65-7.54 (m, 2H), 4.70-4.56 (m, 1H), 3.19 (dd, J = 6, 6 Hz, 2H), 2.26-2.15 (m, 2H), 2.02-1.87 (m, 4H), 1.77-1.62 (m, 1H), 1.32-1.17 (m, 2H); 464.1 |
| 189 | Example 8; P15 | 10.85 (s, 1H), 9.34 (br s, 1H), 9.27 (d, J = 1.3 Hz, 1H), 8.76 (br s, 1H), 8.59 (br s, 1H), 8.53-8.45 (m, 2H), 8.24-8.21 (m, 1H), 7.64-7.55 (m, 2H), 7.50 (dd, J = 8.2, 4.6 Hz, 1H), 4.64-4.52 (m, 1H), 3.19 (dd, J = 6, 6 Hz, 2H), 2.25-2.13 (m, 2H), 2.01-1.85 (m, 4H), 1.76-1.61 (m, 1H), 1.31-1.16 (m, 2H); 464.1 |
| 190 | Example 126[46]; P7 | $^1$H NMR (400 MHz, chloroform-d) d 8.17 (br d, J = 7.7 Hz, 1H), 8.11-8.09 (m, 1H), 7.66 (dd, J = 8.2, 7.9 Hz, 1H), 7.56 (br dd, component of ABX system, J = 8.2, 2.3 Hz, 1H), 7.43-7.33 (m, 2H), 6.00 (br t, J = 6 Hz, 1H), 5.78 (br s, 1H), 3.29 (d, J = 6.4 Hz, 2H), 2.07-1.97 (m, 6H), 1.67-1.56 (m, 6H); 538.1 |
| 191 | Example 4[20]; P1 | 10.86 (br s, 1H), 9.42-9.40 (m, 1H), 9.39-9.37 (m, 1H), 8.30 (br t, J = 6.3 Hz, 1H), 7.65-7.55 (m, 2H), 3.10 (d, J = 6.2 Hz, 2H), 2.04-1.94 (m, 6H), 1.60-1.50 (m, 6H); 510.2 |
| 192 | P1[47] | 10.81 (br s, 1H), 8.17 (t, J = 6.3 Hz, 1H), 7.62-7.51 (m, 2H), 6.30 (br s, 1H), 2.98 (d, J = 6.2 Hz, 2H), 1.74-1.64 (m, 6H), 1.45-1.37 (m, 6H), 1.34 (s, 9H); 411.2 |
| 193 | Example 22; P8 | 8.64 (s, 1H), 8.18-8.14 (m, 1H), 8.02 (br s, 1H), 7.80 (d, J = 9.1 Hz, 1H), 7.42 (dd, J = 9.1, 1.8 Hz, 1H), 7.22 (ddd, J = 11.6, 6.7, 2.2 Hz, 1H), 3.11 (d, J = 6.3 Hz, 2H), 2.23-2.13 (m, 6H), 1.72-1.62 (m, 6H); 498.1 |
| 194 | Example 2[21,48] | 10.83 (br s, 1H), 8.29 (br t, J = 6.3 Hz, 1H), 7.90-7.81 (m, 2H), 7.65-7.55 (m, 2H), 7.44 (dd, J = 7.3, 1.5 Hz, 1H), 3.09 (d, J = 6.2 Hz, 2H), 2.55 (s, 3H), 2.01-1.91 (m, 6H), 1.59-1.49 (m, 6H); 455.2 |
| 195 | Example 5[49] | $^1$H NMR (400 MHz, methanol-$d_4$) d 9.34 (br s, 1H), 8.64 (dd, J = 8.2, 2.1 Hz, 1H), 7.98 (d, J = 8.2 Hz, 1H), 7.98-7.90 (m, 1H), 7.45 (dd, J = 11.3, 6.9 Hz, 1H), 6.75 (dd, J = 12.1, 6.9 Hz, 1H), 3.25-3.21 (m, 2H), 2.15-2.05 (m, 6H), 1.73-1.62 (m, 6H); 509.3 |
| 196 | Example 5[49] | $^1$H NMR (400 MHz, methanol-$d_4$) d 9.34 (br s, 1H), 8.65 (dd, J = 8.2, 2.0 Hz, 1H), 8.17-8.08 (m, 1H), 7.98 (d, J = 8.2 Hz, 1H), 7.25 (ddd, J = 11.0, 6.3, 2.3 Hz, 1H), 3.26-3.21 (m, 2H), 2.16-2.06 (m, 6H), 1.73-1.63 (m, 6H); 527.3 |
| 197 | Example 5[49] | $^1$H NMR (400 MHz, methanol-$d_4$) d 9.37-9.33 (m, 1H), 8.65 (dd, J = 8.2, 2.1 Hz, 1H), 7.99 (d, J = 8.2 Hz, 1H), 7.47 (dd, J = 11.3, 6.9 Hz, 1H), 6.74 (dd, J = 12.1, 6.9 Hz, 1H), 3.36-3.26 (m, 2H, assumed; completely obscured by solvent peak), 3.15-3.04 (m, 1H), 2.33-2.24 (m, 2H), 2.06-1.96 (m, 2H), 1.80-1.64 (m, 3H), 1.32-1.18 (m, 2H); 483.1 |
| 198 | Example 3; C34 | 9.50 (s, 2H), 8.15-8.05 (m, 1H), 7.42 (dd, J= 11.4, 6.9 Hz, 1H), 6.79 (dd, J = 11.5, 7.1 Hz, 1H), 3.19-3.07 (m, 3H), 2.26-2.15 (m, 2H), 1.93-1.82 (m, 2H), 1.68-1.51 (m, 3H), 1.22-1.07 (m, 2H); 484.1 |
| 199 | Example 8[9] | 10.88 (br s, 1H), 9.31-9.26 (m, 2H), 8.64 (br s, 1H), 8.55 (br d, J = 4.6 Hz, 1H), 8.48 (br t, J = 5.6 Hz, 1H), 8.44 (br d, J = 8.0 Hz, 1H), 8.31 (d, J = 1.5 Hz, 1H), 7.64-7.54 (m, 2H), 7.49 (dd, J = 8.0, 4.7 Hz, 1H), 4.68-4.57 (m, 1H), 3.19 (dd, J = 6, 6 Hz, 2H), 2.25-2.14 (m, 2H), 2.03-1.87 (m, 4H), 1.77-1.62 (m, 1H), 1.32-1.16 (m, 2H); 464.1 |

TABLE 2-continued

Method of synthesis and physicochemical data for Examples 22-214.

| Example | Method of synthesis; Non-commercial starting materials | $^1$H NMR (400 MHz, DMSO-$d_6$) d; Mass spectrum, observed ion m/z $[M + H]^+$ or HPLC retention time; Mass spectrum m/z $[M + H]^+$ (unless otherwise indicated) |
|---|---|---|
| 200 | Example 8[9,2] | 10.85 (s, 1H), 9.21 (br s, 1H), 8.55 (br s, 1H), 8.49 (br t, J = 5.8 Hz, 1H), 8.20 (s, 1H), 7.97 (s, 1H), 7.90 (br s, 1H), 7.65-7.54 (m, 2H), 4.67-4.53 (m, 1H), 3.88 (s, 3H), 3.22-3.15 (m, 2H), 2.23-2.13 (m, 2H), 2.01-1.86 (m, 4H), 1.77-1.62 (m, 1H), 1.31-1.15 (m, 2H); 467.1 |
| 201 | Example 8[9,2] | $^1$H NMR (400 MHz, DMSO-$d_6$), characteristic peaks: d 9.27 (br s, 1H), 9.24 (s, 2H), 8.64 (br s, 1H), 8.45-8.37 (m, 1H), 8.27 (d, J = 1.5 Hz, 1H), 7.60-7.49 (m, 2H), 4.68-4.56 (m, 1H), 3.98 (s, 3H), 2.25-2.13 (m, 2H), 2.03-1.87 (m, 4H), 1.77-1.61 (m, 1H); 495.1 |
| 202 | Example 125; P1 | 8.37 (d, J = 1.0 Hz, 1H), 8.30-8.23 (m, 1H), 7.65 (ddd, J = 8.4, 1, 1 Hz, 1H), 7.63-7.53 (m, 3H), 7.19 (ddd, J = 8.7, 6.6, 1.2 Hz, 1H), 6.99 (ddd, J = 8.3, 6.6, 0.9 Hz, 1H), 3.12 (d, J = 6.2 Hz, 2H), 2.20-2.10 (m, 6H), 1.70-1.61 (m, 6H); 412.2 |
| 203 | Example 3[50]; C32, P1 | 10.84 (br s, 1H), 9.48 (s, 2H), 8.34-8.24 (m, 1H), 7.65-7.53 (m, 2H), 3.10 (d, J = 6.2 Hz, 2H), 2.03-1.93 (m, 6H), 1.60-1.50 (m, 6H); 510.1 |
| 204 | Example 8[51]; P1 | 10.85 (s, 1H), 8.35-8.28 (m, 2H), 8.14 (s, 1H), 7.90 (br s, 1H), 7.77-7.73 (m, 1H), 7.66-7.56 (m, 3H), 7.24 (dd, J = 8.7, 1.5 Hz, 1H), 3.86 (s, 3H), 3.12 (d, J = 6.2 Hz, 2H), 2.20-2.10 (m, 6H), 1.71-1.60 (m, 6H); 492.1 |
| 205 | P1[52] | 8.45 (s, 1H), 8.17-8.08 (m, 1H), 7.84 (br s, 1H), 7.65 (d, J = 8.8 Hz, 1H), 7.55-7.42 (m, 2H), 7.10 (dd, J = 8.8, 1.7 Hz, 1H), 3.10 (d, J = 6.3 Hz, 2H), 2.18-2.09 (m, 6H), 1.69-1.59 (m, 6H); 490.0 (bromine isotope pattern observed) |
| 206 | Example 204 | 10.86 (br s, 1H), 9.20 (s, 2H), 9.18 (s, 1H), 8.47 (d, J = 1.0 Hz, 1H), 8.32 (br t, J = 6.3 Hz, 1H), 8.10-8.07 (m, 1H), 7.83 (dd, J = 8.7, 0.9 Hz, 1H), 7.66-7.55 (m, 2H), 7.44 (dd, J = 8.7, 1.6 Hz, 1H), 3.13 (d, J = 6.2 Hz, 2H), 2.24-2.13 (m, 6H), 1.73-1.62 (m, 6H); 490.1 |
| 207 | Example 7[51] | 10.84 (br s, 1H), 8.91 (d, J = 4.8 Hz, 2H), 8.68-8.64 (m, 1H), 8.46 (d, J = 1.0 Hz, 1H), 8.33 (br t, J = 6.3 Hz, 1H), 8.08 (dd, J = 8.8, 1.4 Hz, 1H), 7.78 (dd, J = 8.9, 1 Hz, 1H), 7.67-7.56 (m, 2H), 7.43 (t, J = 4.8 Hz, 1H), 3.13 (d, J = 6.2 Hz, 2H), 2.25-2.14 (m, 6H), 1.73-1.63 (m, 6H); 490.1 |
| 208 | Example 7[51] | 9.34 (d, J = 1.6 Hz, 1H), 8.72 (dd, J = 2.6, 1.5 Hz, 1H), 8.59 (d, J = 2.5 Hz, 1H), 8.48-8.46 (m, 1H), 8.43-8.41 (m, 1H), 8.28 (br t, J = 6.2 Hz, 1H), 7.83-7.80 (m, 2H), 7.64-7.53 (m, 2H), 3.13 (d, J = 6.2 Hz, 2H), 2.25-2.13 (m, 6H), 1.73-1.62 (m, 6H); 490.1 |
| 209 | Example 8; P16 | 11.40 (br s, 1H), 8.32 (d, J = 0.9 Hz, 1H), 8.21-8.13 (m, 1H), 8.15 (s, 1H), 7.90 (br s, 1H), 7.75 (br s, 1H), 7.64 (dd, J = 8.6, 0.9 Hz, 1H), 7.27 (ddd, J = 11.0, 6.4, 2.2 Hz, 1H), 7.24 (dd, J = 8.6, 1.5 Hz, 1H), 3.87 (s, 3H), 3.11 (d, J = 6.2 Hz, 2H), 2.22-2.09 (m, 6H), 1.72-1.61 (m, 6H); 510.1 |
| 210 | Example 4[53] | 11.37 (br s, 1H), 9.19-9.15 (m, 1H), 8.45 (dd, component of ABX system, J = 8.4, 2.4 Hz, 1H), 8.34-8.27 (m, 1H), 8.27 (d, half of AB quartet, J = 8.3 Hz, 1H), 7.29 (ddd, J = 11.1, 6.3, 2.4 Hz, 1H), 3.19-3.06 (m, 3H), 2.25-2.15 (m, 2H), 1.93-1.83 (m, 2H), 1.67-1.52 (m, 3H), 1.22-1.09 (m, 2H); 501.1 |
| 211 | Example 4[54]; P1 | 10.85 (br s, 1H), 8.45 (br t, J = 5.8 Hz, 1H), 8.15 (d, J = 8.7 Hz, 1H), 7.79 (d, J = 8.7 Hz, 1H), 7.64-7.52 (m, 2H), 3.20-3.07 (m, 3H), 2.73 (s, 3H), 2.25-2.15 (m, 2H), 1.93-1.82 (m, 2H), 1.68-1.51 (m, 3H), 1.23-1.08 (m, 2H); 430.2 |
| 212 | Footnotes [54], 55 | 2.50 minutes[15]; 448.5 |
| 213 | Example 3[56] | 10.94 (br s, 1H), 8.40 (t, J = 5.8 Hz, 1H), 7.62-7.50 (m, 2H), 3.12 (t, J = 6.3 Hz, 2H), 2.93 (tt, J = 12.1, 3.6 Hz, 1H), 2.29 (s, 3H), 2.12-2.02 (m, 2H), 1.87-1.78 (m, 2H), 1.63-1.50 (m, 1H), 1.52-1.39 (m, 2H), 1.16-1.02 (m, 2H); 352.2 |

TABLE 2-continued

Method of synthesis and physicochemical data for Examples 22-214.

| Example | Method of synthesis; Non-commercial starting materials | $^1$H NMR (400 MHz, DMSO-$d_6$) d; Mass spectrum, observed ion m/z $[M + H]^+$ or HPLC retention time; Mass spectrum m/z $[M + H]^+$ (unless otherwise indicated) |
|---|---|---|
| 214 | Example 3[56] | 10.44 (br s, 1H), 8.31 (t, J = 5.8 Hz, 1H), 7.65 (dd, J = 12.4, 2.1 Hz, 1H), 7.56 (dd, J = 8.4, 2.1 Hz, 1H), 6.98 (t, J = 8.6 Hz, 1H), 3.11 (t, J = 6.3 Hz, 2H), 2.93 (tt, J = 12.1, 3.6 Hz, 1H), 2.29 (s, 3H), 2.12-2.02 (m, 2H), 1.87-1.78 (m, 2H), 1.63-1.51 (m, 1H), 1.51-1.38 (m, 2H), 1.16-1.02 (m, 2H); 334.2 |

[1]Reaction of P3 with 2-nitrobenzaldehyde, followed by ring closure of the resulting imine with triethyl phosphite and deprotection using hydrogen chloride in 1,4-dioxane, afforded Example 22.

[2]Trifluoroacetic acid was used for the final deprotection, rather than hydrogen chloride.

[3]The requisite 1-[(1r,4r)-4-(6-methoxy-2H-indazol-2-yl)cyclohexyl]methanamine, hydrochloride salt, was prepared using the method described for synthesis of C25 in Preparation P15.

[4]In this case, the boronate coupling was catalyzed by tetrakis(triphenylphosphine)palladium(0) rather than [1,1'-bis(diphenylphosphino)ferrocene]dichloropalladium(II).

[5]The requisite chloro-substituted 1-[(1r,4r)-4-(2H-indazol-2-yl)cyclohexyl]methanamine, hydrochloride salt, was prepared using the method described for synthesis of C25 in Preparation P15.

[6]The requisite 1-{(1r,4r)-4-[6-(pyrimidin-2-yl)-2H-indazol-2-yl]cyclohexyl}methanamine, hydrochloride salt, was prepared using the method described for synthesis of P13 in Preparation P13.

[7]The requisite 1-{(1r,4r)-4-[6-(pyrazin-2-yl)-2H-indazol-2-yl]cyclohexyl}methanamine, hydrochloride salt, was prepared using the method described for synthesis of P13 in Preparation P13.[8]Synthesis of tert-butyl {[(1r,4r)-4-(6-bromoimidazo[1,2-a]pyridin-2-yl)cyclohexyl]methyl}carbamate was carried out from C19, using the method described for synthesis of P11 in Preparation P11. This material was converted to the requisite 1-{(1r,4r)-4-[6-(1-methyl-1H-pyrazol-4-yl)imidazo[1,2-a]pyridin-2-yl]cyclohexyl}methanamine, hydrochloride salt, by reaction with 1-methyl-4-(4,4,5,5-tetramethyl-1,3,2-dioxaborolan-2-yl)-1H-pyrazole in the presence of [1,1'-bis(diphenylphosphino)ferrocene]dichloropalladium(II) and potassium carbonate, followed by deprotection with hydrogen chloride.

[9]The requisite N-{[(1r,4r)-4-(5-chloro-2H-pyrazolo[3,4-c]pyridin-2-yl)cyclohexyl]methyl}-3,5-difluoro-4-[(4-methoxyphenyl)methoxy]benzamide was synthesized according to the method described for preparation of P15 in Preparation P15.

[10]Cyclopropylmethanol was deprotected with sodium hydride in tetrahydrofuran at 0° C., whereupon N-{[(1r,4r)-4-(5-chloro-2H-pyrazolo[3,4-c]pyridin-2-yl)cyclohexyl]methyl}-3,5-difluoro-4-[(4-methoxyphenyl)methoxy]benzamide (see footnote[9]) was added, and the reaction mixture was heated at 80° C. for 16 hours. Subsequent deprotection using trifluoroacetic acid provided Example 32.

[11]Conditions for analytical HPLC. Column: Waters XBridge C18, 2.1 × 50 mm, 5 μm; Mobile phase A: water containing 0.0375% trifluoroacetic acid; Mobile phase B: acetonitrile containing 0.01875% trifluoroacetic acid; Gradient: 10% B for 0.50 minutes; 10% to 100% B over 3.5 minutes; Flow rate: 0.8 mL/minute.

[12]A mixture of N-{[(1r,4r)-4-(5-chloro-2H-pyrazolo[3,4-c]pyridin-2-yl)cyclohexyl]methyl}-3,5-difluoro-4-[(4-methoxyphenyl)methoxy]benzamide (see footnote[9]), [6-(trifluoromethyl)pyridin-2-yl]methanol, tris(dibenzylideneacetone)dipalladium(0), 5-(di-tert-butylphosphanyl)-1',3',5'-triphenyl-1'H-1,4'-bipyrazole (BippyPhos), and sodium hydroxide was heated in a 4:1 mixture of 2-methylbutan-2-ol and dichloromethane at 105° C. for 16 hours. Subsequent deprotection using trifluoroacetic acid provided Example 33.

[13]Conditions for analytical HPLC. Column: Waters XBridge C18, 2.1 × 50 mm, 5 μm; Mobile phase A: water containing 0.0375% trifluoroacetic acid; Mobile phase B: acetonitrile containing 0.01875% trifluoroacetic acid; Gradient: 1% to 5% B over 0.6 minutes; 5% to 100% B over 3.4 minutes; Flow rate: 0.8 mL/minute.

[14]Intermediate P14 was reacted with the appropriate aromatic bromide in the presence of [1,1'-bis(diphenylphosphino)ferrocene]dichloropalladium(II) and tripotassium phosphate, followed by deprotection with hydrogen chloride.

[15]Column: Waters Atlantis dC18, 4.6 × 50 mm, 5 μm; Mobile phase A: water containing 0.05% trifluoroacetic acid (v/v); Mobile phase B: acetonitrile containing 0.05% trifluoroacetic acid (v/V); Gradient: 5.0% to 95% B, linear over 4.0 minutes, then 95% B for 1.0 minute; Flow rate: 2 mL/minute.

[16]In this case, [1,1'-bis(diphenylphosphino)ferrocene]dichloropalladium(II) was used in place of chloro[(di(1-adamantyl)-N-butylphosphine)-2-(2-aminobiphenyl)]palladium(II) (cataCXium ® A Pd G2).

[17]The coupling was carried out using the conditions described in Step 1 of Example 10; deprotection of the product was then effected using trifluoroacetic acid.

[18]In this case, the chloro reactant was used, rather than the bromide.

[19]In this case, 5-bromo-1H-pyrrolo[2,3-b]pyridine was reacted with p-toluenesulfonyl chloride in the presence of N, N-diisopropylethylamine, and the resultant 5-bromo-1-(4-methylbenzene-1-sulfonyl)-1H-pyrrolo[2,3-b]pyridine was used in the coupling reaction.

[20]In this case, the acyl intermediate was cyclized by treatment with sodium acetate, rather than tetrabutylammonium fluoride.

[21]The requisite 4-({3,5-difluoro-4-[(4-methoxyphenyl)methoxy]benzamido}methyl)bicyclo[2.2.2]octane-1-carboxylic acid was synthesized using the method described for preparation of P9 in Preparation P9, but employing P1 as starting material.

[22]The final deprotection was carried out using methanesulfonic acid in 1,1,1,3,3,3-hexafluoropropan-2-ol, rather than hydrogen chloride.[23]Conversion of P1 to the requisite N-[(4-aminobicyclo[2.2.2]octan-1-yl)methyl]-3,5-difluoro-4-[(4-methoxyphenyl)methoxy]benzamide was carried out using the method described in Preparation P3. This intermediate was condensed with 2-nitro-5-(trifluoromethyl)benzaldehyde, followed by ring closure of the resulting imine with triethyl phosphite and deprotection using hydrogen chloride, to afford Example 125.[24]Reaction of P7 with 4-[(fluorosulfonyl)oxy]benzoic acid (A. Baranczak et al., *J. Am. Chem. Soc.* 2015, 137, 7404-7414), 1-[3-(dimethylamino)propyl]-3-ethylcarbodiimide hydrochloride, 1H-benzotriazol-1-ol, and N,N-diisopropylethylamine afforded the acyl intermediate; this was subjected to tetrabutylammonium fluoride, providing 3,5-difluoro-N-({4-[5-(4-hydroxyphenyl)-1,2,4-oxadiazol-3-yl]bicyclo[2.2.2]octan-1-yl}methyl)-4-[(4-methoxyphenyl)methoxy]benzamide. Reaction with (4-acetamidophenyl)imidodisulfuryl difluoride (AISF) and cesium carbonate, followed by deprotection via hydrogen chloride treatment, afforded Example 126.

[25]p-Toluenesulfonic acid was used for the final deprotection, rather than hydrogen chloride.[26]In this case, the acyl intermediate was cyclized by heating in 1-methylpyrrolidin-2-one, rather than treatment with sodium acetate.[27]Methyl 4-(aminomethyl)bicyclo[2.2.2]octane-1-carboxylate was protected by reaction with benzyl chloroformate and triethylamine, whereupon the ester was cleaved using sodium hydroxide. The resulting 4-({[(benzyloxy)carbonyl]amino}methyl)bicyclo[2.2.2]octane-1-carboxylic acid was converted to benzyl {[4-(1,3-benzoxazol-2-yl)bicyclo[2.2.2]octan-1-yl]methyl}carbamate using the method described for synthesis of C26 from P4 in Example 1; subsequent hydrogenation over palladium on carbon afforded the requisite 1-[4-(1,3-benzoxazol-2-yl)bicyclo[2.2.2]octan-1-yl]methanamine.

[28]The requisite 1-(4-{3-[6-(trifluoromethyl)pyridazin-3-yl]-1,2,4-oxadiazol-5-yl}bicyclo[2.2.2]octan-1-yl)methanamine was prepared using the method described for synthesis of C32 in Example 3.

[29]The requisite chloro-substituted 1-[(1r,4r)-4-(2H-indazol-2-yl)cyclohexyl]methanamine, hydrochloride salt, was prepared using the method employed for synthesis of C25 in Preparation P15.[30]Reaction of C49 with P1, mediated by O-(7-azabenzotriazol-1-yl)-N,N,N',N'-tetramethyluronium hexafluorophosphate and N,N-diisopropylethylamine, provided 3,5-difluoro-4-[(4-methoxyphenyl)methoxy]-N-({4-[3-(6-methoxypyridazin-3-yl)-1,2,4-oxadiazol-5-yl]bicyclo[2.2.2]octan-1-yl}methyl)benzamide. This material was demethylated using trimethylsilyl chloride and potassium iodide to afford 3,5-difluoro-4-[(4-methoxyphenyl)methoxy]-N-({4-[3-(6-oxo-1,6-dihydropyridazin-3-yl)-1,2,4-oxadiazol-5-yl]bicyclo[2.2.2]octan-1-yl}methyl)benzamide, which was N-methylated using methyl 4-nitrobenzene-1-sulfonate and cesium carbonate; deprotection with trifluoroacetic acid provided Example 146.

TABLE 2-continued

| Method of synthesis and physicochemical data for Examples 22-214. | | |
|---|---|---|
| Example | Method of synthesis; Non-commercial starting materials | $^1$H NMR (400 MHz, DMSO-$d_6$) d; Mass spectrum, observed ion m/z $[M + H]^+$ or HPLC retention time; Mass spectrum m/z $[M + H]^+$ (unless otherwise indicated) |

[31] tert-Butyl {[(1r,4r)-4-aminocyclohexyl]methyl}carbamate was converted to the requisite 1-{(1r,4r)-4-[5-(trifluoromethyl)-2H-pyrazolo[3,4-c]pyridin-2-yl]cyclohexyl}methanamine, hydrochloride salt using the procedure described in Example 6 for the synthesis of 6 from P3.

[32] 1-{(1r,4r)-4-[6-(1-Ethyl-1H-pyrazol-4-yl)-2H-indazol-2-yl]cyclohexyl}methanamine, hydrochloride salt, was prepared from P12 using the method described for synthesis of P13 in Preparation P13.

[33] 1-{(1r,4r)-4-[6-(Difluoromethyl)-2H-indazol-2-yl]cyclohexyl}methanamine, trifluoroacetate salt, was prepared from C20 by reaction with 2-(difluoromethanesulfonyl)pyridine and zinc in the presence of nickel(II) chloride ethylene glycol dimethyl ether complex, 4-methylpyridine-2,6-dicarboximidamide (see J. M. E. Hughes and P. S. Fier, *Org. Lett.* 2019, 21, 5650-5654), and tetraethylammonium iodide; subsequent deprotection was carried out with trifluoroacetic acid.

[34] tert-Butyl ({(1r,4r)-4-[5-(4,4,5,5-tetramethyl-1,3,2-dioxaborolan-2-yl)-2H-indazol-2-yl]cyclohexyl}methyl) carbamate was prepared in the same manner as P12 in Preparation P12. It was subsequently converted to the requisite 1-{(1r,4r)-4-[5-(pyrimidin-2-yl)-2H-indazol-2-yl]cyclohexyl}methanamine, hydrochloride salt, using the method described in Preparation P13.

[35] tert-Butyl ({(1r,4r)-4-[5-(4,4,5,5-tetramethyl-1,3,2-dioxaborolan-2-yl)-2H-indazol-2-yl]cyclohexyl}methyl) carbamate (see footnote[34]) was converted to the requisite 1-{(1r,4r)-4-[5-(1-methyl-1H-pyrazol-4-yl)-2H-indazol-2-yl]cyclohexyl}methanamine, hydrochloride salt, via the method described for synthesis of C41 from P12 in Example 10, followed by deprotection with hydrogen chloride.

[36] Conversion of P12 to the requisite 2-(4-{2-[(1r,4r)-4-(aminomethyl)cyclohexyl]-2H-indazol-6-yl}-1H-pyrazol-1-yl)ethan-1-ol was carried out using the method described for synthesis of C41 from P12 in Example 10, followed by deprotection with hydrogen chloride.[37] Reaction of P12 with 4-bromo-1-(oxetan-3-yl)-1H-pyrazole was carried out using the method described for synthesis of C41 from P12 in Example 10. Subsequent deprotection with hydrogen chloride also cleaved the oxetane ring, providing 2-(4-{2-[(1r,4r)-4-(aminomethyl)cyclohexyl]-2H-indazol-6-yl}-1H-pyrazol-1-yl)-3-chloropropan-1-ol.[38] Synthesis of tert-butyl {[(1r,4r)-4-(6-bromoimidazo[1,2-a]pyridin-2-yl)cyclohexyl]methyl}carbamate was carried out from C19, using the method described for synthesis of P11 in Preparation P11. Coupling of this material with 1-(difluoromethyl)-4-(4,4,5,5-tetramethyl-1,3,2-dioxaborolan-2-yl)-1H-pyrazole, in the presence of [1,1'-bis(di-tert-butylphosphino)ferrocene]dichloropalladium(II) and potassium carbonate, followed by deprotection with hydrogen chloride, afforded the requisite 1-[(1r,4r)-4-{6-[1-(difluoromethyl)-1H-pyrazol-4-yl]imidazo[1,2-a]pyridin-2-yl}cyclohexyl]methanamine, hydrochloride salt.

[39] In this case, 2,3-difluoro-4-hydroxybenzoic acid was employed for the final amide formation, rather than P1.[40] The requisite 1-(4-{3-[5-(trifluoromethyl)pyrazin-2-yl]-1,2,4-oxadiazol-5-yl}bicyclo[2.2.2]octan-1-yl)methanamine, hydrochloride salt was prepared in the following manner. Reaction of 4-{[(tert-butoxycarbonyl)amino]methyl}bicyclo[2.2.2]octane-1-carboxylic acid and N-hydroxy-5-(trifluoromethyl)pyrazine-2-carboximidamide was carried out using 1-[3-(dimethylamino)propyl]-3-ethylcarbodiimide hydrochloride and 1-methyl-1H-imidazole; the resulting acyl intermediate was cyclized by heating at 120° C. in 1-methylpyrrolidin-2-one, then deprotected with hydrogen chloride.

[41] In this case, hydrogen chloride was used for the intermediate deprotection, rather than trifluoroacetic acid. Additionally, the final coupling was carried out with O-(7-azabenzotriazol-1-yl)-N,N,N',N'-tetramethyluronium hexafluorophosphate and N,N-diisopropylethylamine, rather than the reagents described in Example 15.

[42] tert-Butyl {[(1r,4r)-4-aminocyclohexyl]methyl}carbamate was condensed with 2-nitro-5-(trifluoromethyl)benzaldehyde, followed by ring closure of the resulting imine with triethyl phosphite and deprotection using hydrogen chloride, to afford the requisite 1-{(1r,4r)-4-[5-(trifluoromethyl)-2H-indazol-2-yl]cyclohexyl}methanamine, hydrochloride salt.

[43] In this case, hydrogen chloride was used for the intermediate deprotection, rather than trifluoroacetic acid.

[44] Reaction of tert-butyl {[(1r,4r)-4-aminocyclohexyl]methyl}carbamate with methyl 2-(bromomethyl)-4-chlorobenzoate and triethylamine, followed by deprotection with hydrogen chloride, provided the requisite 2-[(1r,4r)-4-(aminomethyl)cyclohexyl]-5-chloro-2,3-dihydro-1H-isoindol-1-one, hydrochloride salt.

[45] The requisite 1-[(1r,4r)-4-(5-chloro-2H-pyrazolo[3,4-c]pyridin-2-yl)cyclohexyl]methanamine, hydrochloride salt, was prepared using the method described for synthesis of C25 in Preparation P15.

[46] In this case, 3-hydroxybenzoic acid was used in place of 4-[(fluorosulfonyl)oxy]benzoic acid.

[47] Treatment of tert-butyl [4-(hydroxymethyl)bicyclo[2.2.2]octan-1-yl]carbamate with methanesulfonyl chloride and triethylamine, followed by displacement of the resulting methanesulfonate group using sodium azide and potassium carbonate, provided tert-butyl [4-(azidomethyl)bicyclo[2.2.2]octan-1-yl]carbamate. This material was hydrogenated over palladium on carbon, and the resulting primary amine was acylated with P1 by reaction with 1-[3-(dimethylamino)propyl]-3-ethylcarbodiimide hydrochloride and 1H-benzotriazol-1-ol. The product was deprotected via hydrogenation over palladium on carbon to provide Example 192.

[48] In this case, the acyl intermediate was cyclized by treatment with tetrabutylammonium fluoride, rather than sodium acetate.

[49] Reaction of 4-{[(tert-butoxycarbonyl)amino]methyl}bicyclo[2.2.2]octane-1-carboxylic acid with N-hydroxy-6-(trifluoromethyl)pyridine-3-carboximidamide N'-hydroxy-4-(trifluoromethyl)benzene-1-carboximidamide, mediated by 1-[3-(dimethylamino)propyl]-3-ethylcarbodiimide hydrochloride and 1-methyl-1H-imidazole, was followed by heating of the acyl intermediate in 1-methylpyrrolidin-2-one. The resulting cyclized material was deprotected with hydrogen chloride to provide the requisite 1-(4-{3-[6-(trifluoromethyl)pyridin-3-yl]-1,2,4-oxadiazol-5-yl}bicyclo[2.2.2]octan-1-yl)methanamine, hydrochloride salt.

[50] In this case, a final deprotection step was carried out using hydrogen chloride.[51] The requisite N-{[4-(6-bromo-2H-indazol-2-yl)bicyclo[2.2.2]octan-1-yl]methyl}-3,5-difluoro-4-[(4-methoxyphenyl)methoxy]benzamide was prepared using the methods described for synthesis of P16 in Preparations P8 and P16.

[52] N-{[4-(6-Bromo-2H-indazol-2-yl)bicyclo[2.2.2]octan-1-yl]methyl}-3,5-difluoro-4-[(4-methoxyphenyl) methoxy]benzamide, described in footnote[51], was deprotected using hydrogen chloride to afford Example 205.

[53] The final coupling was carried out with 2,3,5-trifluoro-4-hydroxybenzoic acid, rather than with P1.

[54] The requisite 1-{(1r,4r)-4-[3-(6-methylpyridazin-3-yl)-1,2,4-oxadiazol-5-yl]cyclohexyl}methanamine was prepared using the method described in Example 3 for the conversion of C29 to C32, except that cyclization to form the oxadiazole was carried out with heat, rather than microwave irradiation and NaOAc.

55. Coupling of 2,3,5-trifluoro-4-hydroxybenzoic acid and 1-{(1r,4r)-4-[3-(6-methylpyridazin-3-yl)-1,2,4-oxadiazol-5-yl]cyclohexyl}methanamine was carried out using O-(7-azabenzotriazol-1-yl)-N,N,N',N'-tetramethyluronium hexafluorophosphate and N, N-diisopropylethylamine.

[56] Reaction of (1r,4r)-4-{[(tert-butoxycarbonyl)amino]methyl}cyclohexane-1-carboxylic acid and N-hydroxyethanimidamide in the presence of 1-[3-(dimethylamino)propyl]-3-ethylcarbodiimide hydrochloride and triethylamine provided the coupled product, which was cyclized to the oxadiazole via reflux in toluene. Removal of the protecting group by treatment with hydrogen chloride in methanol provided the requisite 1-[(1r,4r)-4-(3-methyl-1,2,4-oxadiazol-5-yl)cyclohexyl]methanamine, hydrochloride salt.

The following protocols may of course be varied by those skilled in the art. hHSD17B13 $IC_{50}$ Assay (FAC beta-estradiol)

HSD17B13 enzyme inhibition potency of test compounds was determined using a purified protein biochemical enzyme activity assay, using NAD(P)H-Glo luciferase readout (Promega). HSD17B13 enzyme uses the oxidized form of nicotinamide adenine dinucleotide (NAD+) as a cofactor during metabolism of Beta-Estradiol (substrate) to estradiol (product), while converting NAD+ to the reduced form (NADH). The Promega NAD(P)H-Glo™ assay is a homogeneous bioluminescent assay that generates a light signal from biochemical reactions that contain NADH (or nicotinamide adenine dinucleotide phosphate, NADPH). In the presence of NADH (or NADPH), the enzyme Reductase reduces a proluciferin reductase substrate to form luciferin. Luciferin then is quantified using Ultra-Glo™ Recombinant Luciferase (rLuciferase), and the light signal produced is proportional to the amount of NAD(P)H in the sample. Substrate mix composed of 12 μM final assay concentration (FAC) beta-estradiol (Sigma, E8875) and 500 μM FAC NAD+ (Sigma, N8285) in assay buffer (25 mM Tris-HCl and 0.02% triton, pH 7.6, Sigma T2444 and X-100) was added (2 μL/well) to 384-well assay plates (Corning 3824) containing 80 nL of 50×FAC compound, serial diluted 1 in 3.162 in 100% DMSO for an 11 point concentration response curve (80 μM top concentration), with duplicate points at each concentration. The reaction was initiated by the addition of 2 μL/well purified HSD17B13 protein (30 nM FAC in assay buffer). Compound, substrate mix and HSD17B13 protein was incubated in the dark at room temperature for 2 hours before the addition of 3 μL/well NAD(P)H-Glo detection reagent, prepared from luciferase detection reagent and reductase/reductase substrate, as per manufacturer's instructions (Promega, G9061). Detection reagent was incubated in the dark for 1 hour at room temperature before plates were read on the Envision plate reader (Perkin Elmer) using a luminescent protocol. Data expressed as relative luminescent units (RLUs) were then normalized to control wells using Activity Base (IDBS). Zero percent effect (ZPE) was defined as RLUs generated from uninhibited HSD17B13 protein (vehicle control). One hundred percent effect (HPE) was defined RLUs generated from wells containing 40 μM FAC of a Pfizer proprietary compound known to cause 100% inhibition of HSD17B13 protein. The concentration and % effect values for each compound were plotted by Activity Base using a four-parameter logistic dose response equation, and the concentration required for 50% inhibition ($IC_{50}$) was determined.

HEK_Beta-Est LCMS_$IC_{50}$_Tekcel

Inhibition potency of test compounds was determined using a whole-cell HEK-HSD17B13 inhibition assay, utilizing a LCMS readout.

HSD17B13 uses the oxidized form of nicotinamide adenine dinucleotide (NAD+) as a cofactor during metabolism of beta-estradiol (substrate), converting NAD+ to the reduced form (NADH) and beta-estradiol to its product (estrone). Estrone production is quantified by LCMS, and used as a measure of HSD17B13 enzyme activity.

HEK-cells stably expressing wild type human HSD17B13 were plated at 10,000 cells/well in 50 μL growth media (DMEM containing 10% heat inactivated FBS, 400 μg/ml geneticin, 1× L-Glutamine, and 1× Non-essential amino acids, Invitrogen 11965-092, 16140-071, 10131-027, 25030-081, 11140-050), into poly-D-lysine-coated 384-well plates (Corning Biocoat, 354663), and incubated overnight (with lid) at 37° C. (95% $O_2$: 5% $CO_2$). Following overnight incubation, intermediate compound plates (Greiner, 781280) containing 160 nL of 375×FAC test compound which had been serial diluted 1 in 3.162 in 100% DMSO for an 11 point concentration response curve, with duplicate points at each concentration, were diluted 1 in 187.5 with 30 μL warmed assay media (DMEM, 1× L-Glutamine, and 1× Non-essential amino acids) to give 2×FAC compound (80 μM top concentration) in 0.53% DMSO. Growth media was then removed from the cell plates and replaced with 10 μL of 2×FAC test compound, and incubated for 1 hour (with lid) at 37° C. (95% $O_2$: 5% $CO_2$), before the addition of 25 μM FAC beta-estradiol in assay media/0.2% DMSO. The reaction was incubated for 2 hours (with lid) at 37° C. (95% $O_2$: 5% $CO_2$), after which 10 μL of reaction was transferred from assay plate to a new 384-well deep-well plate (Matrix 4325) and diluted 1 in 10 with 90 μL of stop reagent (50% methanol in water containing internal standard 17b-estradiol-2,3,4-$^{13}C_3$). Amount of product (estrone) was then quantified by LCMS. Data expressed as product area ratio (PAR) were then normalized to control wells using Activity Base (IDBS). Zero percent effect (ZPE) was defined as PAR generated from uninhibited HSD17B13 (vehicle control). One hundred percent effect (HPE) was defined PAR generated from wells containing 20 μM FAC of a Pfizer proprietary compound known to cause 100% inhibition of HSD17B13. The concentration and % effect values for each compound were plotted by Activity Base using a four-parameter logistic dose response equation, and the concentration required for 50% inhibition ($IC_{50}$) was determined.

In Table 3, assay data ($IC_{50}$s) are presented for the Examples below in accordance with the above-described assay (to two (2) significant figures as the geometric mean, based on the number of replicates tested (Number).

TABLE 3

Biological Assay Data

| Example | hHSD17B13_$IC_{50}$ GMean $IC_{50}$ (nM) (# Replicates) | HEK_Beta-Est LCMS_$IC_{50}$_Tekcel GMean $IC_{50}$ (μM) (# Replicates) |
|---|---|---|
| 1 | 14 (9) | 0.49 (4) |
| 2 | 12 (3) | 0.47 (3) |
| 3 | N.D. | 0.13 (3) |
| 4 | 5.5 (5) | 0.29 (3) |
| 5 | >2500 (1) | 0.072 (2) |
| 6 | 21 (3) | 0.44 (2) |
| 7 | N.D. | 0.18 (2) |
| 8 | 18 (1) | 0.32 (1) |
| 9 | 13 (3) | 0.17 (3) |
| 10 | N.D. | 0.12 (3) |
| 11 | N.D. | 0.24 (3) |
| 12 | 11 (3) | 0.29 (3) |
| 13 | 17 (3) | 0.47 (3) |
| 14 | N.D. | N.D. |
| 15 | 7.1 (3) | 0.22 (2) |
| 16 | 17 (3) | 0.31 (2) |
| 17 | 12 (3) | 0.27 (3) |
| 18 | 18 (3) | 0.42 (2) |
| 19 | N.D. | N.D. |
| 20 | 16 (5) | 0.49 (3) |
| 21 | N.D. | N.D. |
| 22 | 20 (9) | 0.39 (2) |
| 23 | 20 (3) | N.D. |
| 24 | 14 (4) | 0.12 (1) |
| 25 | 14 (5) | 0.30 (3) |
| 26 | N.D. | 0.19 (1) |
| 27 | 12 (1) | 0.18 (3) |
| 28 | 8.7 (3) | 0.17 (3) |
| 29 | N.D. | 0.35 (2) |
| 30 | N.D. | 0.36 (2) |

TABLE 3-continued

Biological Assay Data

| Example | hHSD17B13_$IC_{50}$ GMean $IC_{50}$ (nM) (# Replicates) | HEK_Beta-Est LCMS_$IC_{50}$_Tekcel GMean $IC_{50}$ (μM) (# Replicates) |
|---|---|---|
| 31 | N.D. | N.D. |
| 32 | 25 (3) | 0.40 (2) |
| 33 | N.D. | 0.38 (2) |
| 34 | 4.3 (4) | 0.31 (3) |
| 35 | 10 (3) | 0.35 (3) |
| 36 | 2.7 (4) | 0.18 (3) |
| 37 | 8.4 (3) | 0.15 (3) |
| 38 | 4.6 (3) | 0.15 (3) |
| 39 | 5.7 (5) | 0.25 (3) |
| 40 | 4.3 (3) | 0.16 (3) |
| 41 | 21 (3) | 0.44 (3) |
| 42 | 11 (3) | 0.26 (3) |
| 43 | 2.8 (4) | 0.14 (3) |
| 44 | <2.6 (4) | 0.092 (3) |
| 45 | 5.4 (5) | 0.22 (3) |
| 46 | 9.5 (3) | 0.45 (3) |
| 47 | <4.4 (4) | 0.11 (3) |
| 48 | 3.2 (4) | 0.13 (3) |
| 49 | 3.4 (5) | 0.43 (3) |
| 50 | 11 (3) | 0.25 (3) |
| 51 | 6.5 (3) | 0.12 (3) |
| 52 | 15 (4) | 0.33 (2) |
| 53 | 4.4 (4) | 0.20 (2) |
| 54 | 9.5 (3) | 0.23 (2) |
| 55 | 17 (3) | 0.23 (2) |
| 56 | 3.8 (3) | 0.16 (2) |
| 57 | 26 (3) | 0.31 (2) |
| 58 | 25 (4) | 0.28 (2) |
| 59 | 11 (3) | 0.47 (2) |
| 60 | 5.8 (4) | 0.094 (3) |
| 61 | 4.8 (4) | 0.12 (2) |
| 62 | 8.7 (3) | 0.35 (2) |
| 63 | 11 (4) | 0.37 (2) |
| 64 | 5.6 (4) | 0.35 (2) |
| 65 | 13 (3) | 0.17 (2) |
| 66 | 7.5 (4) | 0.18 (2) |
| 67 | 31 (3) | 0.27 (2) |
| 68 | 7.8 (4) | 0.27 (2) |
| 69 | 8.4 (3) | 0.13 (3) |
| 70 | 3.8 (5) | 0.19 (2) |
| 71 | 9.6 (3) | 0.43 (2) |
| 72 | 7.8 (3) | 0.17 (2) |
| 73 | 13 (3) | 0.17 (3) |
| 74 | 12 (3) | 0.17 (2) |
| 75 | 19 (4) | 0.21 (2) |
| 76 | 19 (3) | 0.19 (2) |
| 77 | 13 (3) | 0.16 (2) |
| 78 | N.D. | 0.19 (4) |
| 79 | N.D. | 0.37 (4) |
| 80 | N.D. | 0.20 (3) |
| 81 | N.D. | 0.12 (3) |
| 82 | N.D. | 0.12 (4) |
| 83 | N.D. | 0.094 (3) |
| 84 | N.D. | 0.39 (3) |
| 85 | N.D. | 0.18 (3) |
| 86 | N.D. | 0.27 (1) |
| 87 | N.D. | 0.13 (1) |
| 88 | N.D. | 0.17 (4) |
| 89 | N.D. | 0.13 (4) |
| 90 | N.D. | 0.20 (1) |
| 91 | N.D. | 0.28 (2) |
| 92 | N.D. | 0.13 (4) |
| 93 | N.D. | 0.18 (4) |
| 94 | N.D. | 0.14 (3) |
| 95 | N.D. | 0.24 (4) |
| 96 | N.D. | 0.085 (3) |
| 97 | N.D. | 0.30 (1) |
| 98 | N.D. | 0.11 (3) |
| 99 | N.D. | 0.22 (2) |
| 100 | N.D. | 0.065 (3) |
| 10 | N.D. | 0.14 (3) |
| 102 | N.D. | 0.20 (4) |
| 103 | N.D. | 0.36 (1) |
| 104 | N.D. | 0.37 (3) |
| 105 | N.D. | 0.37 (2) |
| 106 | N.D. | 0.15 (3) |
| 107 | N.D. | 0.16 (4) |
| 108 | N.D. | 0.14 (1) |
| 109 | N.D. | 0.17 (4) |
| 110 | N.D. | 0.11 (1) |
| 111 | N.D. | 0.081 (3) |
| 112 | N.D. | 0.22 (2) |
| 113 | N.D. | 0.32 (2) |
| 114 | N.D. | 0.17 (3) |
| 115 | N.D. | 0.19 (4) |
| 116 | N.D. | 0.19 (4) |
| 117 | N.D. | 0.18 (3) |
| 118 | N.D. | 0.23 (4) |
| 119 | N.D. | 0.15 (3) |
| 120 | N.D. | 0.25 (4) |
| 12 | N.D. | 0.15 (3) |
| 122 | 14 (3) | 0.31 (2) |
| 123 | 10 (6) | 0.46 (4) |
| 124 | 7.1 (6) | 0.16 (4) |
| 125 | 17 (3) | 0.25 (2) |
| 126 | 16 (5) | 0.43 (4) |
| 127 | 13 (3) | 0.35 (3) |
| 128 | 16 (6) | 0.40 (3) |
| 129 | 33 (3) | 0.40 (2) |
| 130 | 27 (3) | 0.33 (3) |
| 131 | 27 (3) | 0.27 (3) |
| 132 | 14 (3) | 0.14 (3) |
| 133 | 29 (3) | 0.28 (3) |
| 134 | 32 (3) | 0.47 (3) |
| 135 | 21 (3) | 0.25 (2) |
| 136 | 15 (3) | 0.30 (4) |
| 137 | 25 (3) | 0.28 (3) |
| 138 | 16 (3) | 0.20 (3) |
| 139 | 22 (3) | 0.41 (3) |
| 140 | 16 (3) | 0.22 (3) |
| 141 | 8.8 (3) | 0.19 (3) |
| 142 | 10 (3) | 0.16 (2) |
| 143 | 13 (3) | 0.18 (3) |
| 144 | 14 (3) | 0.44 (3) |
| 145 | 18 (4) | 0.26 (3) |
| 146 | 5.6 (8) | 0.29 (5) |
| 147 | 17 (5) | 0.43 (2) |
| 148 | N.D. | 0.47 (1) |
| 149 | N.D. | 0.43 (1) |
| 150 | 4.8 (1) | 0.12 (2) |
| 151 | 8.2 (3) | 0.17 (3) |
| 152 | 10 (3) | 0.14 (3) |
| 153 | 31 (3) | 0.27 (2) |
| 154 | N.D. | 0.11 (3) |
| 155 | N.D. | 0.12 (3) |
| 156 | N.D. | 0.17 (3) |
| 157 | N.D. | 0.27 (2) |
| 158 | N.D. | 0.19 (3) |
| 159 | N.D. | 0.091 (3) |
| 160 | N.D. | 0.40 (3) |
| 161 | N.D. | 0.18 (3) |
| 162 | N.D. | 0.31 (3) |
| 163 | N.D. | 0.33 (3) |
| 164 | N.D. | 0.23 (3) |
| 165 | N.D. | 0.42 (3) |
| 166 | N.D. | 0.41 (3) |
| 167 | N.D. | 0.20 (3) |
| 168 | N.D. | 0.38 (2) |
| 169 | N.D. | N.D. |
| 170 | N.D. | N.D. |
| 171 | N.D. | N.D. |
| 172 | N.D. | N.D. |
| 173 | N.D. | N.D. |
| 174 | N.D. | N.D. |
| 175 | N.D. | N.D. |
| 176 | 11 (3) | 0.19 (3) |

TABLE 3-continued

| Biological Assay Data | | |
|---|---|---|
| Example | hHSD17B13_$IC_{50}$ GMean $IC_{50}$ (nM) (# Replicates) | HEK_Beta-Est LCMS_$IC_{50}$_Tekcel GMean $IC_{50}$ (μM) (# Replicates) |
| 177 | 17 (4) | 0.37 (3) |
| 178 | 7.9 (6) | 0.15 (5) |
| 179 | 16 (3) | 0.15 (3) |
| 180 | 11 (4) | 0.47 (3) |
| 181 | 16 (3) | 0.23 (2) |
| 182 | 16 (3) | 0.23 (3) |
| 183 | 10 (6) | 0.45 (3) |
| 184 | 5.5 (5) | 0.22 (3) |
| 185 | 3.7 (5) | 0.14 (3) |
| 186 | 15 (3) | 0.48 (2) |
| 187 | 10 (2) | 0.40 (2) |
| 188 | 11 (1) | 0.24 (2) |
| 189 | N.D. | 0.43 (3) |
| 190 | 8.6 (4) | 0.42 (4) |
| 191 | 9.7 (4) | 0.12 (3) |
| 192 | N.D. | 0.48 (3) |
| 193 | 22 (1) | 0.44 (1) |
| 194 | N.D. | 0.23 (1) |
| 195 | 16 (3) | 0.39 (2) |
| 196 | 12 (3) | 0.34 (2) |
| 197 | 39 (3) | 0.47 (2) |
| 198 | 6.5 (5) | 0.31 (3) |
| 199 | 8.8 (3) | 0.37 (2) |
| 200 | 10 (4) | 0.35 (2) |
| 201 | N.D. | 0.35 (2) |
| 202 | 49 (3) | 0.22 (2) |
| 203 | N.D. | 0.098 (3) |
| 204 | N.D. | 0.099 (3) |
| 205 | N.D. | 0.22 (2) |
| 206 | N.D. | 0.15 (3) |
| 207 | N.D. | 0.14 (4) |
| 208 | N.D. | 0.12 (4) |
| 209 | N.D. | 0.15 (4) |
| 210 | 18 (3) | 0.45 (3) |
| 211 | 15 (12) | 2.7 (3) |
| 212 | 26 (10) | 2.3 (1) |
| 213 | 64 (7) | N.D. |
| 214 | 290 (6) | N.D. |

Throughout this application, various publications are referenced. The disclosures of these publications in their entireties are hereby incorporated by reference into this application for all purposes.

It will be apparent to those skilled in the art that various modifications and variations can be made without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of Formula I

Formula I

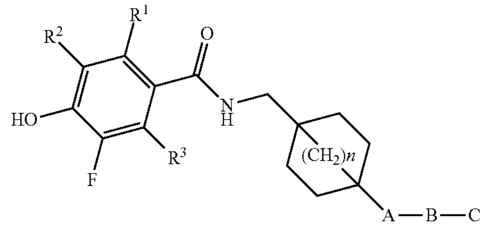

wherein

A is —NH—C(O)— or a heteroaryl having 1, 2, 3, or 4 heteroatoms selected from O, N, and S and wherein A is optionally substituted with one or two $R^4$;

B is absent or is H, aryl, heteroaryl, heterocyclyl, fluoro, chloro, bromo, oxo, cyano, hydroxyl, $(C_1-C_6)$alkyl, $(C_3-C_6)$cycloalkyl, $(C_1-C_6)$fluoroalkyl, $(C_1-C_6)$alkoxy, or $(C_1-C_6)$fluoroalkoxy, wherein the heteroaryl or heterocyclyl has 1, 2, or 3 heteroatoms selected from O,N, and S and wherein B is optionally substituted with one or two $R^5$;

C is absent or is H, —NH—C(O)—$R^7$, —$S(O)_2$—$R^7$, —O—$S(O)_2$—$R^7$, fluoro, chloro, bromo, oxo, cyano, hydroxyl, $(C_1-C_6)$alkyl, $(C_3-C_6)$cycloalkyl, $(C_1-C_6)$alkoxy, $(C_3-C_6)$cycloether, $(C_1-C_6)$fluoroalkyl, $(C_1-C_6)$fluoroalkoxy, aryl, heteroaryl or heterocyclyl, wherein the heteroaryl or heterocyclyl has 1, 2, or 3 heteroatoms selected from ON, and S, and wherein C is optionally substituted with one, two or three $R^6$;

$R^1$, $R^2$, and $R^3$ are each independently selected from H and fluoro;

each $R^4$, $R^5$ and $R^6$ are independently selected from oxo, hydroxyl, chloro, fluoro, $(C_1-C_6)$alkyl, $(C_1-C_6)$alkoxy, $(C_1-C_6)$fluoroalkyl, $(C_3-C_6)$cycloalkyl, and heterocyclyl having 1, 2, or 3 heteroatoms selected from O and N;

$R^7$ is hydroxyl, chloro, fluoro, $(C_1-C_6)$alkyl, $(C_1-C_6)$alkoxy, $(C_1-C_6)$fluoroalkyl, or $(C_3-C_6)$cycloalkyl; and n is 0, 1 or 2;

or a pharmaceutically acceptable salt of said compound.

2. The compound of claim 1, wherein the compound has the Formula IA

Formula IA

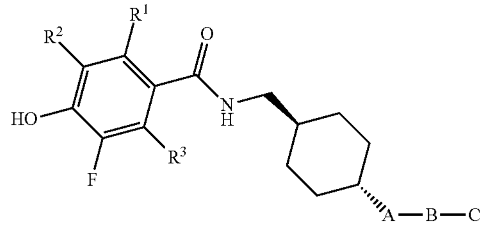

or a pharmaceutically acceptable salt of said compound.

3. The compound of claim 1, wherein the compound has the Formula IB

Formula IB

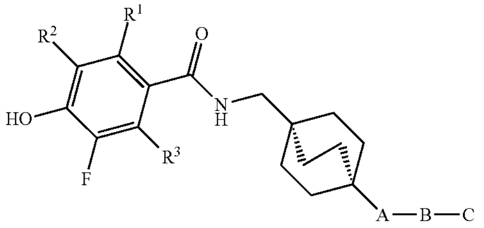

or a pharmaceutically acceptable salt of said compound.

4. The compound of claim 1, wherein at least one of $R^1$, $R^2$, and $R^3$ are fluoro; or a pharmaceutically acceptable salt of said compound.

5. The compound of claim 1, wherein A is thiazolyl, pyrazolyl, oxazolyl, imidazolyl, isoxazolyl, isothiazolyl, imidazotriazinyl, imidazopyridazinyl, imidazopyridinyl, benzoimidazolyl, benzothiazolyl, purinyl, pyridopyridazinyl, quinazolinyl, indazolyl, imidazopyridinyl, benzooxazolyl, pyrazolopyridinyl, isoindolinonyl, triazolyl, or oxadiazolyl, or a pharmaceutically acceptable salt of said compound.

6. The compound of claim 1, wherein

A is

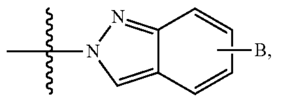 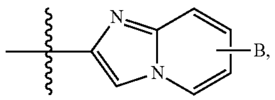

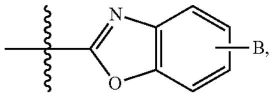

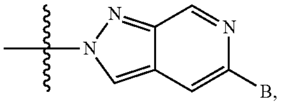

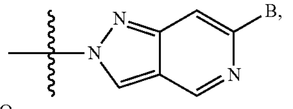

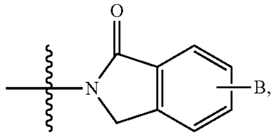 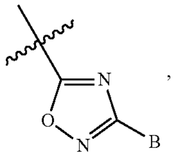 ,

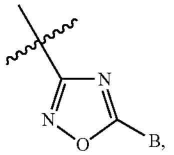 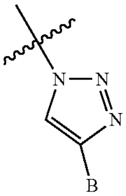 , or

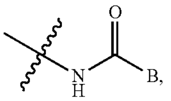

or a pharmaceutically acceptable salt of said compound.

7. The compound of claim 1, wherein B is absent or is H, pyridinyl, pyrimidinyl, pyridazinyl, pyrazinyl, pyrazolyl, piperazinyl, quinoxalinyl, phenyl, triazolyl, thiazolyl, thiadiazolyl, oxazolyl, imidazolyl, indazolyl, $(C_1\text{-}C_6)$alkyl, $(C_1\text{-}C_6)$fluoroalkyl, $(C_1\text{-}C_6)$alkoxy, bromo, chloro, fluoro, or oxo, and wherein B is optionally substituted with one or two fluoro, oxo, hydroxyl, $(C_1\text{-}C_6)$alkyl, $(C_3\text{-}C_6)$cycloalkyl, $(C_1\text{-}C_6)$fluoroalkyl, $(C_1\text{-}C_6)$alkoxy, or $(C_3\text{-}C_6)$cycloether; or a pharmaceutically acceptable salt of said compound.

8. The compound of claim 1, wherein B is pyrimidinyl, $(C_1\text{-}C_3)$fluoroalkyl substituted pyrimidinyl, $(C_1\text{-}C_3)$alkyl substituted pyrazolyl, methoxy substituted pyridazinyl, difluoromethyl substituted pyrazinyl, trifluoromethyl substituted pyrimidinyl, or methoxy substituted pyrimidinyl; or a pharmaceutically acceptable salt of said compound.

9. The compound of claim 1, wherein C is absent or is H, pyridinyl, piperazinyl, oxolanyl, $(C_3\text{-}C_6)$cycloalkyl, $(C_1\text{-}C_6)$alkyl, $(C_1\text{-}C_6)$fluoroalkyl, $(C_1\text{-}C_6)$alkoxy, cyano, bromo, chloro, fluoro, or oxo, and wherein C is optionally substituted with one, two or three fluoro, oxo, hydroxyl, $(C_1\text{-}C_6)$alkyl, $(C_3\text{-}C_6)$cycloalkyl, $(C_1\text{-}C_6)$fluoroalkyl, or $(C_1\text{-}C_6)$alkoxy; or a pharmaceutically acceptable salt of said compound.

10. The compound of claim 1, wherein C is absent or is pyridinyl, piperazinyl, $(C_3\text{-}C_6)$cycloalkyl, $(C_1\text{-}C_6)$alkyl, $(C_1\text{-}C_6)$fluoroalkyl; and wherein C is optionally substituted with one, two or three fluoro, oxo, hydroxyl, or $(C_1\text{-}C_5)$alkyl; or a pharmaceutically acceptable salt of said compound.

11. The compound of claim 1, wherein the compound is selected from the group consisting of:

2,3,5-Trifluoro-4-hydroxy-N-[(4-{3-[5-(trifluoromethyl)pyrimidin-2-yl]-1,2,4-oxadiazol-5-yl}bicyclo[2.2.2]octan-1-yl)methyl]benzamide;

2,3,5-Trifluoro-4-hydroxy-N-({4-[6-(pyrimidin-2-yl)-2H-indazol-2-yl]bicyclo[2.2.2]octan-1-yl}methyl)benzamide;

2,3,5-Trifluoro-4-hydroxy-N-({(1r,4r)-4-[6-(pyrimidin-5-yl)-2H-indazol-2-yl]cyclohexyl}methyl)benzamide;

2,3,5-Trifluoro-4-hydroxy-N-({4-[3-(6-methoxy-pyridazin-3-yl)-1,2,4-oxadiazol-5-yl]bicyclo[2.2.2]octan-1-yl}methyl)benzamide:

N-[(4-{5-[5-(Difluoromethyl)pyrazin-2-yl]-1,2,4-oxadiazol-3-yl}bicyclo[2.2.2]octan-1-yl)methyl]-3,5-difluoro-4-hydroxybenzamide;

3,5-Difluoro-4-hydroxy-N-{[(1r,4r)-4-{3-[5-(trifluoromethyl)pyrimidin-2-yl]-1,2,4-oxadiazol-5-yl}cyclohexyl]methyl}benzamide;

3,5-Difluoro-4-hydroxy-N-({(1r,4r)-4-[6-(2-methoxypyrimidin-5-yl)-2H-pyrazolo[4,3-c]pyridin-2-yl]cyclohexyl}methyl)benzamide, 2,3,5-Trifluoro-4-hydroxy-N-[(4-{5-[2-(piperazin-1-yl)pyrimidin-4-yl]-1,2,4-oxadiazol-3-yl}bicyclo[2.2.2]octan-1-yl)methyl]benzamide, or 2,3,5-Trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide, or a pharmaceutically acceptable salt of said compound.

12. The compound of claim 1, wherein the compound is 2,3,5-Trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide, or a pharmaceutically acceptable salt of said compound.

13. The compound of claim 1, wherein the compound is 2,3,5-Trifluoro-4-hydroxy-N-[(4-{5-[2-(4-methylpiperazin-1-yl)pyrimidin-4-yl]-1,2,4-oxadiazol-3-yl}bicyclo[2.2.2]octan-1-yl)methyl]benzamide, hydrochloride salt.

14. The compound of claim 1, wherein the compound is

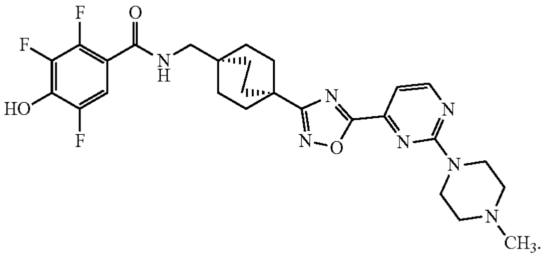 [SMILES: CN1CCN(c2nccc(-c3nc([C@]45CC[C@](CNC(=O)c6cc(F)c(O)c(F)c6F)(CC4)CC5)no3)n2)CC1]

15. A pharmaceutical composition which comprises a therapeutically effective amount of a compound of Formula I:

Formula I

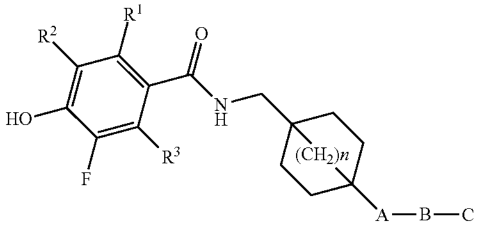

wherein

A is —NH—C(O)— or a heteroaryl having 1, 2, 3, or 4 heteroatoms selected from O, N, and S and wherein A is optionally substituted with one or two $R^4$;

B is absent or is H, aryl, heteroaryl, heterocyclyl, fluoro, chloro, bromo, oxo, cyano, hydroxyl, $(C_1\text{-}C_6)$alkyl, $(C_3\text{-}C_6)$cycloalkyl, $(C_1\text{-}C_6)$fluoroalkyl, $(C_1\text{-}C_6)$alkoxy, or $(C_1\text{-}C_6)$fluoroalkoxy, wherein the heteroaryl or heterocyclyl has 1, 2, or 3 heteroatoms selected from ON, and S and wherein B is optionally substituted with one or two $R^5$;

C is absent or is H, —NH—C(O)—$R^7$, —$S(O)_2$—$R^7$, —O—$S(O)_2$—$R^7$, fluoro, chloro, bromo, oxo, cyano, hydroxyl, $(C_1\text{-}C_6)$alkyl, $(C_3\text{-}C_6)$cycloalkyl, $(C_1\text{-}C_6)$alkoxy, $(C_3\text{-}C_6)$cycloether, $(C_1\text{-}C_6)$fluoroalkyl, $(C_1\text{-}C_6)$fluoroalkoxy, aryl, heteroaryl or heterocyclyl, wherein the heteroaryl or heterocyclyl has 1, 2, or 3 heteroatoms selected from ON, and S, and wherein C is optionally substituted with one, two or three $R^6$;

$R^1$, $R^2$, and $R^3$are each independently selected from H and fluoro;

each $R^4$, $R^5$ and $R^6$ are independently selected from oxo, hydroxyl, chloro, fluoro, $(C_1\text{-}C_6)$alkyl, $(C_1\text{-}C_6)$alkoxy, $(C_1\text{-}C_6)$fluoroalkyl, $(C_3\text{-}C_6)$cycloalkyl, and heterocyclyl having 1, 2, or 3 heteroatoms selected from O and N;

$R^7$ is hydroxyl, chloro, fluoro, $(C_1\text{-}C_6)$alkyl, $(C_1\text{-}C_6)$alkoxy, $(C_1\text{-}C_6)$fluoroalkyl, or $(C_3\text{-}C_6)$cycloalkyl; and n is 0, 1 or 2;

or a pharmaceutically acceptable salt of said compound; and a pharmaceutically acceptable carrier, vehicle or diluent.

16. The pharmaceutical composition of claim 15, further comprising a second compound, the second compound being an anti-diabetic agent; a non-alcoholic steatohepatitis treatment agent, a non-alcoholic fatty liver disease treatment agent or an anti-heart failure treatment agent.

* * * * *